US012522648B2

(12) United States Patent
Igawa et al.

(10) Patent No.: US 12,522,648 B2

(45) Date of Patent: Jan. 13, 2026

(54) ANTIGEN-BINDING MOLECULE CONTAINING MODIFIED Fc REGION

(71) Applicant: Chugai Seiyaku Kabushiki Kaisha, Tokyo (JP)

(72) Inventors: Tomoyuki Igawa, Shizuoka (JP); Naoka Hironiwa, Shizuoka (JP); Shojiro Kadono, Kanagawa (JP); Atsushi Matsuo, Shizuoka (JP); Taichi Kuramochi, Shizuoka (JP); Futa Mimoto, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 967 days.

(21) Appl. No.: 17/484,003

(22) Filed: Sep. 24, 2021

(65) Prior Publication Data

US 2022/0242934 A1 Aug. 4, 2022

Related U.S. Application Data

(62) Division of application No. 14/406,232, filed as application No. PCT/JP2013/066428 on Jun. 14, 2013, now Pat. No. 11,142,563.

(30) Foreign Application Priority Data

Jun. 14, 2012 (JP) ................................ 2012-134908

(51) Int. Cl.
*C07K 16/00* (2006.01)
*C07K 16/22* (2006.01)
*C07K 16/28* (2006.01)

(52) U.S. Cl.
CPC .............. *C07K 16/00* (2013.01); *C07K 16/22* (2013.01); *C07K 16/2848* (2013.01); *C07K 2317/52* (2013.01); *C07K 2317/524* (2013.01); *C07K 2317/71* (2013.01); *C07K 2317/72* (2013.01); *C07K 2317/732* (2013.01); *C07K 2317/94* (2013.01); *C07K 2319/30* (2013.01)

(58) Field of Classification Search
CPC .............. C07K 16/00; C07K 2317/524; C07K 2317/52; C07K 2317/71; C07K 2317/72
See application file for complete search history.

(56) References Cited

U.S. PATENT DOCUMENTS

| | | | |
|---|---|---|---|
| 6,344,443 | B1 | 2/2002 | Liu et al. |
| 6,737,056 | B1 | 5/2004 | Presta et al. |
| 7,317,091 | B2 | 1/2008 | Lazar et al. |
| 7,662,925 | B2 | 2/2010 | Lazar et al. |
| 7,951,917 | B1 | 5/2011 | Arathoon et al. |
| 8,063,187 | B2 | 11/2011 | Chu et al. |
| 8,524,867 | B2 | 9/2013 | Bernett et al. |
| 8,551,485 | B2 | 10/2013 | Bernett et al. |
| 8,592,562 | B2 | 11/2013 | Kannan et al. |
| 8,802,823 | B2 | 8/2014 | Lazar et al. |
| 9,051,373 | B2 | 6/2015 | Lazar et al. |
| 9,200,060 | B2 | 12/2015 | Kannan et al. |
| 9,890,218 | B2 | 2/2018 | Mimoto et al. |
| 10,766,960 | B2 | 9/2020 | Igawa et al. |
| 11,142,563 | B2 | 10/2021 | Igawa et al. |
| 11,154,615 | B2 | 10/2021 | Igawa et al. |
| 11,739,149 | B2 | 8/2023 | Igawa et al. |
| 11,952,422 | B2 | 4/2024 | Shimizu et al. |
| 2004/0110226 | A1 | 6/2004 | Lazar et al. |
| 2005/0260213 | A1 | 11/2005 | Koenig et al. |
| 2006/0121042 | A1 | 6/2006 | Dallacqua et al. |
| 2006/0134709 | A1 | 6/2006 | Stavenhagen et al. |
| 2006/0140934 | A1 | 6/2006 | Gegg et al. |
| 2006/0275283 | A1 | 12/2006 | van Vlijmen et al. |
| 2007/0237767 | A1 | 10/2007 | Lazar et al. |
| 2007/0286859 | A1 | 12/2007 | Lazar et al. |
| 2008/0014205 | A1 | 1/2008 | Horowitz et al. |
| 2008/0051563 | A1 | 2/2008 | Lazar et al. |
| 2009/0076251 | A1 | 3/2009 | Koenig et al. |
| 2009/0136485 | A1 | 5/2009 | Chu et al. |
| 2010/0150918 | A1 | 6/2010 | Kufer et al. |
| 2010/0249482 | A1 | 9/2010 | Chung et al. |
| 2010/0316641 | A1 | 12/2010 | Dimitrov |
| 2010/0322946 | A1 | 12/2010 | Bostrom et al. |
| 2010/0331527 | A1 | 12/2010 | Davis et al. |
| 2011/0021755 | A1 | 1/2011 | Lazar et al. |
| 2011/0027276 | A1 | 2/2011 | Bernett et al. |
| 2012/0149876 | A1 | 6/2012 | Kreudenstein et al. |

(Continued)

FOREIGN PATENT DOCUMENTS

| | | |
|---|---|---|
| CA | 2 815 266 | 5/2012 |
| CN | 1069124 | 2/1993 |

(Continued)

OTHER PUBLICATIONS

U.S. Appl. No. 18/022,342, Katada et al., filed Feb. 21, 2023.

(Continued)

*Primary Examiner* — Meera Natarajan

*Assistant Examiner* — Francesca Edgingtongiordano

(74) *Attorney, Agent, or Firm* — Fish & Richardson P.C.

(57) ABSTRACT

The present inventors have successfully prepared an antibody Fc region dimer that has binding activity against each of an antigen and FcγR, but does not bind to the antigen and the FcγR at the same time, and a polypeptide comprising the Fc region dimer. The present invention enables the preparation of a multispecific binding polypeptide capable of avoiding an adverse reaction that may be caused by its binding to an antigen and FcγR at the same time. Thus, the present invention provides a polypeptide suitable as a drug.

25 Claims, 22 Drawing Sheets

Specification includes a Sequence Listing.

(56) References Cited

U.S. PATENT DOCUMENTS

| | | | |
|---|---|---|---|
| 2012/0244578 | A1 | 9/2012 | Kannan et al. |
| 2013/0101581 | A1 | 4/2013 | Kuramochi et al. |
| 2014/0093496 | A1 | 4/2014 | Mimoto et al. |
| 2014/0105889 | A1 | 4/2014 | Igawa et al. |
| 2014/0112914 | A1 | 4/2014 | Nezu et al. |
| 2014/0112926 | A1 | 4/2014 | Liu |
| 2014/0199294 | A1 | 7/2014 | Mimoto et al. |
| 2014/0242077 | A1 | 8/2014 | Choi et al. |
| 2014/0335089 | A1 | 11/2014 | Igawa et al. |
| 2015/0166636 | A1 | 6/2015 | Igawa et al. |
| 2015/0166654 | A1 | 6/2015 | Igawa et al. |
| 2015/0203577 | A1 | 7/2015 | Igawa et al. |
| 2015/0210763 | A1 | 7/2015 | Kuramochi et al. |
| 2015/0299296 | A1 | 10/2015 | Katada et al. |
| 2015/0344570 | A1 | 12/2015 | Igawa et al. |
| 2016/0200807 | A1 | 7/2016 | Ruike et al. |
| 2016/0229915 | A1 | 8/2016 | Igawa et al. |
| 2016/0280787 | A1 | 9/2016 | Igawa et al. |
| 2018/0155451 | A1 | 6/2018 | Mimoto et al. |
| 2018/0319877 | A1 | 11/2018 | Ruike et al. |
| 2020/0332001 | A1 | 10/2020 | Igawa et al. |
| 2020/0377595 | A1 | 12/2020 | Shimizu et al. |
| 2021/0261648 | A1 | 8/2021 | Katada et al. |
| 2021/0388087 | A1 | 12/2021 | Ho et al. |
| 2022/0040297 | A1 | 2/2022 | Igawa et al. |
| 2023/0174655 | A1 | 6/2023 | Mimoto et al. |
| 2023/0416371 | A1 | 12/2023 | Katada et al. |
| 2024/0026000 | A1 | 1/2024 | Igawa et al. |
| 2024/0043515 | A1 | 2/2024 | Katada et al. |
| 2024/0270846 | A1 | 8/2024 | Shimizu et al. |

FOREIGN PATENT DOCUMENTS

| | | | |
|---|---|---|---|
| CN | 1291198 | | 4/2001 |
| CN | 1763097 | | 4/2006 |
| CN | 101123983 | | 2/2008 |
| CN | 103827300 | | 5/2014 |
| CN | 105102618 | A | 11/2015 |
| EP | 1 293 514 | | 3/2003 |
| EP | 1 752 471 | | 2/2007 |
| EP | 2 196 541 | | 6/2010 |
| EP | 2 647 707 | | 10/2013 |
| EP | 2 728 002 | | 5/2014 |
| EP | 2 731 970 | A | 5/2014 |
| EP | 2 762 493 | A1 | 8/2014 |
| EP | 2 862 875 | A1 | 4/2015 |
| EP | 2 940 135 | | 11/2015 |
| EP | 3 070 168 | | 9/2016 |
| EP | 3 130 606 | | 2/2017 |
| EP | 3 219 724 | | 9/2017 |
| EP | 4 082 570 | A1 | 11/2022 |
| EP | 4 361 273 | A1 | 5/2024 |
| JP | 2003-512019 | | 4/2003 |
| JP | 2006-512407 | | 4/2006 |
| JP | 2006-524039 | | 10/2006 |
| JP | 2007-532139 | | 11/2007 |
| JP | 2007-536912 | | 12/2007 |
| JP | 2008-514201 | | 5/2008 |
| JP | 2008-518023 | | 5/2008 |
| JP | 2008-526809 | | 7/2008 |
| JP | 2009-511067 | | 3/2009 |
| JP | 2009-511587 | | 3/2009 |
| JP | 2009-538273 | | 11/2009 |
| JP | 2009/540837 | | 11/2009 |
| JP | 2010-524851 | | 7/2010 |
| JP | 2012-501648 | | 1/2012 |
| JP | 2014-504265 | A | 2/2014 |
| JP | 2014-509857 | A | 4/2014 |
| JP | 6433297 | | 12/2018 |
| JP | 6628966 | | 1/2020 |
| RU | 2236222 | | 9/2004 |
| RU | 2005/112742 | | 1/2006 |
| RU | 2006/142852 | | 6/2008 |
| RU | 2390527 | | 5/2010 |
| RU | 2398777 | | 9/2010 |
| TW | 2011/16625 | | 5/2011 |
| WO | WO 92/19973 | | 11/1992 |
| WO | WO 94/18221 | | 8/1994 |
| WO | WO 95/14714 | | 6/1995 |
| WO | WO 99/40117 | | 8/1999 |
| WO | WO 99/58572 | | 11/1999 |
| WO | WO 00/15214 | | 3/2000 |
| WO | WO 00/42072 | | 7/2000 |
| WO | WO 2004/029207 | | 4/2004 |
| WO | WO 2004/063351 | | 7/2004 |
| WO | WO 2004/099249 | | 11/2004 |
| WO | WO 2005/056606 | | 6/2005 |
| WO | WO 2005/059106 | | 6/2005 |
| WO | WO 2005/070966 | | 8/2005 |
| WO | WO 2005/115452 | | 12/2005 |
| WO | WO 2006/015371 | | 2/2006 |
| WO | WO 2006/019447 | | 2/2006 |
| WO | WO 2006/023403 | | 3/2006 |
| WO | WO 2006/023420 | | 3/2006 |
| WO | WO 2006/036291 | | 4/2006 |
| WO | WO 2006/036834 | | 4/2006 |
| WO | WO 2006/047639 | | 5/2006 |
| WO | WO 2006/072620 | | 7/2006 |
| WO | WO 2006/076594 | | 7/2006 |
| WO | WO 2006/083706 | | 8/2006 |
| WO | WO 2006/085938 | | 8/2006 |
| WO | WO 2006/088494 | | 8/2006 |
| WO | WO 2006/106905 | | 10/2006 |
| WO | WO 2006/133486 | | 12/2006 |
| WO | WO 2007/022520 | | 2/2007 |
| WO | WO 2007/024249 | | 3/2007 |
| WO | WO 2007/047291 | | 4/2007 |
| WO | WO 2007/047578 | | 4/2007 |
| WO | WO 2007/114325 | | 10/2007 |
| WO | WO 2007/121354 | | 10/2007 |
| WO | WO 2008/003103 | | 1/2008 |
| WO | WO 2008/119567 | | 10/2008 |
| WO | WO 2008/150494 | | 12/2008 |
| WO | WO 2009/041062 | | 4/2009 |
| WO | WO 2009/062083 | | 5/2009 |
| WO | WO 2010/027981 | | 3/2010 |
| WO | WO 2011/107989 | | 9/2011 |
| WO | WO 2011/108714 | | 9/2011 |
| WO | WO 2011/133886 | | 10/2011 |
| WO | WO 2012/058768 | | 5/2012 |
| WO | WO 2012/073985 | | 6/2012 |
| WO | WO 2012/096994 | | 7/2012 |
| WO | WO 2012/115241 | | 8/2012 |
| WO | WO 2012/125850 | | 9/2012 |
| WO | WO 2012/143524 | | 10/2012 |
| WO | WO 2012/162067 | | 11/2012 |
| WO | WO 2013/002362 | | 1/2013 |
| WO | WO 2013/026833 | | 2/2013 |
| WO | WO 2013/047748 | A1 | 4/2013 |
| WO | WO 2013/059593 | | 4/2013 |
| WO | WO 2013/063702 | | 5/2013 |
| WO | WO 2013/187495 | | 12/2013 |
| WO | WO 2014/104165 | | 7/2014 |
| WO | WO 2014/116846 | | 7/2014 |
| WO | WO 2014/163101 | | 10/2014 |
| WO | WO 2014/177459 | A2 | 11/2014 |
| WO | WO 2015/068847 | | 5/2015 |
| WO | WO 2015/156268 | | 10/2015 |
| WO | WO 2016/076345 | | 5/2016 |
| WO | WO 2018/146317 | A1 | 8/2018 |
| WO | WO 2019/111871 | | 6/2019 |
| WO | WO 2020/067419 | | 4/2020 |
| WO | WO 2021/131021 | A1 | 7/2021 |
| WO | WO 2022/044248 | A1 | 3/2022 |
| WO | WO 2022/045276 | A1 | 3/2022 |
| WO | WO 2022/270611 | A1 | 12/2022 |

OTHER PUBLICATIONS

U.S. Appl. No. 18/023,038, Katada et al., filed Feb. 24, 2023.
U.S. Appl. No. 18/345,750, Igawa et al., filed Jun. 30, 2023.
U.S. Appl. No. 18/022,342, filed Feb. 21, 2023, Katada et al.
U.S. Appl. No. 18/023,038, filed Feb. 24, 2023, Katada et al.

(56) References Cited

OTHER PUBLICATIONS

U.S. Appl. No. 18/345,750, filed Jun. 30, 2023, Igawa et al.
U.S. Pat. No. 11,739,149, Igawa et al., issued Aug. 29, 2023.
U.S. Appl. No. 15/035,098, filed May 6, 2016, Igawa et al.
U.S. Appl. No. 15/525,603, filed May 10, 2017, Igawa et al.
U.S. Appl. No. 15/860,163, filed Jan. 2, 2018, Mimoto et al.
U.S. Appl. No. 16/704,464, filed Dec. 5, 2019, Igawa et al.
U.S. Appl. No. 16/769,299, filed Jun. 3, 2020, Shimizu et al.
U.S. Appl. No. 17/272,972, filed Mar. 3, 2021, Ho et al.
Amigorena et al., "Cytoplasmic domain heterogeneity and functions of IgG Fc receptors in B lymphocytes," Science, 1992, 252(5065):1808-1812.
Amigorena et al., "Fc gamma RII expression in resting and activated B lymphocytes," Eur J Immunol, 1989, 19(8):1379-1385.
Armour et al., "Differential binding to human FcgammaRIIa and FcgammaRIIb receptors by human IgG wildtype and mutant antibodies," Mol Immunol, 2003, 40(9):585-593.
Atwell et al., "Stable heterodimers from remodeling the domain interface of a homodimer using a phage display library," J Mol Biol, Jul. 4, 1997, 270(1):26-35.
Baeuerle et al., "Bispecific T-Cell Engaging Antibodies for Cancer Therapy," Cancer Res, Jun. 15, 2009, 69(12):4941-4944. doi: 10.1158/0008-5472.CAN-09-0547. Epub Jun. 9, 2009.
Beljaars et al., "The preferential homing of a platelet derived growth factor receptor-recognizing macromolecule to fibroblast-like cells in fibrotic tissue," Biochemical Pharmacology, 2003, 66(7):1307-1317.
Berntzen et al., "Identification of a High Affinity FcγRIIA-binding Peptide That Distinguishes FcγRIIA from FcγRIIB and Exploits FcγRIIA-mediated Phagocytosis and Degradation," Biol Chem, Jan. 9, 2009, 284(2):1126-1135. doi: 10.1074/jbc.M803584200. Epub Oct. 28, 2008.
Binetruy-Tournaire et al., "Identification of a peptide blocking vascular endothelial growth factor (VEGF)-mediated angiogenesis," Embo J, Apr. 3, 2000, 19(7):1525-1533.
Bjellqvist et al., "The focusing positions of polypeptides in immobilized pH gradients can be predicted from their amino acid sequences," Electrophoresis, Oct. 1993, 14(10):1023-1031.
Blank et al., "Decreased transcription of the human FCGR2B gene mediated by the -343 G/C promoter polymorphism and association with systemic lupus erythematosus," Hum Genet, 2005, 117(2-3):220-227. Epub May 14, 2005.
Boder et al., "Directed evolution of antibody fragments with monovalent femtomolar antigen-binding affinity," Proc Natl Acad Sci USA, Sep. 26, 2000, 97(20):10701-10705.
Boruchov et al., "Activating and inhibitory IgG Fc receptors on human DCs mediate opposing functions," J Clin Invest, 2005, 115(10):2914-2923. Epub Sep. 15, 2005.
Bostrom et al., "Variants of the Antibody Herceptin That Interact with HER2 and VEGF at the Antigen Binding Site," Science, Mar. 20, 2009, 323(5921):1610-1614.
Boumpas et al., "A short course of BG9588 (anti-CD40 ligand antibody) improves serologic activity and decreases hematuria in patients with proliferative lupus glomerulonephritis," Arthritis Rheum, 2003, 48(3):719-727.
Brennand et al., "A cyclic peptide analogue of loop III of PDGF-BB causes an apoptosis in human fibroblasts," FEBS Lett, Dec. 15, 1997, 419(2-3):166-170.
Bruhns et al., "Specificity and affinity of human Fcgamma receptors and their polymorphic variants for human IgG subclasses," Blood, 2009, 113(16):3716-3725. Epub Nov. 18, 2008.
Cartron et al., "Therapeutic activity of humanized anti-CD20 monoclonal antibody and polymorphism in IgG Fc receptor FcgammaRIIIa gene," Blood, Feb. 1, 2002, 99(3):754-758.
Cemerski et al., "Suppression of mast cell degranulation through a dual-targeting tandem IgE-IgG Fc domain biologic engineered to bind with high affinity to FcγRIIb," Immunol Lett, 143(1):34-43 (2012). Epub Jan. 25, 2012.
Chamarthy et al., "Gene delivery to dendritic cells facilitated by a tumor necrosis factor alpha-competing peptide," The Mol Immunol, Jul. 2004, 41(8):741-749.
Chan et al., "Therapeutic antibodies for autoimmunity and inflammation," Nat Rev Immunol, May 2010, 10(5):301-316. doi: 10.1038/nri2761.
Chen et al., "Enhancement and destruction of antibody function by somatic mutation: unequal occurrence is controlled by V gene combinatorial associations," Embo J, 1995, 14:2784-2794.
Chen et al., "Association of a transmembrane polymorphism of Fcgamma receptor IIb (FCGR2B) with systemic lupus erythematosus in Taiwanese patients," Arthritis Rheum, 2006, 54(12):3908-3917.
Chen et al., "Characterization of human IgG repertoires in an acute HIV-1 infection," Exp Mol Pathol, Dec. 2012, 93(3):399-407. doi: 10.1016/j.yexmp.2012.09.022. Epub Oct. 1, 2012.
Chu et al., "Inhibition of B cell receptor-mediated activation of primary human B cells by coengagement of CD19 and FcgammaRIIb with Fc-engineered antibodies," Mol Immunol, Sep. 2008, 45(15):3926-3933. doi: 10.1016/j.molimm.2008.06.027. Epub Aug. 8, 2008.
Chu et al., "Reduction of total IgE by targeted coengagement of IgE B-cell receptor and FcγRIIb with Fc-engineered antibody," J Allergy Clin Immunol, 2012, 129(4):1102-1115. Epub Jan. 16, 2012.
Chuntharapai et al., "Isotype-dependent inhibition of tumor growth in vivo by monoclonal antibodies to death receptor 4," J Immunol, 2001, 166(8):4891-4898.
Clackson et al., "Making antibody fragments using phage display libraries," Nature, Aug. 15, 1991, 352(6336):624-628.
Clark, "IgG effector mechanisms," Chem Immunol, 1997, 65:88-110.
Clynes et al., "Fc receptors are required in passive and active immunity to melanoma," Proc Natl Acad Sci USA, Jan. 20, 1998, 95(2):652-656.
Clynes et al., "Inhibitory Fc receptors modulate in vivo cytotoxicity against tumor targets," Nat Med, Apr. 2000, 6(4):443-446.
Conrad, et al, "TCR and CD3 antibody cross-reactivity in 44 species," Cytometry A, Nov. 2007, 71(11):925-933.
Dall'Acqua et al., "Modulation of the effector functions of a human IgG1 through engineering of its hinge region," J Immunol, Jul. 15, 2006, 177(2):1129-1138.
Davis et al., "SEEDbodies: fusion proteins based on strand-exchange engineered domain (SEED) CH3 heterodimers in an Fc analogue platform for asymmetric binders or immunofusions and bispecific antibodies," Protein Eng Des Sel, Apr. 2010, 23(4):195-202. doi: 10.1093/protein/gzp094. Epub Feb. 4, 2010.
De Pascalis et al., "Grafting of 'Abbreviated' Complementarity-Determining Regions Containing Specificity-Determining Residues Essential for Ligand Contact to Engineer a Less Immunogenic Humanized Monoclonal Antibody," The Journal of Immunology, 2002, 169:3076-3084.
Deambrosis et al., "Inhibition of CD40-CD154 costimulatory pathway by a cyclic peptide targeting CD154," J Mol Med, Feb. 2009, 87(2):181-197.
Dermer et al., "Another Anniversary for the War on Cancer," BioTechnology, 1994, 12:320.
Dhodapkar et al., "Selective blockade of inhibitory Fcgamma receptor enables human dendritic cell maturation with IL-12p70 production and immunity to antibody-coated tumor cells," Proc Natl Acad Sci USA, 2005, 102(8):2910-2915. Epub Feb. 9, 2005.
Dubrot, "Treatment with anti-CD137 mAbs causes intense accumulations of liver T cells without selective antitumor immunotherapeutic effects in this organ," Cancer Immunol Immunother, Aug. 2010, 59(8):1223-1233.
Duffau et al., "Platelet CD154 potentiates interferon-alpha secretion by plasmacytoid dendritic cells in systemic lupus erythematosus," Sci Transl Med, 2010, 2(47):47ra63. doi: 10.1126/scitranslmed.3001001.
Dufner et al., "Harnessing phage and ribosome display for antibody optimisation," Trends Biotechnology, Nov. 2006, 24(11):523-529.
Eigenbrot et al., "Two-in-One antibodies with dual action Fabs," Curr Opin Chem Biol, Jun. 2013, 17(3):400-405. doi: 10.1016/j.cbpa.2013.04.015. Epub May 14, 2013.

(56) References Cited

OTHER PUBLICATIONS

Faham et al., "Antigen-Containing Liposomes Engrafted with Flagellin-Related Peptides Are Effective Vaccines That Can Induce Potent Antitumor Immunity and Immunotherapeutic Effect," The J Immunol, 2010, 185:1744-1754.
Ferran et al., "Cytokine-related syndrome following injection of anti-CD3 monoclonal antibody: Further evidence for transient in vivo T cell activation," Eur J Immunol, Mar. 1990, 20(3):509-515.
Fillipovic, Biochemical basis of human life activity, Vlados, 2005:38-43 (with English translation).
Fillipovich, Biochemical basis of human life, Vlados, 2005:49-50 (with English translation).
Flores et al., "Dominant Expression of the Inhibitory FcγRIIB Prevents Antigen Presentation by Murine Plasmacytoid Dendritic Cells," J Immunol, Dec. 1, 2009, 183(11):7129-7139. doi: 10.4049/jimmunol.0901169.
Floto et al., "Loss of function of a lupus-associated FcgammaRIIb polymorphism through exclusion from lipid rafts," Nat Med, 2005, 11(10):1056-1058. Epub Sep. 18, 2005.
Fournier et al., "Activation of human peripheral IgM+ B cells is transiently inhibited by BCR-independent aggregation of Fc gammaRIIB," J Immunol, 2008, 181(8):5350-5359.
Frey et al., "Cytokine release syndrome with novel therapeutics for acute lymphoblastic leukemia," Hematology Am Soc Hematol Educ Program, Dec. 2, 2016, 2016(1):567-572.
Fukuda et al., "In vitro evolution of a single-chain antibodies using mRNA display," Nucleic Acids Res, Oct. 1, 2006, 34(19):e127.
Gary et al., Chapter 8 "Making Antibodies in Bacteria," Making and Using Antibodies: A Practical Handbook, CRC Press, Taylor & Francis Group, 2006, pp. 157-177.
Greenwood et al., "Structural motifs involved in human IgG antibody effector functions," Eur J Immunol, May 1993, 23(5):1098-1104.
Guilliams et al., "The function of Fcγ receptors in dendritic cells and macrophages," Nat Rev Immunol, Feb. 2014, 14(2):94-108. doi: 10.1038/nri3582. Epub Jan. 21, 2014.
Gunaskaran et al., "Enhancing antibody Fc heterodimer formation through electrostatic steering effects: applications to bispecific molecules and monovalent IgG," J Biol Chem, 2010, 285(25):19637-19646. doi: 10.1074/jbc.M110.117382. Epub Apr. 16, 2010.
Gura, "Systems for Identifying New Drugs Are Often Faulty," Science, Nov. 7, 1997, 278(5340):1041-1042.
Hanes et al., "Picomolar affinity antibodies from a fully synthetic naïve library selected and evolved by ribosome display," Nat Biotechnol, Dec. 2000, 18(12):1287-1292.
Harvey et al., "Anchored periplasmic expression, a versatile technology for the isolation of high-affinity antibodies from *Escherichia coli*-expressed libraries," Proc Natl Acad Sci USA, Jun. 22, 2004, 101(25):9193-9198.
Hawkins et al., "Selection of Phage Antibodies by Binding Affinity Mimicking Affinity Maturation," J Mol Biol, Aug. 5, 1992, 226(3):889-896.
Hess et al., "Cancer therapy with trifunctional antibodies: linking innate and adaptive immunity," Future Oncol, Jan. 2012, 8(1):73-85. doi: 10.2217/fon.11.138.
Hetian et al., "A Novel Peptide Isolated from a Phage Display Library Inhibits Tumor Growth and Metastasis by Blocking the Binding of Vascular Endothelial Growth Factor to Its Kinase Domain Receptor," J Biol Chem, Nov. 8, 2002, 277(45):43137-43142.
Heyman, "Feedback regulation by IgG antibodies," Immunol Lett, 2003, 88(2):157-161.
Hezareh et al., "Effector Function Activities of a Panel of Mutants of a Broadly Neutralizing Antibody against Human Immunodeficiency Virus Type 1," J Virol, Dec. 2001, 75(24):12161-12168.
Holen et al., "Activation of EphA receptors on $CD4^+CD45RO^+$ memory cells stimulates migration," J Leukoc Biol, Jun. 2010, 87(6):1059-1068. doi: 10.1189/jlb.0709497. Epub Feb. 16, 2010.
Horton et al., "Potent in vitro and in vivo activity of an Fc-engineered anti-CD19 monoclonal antibody against lymphoma and leukemia," Cancer Res, Oct. 1, 2008, 68(19):8049-8057. doi: 10.1158/0008-5472. CAN-08-2268.
Houot et al., "Therapeutic effect of CD137 immunomodulation in lymphoma and its enhancement by $T_{reg}$ depletion," Blood, Oct. 15, 2009, 114(16):3431-3438.
Igawa et al., "Antibody Optimization Technologies for Developing Next Generation Antibody Therapeutics," Bio Industry, 2011, 28(7):15-21.
Ikuta, et al, "Expression of human immunodeficiency virus type 1 (HIV-1) gag antigens on the surface of a cell line persistently infected with HIV-1 that highly expresses HIV-1 antigens," Virology, Jun. 1989, 170(2):408-417.
Information Meeting on Antibody Engineering Technologies, Copyright © Chugai Pharmaceutical Co., Ltd., Dec. 18, 2012.
Jefferis et al., "Interaction sites on human IgG-Fc for Fc gamma R: current models," Immunol Lett, Jun. 3, 2002, 82(1-2):57-65.
Jones et al., "Growth factor receptor interplay and resistance in cancer," Endocr Relat Cancer, Dec. 2006, 13 Suppl 1:S45-51.
Kabat et al., "Sequences of proteins of immunological interest," Diane publishing, 5th ed, 1991, vol. 1, pp. 679-687.
King, Chapter 5 "Production of Monoclonal Antibodies," Applications and Engineering of Monoclonal Antibodies, Taylor & Francis, ISBN 0-203-21169-3, 2005, pp. 151-159 and 162-164.
Kohrt et al., "Stimulation of natural killer cells with a CD137-specific antibody enhances trastuzumab efficacy in xenotransplant models of breast cancer," J Clin Invest, 2012, 122(3):1066-1075. Epub Feb. 13, 2012.
Kontermann, "Dual targeting strategies with bispecific antibodies," mAbs, Mar.-Apr. 2012, 4(2):182-197. doi: 10.4161/mabs.4.2.19000. Epub Mar. 1, 2012.
Kraft et al., "Definition of an Unexpected Ligand Recognition Motif for αvβ6 Integrin," J Biol Chem, 1999, 274:1979-1985.
Kramer, et al, "Molecular basis for the binding promiscuity of an anti-p24 (HIV-1) monoclonal antibody," Cell, Dec. 12, 1997, 91(6):799-809.
Kronqvist et al., "A novel affinity protein selection system based on staphylococcal cell surface display and flow cytometry," Protein Eng Des Sel, Apr. 2008, 21(4):247-255.
Kussie et al., "A Single Engineered Amino Acid Substitution Changes Antibody Fine Specificity," J Immunol, 1994, 152:146-152.
Lazar et al., "Engineered antibody Fc variants with enhanced effector function," Proc Natl Acad Sci USA, Mar. 2006, 103(11):4005-4010. Epub Mar. 6, 2006.
Lederman et al., "A Single Amino Acid Substitution in a Common African Allele of the CD4 Molecule Ablates Binding of the Monoclonal Antibody, OKT4," Molecular Immunology, 1991, 28:1171-1181.
Li et al., Activation of the Proapoptotic Death Receptor DR5 by Oligomeric Peptide and Antibody Agonists, J Mol Biol, 2006, 361(3): 522-536.
Li et al., "β-Endorphin omission analogs: Dissociation of immunoreactivity from other biological activities," Proc Natl Acad Sci USA, Jun. 1980, 77(6): 3211-3214.
Li et al., "CD72 down-modulates BCR-induced signal transduction and diminishes survival in primary mature B lymphocytes," J Immunol, 2006, 176(9):5321-5328.
Li et al., "Inhibitory Fcγ receptor engagement drives adjuvant and anti-tumor activities of agonistic CD40 antibodies," Science, 2011, 333(6045):1030-1034.
Li et al., "Antitumor activities of agonistic anti-TNFR antibodies require differential FcKRIIB coengagement in vivo," Proc Natl Acad Sci USA, Nov. 26, 2013, 110(48):19501-19506.
Lightfield, "Critical function for Naip5 in inflammasome activation by a conserved carboxy-terminal domain of flagellin," Nat Immunol, Oct. 2008, 9(10):1171-1178. doi: 10.1038/ni.1646. Epub Aug. 24, 2008.
Liu et al., "Asymmetrical Fc engineering greatly enhances antibody-dependent cellular cytotoxicity (ADCC) effector function and sta-

(56) References Cited

OTHER PUBLICATIONS bility of the modified antibodies," J Biol Chem, Feb. 7, 2014, 289(6):3571-3590. doi: 10.1074/jbc.M113.513366. Epub Dec. 5, 2013.
Lum et al., "Targeting T Cells with Bispecific Antibodies for Cancer Therapy," BioDrugs, Dec. 1, 2011, 25(6):365-379. doi: 10.2165/11595950-000000000-00000.
Lutterbuese et al., "T cell-engaging BiTE antibodies specific for EGFR potently eliminate KRAS- and BRAF-mutated colorectal cancer cells," Pro Natl Acad Sci USA, 2010, 107(28):12605-12610. doi: 10.1073/pnas.1000976107. Epub Jun. 28, 2010.
MacCalum et al., "Antibody-antigen interactions: contact analysis and binding site topography," J Mol Biol, Oct. 11, 1996, 262(5):732-745.
Mackay et al., "Selective dysregulation of the FcgammaIIB receptor on memory B cells in SLE," J Exp Med, 2006, 203(9):2157-2164. Epub Aug. 21, 2006.
Manger et al., "Fcgamma receptor IIa polymorphism in Caucasian patients with systemic lupus erythematosus: association with clinical symptoms," Arthritis Rheum, 1998, 41(7):1181-1189 (1998).
Marino et al., "Prevention of systemic lupus erythematosus in MRL//pr mice by administration of an immunoglobulin-binding peptide," Nat Biotechnol, Jul. 2000, 18(7):735-739.
Marks et al., "By-passing Immunization—Human Antibodies from V-gene Libraries Displayed on Phage," J Mol Biol, Dec. 5, 1991, 222(3):581-597.
Marvin et al., "Recombinant approaches to IgG-like bispecific antibodies," Acta Pharmacol Sin, Jun. 2005, 26(6):649-658.
Mendez-Fernandez et al., "The inhibitory FcγRIIb modulates the inflammatory response and influences atherosclerosis in male apoE$^{-/-}$ mice," Atherosclerosis, Jan. 2011, 214(1):73-80. doi: 10.1016/j.atherosclerosis.2010.10.018.
Meyer et al., "Bevacizumab immune complexes activate platelets and induce thrombosis in FCGR2A transgenic mice," J Thromb Haemost, 2009, 7(1):171-181. Epub Oct. 30, 2008.
Mimoto et al., "Novel asymmetrically engineered antibody Fc variant with superior FcγR binding affinity and specificity compared with afucosylated Fc variant," mAbs, Mar.Apr. 2013, 5(2):229-236. doi: 10.4161/mabs.23452. Epub Feb. 13, 2013.
Morgan et al., "The N-terminal end of the CH2 domain of chimeric human IgGI anti-HLA-DR is necessary for C1q, Fc gamma RI and Fc gamma RIII binding," Immunology, Oct. 1995, 86(2):319-324.
Muta et al., "A 13-amino-acid motif in the cytoplasmic domain of Fc gamma RIIB modulates B-cell receptor signalling," Nature, 1994, 368(6466):70-73.
Nagaoka et al., "Single amino acid substitution in the mouse IgG1 Fc region induces drastic enhancement of the affinity to protein A," Protein Eng, Apr. 2003, 16(4):243-245. doi: 10.1093/proeng/gzg037.
Nakamura et al., "Fcgamma receptor IIB-deficient mice develop Goodpasture's syndrome upon immunization with type IV collagen: a novel murine model for autoimmune glomerular basement membrane disease," J Exp Med, 2000, 191(5):899-906.
Nakamura et al., "Peptide mimics of epidermal growth factor (EGF) with antagonistic activity," Journal of Biotechnology, 2005, 116(3):211-219.
Natsume et al., "Engineered antibodies of IgG1/IgG3 mixed isotype with enhanced cytotoxic activities," Cancer Res, May 15, 2008, 68(10):3863-3872. doi: 10.1158/0008-5472.CAN-07-6297.
Nicholas et al., "Regulation of the immune response. I. Reduction in ability of specific antibody to inhibit long-lasting IgG immunological priming after removal of the Fc fragment," J Exp Med, 1969, 129(6):1183-1201.
Nimmerjahn et al., "Divergent immunoglobulin g subclass activity through selective Fc receptor binding," Science, Dec. 2, 2005, 310(5753):1510-1512.
Nimmerjahn et al., "Fcgamma receptors as regulators of immune responses," Nat Rev Immunol, Jan. 2008, 8(1):34-47.
Odegrip et al., "CIS display: In vitro selection of peptides from libraries of protein-DNA complexes," Proc Natl Acad Sci USA, Mar. 2, 2004, 101(9):2806-2810.
Okabe, "Proprietary Innovative Antibody Engineering Technologies in Chugai Pharmaceutical," Information meeting on Antibody Engineering Technologies, Dec. 18, 2012.
Olferiev et al., "The role of activating protein 1 in the transcriptional regulation of the human FCGR2B promoter mediated by the -343 G -> C polymorphism associated with systemic lupus erythematosus," J Biol Chem, 2007, 282(3):1738-1746. Epub Nov. 27, 2006.
Response to Search Report filed on Jul. 16, 2015) (document submitted by the Opponent on May 6, 2020 in EPO opposition proceedings of EP 2 679 681).
Pavlou et al., "The therapeutic antibodies market to 2008," Eur J Pharm Biopharm, Apr. 2005, 59(3):389-396.
Porter et al., "Chimeric Antigen Receptor-Modified T Cells in Chronic Lymphoid Leukemia," N Engl J Med, Aug. 25, 2011, 365(8):725-733.
Properties of human lgG subclasses, Feb. 28, 2017, retrieved from the internet on Mar. 23, 2017 http://ednieuw.home.xs4all.nl/IgGsubclasses/subk123.htm>, 5 pages.
Radaev et al., "Recognition of IgG by Fcgamma receptor. The role of Fc glycosylation and the binding of peptide inhibitors," J Biol Chem, 2001, 276(19):16478-16483. Epub Jan. 31, 2001.
Radaev et al., "The structure of a human type III Fcgamma receptor in complex with Fc," J Biol Chem, May 11, 2001, 276(19):16469-16477. Epub Jan. 31, 2001.
Rao et al., "Novel cyclic and linear oligopeptides that bind to integrin β1 chain and either inhibit or costimulate T lymphocytes," Int Immunopharmacol, Mar. 2003, 3(3):435-443.
Ravetch et al., "Immune inhibitory receptors," Science, 2000, 290(5489):84-89.
Reichert et al., "Monoclonal antibody successes in the clinic," Nat Biotechnol, Sep. 2005, 23(9):1073-1078.
Richards et al., "A peptide containing a novel FPGN CD40-binding sequence enhances adenoviral infection of murine and human dendritic cells," Eur J Biochem, May 2003, 270(10):2287-2294.
Richards et al., "Optimization of antibody binding to FcgammaRIIa enhances macrophage phagocytosis of tumor cells," Mol Cancer Ther, 2008, 7(8):2517-2527.
Riechelmann et al., "Adoptive therapy of head and neck squamous cell carcinoma with antibody coated immune cells: a pilot clinical trial," Cancer Immunol Immunother, Sep. 2007, 56(9):1397-1406. Epub Feb. 2, 2007.
Robles-Carrillo et al., "Anti-CD40L immune complexes potently activate platelets in vitro and cause thrombosis in FCGR2A transgenic mice," J Immunol, 2010, 185(3):1577-1583. Epub Jun. 28, 2010.
Roitt et al., Chapter 19 "Vaccination," Immunology, Moscow, Mir, 2000, pp. 373-374 (with English translation).
Rothe et al., "Recombinant proteins in rheumatology—recent advances," N Biotechnol, Sep. 2011, 28(5):502-510. doi: 10.1016/j.nbt.2011.03.019. Epub Apr. 5, 2011.
Rudikoff et al., "single amino acid substitution altering antigen-binding specificity," Proc Natl Acad Sci USA, Mar. 1982, 79(6):1979-1983.
Salmon et al., "Fc gamma RIIA alleles are heritable risk factors for lupus nephritis in African Americans," J Clin Invest, 1996, 97(5):1348-1354.
Samuelsson et al., "Anti-inflammatory activity of IVIG mediated through the inhibitory Fc receptor," Science, Jan. 19, 2001, 291(5503):484-486.
Sazinsky et al., "Aglycosylated immunoglobulin $G_1$ variants productively engage activating Fc receptor," Proc Natl Acad Sci USA, Dec. 23, 2008, 105(51):20167-20172. doi: 10.1073/pnas.0809257105. Epub Dec. 12, 2008.
Scappaticci et al., "Arterial thromboembolic events in patients with metastatic carcinoma treated with chemotherapy and bevacizumab," J Natl Cancer Inst, 2007, 99(16):1232-1239.
Schaefer et al., "A two-in-one antibody against HER3 and EGFR has superior inhibitory activity compared with monospecific antibodies," Cancer Cell, 2011, 20(4):472-486. doi: 10.1016/j.ccr.2011.09.003.

(56) References Cited

OTHER PUBLICATIONS

Schabowsky et al., "A Novel Form of 4-1BBL Has Better Immunomodulatory Activity than an Agonistic Anti-4-1BB Ab without Ab Associated Severe Toxicity," Vaccine, Dec. 11, 2009, 28(2):512- 522.
Schlothauer et al., "Novel human IgG1 and IgG4 Fc-engineered antibodies with completely abolished immune effector functions," Protein Eng Des Sel, Oct. 2016, 29(10):457-466. doi: 10.1093/protein/gzw040. Epub Aug. 29, 2016.
Schraa et al., "RGD-Modified Anti-CD3 Antibodies Redirect Cytolytic Capacity of Cytotoxic T Lymphocytes Toward αvβ3-Expressing Endothelial Cells," Int J Cancer, Nov. 1, 2004, 112(2):279-285.
Seimetz et al., "Development and approval of the trifunctional antibody catumaxomab (anti-EpCAM x anti-CD3) as a targeted cancer immunotherapy," Cancer Treat Rev, Oct. 2010, 36(6):458-467. doi: 10.1016/j.ctrv.2010.03.001. Epub Mar. 27, 2010.
Sepp et al., Chapter 12 "Cell-Free Selection of Domain Antibodies by In Vitro Compartmentalization," Methods Mol Biol, 2012, 911:183-198.
Shanmugam et al., "Synthetic Toll Like Receptor-4 (TLR-4) Agonist Peptides as a Novel Class of Adjuvants," PLoS One, Feb. 2012, 7(2):e30839.
Shields et al., "High resolution mapping of the binding site on human IgGI for Fc gamma RI, Fc gamma RII, Fc gamma RIII, and FcRn and design of IgG1 variants with improved binding to the Fc gamma R," J Biol Chem, Mar. 2, 2001, 276(9):6591-6604. Epub Nov. 28, 2000.
Shinkawa et al., "The absence of fucose but not the presence of galactose or bisecting N-acetylglucosamine of human IgG1 complex-type oligosaccharides shows the critical role of enhancing antibody-dependent cellular cytotoxicity," J Biol Chem, Jan. 31, 2003, 278(5):3466-3473. Epub Nov. 8, 2002.
Siberil et al., "Molecular aspects of human FcgammaR interactions with IgG: functional and therapeutic consequences," Immunol Lett, Aug. 15, 2006, 106(2):111-118. Epub Jun. 12, 2006.
Singer et al., Chapter 3 "The Logic and Machinery of Gene Expression," Genes & Genomes, Moscow, Mir, 1998; 115-88 (with what are believed to be the corresponding pages from an English version of Genes & Genomes).
Smith et al., "FcgammaRIIB in autoimmunity and infection: evolutionary and therapeutic implications," Nat Rev Immunol, 2010, 10(5):328-343.
Stancovski et al., "Mechanistic aspects of the opposing effects of monoclonal antibodies to the ERBB2 receptor on tumor growth," Proc Natl Acad Sci USA, 1991, 88:8691-8695.
Stevenson et al., "A chimeric antibody with dual Fc regions (bisFabFc) prepared by manipulations at the IgG hinge," Anticancer Drug Des, Mar. 1989, 3(4):219-230.
Su et al., "Expression profile of FcgammaRIIb on leukocytes and its dysregulation in systemic lupus erythematosus," J Immunol, 2007, 178(5):3272-3280.
Tackenberg et al., "Impaired inhibitory Fcγ receptor IIB expression on B cells in chronic inflammatory demyelinating polyneuropathy," Proc Natl Acad Sci USA, Mar. 24, 2009, 106(12):4788-4792. doi: 10.1073/pnas.0807319106.
Traxlmayr et al., "Integrin binding human antibody constant domains—probing the C-terminal structural loops for grafting the RGD motif," J Biotechnol, Sep. 10, 2011, 155(2):193-202. doi: 10.1016/j.jbiotec.2011.06.042. Epub Jul. 8, 2011.
Tutt et al., "Trispecific F(ab')3 derivatives that use cooperative signaling via the TCR/CD3 complex and CD2 to activate and redirect resting cytotoxic T cells," J Immunol, Jul. 1, 1991, 147(1):60-69.
Unkeless et al., "Structure and function of human and murine receptors for IgG," Annu Rev Immunol, 1988, 6:251-281.
Vajdos et al., "Comprehensive Functional Maps of the Antigen-binding Site of an Anti-ErbB2 Antibody Obtained with Shotgun Scanning Mutagenesis," J Mol Biol, 2002, 320:415-428.
Vaughan et al., "Human Antibodies with Sub-nanomolar Affinities Isolated from a Large Non-immunized Phage Display Library," Nat Biotechnol, Mar. 1996, 14(3):309-314.
Veri et al., "Monoclonal antibodies capable of discriminating the human inhibitory Fcgamma-receptor IIB (CD32B) from the activating Fcgamma-receptor IIA (CD32A): biochemical, biological and functional characterization," Immunology, 2007, 21(3):392-404. Epub Mar. 26, 2007.
Veri et al., "Therapeutic control of B cell activation via recruitment of Fcgamma receptor IIb (CD32B) inhibitory function with a novel bispecific antibody scaffold," Arthritis Rheum, 2010, 62(7):1933-1943.
Vidarsson et al., "IgG subclasses and allotypes: from structure to effector functions," Front Immunol, Oct. 20, 2014, 5:520. doi: 10.3389/fimmu.2014.00520. eCollection 2014.
Vinay et al., "4-1BB signaling beyond T cells," Cell Mol Immunol, Jul. 2011, 8(4):281-284.
Warmerdam et al., "Molecular basis for a polymorphism of human Fc gamma receptor II (CD32)," J Exp Med, 1990, 172(1):19-25.
Warmerdam et al., "The human low affinity immunoglobulin G Fc receptor IIC gene is a result of an unequal crossover event," J Biol Chem, Apr. 5, 1993, 268(10):7346-7349.
Warncke et al., "Different adaptations of IgG effector function in human and nonhuman primates and implications for therapeutic antibody treatment," J Immunol, May 1, 2012, 188(9):4405-4411. doi: 10.4049/jimmunol. 1200090. Epub Mar. 28, 2012.
Wernersson et al., "IgG-mediated enhancement of antibody responses is low in Fc receptor gamma chain-deficient mice and increased in Fc gamma RII-deficient mice," J Immunol, 1999, 163(2):618-622.
Werwitzke et al., "Treatment of lupus-prone NZB/NZW F1 mice with recombinant soluble Fc gamma receptor II (CD32)," Ann Rheum Dis, Feb. 2008, 67(2):154-161. Epub Jun. 8, 2007.
Witte et al., "Monoclonal antibodies targeting the VEGF receptor-2 (Flk1/KDR) as an anti-angiogenic therapeutic strategy," Cancer and Metastasis Reviews, 1998, 17:155-161.
Wilson et al., "An Fcγ receptor-dependent mechanism drives antibody-mediated target-receptor signaling in cancer cells," Cancer Cell, 2011, 19(1):101-113.
Wozniak-Knopp et al., "Introducing antigen-binding sites in structural loops of immunoglobulin constant domains: Fc fragments with engineered HER2/neu-binding sites and antibody properties," Protein Eng Des Sel, Apr. 2010, 23(4):289-297. doi: 10.1093/protein/gzq005. Epub Feb. 11, 2010.
Wu et al., "Humanization of a Murine Monoclonal Antibody by Simultaneous Optimization of Framework and CDR Residues," J Mol Biol, 1999, 294:151-162.
Wu et al., "Structures of the CXCR4 Chemokine GPCR with Small-Molecule and Cyclic Peptide Antagonists," Science, 2010, 330:1066-1071.
Xi et al., "Increased survival and reduced renal injury in MRL/lpr mice treated with a human Fcγ receptor II (CD32) peptide," Immunology, May 2012, 136(1):46-53. doi: 10.1111/j.1365-2567.2012.03553.x.
Xiao et al., "A large library based on a novel (CH2) scaffold: Identification of HIV-1 inhibitors," Biochem Biophys Res Commun, Sep. 18, 2009, 387(2):387-392. doi: 10.1016/j.bbrc.2009.07.044. Epub Jul. 15, 2009.
Xie et al., "A new format of bispecific antibody: highly efficient heterodimerization, expression and tumor cell lysis," J Immunol Methods, Jan. 2005, 296(1-2):95-101. Epub Nov. 19, 2004.
Xu et al., "Fc gamma Rs modulate cytotoxicity of anti-Fas antibodies: implications for agonistic antibody-based therapeutics," J Immunol, 2003, 17(2):562-568.
Yarilin, Fundamentals of Immunology, M: Medicina, 1999, pp. 169-172 and 354-8 (with English translation).
Yarilin, Fundamentals of Immunology, M.: Medicina, 1999, pp. 172-174 (with English translation).
Yuasa et al., "Deletion of fcgamma receptor IIB renders H-2(b) mice susceptible to collagen-induced arthritis," J Exp Med, 1999, 198(1):187-194.
Yu et al., "Interaction between Bevacizumab and Murine VEGF-A: A Reassessment," Investigative Opthalmology and Visual Science, Feb. 2008, 49(2):522-527.

(56) References Cited

OTHER PUBLICATIONS

Zalevsky et al., "The impact of Fc engineering on an anti-CD19 antibody: increased Fcgamma receptor affinity enhances B-cell clearing in nonhuman primates," Blood, 2009, 113(16):3735-3743. Epub Dec. 24, 2008.
Zeidler et al., "Simultaneous activation of T cells and accessory cells by a new class of intact bispecific antibody results in efficient tumor cell killing," J Immunol, Aug. 1, 1999, 163(3):1246-1252.
Zhang et al., "Effective therapy for a murine model of human anaplastic large-cell lymphoma with the anti-CD30 monoclonal antibody, HeFi-1, does not require activating Fc receptors," Blood, 2006, 108(2):705-710. Epub Mar. 21, 2006.
Zhou et al., "Development of a novel mammalian cell surface antibody display platform," mAbs, Sep.-Oct. 2010, 2(5):508-518.
International Search Report for App. Ser. No. PCT/JP2013/084809, mailed Apr. 1, 2014, 4 pages.
International Preliminary Report on Patentability for App. Ser. No. PCT/JP2013/084809, dated Jun. 30, 2015, 7 pages.
USPTO Restriction Requirement in U.S. Appl. No. 14/127,576, dated Jun. 1, 2016, 8 pages.
Fish & Richardson P.C., Reply to Restriction Requirement dated Jun. 1, 2016 in U.S. Appl. No. 14/127,576, filed Aug. 24, 2016, 2 pages.
USPTO Non-Final Office Action in U.S. Appl. No. 14/127,576, dated Sep. 20, 2016, 17 pages.
USPTO Interview Summary in U.S. Appl. No. 14/127,576, dated Dec. 23, 2016, 3 pages.
Fish & Richardson P.C., Reply to Non-Final Office Action of Sep. 20, 2016 in U.S. Appl. No. 14/127,576, dated Mar. 16, 2017, 21 pages.
USPTO Notice of Allowance in U.S. Appl. No. 14/127,576, dated Jun. 2, 2017, 13 pages.
USPTO Notice of Allowance in U.S. Appl. No. 14/127,576, dated Jun. 21, 2017, 9 pages.
USPTO Notice of Allowance in U.S. Appl. No. 14/127,576 dated Oct. 19, 2017, 7 pages.
USPTO Notice of Allowance in U.S. Appl. No. 14/127,576, dated Dec. 15, 2017, 8 pages.
USPTO Restriction Requirement in U.S. Appl. No. 14/001,218, dated Dec. 2, 2015, 8 pages.
Fish & Richardson P.C., Reply to Restriction Requirement dated Dec. 2, 2015 in U.S. Appl. No. 14/001,218, filed Feb. 1, 2016, 1 page.
USPTO Office Action in U.S. Appl. No. 14/001,218, dated Apr. 4, 2016, 13 pages.
Fish & Richardson P.C., Reply to Office Action dated Apr. 4, 2016 in U.S. Appl. No. 14/001,218, filed Oct. 3, 2016, 15 pages.
USPTO Office Action in U.S. Appl. No. 14/001,218, dated Dec. 2, 2016, 10 pages.
USPTO Interview Summary in U.S. Appl. No. 14/001,218, dated Jan. 12, 2017, 3 pages.
USPTO Office Action in U.S. Appl. No. 14/001,218, dated Dec. 16, 2016, 11 pages.
Fish & Richardson P.C., Reply to Office Action dated Dec. 16, 2016 in U.S. Appl. No. 14/001,218, filed Jun. 16, 2017, 12 pages.
USPTO Office Action in U.S. Appl. No. 14/001,218, dated Jun. 27, 2017, 12 pages.
USPTO Final Office Action in U.S. Appl. No. 14/001,218, dated Jan. 29, 2018, 11 pages.
USPTO Advisory Action in U.S. Appl. No. 14/001,218, dated Apr. 11, 2018, 3 pages.
USPTO Non-Final Office Action in U.S. Appl. No. 14/001,218, dated Mar. 18, 2019, 32 pages.
USPTO AFCP 2.0 Decision and Applicant-Initiated Interview Summary in U.S. Appl. No. 14/001,218, dated Apr. 11, 2018, 3 pages.
USPTO Final Office Action in U.S. Appl. No. 14/001,218, dated Nov. 21, 2019, 24 pages.
USPTO Non-Final Office Action in U.S. Appl. No. 14/001,218, dated Jun. 16, 2020, 15 pages.
USPTO Final Office Action in U.S. Appl. No. 14/001,218, dated Feb. 2, 2021, 19 pages.
USPTO Non-final Office Action in U.S. Appl. No. 15/024,063, dated Feb. 7, 2018, 91 pages.
USPTO Restriction Requirement in U.S. Appl. No. 14/422,207, dated Nov. 20, 2015, 6 pages.
USPTO Non-Final Office Action for U.S. Appl. No. 14/422,207, dated Feb. 11, 2016, 11 pages.
Fish & Richardson P.C., Reply to Non-Final Office Action of Feb. 11, 2016, in U.S. Appl. No. 14/422,207, filed Aug. 10, 2016, 24 pages.
Fish & Richardson P.C., Supplemental Reply to Non-Final Office Action of Feb. 11, 2016, in U.S. Appl. No. 14/422,207, filed Oct. 13, 2016, 24 pages.
USPTO Non-Final Office Action for U.S. Appl. No. 14/422,207, dated Feb. 7, 2017, 17 pages.
USPTO Final Office Action for U.S. Appl. No. 14/422,207, dated Nov. 16, 2017, 30 pages.
USPTO Non-Final Office Action for U.S. Appl. No. 14/422,207, dated Jun. 18, 2019, 43 pages.
USPTO Final Office Action for U.S. Appl. No. 14/422,207, dated Mar. 27, 2020, 22 pages.
USPTO Applicant-Initiated Interview Summary for U.S. Appl. No. 14/422,207, dated Oct. 21, 2020, 3 pages.
USPTO Advisory Action for U.S. Appl. No. 14/422,207, dated Jan. 1, 2021, 4 pages.
USPTO Applicant-Initiated Interview Summary for U.S. Appl. No. 14/422,207, dated Apr. 16, 2021, 2 pages.
USPTO Applicant-Initiated Interview Summary for U.S. Appl. No. 14/422,207, dated May 28, 2021, 2 pages.
USPTO Notice of Allowance for U.S. Appl. No. 14/422,207, dated Jun. 8, 2021, 16 pages.
International Search Report for App. Ser. No. PCT/JP2015/081693, mailed Feb. 2, 2016, 2 pages (with English translation).
International Preliminary Report on Patentability in International Application No. PCT/JP2005/081693, dated May 26, 2017, 10 pages.
USPTO Restriction Requirement in U.S. Appl. No. 14/654,895, dated Sep. 21, 2017, 8 pages.
USPTO Non-Final Office Action in U.S. Appl. No. 14/654,895, dated Feb. 7, 2018, 39 pages.
USPTO Final Office Action and Examiner-Initiated Interview Summary in U.S. Appl. No. 14/654,895, dated Oct. 11, 2018, 17 pages.
USPTO Applicant-Initiated Interview Summary in U.S. Appl. No. 14/654,895, dated Oct. 16, 2018, 3 pages.
USPTO Applicant-Initiated Interview Summary in U.S. Appl. No. 14/654,895, dated Nov. 19, 2018, 3 pages.
USPTO Advisory Action Before the Filing of an Appeal Brief in U.S. Appl. No. 14/654,895, dated Jan. 11, 2019, 3 pages.
USPTO Notice of Allowance in U.S. Appl. No. 14/654,895, dated Jun. 27, 2019, 12 pages.
USPTO Notice of Allowance in U.S. Appl. No. 14/654,895, dated Dec. 26, 2019, 11 pages.
U.S. Appl. No. 18/436,917, Shimizu et al., filed Feb. 8, 2024.
U.S. Appl. No. 18/436,917, filed Feb. 8, 2024, Shimizu et al.
Latypov et al., "Elucidation of acid-induced unfolding and aggregation of human immunoglobulin IgG1 and IgG2 Fc," J Biol Chem, Jan. 6, 2012, 287(2):1381-1396. doi: 10.1074/jbc.M111.297697. Epub Nov. 14, 2011.
Escobar-Cabrera et al., "Asymmetric Fc Engineering for Bispecific Antibodies with Reduced Effector Function," Antibodies (Basel), May 16, 2017, 6(2):7, 16 pages.
Mimoto et al., Engineered antibody Fc variant with selectively enhanced FcγRIIb binding over both FcγRIIa$^{R131}$ and FcγRIIa$^{H131}$, Protein Eng Des Sel, Oct. 2013, 26(10):589-598. doi: 10.1093/protein/gzt022. Epub Jun. 5, 2013.
Tamura et al., "FcγR2A and 3A polymorphisms predict clinical outcome of trastuzumab in both neoadjuvant and metastatic settings in patients with HER2-positive breast cancer," Ann Oncol, Jun. 2011, 22(6):1302-1307.

(56) References Cited

OTHER PUBLICATIONS

Tsao et al., "CD47 blockade augmentation of trastuzumab antitumor efficacy dependent on antibody-dependent cellular phagocytosis," JCI Insight, Dec. 19, 2019, 4(24):e131882, 21 pages. doi: 10.1172/jci.insight.131882.
U.S. Pat. No. 9,890,218, Mimoto et al., issued Feb. 13, 2018.
U.S. Appl. No. 15/860,163, Mimoto et al., filed Jan. 2, 2018.
U.S. Pat. No. 10,766,960, Igawa et al., issued Sep. 8, 2020.
U.S. Appl. No. 14/001,218, Mimoto et al., filed Dec. 2, 2013.
U.S. Pat. No. 11,142,563, Igawa et al., issued Oct. 12, 2021.
U.S. Appl. No. 15/035,098, Igawa et al., filed May 6, 2016 (abandoned).
U.S. Appl. No. 16/704,464, Igawa et al., filed Dec. 5, 2019.
U.S. Pat. No. 11,154,615, Igawa et al., issued Oct. 26, 2021.
U.S. Appl. No. 16/769,299, Shimizu et al., filed Jun. 3, 2020.
U.S. Appl. No. 17/272,972, Ho et al., filed Mar. 3, 2021.
U.S. Appl. No. 15/963,455, filed Apr. 26, 2018, Ruike et al.
U.S. Appl. No. 17/028,210, filed Sep. 22, 2020, Katada et al.
U.S. Appl. No. 17/506,733, filed Oct. 21, 2021, Igawa et al.
Bardwell et al., "Potent and conditional redirected T cell killing of tumor cells using Half DVD-Ig," Protein Cell, Jan. 2018, 9(1):121-129.
Crowe et al., "Humanized monoclonal antibody CAMPATH-1H: myeloma cell expression of genomic constructs, nucleotide sequence of cDNA constructs and comparison of effector mechanisms of myeloma and Chinese hamster ovary cell-derived material," Clin Exp Immunol, Jan. 1992, 87(1):105-110.
Dickopf et al., "Format and geometries matter: Structure-based design defines the functionality of bispecific antibodies," Comput Struct Biotechnol J, May 14, 2020, 18:1221-1227.
Edelman et al., "The Covalent Structure of an Entire KG Immunoglobulin Molecule," Proc Natl Acad Sci USA, May 1969, 63(1):78-85.
Ellmark et al., "Selective FcγR engagement by human agonistic anti-CD40 antibodies," Transl Cancer Res 2016, 5(Suppl 4):S839-S841.
James et al., "1.9 Å structure of the therapeutic antibody CAMPATH-1H fab in complex with a synthetic peptide antigen," J Mol Biol, Jun. 4, 1999, 289(2):293-301.
USPTO Restriction Requirement in U.S. Appl. No. 14/406,232, dated Apr. 27, 2016, 15 pages.
Fish & Richardson P.C., Reply to Restriction Requirement in U.S. Appl. No. 14/406,232, filed Jul. 26, 2016, 2 pages.
Fish & Richardson P.C., Supplemental Reply to Restriction Requirement dated Apr. 27, 2016 in U.S. Appl. No. 14/406,232, filed Oct. 5, 2016, 2 pages.
USPTO Non-Final Office Action in U.S. Appl. No. 14/406,232, dated Oct. 20, 2016, 37 pages.
Fish & Richardson P.C., Response to Non-Final Office Action in U.S. Appl. No. 14/406,232, dated Apr. 20, 2017, 39 pages.
USPTO Notice of Non-Compliant Amendment in U.S. Appl. No. 14/406,232, dated Jul. 25, 2017, 3 pages.
Fish & Richardson P.C., Reply to Notice of Non-Compliant Amendment and Supplemental Reply to Action of Oct. 20, 2016, Correcting the "Amendments to the Specification," Section, in U.S. Appl. No. 14/406,232, dated Aug. 10, 2017, 9 pages.
USPTO Final Office Action in U.S. Appl. No. 14/406,232, dated Nov. 13, 2017, 26 pages.
USPTO Applicant-Initiated Interview Summary in U.S. Appl. No. 14/406,232, dated May 15, 2018, 3 pages.
Fish & Richardson P.C., Amendment and Reply to Action of Nov. 13, 2017 in U.S. Appl. No. 14/406,232, dated Jul. 10, 2018, 473 pages.
Fish & Richardson P.C., Second Supplemental Amendment and Reply to Action of Nov. 14, 2017 in U.S. Appl. No. 14/406,232, dated Jul. 11, 2018, 473 pages.
USPTO Final Office Action in U.S. Appl. No. 14/406,232, dated Apr. 5, 2019, 38 pages.
Fish & Richardson P.C., Amendment in Reply to Final Action of Apr. 5, 2019 in U.S. Appl. No. 14/406,232, dated Apr. 30, 2020, 454 pages.
USPTO Non-Final Office Action in U.S. Appl. No. 14/406,232, dated Aug. 11, 2020, 47 pages.
Fish & Richardson P.C., Amendment and Reply to Action of Aug. 11, 2020 in U.S. Appl. No. 14/406,232, dated Feb. 10, 2021, 22 pages.
USPTO Notice of Allowance in U.S. Appl. No. 14/406,232, dated Mar. 25, 2021, 10 pages.
Fish & Richardson P.C., Supplemental Amendment in U.S. Appl. No. 14/406,232, dated Jul. 15, 2021, 11 pages.
USPTO Notice of Allowance and Examiner-Initiated Interview Summary in U.S. Appl. No. 14/406,232, dated Jul. 23, 2021, 12 pages.
Fish & Richardson P.C., Reply to Notice of Allowance in U.S. Appl. No. 14/406,232, dated Sep. 9, 2021, 3 pages.
International Search Report for App. Ser. No. PCT/JP2013/066428, mailed Aug. 6, 2013.
International Preliminary Report on Patentability for App. Ser. No. PCT/JP2013/066428, dated Dec. 16, 2014.
USPTO Non-Final Office Action in U.S. Appl. No. 14/001,218, dated Dec. 29, 2021, 20 pages.
U.S. Appl. No. 17/846,672, Mimoto et al., filed Jun. 22, 2022.
U.S. Appl. No. 17/506,733, Igawa et al., filed Oct. 21, 2021.
U.S. Appl. No. 17/846,672, filed Jun. 22, 2022, Mimoto et al.
Ridgway et al., "'Knobs-into-holes' engineering of antibody $C_H3$ domains for heavy chain heterodimerization," Prot Eng, Jul. 1996, 9(7):617-621.
U.S. Pat. No. 11,952,422, Shimizu et al., issued Apr. 9, 2024.
Chen et al., "Advance in research on antibody half-life related engineering," China Biotechnology, 2017, 37(5):87-96 (with English abstract).
Wang et al., "IgG Fc engineering to modulate antibody effector functions," Protein Cell, Jan. 2018, 9(1):63-73.
Yang et al., "Engineering of Fc Fragments with Optimized Physicochemical Properties Implying Improvement of Clinical Potentials for Fc-Based Therapeutics," Front Immunol, Jan. 8, 2018, 8:1860, 14 pages.

(A)

(B)

Diagram in which FcγR and Fc region complex is viewed from N-terminal side of the Fc region (top view)

ANTIGEN-BINDING MOLECULE CONTAINING MODIFIED Fc REGION

CROSS-REFERENCE TO RELATED APPLICATIONS

This application is a divisional of U.S. application Ser. No. 14/406,232, filed Dec. 8, 2014, which is the National Stage of International Application No. PCT/JP2013/066428, filed Jun. 14, 2013, which claims the benefit of Japanese Application No. 2012-134908, filed Jun. 14, 2012.

SEQUENCE LISTING

This application contains a Sequence Listing that has been submitted electronically as an ASCII text file named SequenceListing.txt. The ASCII text file, created on Sep. 22, 2021, is 190 kilobytes in size. The material in the ASCII text file is hereby incorporated by reference in its entirety.

TECHNICAL FIELD

The present invention relates to an antibody Fc region dimer that binds to each of a molecule incapable of binding to a natural antibody Fc region, and FcγR, but does not bind to the molecule and the FcγR at the same time, a polypeptide comprising the Fc region dimer, a pharmaceutical composition comprising the polypeptide, and a method for producing the polypeptide.

BACKGROUND ART

Antibodies have received attention as drugs because of their high stability in plasma and few adverse reactions (Nat. Biotechnol. (2005) 23, 1073-1078 (Non Patent Literature 1) and Eur J Pharm Biopharm. (2005) 59 (3), 389-396 (Non Patent Literature 2)). The antibodies induce not only an antigen-binding effect, an agonistic effect, or an antagonistic effect but the cytotoxic activities of effector cells (also referred to as effector functions), such as ADCC (antibody-dependent cytotoxicity), ADCP (antibody-dependent cell phagocytosis), and CDC (complement-dependent cytotoxicity). Particularly, antibodies of IgG1 subclass exhibit effector functions against cancer cells. A large number of antibody drugs have therefore been developed in the oncology field.

For exerting the ADCC, ADCP, or CDC of the antibodies, their Fc regions must bind to antibody receptors (FcγR) present on effector cells (such as NK cells or macrophages) and various complement components. In humans, FcγRIa, FcγRIIa, FcγRIIb, FcγRIIIa, and FcγRIIIb isoforms have been reported as the protein family of FcγR, and their respective allotypes have also been reported (Immunol. Lett. (2002) 82, 57-65 (Non Patent Literature 3)). Of these isoforms, FcγRIa, FcγRIIa, and FcγRIIIa have, in their intracellular domains, a domain called ITAM (immunoreceptor tyrosine-based activation motif), which transduces activation signals. By contrast, only FcγRIIb has, in its intracellular domain, a domain called ITIM (immunoreceptor tyrosine-based inhibitory motif), which transduces inhibition signals. These isoforms of FcγR are all known to transduce signals through cross-link by immune complexes or the like (Nat. Rev. Immunol. (2008) 8, 34-47 (Non Patent Literature 4)). In fact, when the antibodies exert effector functions against cancer cells, FcγR molecules on effector cell membranes are clustered by the Fc regions of a plurality of antibodies bound onto cancer cell membranes and thereby transduce activation signals through the effector cells. As a result, a cell-killing effect is exerted. In this respect, the cross-link of FcγR is restricted to effector cells located near the cancer cells, showing that the activation of immunity is localized to the cancer cells (Ann. Rev. Immunol. (1988). 6. 251-81 (Non Patent Literature 5)).

For the binding between FcγR and the Fc region of an antibody, some amino acid residues in the hinge regions and the CH2 domains of the antibody and sugar chains added to Asn 297 (EU numbering) of the CH2 domains have been found important (Chem. Immunol. (1997), 65, 88-110 (Non Patent Literature 6), Eur. J. Immunol. (1993) 23, 1098-1104 (Non Patent Literature 7), and Immunol. (1995) 86, 319-324 (Non Patent Literature 8)). Fc region variants having various FcγR-binding properties have previously been studied by focusing on this binding site, to yield Fc region variants having higher binding activity against activated FcγR (WO2000/042072 (Patent Literature 1) and WO2006/019447 (Patent Literature 2)). For example, Lazar et al. have successfully increased the binding activity of human IgG1 against human FcγRIIIa (V158) to approximately 370 times by substituting Ser 239, Ala 330, and Ile 332 (EU numbering) of the human IgG1 by Asp, Leu, and Glu, respectively (Proc. Natl. Acad. Sci. U.S.A (2006) 103, 4005-4010 (Non Patent Literature 9) and WO2006/019447 (Patent Literature 2)). This altered form has approximately 9 times the binding activity of a wild type in terms of the ratio of FcγRIIIa to FcγIIb (A/I ratio). Alternatively, Shinkawa et al. have successfully increased binding activity against FcγRIIIa to approximately 100 times by deleting fucose of the sugar chains added to Asn 297 (EU numbering) (J. Biol. Chem. (2003) 278, 3466-3473 (Non Patent Literature 10)). These methods enable drastic improvement in the ADCC activity of human IgG1 compared with naturally occurring human IgG1.

Enhancement in the ADCC activity, prolonging of blood retention properties, improvement in binding activity against an antigen, and reduction in immunogenicity risk have been practiced as techniques of improving antibodies. A conventional antibody recognizes and binds to one epitope on an antigen. Hence, only one type of antigen is targeted by one antibody even if these improvement techniques are applied thereto. Meanwhile, many types of proteins are known to participate in cancer or inflammation, and these proteins may crosstalk with each other. For example, some inflammatory cytokines (TNF, IL1, and IL6) are known to participate in immunological disease (Nat. Biotech., (2011) 28, 502-10 (Non Patent Literature 11)). Also, the activation of other receptors is known as one mechanism underlying the acquisition of drug resistance by cancer (Endocr Relat Cancer (2006) 13, 45-51 (Non Patent Literature 12)). In such a case, the conventional antibody, which recognizes one epitope, cannot inhibit a plurality of proteins.

Antibodies that bind to two or more types of antigens by one molecule (these antibodies are referred to as bispecific antibodies) have been studied as molecules inhibiting a plurality of targets. Each bispecific antibody interacts with two or more types of antigens and therefore has not only the effect of neutralizing these two or more types of antigens by one molecule but the effect of enhancing antitumor activity through the cross-link between cells having cytotoxic activity and cancer cells. A molecule comprising an antigen-binding site added to the N or C terminus of an antibody (DVD-Ig and scFv-IgG), a molecule having different sequences of two Fab regions of an antibody (common L-chain bispecific antibody and hybrid hybridoma), a molecule in which one Fab region recognizes two antigens (two-in-one IgG), and a molecule having a CH3 region loop site as another antigen-binding site (Fcab) have previously been reported as molecular forms of the bispecific antibody (Nat. Rev. (2010), 10, 301-316 (Non Patent Literature 13) and Peds (2010), 23 (4), 289-297 (Non Patent Literature 14)). Since any of these bispecific antibodies interact at their Fc regions with FcγR, antibody effector functions are preserved therein. Thus, the bispecific antibody binds to any antigens recognized thereby (by its Fab domain) at the same time with binding to FcγR and exhibits ADCC activity against cells expressing the antigen.

Provided that all the antigens recognized by the bispecific antibody are antigens specifically expressed in cancer, the bispecific antibody exhibits cytotoxic activity upon expression of any of the antigens and as such, can be used as an anticancer agent more versatile than the conventional antibody drug that merely recognizes one antigen. However, in the case where any one of the antigens recognized by the bispecific antibody is expressed in a normal tissue or is a cell expressed on immunocytes, damage on the normal tissue or release of cytokines occurs due to cross-link with FcγR (J. Immunol. (1999) August 1, 163 (3), 1246-52 (Non Patent Literature 15)). As a result, strong adverse reactions are induced.

Catumaxomab is known as a bispecific antibody that recognizes a protein expressed on T cells and a protein expressed on cancer cells (cancer antigen). Catumaxomab binds, at two Fab domains, the cancer antigen (EpCAM) and a CD3 epsilon chain expressed on T cells, respectively. Catumaxomab induces T cell-mediated cytotoxic activity through binding to the cancer antigen and the CD3 epsilon at the same time and induces effector cell-mediated cytotoxic activity through binding to the cancer antigen and FcγR at the same time. By use of these two cytotoxic activities, catumaxomab exhibits a high therapeutic effect on malignant ascites by intraperitoneal administration and has thus been approved in Europe (Cancer Treat Rev. (2010) October 36 (6), 458-67 (Non Patent Literature 16)). In addition, the administration of catumaxomab reportedly yields cancer cell-reactive antibodies in some cases, demonstrating that acquired immunity is induced (Future Oncol. (2012) January 8 (1), 73-85 (Non Patent Literature 17)). From this result, such antibodies having both of T cell-mediated cytotoxic activity and the effect of cells such as NK cells or macrophages via FcγR (these antibodies are particularly referred to as trifunctional antibodies) have received attention because a strong antitumor effect and induction of acquired immunity can be expected.

The trifunctional antibodies, however, bind to CD3 epsilon and FcγR at the same time even in the absence of a cancer antigen and therefore cross-link CD3 epsilon-expressing T cells to FcγR-expressing cells even in an environment lacking cancer cells, leading to production of various cytokines in large amounts. Such cancer antigen-independent induction of production of various cytokines restricts the current administration of the trifunctional antibodies to an intraperitoneal route (Cancer Treat Rev. 2010 October 36 (6), 458-67 (Non Patent Literature 16)). The trifunctional antibodies are very difficult to administer systemically due to severe cytokine storm-like adverse reactions (Cancer Immunol Immunother. 2007 September; 56 (9): 1397-406 (Non Patent Literature 18)). The bispecific antibody of the conventional technique is capable of binding to both antigens, i.e., a first antigen cancer antigen (EpCAM) and a second antigen CD3 epsilon, at the same time with binding to FcγR, and therefore, cannot avoid, in view of its molecular structure, such adverse reactions caused by the binding to FcγR and the second antigen CD3 epsilon at the same time. Since the conventional bispecific antibody cannot avoid adverse reactions caused by the binding to the second antigen (which is not limited to CD3 epsilon) and FcγR at the same time as mentioned above, a bispecific antibody having molecular structure that can avoid such adverse reactions has been demanded.

CITATION LIST

Patent Literature

Patent Literature 1: WO2000/042072
Patent Literature 2: WO2006/019447

Non Patent Literature

Non Patent Literature 1: Nat. Biotechnol. (2005) 23, 1073-1078
Non Patent Literature 2: Eur J Pharm Biopharm. (2005) 59 (3), 389-396
Non Patent Literature 3: Immunol. Lett. (2002) 82, 57-65
Non Patent Literature 4: Nat. Rev. Immunol. (2008) 8, 34-47
Non Patent Literature 5: Ann. Rev. Immunol. (1988). 6. 251-81
Non Patent Literature 6: Chem. Immunol. (1997), 65, 88-110
Non Patent Literature 7: Eur. J. Immunol. (1993) 23, 1098-1104
Non Patent Literature 8: Immunol. (1995) 86, 319-324
Non Patent Literature 9: Proc. Natl. Acad. Sci. U.S.A (2006) 103, 4005-4010
Non Patent Literature 10: J. Biol. Chem. (2003) 278, 3466-3473
Non Patent Literature 11: Nat. Biotech., (2011) 28, 502-10
Non Patent Literature 12: Endocr Relat Cancer (2006) 13, 45-51
Non Patent Literature 13: Nat. Rev. (2010), 10, 301-316
Non Patent Literature 14: Peds (2010), 23 (4), 289-297
Non Patent Literature 15: J. Immunol. (1999) August 1, 163 (3), 1246-52
Non Patent Literature 16: Cancer Treat Rev. (2010) October 36 (6), 458-67
Non Patent Literature 17: Future Oncol. (2012) January 8 (1), 73-85
Non Patent Literature 18: Cancer Immunol Immunother. 2007 September; 56 (9): 1397-406

SUMMARY OF THE INVENTION

Problems to be Solved by the Invention

The present invention has been made in light of these situations, and an object of the present invention is to provide an antibody Fc region dimer that has binding activity against each of an antigen and FcγR, but does not bind to the antigen and the FcγR at the same time, a polypeptide comprising the Fc region dimer, a pharmaceutical composition comprising the polypeptide, and a method for producing the polypeptide.

Means for Solving the Problems

The present inventors have conducted diligent studies to attain the object. As a result, the present inventors have successfully prepared an antibody Fc region dimer that has binding activity against each of an antigen and FcγR, but does not bind to the antigen and the FcγR at the same time, and a polypeptide comprising the Fc region dimer.

More specifically, the present invention relates to the following:

[1] An Fc region dimer comprising an antigen-binding site and an FcγR-binding site, wherein the Fc region dimer does not bind to an antigen and FcγR at the same time.

[2] The Fc region dimer according to [1], wherein the Fc region of the Fc region dimer is an IgG Fc region.

[3] The Fc region dimer according to [1] or [2], wherein the Fc region dimer is a heterodimer consisting of two Fc regions (first Fc region and second Fc region) differing in their amino acid sequences.

[4] The Fc region dimer according to any of [1] to [3], wherein the antigen-binding site is a site introduced by the alteration of at least one amino acid in the Fc region or a site having an amino acid sequence identical thereto.

[5] The Fc region dimer according to [4], wherein the amino acid to be altered is an amino acid in a CH2 domain of the Fc region.

[6] The Fc region dimer according to [4] or [5], wherein the amino acid to be altered is an amino acid in a loop region.

[7] The Fc region dimer according to [6], wherein the amino acid to be altered is at least one amino acid selected from EU numbering positions 231 to 239, EU numbering positions 265 to 271, EU numbering positions 295 to 300, and EU numbering positions 324 to 337.

[8] The Fc region dimer according to [4], wherein the amino acid to be altered in the heterodimer is at least one amino acid selected from EU numbering positions 265 to 271 and EU numbering positions 295 to 300 of the first Fc region, and EU numbering positions 265 to 271 and EU numbering positions 324 to 332 of the second Fc region.

[9] The Fc region dimer according to [4], wherein the alteration in the antigen-binding site is the insertion of at least one amino acid.

[10] The Fc region dimer according to [9], wherein the number of the amino acid to be inserted is 9 or less.

[11] The Fc region dimer according to [9] or [10], wherein the at least one amino acid to be inserted is a peptide having binding activity against the antigen.

[12] The Fc region dimer according to any of [1] to [11], wherein the FcγR-binding site is a site with at least one amino acid altered in the Fc region or a site having an amino acid sequence identical thereto.

[13] The Fc region dimer according to [12], wherein the amino acid to be altered is an amino acid in a CH2 domain of the Fc region.

[14] The Fc region dimer according to [12] or [13], wherein the FcγR-binding site has the introduced alteration of at least one amino acid wherein the amino acid to be altered is selected from the group consisting of Leu at EU numbering position 234, Leu at EU numbering position 235, Gly at EU numbering position 236, Ser at EU numbering position 239, His at EU numbering position 268, Asp at EU numbering position 270, Ser at EU numbering position 298, Lys at EU numbering position 326, Ala at EU numbering position 330, Ile at EU numbering position 332, and Lys at EU numbering position 334, or has an amino acid sequence identical thereto.

[15] The Fc region dimer according to [12] or [13], wherein the FcγR-binding site has the introduced alteration of at least one or more amino acid(s) wherein the alteration is selected from the group consisting of the substitution of an amino acid L at EU numbering position 234 by Y, the substitution of an amino acid L at EU numbering position 235 by Y or Q, the substitution of an amino acid G at EU numbering position 236 by W, the substitution of an amino acid S at EU numbering position 239 by D or M, the substitution of an amino acid H at EU numbering position 268 by D, the substitution of an amino acid D at EU numbering position 270 by E, the substitution of an amino acid S at EU numbering position 298 by A, the substitution of an amino acid K at EU numbering position 326 by D, the substitution of an amino acid A at EU numbering position 330 by L or M, the substitution of an amino acid I at EU numbering position 332 by E, and the substitution of an amino acid K at EU numbering position 334 by E, or has an amino acid sequence identical thereto.

[16] The Fc region dimer according to [12] or [13], wherein the amino acid sequence of either one of the Fc regions in the Fc region dimer has the introduced alteration of at least one or more amino acid(s), selected from the group consisting of the substitution of an amino acid L at EU numbering position 234 by Y, the substitution of an amino acid L at EU numbering position 235 by Y or Q, the substitution of an amino acid G at EU numbering position 236 by W, the substitution of an amino acid S at EU numbering position 239 by M, the substitution of an amino acid H at EU numbering position 268 by D, the substitution of an amino acid D at EU numbering position 270 by E, and the substitution of an amino acid S at EU numbering position 298 by A, or has an amino acid sequence identical thereto, and the amino acid sequence of the other Fc region has the introduced alteration of at least one or more amino acid(s), selected from the group consisting of the substitution of an amino acid S at EU numbering position 239 by D, the substitution of an amino acid D at EU numbering position 270 by E, the substitution of an amino acid K at EU numbering position 326 by D, the substitution of an amino acid A at EU numbering position 330 by L or M, the substitution of an amino acid I at EU numbering position 332 by E, and the substitution of an amino acid K at EU numbering position 334 by E, or has an amino acid sequence identical thereto.

[17] The Fc region dimer according to [12] or [13], wherein either one of the Fc regions in the Fc region dimer has any of amino acid sequences (i) to (iii), and the other Fc region has any of amino acid sequences (iv) to (vi):

(i) an amino acid sequence in which the substitution of an amino acid L at EU numbering position 234 by Y, the substitution of an amino acid G at EU numbering position 236 by W, and the substitution of an amino acid S at EU numbering position 298 by A are introduced, or an amino acid sequence identical thereto;

(ii) an amino acid sequence in which the substitution of an amino acid L at EU numbering position 234 by Y, the substitution of an amino acid L at EU numbering position 235 by Y, the substitution of an amino acid G at EU numbering position 236 by W, the substitution of an amino acid H at EU numbering position 268 by D, and the substitution of an amino acid S at EU numbering position 298 by A are introduced, or an amino acid sequence identical thereto; and (iii) an amino acid sequence in which the substitution of an amino acid L at EU numbering position 234 by Y, the substitution of an amino acid L at EU numbering position 235 by Q, the substitution of an amino acid G at EU numbering position 236 by W, the substitution of an amino acid S at EU numbering position 239 by M, the substitution of an amino acid H at EU numbering position 268 by D, the substitution of an amino acid D at EU numbering position 270 by E, and the substitution of an amino acid S at EU numbering position 298 by A are introduced, or an amino acid sequence identical thereto; and (iv) an amino acid sequence in which the substitution of an amino acid S at EU numbering position 239 by D, the substitution of an amino acid A at EU numbering position 330 by L, and the substitution of an amino acid I at EU numbering position 332 by E are introduced, or an amino acid sequence identical thereto;

(v) an amino acid sequence in which the substitution of an amino acid K at EU numbering position 326 by D, the substitution of an amino acid A at EU numbering position 330 by M, and the substitution of an amino acid K at EU numbering position 334 by E are introduced, or an amino acid sequence identical thereto; and (vi) an amino acid sequence in which the substitution of an amino acid D at EU numbering position 270 by E, the substitution of an amino acid K at EU numbering position 326 by D, the substitution of an amino acid A at EU numbering position 330 by M, and the substitution of an amino acid K at EU numbering position 334 by E are introduced, or an amino acid sequence identical thereto.

[18] The Fc region dimer according to any of [12] to [17], wherein the FcγR-binding site has FcγR-binding activity higher than that of naturally occurring IgG1.

[19] The Fc region dimer according to any of [1] to [18], wherein the FcγR is at least one or more receptor(s) selected from the group consisting of FcγRIa, FcγRIIa, FcγRIIb, FcγRIIIa, and FcγRIIIb.

[20] The Fc region dimer according to [19], wherein the FcγR is FcγRIIIa.

[21] The Fc region dimer according to [19], wherein the Fc region dimer has an amino acid sequence with at least one amino acid altered wherein the amino acid to be altered is selected from the group consisting of amino acids to be mutated as described in Tables 2-1 to 2-3, or has an amino acid sequence identical thereto.

[22] A polypeptide comprising an Fc region dimer according to any of [1] to [21].

[23] The polypeptide according to [22], wherein the polypeptide is an antibody, a multispecific antibody, a peptide-Fc fusion protein, or a scaffold-Fc fusion protein.

[24] The polypeptide according to [22] or [23], wherein the polypeptide comprises variable regions of an antibody, wherein a first antigen binds to the variable regions, and a second antigen different from the first antigen binds to the Fc region.

[25] The polypeptide according to any of [22] to [24], wherein the first antigen is an antigen specific for a tumor cell.

[26] The polypeptide according to any of [22] to [25], wherein the second antigen is a molecule expressed on the surface of an immunocyte or a molecule expressed on a tumor cell and a normal cell.

[27] A pharmaceutical composition comprising a polypeptide according to any of [22] to [26] and a pharmaceutically acceptable carrier.

[28] A method for producing a polypeptide according to any of [22] to [26], the method comprising steps (i) to (iv):

(i) preparing a peptide library consisting of peptides or polypeptides containing CH2 domains having diverse amino acid sequences;

(ii) selecting a CH2 domain-containing peptide or polypeptide from the prepared library, wherein the CH2 domain-containing peptide or polypeptide has binding activity against each of an antigen and FcγR, but does not bind to the antigen and the FcγR at the same time;

(iii) culturing a host cell containing a nucleic acid encoding a polypeptide comprising an Fc region dimer having the same CH2 domains as those of the peptide or the polypeptide selected in step (ii) to express the polypeptide comprising an Fc region dimer; and (iv) recovering the polypeptide comprising an Fc region dimer from cultures of the host cell.

[29] The method according to [28], wherein the CH2 domain-containing peptide or polypeptide used in step (i) is a heterodimer consisting of two CH2 domains (first CH2 domain and second CH2 domain) differing in their amino acid sequences.

[30] The method according to [28] or [29], wherein the CH2 domain-containing peptide or polypeptide used in steps (i) and (ii) is an Fc region dimer or a polypeptide comprising the Fc region dimer.

[31] The method according to any of [28] to [30], wherein step (ii) further comprises the step of selecting a CH2 domain-containing peptide or polypeptide whose CH2 domains have a thermal denaturation temperature of 50° C. or higher.

[32] The method according to any of [28] to [31], wherein the CH2 domain-containing peptide or polypeptide used in step (i) is of IgG type.

[33] The method according to any of [28] to [32], wherein the CH2 domain-containing peptide or polypeptide used in step (i) has a sequence identical to the altered sequence described in any of [14] to [17] and [21] for enhancing binding activity against FcγR.

[34] The method according to any of [28] to [33], wherein the library used in step (i) is a library in which the CH2 domains have diversified amino acid sequences.

[35] The method according to any of [28] to [34], wherein the library used in step (i) is a library in which loop regions have diversified amino acid sequences.

[36] The method according to any of [28] to [35], wherein the amino acid sequences of the loop regions to be diversified each comprise at least one amino acid selected from EU numbering positions 231 to 239, EU numbering positions 265 to 271, EU numbering positions 295 to 300, and EU numbering positions 324 to 337.

[37] The method according to any of [29] to [36], wherein the amino acid sequences of the loop regions to be diversified each comprise at least one amino acid selected from EU numbering positions 265 to 271 and EU numbering positions 295 to 300 of the first Fc region, and EU numbering positions 265 to 271 and EU numbering positions 324 to 332 of the second Fc region.

[38] The method according to any of [28] to [37], wherein the diversification is diversification by the random insertion of a peptide having binding activity against the antigen.

BRIEF DESCRIPTION OF THE DRAWINGS

FIG. 15-1 is a diagram showing the amino acid sequences of a portion of each of several $H_A$ chains, the portion corresponding to EU positions 231-340, wherein a peptide consisting of various combinations of Gly and Ser residues was inserted into a loop region on the Y side of some of the $H_A$ chains. In the listed sequences, the “IgG1” sequence (first line of listed sequences) corresponds to positions 114-223 of SEQ ID NO: 49; the “Parent peptide H1076” sequence corresponds to positions 230-339 of SEQ ID NO: 22; the “H1076-L2-3” sequence corresponds to positions 230-342 of SEQ ID NO: 26; the “H1076-L2-6” sequence corresponds to positions 230-345 SEQ ID NO: 27; the “H1076-L2-9” sequence corresponds to positions 230-348 of SEQ ID NO: 28; the “H1076-L2-GS6_2” sequence corresponds to positions 230-339 of SEQ ID NO: 23; the “H1076-L2-GS8_2” sequence corresponds to positions 230-345 of SEQ ID NO: 24; the “H1076-L2-GS12_2” sequence corresponds to positions 230-345 of SEQ ID NO: 25; the “H1076-L3-3” sequence corresponds to positions 230-342 of SEQ ID NO: 29; the “H1076-L3-6” sequence corresponds to positions 230-345 of SEQ ID NO: 30; and the “H1076-L3-9” sequence corresponds to positions 230-348 of SEQ ID NO: 31.

FIG. 15-2 is a diagram showing amino acid sequences of a portion of each of several $H_B$ chains, the portion corresponding to EU positions 231-340, wherein a peptide consisting of various combinations of Gly and Ser residues was inserted into a loop region on the Y side of some of the $H_B$ chains. The “IgG1” sequence (first line of listed sequences) corresponds to positions 114-223 of SEQ ID NO: 49; the “Parent peptide_Kn125” sequence corresponds to positions 230-339 of SEQ ID NO: 21; the “Kn125-L2a-3” sequence corresponds to positions 230-342 of SEQ ID NO: 35; the “Kn125-L2a-6” sequence corresponds to positions 230-345 of SEQ ID NO: 36; the “Kn125-L2a-9” sequence corresponds to positions 230-348 of SEQ ID NO: 37; the “Kn125-L2b-3” sequence corresponds to positions 230-342 of SEQ ID NO: 38; the “Kn125-L2b-6” sequence corresponds to positions 230-345 of SEQ ID NO: 39; the “Kn125-L2b-9” sequence corresponds to positions 230-348 of SEQ ID NO: 40; the “Kn125-L4-3” sequence corresponds to positions 230-342 of SEQ ID NO: 41; the “Kn125-L4-6” sequence corresponds to positions 230-345 of SEQ ID NO: 42; the “Kn125-L4-9” sequence corresponds to positions 230-348 of SEQ ID NO: 43; the “Kn125-L4-GS5” sequence corresponds to positions 230-339 of SEQ ID NO: 32; the “Kn125-L4-GS7” sequence corresponds to positions 230-341 of SEQ ID NO: 33; and the “Kn125-L4-GS11” sequence corresponds to positions 230-345 of SEQ ID NO: 34.

MODE FOR CARRYING OUT THE INVENTION

Figure 1:
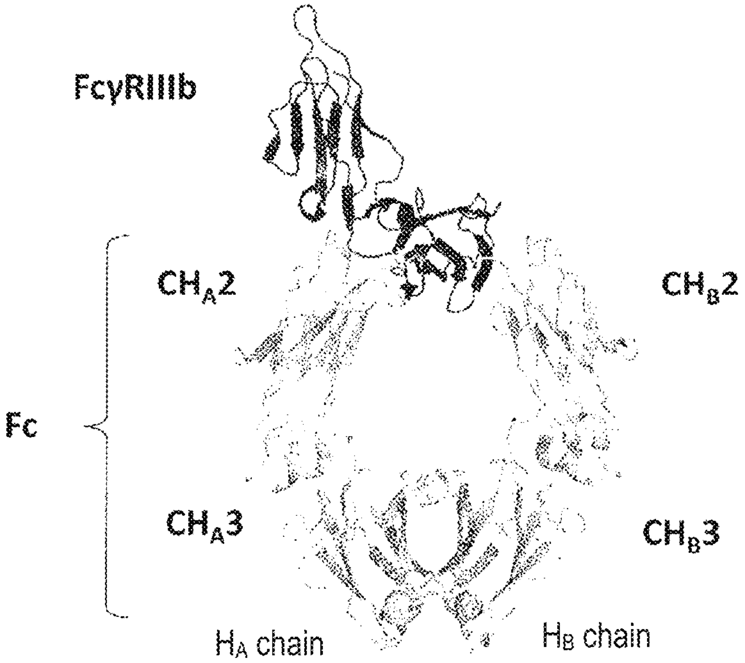
FIG. 1 is a diagram showing the binding of an Fc region to FcγR. FcγR binds to antibody heavy chain CH2 regions. FcγR interacts with the antibody Fc region from the back side of the drawing. In this context, the H chain shown on the left side is referred to as an $H_A$ chain, while the H chain shown on the right side is referred to as an $H_B$ chain.

The following definitions are provided merely for facilitating the understanding of the present invention described herein.

In the present invention, the "antigen-binding site" is not particularly limited as long as the peptide has binding activity against a desired antigen. The antigen-binding site may be a site obtained, for example, by randomly altering amino acids in Fc regions and selecting an Fc region having binding activity against the desired antigen from the Fc regions having the altered amino acids. Alternatively, the antigen-binding site may be a peptide previously known to have binding activity against the desired antigen. Examples of the peptide previously known to have antigen-binding activity include peptides shown in Table 1.

TABLE 1

| Binding partner/ protein of interest | Reference |
|---|---|
| VEGFR | J Biol Chem. 2002 Nov. 8; 277(45): 43137-42. Epub 2002 Aug. 14., EMBO J. 2000 Apr. 3; 19(7): 1525-33., J Med Chem. 2010 Jun. 10; 53(11): 4428-40. |
| TNFR | Mol Immunol. 2004 July; 41(8): 741-9., Eur J Pharmacol. 2011 Apr. 10; 656(1-3): 119-24. |
| TLR5 | J Immunol 2010; 185; 1744-1754 |
| TLR4 | PLoS ONE, February 2012, Volume 7, Issue 2, e30839 |
| TLR2 | WO2006/083706A2 |
| T-cell VLA receptor | Int Immunopharmacol. 2003 March; 3(3): 435-43. |
| PDGFR | Biochemical Pharmacology (2003), 66(7), 1307-1317, FEBS Lett. 1997 Dec. 15; 419(2-3): 166-70. |
| Naip5(NLR) | NATURE IMMUNOLOGY VOLUME 9 NUMBER 10 OCTOBER 2008 1171- |
| integrin | WO 95/14714, WO 97/08203, WO 98/10795, WO 99/24462, J. Biol. Chem. 274: 1979-1985 |
| FcgRIIa | J Biol Chem. 2009 Jan. 9; 284(2): 1126-35 |
| EGFR | Journal of Biotechnology (2005), 116(3) 211-219 |
| DR5 agonist | J Mol Biol (2006), 361(3) 522-536 |
| CXCR4 | Science 330, 1066 (2010); Vol. 330 no. 6007 pp. 1066-1071 |
| CD40 | Eur J Biochem. 2003 May; 270(10): 2287-94. |
| CD154 | J Mol Med (Berl). 2009 February; 87(2): 181-97. |

In the present invention, the "FcγR-binding site" is not particularly limited as long as the peptide has binding activity against FcγR. The FcγR-binding site includes, for example, an FcγR-binding site in the Fc region of IgG such as IgG1, IgG2, IgG3, or IgG4 and also includes FcγR-binding sites with FcγR-binding activity changed by the alteration of amino acids in these binding sites of IgG as long as these sites have binding activity against FcγR.

In the Fc region dimer of the present invention, the phrase "not binding to an antigen and FcγR at the same time" means that the Fc region dimer of the present invention in a state bound with the antigen cannot bind to the FcγR, while the Fc region dimer in a state bound with the FcγR cannot bind to the antigen. Such an Fc region dimer is not particularly limited as long as the Fc region dimer has the functions described above. Examples thereof can include Fc region dimers allowed to bind to the desired antigen by the alteration of amino acid(s) in one of two FcγR-binding sites present in an IgG Fc region dimer. Presumably, such an Fc region dimer changes its three-dimensional structure upon binding to either one of the antigen and FcγR molecules and consequently, can no longer bind to the other molecule. Specific examples thereof include Fc region dimers described in Example 1. Alternatively, for example, the FcγR and the antigen may be recognized by the same amino acid. In such a case, the amino acid bound with one of the molecules cannot bind to the other molecule. Presumably, this Fc region dimer can no longer bind to the other molecule.

The "Fc region dimer" of the present invention means a dimer consisting of two Fc regions. The dimer may be an Fc homodimer consisting of identical Fc regions or may be an Fc region heterodimer consisting of a first Fc region and a second Fc region differing in their amino acid sequences. The homodimer also includes an Fc region dimer consisting of Fc regions having identical amino acid sequences except for an alteration intended for the efficient Fc region dimerization or an alteration intended for the efficient purification of a polypeptide comprising the Fc region dimer, and an Fc region dimer consisting of Fc regions having identical amino acid sequences except for an alteration not intended to improve the functions of the Fc region. For enhancing the binding activity of the FcγR-binding site, an Fc region heterodimer is preferred, and an Fc region heterodimer having different sequences of at least CH2 regions is more preferred.

An Fc region dimer derived from, for example, naturally occurring IgG can be used as the "Fc region dimer" of the present invention. In this context, the naturally occurring IgG means a polypeptide that contains an amino acid sequence identical to that of IgG found in nature and belongs to a class of an antibody substantially encoded by an immunoglobulin gamma gene. The naturally occurring human IgG means, for example, naturally occurring human IgG1, naturally occurring human IgG2, naturally occurring human IgG3, or naturally occurring human IgG4. The naturally occurring IgG also includes variants or the like spontaneously derived therefrom. A plurality of allotype sequences based on gene polymorphism are described as the constant regions of human IgG1, human IgG2, human IgG3, and human IgG4 antibodies in Sequences of proteins of immunological interest, NIH Publication No. 91-3242, any of which can be used in the present invention. Particularly, the sequence of human IgG1 may have DEL or EEM as an amino acid sequence of EU numbering positions 356 to 358.

Figure 11:
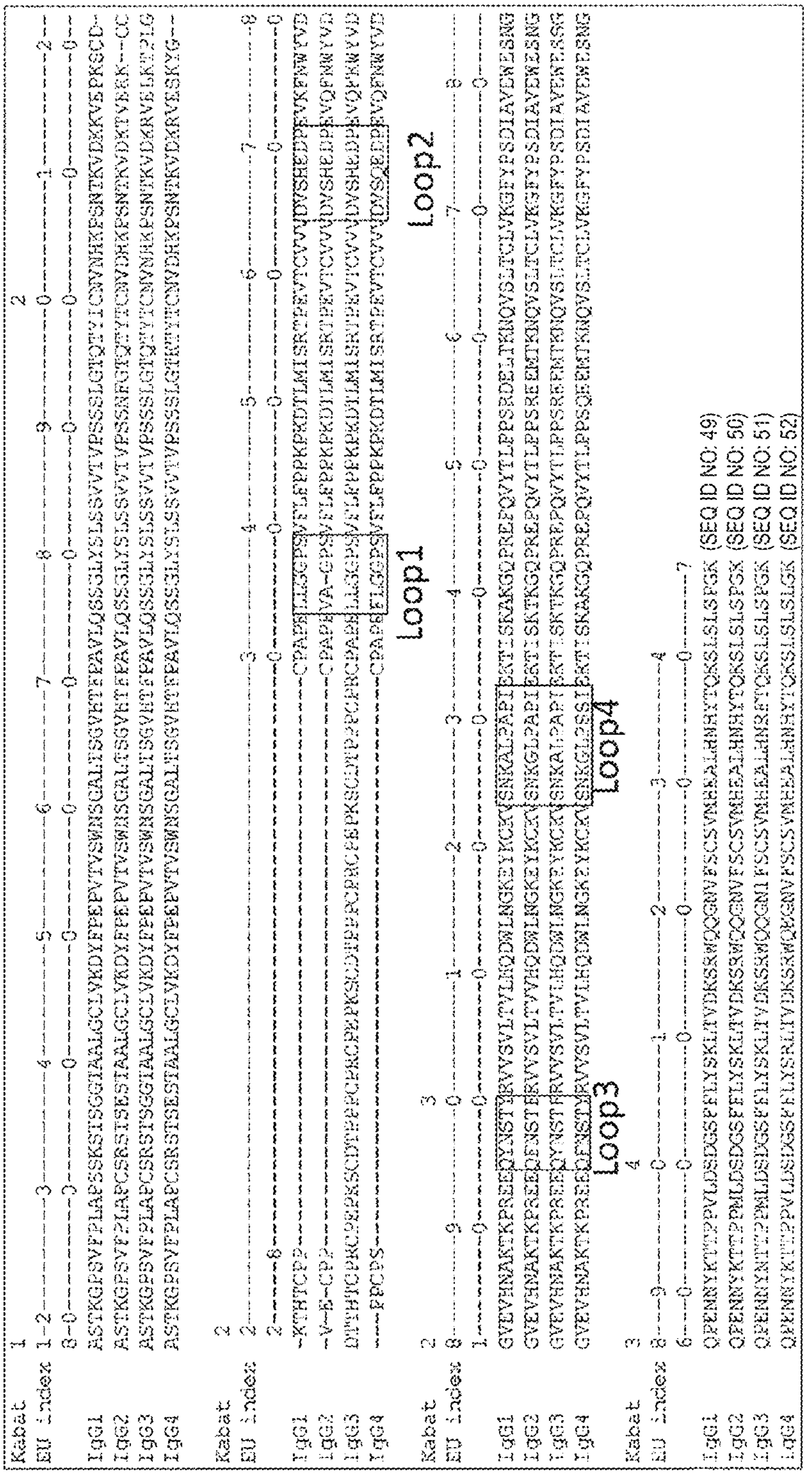
FIG. 11 is a diagram showing loop regions that are made into a library.

The antibody Fc region is found as, for example, the Fc region of IgA1, IgA2, IgD, IgE, IgG1, IgG2, IgG3, IgG4, or IgM type. For example, a human IgG antibody Fc region can be used as the antibody Fc region of the present invention. A human IgG1 antibody Fc region is preferred. For example, an Fc region derived from constant regions of naturally occurring IgG, specifically, constant regions (SEQ ID NO: 49) originated from naturally occurring human IgG1, constant regions (SEQ ID NO: 50) originated from naturally occurring human IgG2, constant regions (SEQ ID NO: 51) originated from naturally occurring human IgG3, or constant regions (SEQ ID NO: 52) originated from naturally occurring human IgG4 can be used as the Fc region of the present invention (FIG. 11). The constant regions of naturally occurring IgG also includes variants or the like spontaneously derived therefrom. A plurality of allotype sequences based on gene polymorphism are described as the constant regions of human IgG1, human IgG2, human IgG3, and human IgG4 antibodies in Sequences of proteins of immunological interest, NIH Publication No. 91-3242, any of which can be used in the present invention. Particularly, the sequence of human IgG1 may have DEL or EEM as an amino acid sequence of EU numbering positions 356 to 358.

Reportedly, the strength of the interaction between the antibody Fc region and FcγR depends on $Zn^{2+}$ ion concentrations (Immunology Letters 143 (2012) 60-69). An Fc region with a higher $Zn^{2+}$ ion concentration interacts more strongly with FcgR. $Zn^{2+}$ chelation by His 310 and His 435 present in CH3 of the antibody Fc region causes distal CH2-CH2 interdomain opening in the Fc region. This facilitates the interaction of the CH2 domains with FcgR, enhancing the interaction between the Fc region and the FcgR. In a non-limiting aspect, examples of the Fc region of the present invention include Fc regions with $Zn^{2+}$ chelated by His 310, His 435, His 433, and/or Asn 434 defined by EU numbering.

In the present invention, the "Fc region" refers to a region comprising a fragment consisting of hinges or a portion thereof and CH2 and CH3 domains in an antibody molecule. The Fc region of IgG class means, but not limited to, a region from, for example, cysteine 226 (EU numbering (also referred to as EU index herein)) to the C terminus or proline 230 (EU numbering) to the C terminus.

In the present invention, the "heterodimer" or the "homodimer" preferably means that CH2 domains in the Fc region are "heterodimerized" or "homodimerized".

The Fc region can be preferably obtained by the partial digestion of, for example, an IgG1, IgG2, IgG3, or IgG4 monoclonal antibody with a proteolytic enzyme such as pepsin followed by re-elution of a fraction adsorbed on a protein A column or a protein G column. Such a proteolytic enzyme is not particularly limited as long as the enzyme is capable of digesting a whole antibody to restrictively form Fab or $F(ab')_2$ under appropriately set reaction conditions (e.g., pH) of the enzyme. Examples thereof can include pepsin and papain.

In the present invention, one amino acid mutation may be used alone, or a plurality of amino acid mutations may be used in combination.

In the case of using a plurality of amino acid mutations in combination, the number of the mutations to be combined is not particularly limited and can be appropriately set within a range that can attain the object of the invention. The number of the mutations to be combined is, for example, 2 or more and 30 or less, preferably 2 or more and 15 or less.

The plurality of amino acid mutations to be combined may be added to only one of the two Fc regions constituting the Fc region dimer or may be appropriately distributed to both of these two Fc regions.

The alteration site is not particularly limited as long as the site is located within the Fc region, and can be appropriately set within a range that can attain the object of the present invention. The alteration site resides in, for example, a hinge region, a CH2 region, or a CH3 region.

More preferably, the alteration site resides in a CH2 region. In this context, the CH2 region means a region of EU numbering positions 231 to 340, and the CH3 region means a region of EU numbering positions 341 to 447.

Further preferably, the alteration site resides in a loop region in the CH2 region. Specific examples thereof include EU numbering positions 231 to 239, EU numbering positions 263 to 275, EU numbering positions 292 to 302, and EU numbering positions 323 to 337. The alteration site in the loop region resides in preferably EU numbering positions 231 to 239, EU numbering positions 265 to 271, EU numbering positions 295 to 300, or EU numbering positions 324 to 337, more preferably EU numbering positions 234 to 239, EU numbering positions 265 to 271, EU numbering positions 295 to 300, or EU numbering positions 324 to 337, further preferably EU numbering positions 265 to 271, EU numbering positions 295 to 300, or EU numbering positions 324 to 332.

In the case of introducing alteration(s), for example, to the amino acid sequence of an Fc region originated from human IgG1, an amino acid residue at one or more position(s) selected from EU numbering positions 265 to 271 in the loop region, EU numbering positions 295 to 300 in the loop region, and EU numbering positions 324 to 332 in the loop region can be altered as the alteration site for the antigen-binding site.

In the present invention, the "loop region" means a region containing residues that are not involved in the maintenance of an immunoglobulin β barrel structure. The alteration of an amino acid residue also involves alteration by the insertion of, to any of the regions mentioned above, a peptide previously known to have binding activity against the desired antigen.

In the case of introducing alteration(s), for example, to the amino acid sequence of a constant region originated from human IgG1, an amino acid residue at one or more position (s) selected from EU numbering positions 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, and 447 can be altered as the alteration site for the FcγR-binding site.

More specifically, in the case of introducing alteration(s) to the amino acid sequence of a human IgG1 constant region, an amino acid residue at one or more position(s) selected from EU numbering positions 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, and 447 can be altered.

More specifically, in the case of introducing alteration(s) to the amino acid sequence of a human IgG1 constant region, an amino acid residue at one or more position(s) selected from EU numbering positions 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, and 340 can be altered.

More specifically, in the case of introducing alteration(s) to the amino acid sequence of a human IgG1 constant region, an amino acid residue at one or more position(s) selected from EU numbering positions 234, 235, 236, 237, 238, 239, 265, 266, 267, 268, 269, 270, 271, 295, 296, 298, 300, 324, 325, 326, 327, 328, 329, 330, 331, 332, 333, 334, 335, 336, 337, 356, 435, and 439 can be altered.

More specifically, in the case of introducing alteration(s) to the amino acid sequence of a human IgG1 constant region, an amino acid residue at one or more position(s) selected from EU numbering positions 234, 235, 236, 237, 238, 239, 265, 266, 267, 268, 269, 270, 271, 295, 296, 298, 300, 324, 325, 326, 327, 328, 329, 330, 331, 332, 333, 334, 335, 336, and 337 can be altered.

In the present invention, the amino acid alteration means substitution, deletion, addition, insertion, or modification, or a combination thereof. In the present invention, the amino acid alteration can be used interchangeably with amino acid mutation and used in the same sense therewith.

The substitution of an amino acid residue is carried out by replacement with another amino acid residue for the purpose of altering, for example, any of the following (a) to (c): (a) the polypeptide backbone structure of a region having a sheet structure or helix structure; (b) the electric charge or hydrophobicity of a target site; and (c) the size of a side chain.

Amino acid residues are classified into the following groups on the basis of general side chain properties: (1) hydrophobic residues: norleucine, Met, Ala, Val, Leu, and Ile; (2) neutral hydrophilic residues: Cys, Ser, Thr, Asn, and Gln; (3) acidic residues: Asp and Glu; (4) basic residues: His, Lys, and Arg; (5) residues that influence chain orientation: Gly and Pro; and (6) aromatic residues: Trp, Tyr, and Phe.

The substitution of amino acid residues within each of these groups is called conservative substitution, while the substitution of an amino acid residue in one of these groups by an amino acid residue in another group is called non-conservative substitution.

The substitution according to the present invention may be the conservative substitution or may be the non-conservative substitution. Alternatively, the conservative substitution and the non-conservative substitution may be combined.

In the present invention, the "polypeptide" typically refers to a peptide of approximately 10 or more amino acids in length, and a protein. The polypeptide is usually an organism-derived polypeptide, though the polypeptide of the present invention is not particularly limited thereto. The polypeptide may be, for example, a polypeptide consisting of an artificially designed sequence. Alternatively, a natural polypeptide, a synthetic polypeptide, a recombinant polypeptide, or the like may be used.

Preferred examples of the polypeptide of the present invention can include human IgG antibodies. Human IgG used as an antibody is not limited by its isotype (subclass), and human IgG of isotype (subclass) such as IgG1, IgG2, IgG3, or IgG4 may be used.

The polypeptide of the present invention is preferably human IgG1. A plurality of allotype sequences based on gene polymorphism are described as the Fc region of human IgG1 in Sequences of proteins of immunological interest, NIH Publication No. 91-3242, any of which can be used in the present invention. Particularly, the sequence of human IgG1 may have DEL or EEM as an amino acid sequence of EU numbering positions 356 to 358.

Also, the polypeptide comprising the Fc region dimer according to the present invention involves the amino acid alteration introduced on the basis of the present invention and can further involve additional alteration. The additional alteration can be selected from, for example, amino acid substitution, deletion, and modification, and a combination thereof.

For example, the polypeptide comprising the Fc region dimer according to the present invention can be further altered arbitrarily, substantially without changing the intended functions of the Fc region dimer. When the polypeptide of the present invention is an antibody, its heavy or light chain can be altered. Such mutations can be performed, for example, by the conservative substitution of amino acid residues. Alternatively, even alteration that changes the intended functions of the polypeptide of the present invention may be carried out as long as the functions changed by such alteration fall within the object of the present invention.

The alteration of an amino acid sequence according to the present invention includes posttranslational modification. Specifically, the posttranslational modification can refer to the addition or deletion of a sugar chain. For example, an amino acid residue at EU numbering position 297 in an IgG1 constant region can be modified with a sugar chain. The sugar chain structure used in the modification is not limited. In general, antibodies expressed by eukaryotic cells involve sugar chain modification in their constant regions. Thus, antibodies expressed by the following cells are usually modified with some sugar chain: mammalian antibody-producing cells; and eukaryotic cells transformed with expression vectors comprising antibody-encoding DNAs.

In this context, the eukaryotic cells include yeast and animal cells. For example, CHO cells or HEK293H cells are typical animal cells for use in transformation with expression vectors comprising antibody-encoding DNAs. On the other hand, the antibody of the present invention also includes antibodies lacking sugar chain modification at the position. The antibodies having sugar chain-unmodified constant regions can be obtained by the expression of their antibody-encoding genes in prokaryotic cells such as *E. coli*.

The additional alteration according to the present invention may be more specifically, for example, the addition of sialic acid to the sugar chain of an Fc region (MAbs. 2010 September-October; 2 (5): 519-27).

When the polypeptide of the present invention is an antibody, for example, amino acid substitution for improving binding activity against FcRn (J Immunol. 2006 Jan. 1; 176 (1): 346-56, J Biol Chem. 2006 Aug. 18; 281 (33): 23514-24., Int Immunol. 2006 December; 18 (12): 1759-69., Nat Biotechnol. 2010 February; 28 (2): 157-9, WO/2006/019447, WO/2006/053301, and WO/2009/086320) or amino acid substitution for improving antibody heterogeneity or stability ((WO/2009/041613)) may be added to constant regions portion of the antibody.

In the Fc region dimer of the present invention or the polypeptide comprising the Fc region dimer, use of a heterodimer as the Fc region dimer requires associating polypeptides differing in their amino acid sequences, or separating the heterodimer of interest or a polypeptide comprising the heterodimer from other homodimers or polypeptides comprising the homodimers.

The association of polypeptides for the heterodimer or the polypeptide comprising the heterodimer can be achieved by the application of a technique of suppressing the unintended association between H chains by introducing electric charge repulsion to the interface of the antibody H chain second constant region (CH2) or third constant region (CH3) (WO2006/106905).

In the technique of suppressing the unintended association between H chains by introducing electric charge repulsion to the CH2 or CH3 interface, examples of amino acid residues contacted with each other at the interface between the H chain constant regions can include regions corresponding to a residue at EU numbering position 356, a residue at EU numbering position 439, a residue at EU numbering position 357, a residue at EU numbering position 370, a residue at EU numbering position 399, and a residue at EU numbering position 409 in the CH3 region.

More specifically, for example, an antibody comprising two types of H chain CH3 regions can be prepared as an antibody in which one to three pair(s) of amino acid residues selected from the following amino acid residue pairs (1) to (3) in the first H chain CH3 region carry the same type of electric charge: (1) amino acid residues at EU numbering positions 356 and 439 contained in the H chain CH3 region; (2) amino acid residues at EU numbering positions 357 and 370 contained in the H chain CH3 region; and (3) amino acid residues at EU numbering positions 399 and 409 contained in the H chain CH3 region.

In addition, the antibody can be prepared as an antibody having one to three pair(s) of the amino acid residues selected from the amino acid residue pairs (1) to (3) in the second H chain CH3 region different from the first H chain CH3 region, wherein the pair(s) of the amino acid residues correspond to the amino acid residue pairs (1) to (3) carrying the same type of electric charge in the first H chain CH3 region and carry opposite electric charges from the corresponding amino acid residues in the first H chain CH3 region.

The amino acid residues described in each of the pairs (1) to (3) are located close to each other during the association. Those skilled in the art can find positions corresponding to the amino acid residues described in each of the pairs (1) to (3) as to the desired H chain CH3 region or H chain constant region by homology modeling or the like using commercially available software and can appropriately alter amino acid residues at the positions.

In the above antibody, each of the "amino acid residues carrying electric charge" is preferably selected from, for example, amino acid residues included in any of the following groups (X) and (Y): (X) glutamic acid (E) and aspartic acid (D); and (Y) lysine (K), arginine (R), and histidine (H).

In the above antibody, the phrase "carrying the same type of electric charge" means that, for example, all of two or more amino acid residues are amino acid residues included in any one of the groups (a) and (b). The phrase "carrying opposite electric charges" means that, for example, at least one amino acid residue among two or more amino acid residues may be an amino acid residue included in any one of the groups (X) and (Y), while the remaining amino acid residue(s) is amino acid residue(s) included in the other group.

In a preferred aspect, the antibody may have the first H chain CH3 region and the second H chain CH3 region cross-linked through a disulfide bond.

The amino acid residue to be altered according to the present invention is not limited to the above-mentioned amino acid residues in antibody variable or constant regions. Those skilled in the art can find amino acid residues constituting the interface as to a polypeptide variant or a heteromultimer by homology modeling or the like using commercially available software and can alter amino acid residues at the positions so as to regulate the association.

The association for the Fc region heterodimer of the present invention consisting of two Fc regions differing in their amino acid sequences or the polypeptide comprising the heterodimer can also be carried out by an alternative technique known in the art. An amino acid side chain present in the variable region of one antibody H chain is substituted by a larger side chain (knob), and its counterpart amino acid side chain present in the variable region of the other H chain is substituted by a smaller side chain (hole). The knob can be placed into the hole to efficiently associate the polypeptides of the Fc regions differing in their amino acid sequences (WO1996/027011, Ridgway J B et al., Protein Engineering (1996) 9, 617-621, and Merchant A M et al. Nature Biotechnology (1998) 16, 677-681).

In addition to this technique, a further alternative technique known in the art may be used in the association for the Fc region heterodimer or the polypeptide comprising the heterodimer. A portion of CH3 of one antibody H chain is converted to an IgA-derived sequence corresponding to the portion, and its complementary portion in CH3 of the other H chain is converted to an IgA-derived sequence corresponding to the portion. The resulting strand-exchange engineered domain CH3 domains can be associated with each other to efficiently associate the polypeptides differing in their sequences (Protein Engineering Design & Selection, 23; 195-202, 2010). Use of this technique known in the art can also achieve the efficient association for the Fc region heterodimer or the polypeptide comprising the heterodimer.

Alternatively, the polypeptide comprising the Fc region heterodimer may be prepared by a heterodimerized antibody preparation technique using antibody CH1-CL association and VH-VL association as described in WO2011/028952.

Even if such a heterodimerized polypeptide cannot be formed efficiently, the heterodimerized polypeptide may be obtained by the separation and purification of the heterodimerized polypeptide from homodimerized polypeptides. A heterodimerized polypeptide comprising a first Fc region and a second Fc region differing in their sequences is contaminated, during its preparation, by a homodimerized polypeptide consisting only of polypeptides comprising two first Fc regions and a homodimerized polypeptide consisting only of polypeptides comprising two second Fc regions, as impurities. These two types of homodimerized polypeptides can be efficiently removed by a method using a technique known in the art. The previously reported method involves introducing amino acid substitution to the variable regions of two types of H chains to impart thereto difference in isoelectric point so that these two types of homodimerized forms and the heterodimerized antibody of interest can be separately purified by ion-exchanged chromatography (WO2007114325). A method using protein A to purify a heterodimerized antibody consisting of a mouse IgG2a H chain capable of binding to protein A and a rat IgG2b H chain incapable of binding to protein A has previously been reported as a method for purifying the heterodimerized antibody (WO98050431 and WO95033844).

Alternatively, amino acid residues at EU numbering positions 435 and 436 that constitute the protein A-binding site of IgG may be substituted by amino acids, such as Tyr and His, which differ therefrom in the strength of protein A binding, and the resulting H chain is used to change the interaction of each H chain with protein A. As a result, only the heterodimerized antibody can be efficiently purified by use of a protein A column.

A plurality of, for example, two or more of these substitution techniques can be used in combination. Also, these alterations can be appropriately added separately to the polypeptide comprising the first Fc region and the polypeptide comprising the second Fc region. In this context, the polypeptide of the present invention may be prepared on the basis of these altered forms.

The alteration of an amino acid sequence can be performed by various methods known in the art. These methods that may be performed can include, but not limited to, methods such as site-directed mutagenesis (Hashimoto-Gotoh, T, Mizuno, T, Ogasahara, Y, and Nakagawa, M. (1995) An oligodeoxyribonucleotide-directed dual amber method for site-directed mutagenesis. Gene 152, 271-275, Zoller, M J, and Smith, M. (1983) Oligonucleotide-directed mutagenesis of DNA fragments cloned into M13 vectors. Methods Enzymol. 100, 468-500, Kramer, W, Drutsa, V, Jansen, H W, Kramer, B, Pflugfelder, M, and Fritz, H J (1984) The gapped duplex DNA approach to oligonucleotide-directed mutation construction. Nucleic Acids Res. 12, 9441-9456, Kramer W, and Fritz H J (1987) Oligonucleotide-directed construction of mutations via gapped duplex DNA Methods. Enzymol. 154, 350-367, Kunkel, TA (1985) Rapid and efficient site-specific mutagenesis without phenotypic selection. Proc Natl Acad Sci USA. 82, 488-492), PCR mutagenesis, and cassette mutagenesis.

In the present invention, the Fcγ receptor (also referred to as FcγR herein) refers to a receptor capable of binding to the Fc region of IgG1, IgG2, IgG3, or IgG4 and means any member of the protein family substantially encoded by Fcγ receptor genes. In humans, this family includes, but not limited to: FcγRI (CD64) including isoforms FcγRIa, FcγRIb, and FcγRIc; FcγRII (CD32) including isoforms FcγRIIa (including allotypes H131 (H type) and R131 (R type)), FcγRIIb (including FcγRIIb-1 and FcγRIIb-2), and FcγRIIc; and FcγRIII (CD16) including isoforms FcγRIIIa (including allotypes V158 and F158) and FcγRIIIb (including allotypes FcγRIIIb-NA1 and FcγRIIIb-NA2); and any yet-to-be-discovered human FcγR or FcγR isoform or allotype. The FcγR includes those derived from humans, mice, rats, rabbits, and monkeys. The FcγR is not limited to these molecules and may be derived from any organism. The mouse FcγRs include, but not limited to, FcγRI (CD64), FcγRII (CD32), FcγRIII (CD16), and FcγRIII-2 (CD16-2), and any yet-to-be-discovered mouse FcγR or FcγR isoform or allotype. Preferred examples of such Fcγ receptors include human FcγRI (CD64), FcγRIIa (CD32), FcγRIIb (CD32), FcγRIIIa (CD16), and/or FcγRIIIb (CD16).

The FcγR is found in the forms of activating receptors having ITAM (immunoreceptor tyrosine-based activation motif) and inhibitory receptors having ITIM (immunoreceptor tyrosine-based inhibitory motif). The FcγR is classified into activating FcγR (FcγRI, FcγRIIa R, FcγRIIa H, FcγRIIIa, and FcγRIIIb) and inhibitory FcγR (FcγRIIb).

The polynucleotide sequence and amino acid sequence of FcγRI are described in NM 000566.3 and NP 000557.1, respectively; the polynucleotide sequence and amino acid sequence of FcγRIIa are described in BC020823.1 and AAH20823.1, respectively; the polynucleotide sequence and amino acid sequence of FcγRIIb are described in BC146678.1 and AA146679.1, respectively; the polynucleotide sequence and amino acid sequence of FcγRIIIa are described in BC033678.1 and AAH33678.1, respectively; and the polynucleotide sequence and amino acid sequence of FcγRIIIb are described in BC128562.1 and AAI28563.1, respectively (RefSeq registration numbers). FcγRIIa has two types of gene polymorphisms that substitute the 131st amino acid of FcγRIIa by histidine (H type) or arginine (R type) (J. Exp. Med, 172, 19-25, 1990). FcγRIIb has two types of gene polymorphisms that substitute the 232nd amino acid of FcγRIIb by isoleucine (I type) or threonine (T type) (Arthritis. Rheum. 46: 1242-1254 (2002)). FcγRIIIa has two types of gene polymorphisms that substitute the 158th amino acid of FcγRIIIa by valine (V type) or phenylalanine (F type) (J. Clin. Invest. 100 (5): 1059-1070 (1997)). FcγRIIIb has two types of gene polymorphisms (NA1 type and NA2 type) (J. Clin. Invest. 85: 1287-1295 (1990)).

In the present invention, whether the antigen-binding site or the FcγR-binding site in the Fc region dimer of the present invention or the polypeptide comprising the Fc region dimer has its binding activity against the desired antigen or various Fcγ receptors can be determined using, for example, a BiaCore™ surface plasmon resonance interaction analyzer (GE Healthcare Japan Corp.) based on a surface plasmon resonance (SPR) phenomenon. The BiaCore™ surface plasmon resonance analyzer includes any model such as BiaCore™ T100, T200, X100, A100, 4000, 3000, 2000, 1000, or C surface plasmon resonance analyzer. Any sensor chip for a BiaCore™ surface plasmon resonance device, such as a CM7, CM5, CM4, CM3, Cl, SA, NTA, L1, HPA, or Au chip, can be used as a sensor chip. HBE-EP+ as well as a buffer pH-adjusted to a near-neutral pH such as pH 7.4 with HEPES, phosphate, ACES, Tris, citrate, or the like can be used as a running buffer. The assay temperature can be selected within the range of 4 to 37° C. Antibody-capturing protein A, protein G, or protein L, or proteins for antibody capture such as anti-human IgG antibodies, anti-human IgG-Fab, anti-human L chain antibodies, anti-human Fc antibodies, antigenic proteins, or antigenic peptides are immobilized onto the sensor chip by a coupling method such as amine coupling, disulfide coupling, or aldehyde coupling. Various Fcγ receptors including Fcγ receptors I, IIa R, IIa H, IIb, IIIa F, IIIa V, and IIIb are injected thereon as analytes. The interaction of a sample with the analytes is measured to obtain sensorgrams. In this procedure, the concentrations of the Fcγ receptors can be selected within the range of a few uM to a few pM according to the interaction strength (e.g., KD) of the assay sample.

Alternatively, various Fcγ receptors may be immobilized instead of the antibody onto the sensor chip, with which the antibody sample to be evaluated is in turn allowed to interact. Whether the antigen-binding site or the FcγR-binding site in the Fc region dimer of the present invention or the polypeptide comprising the Fc region dimer has its binding activity against the desired antigen or various Fcγ receptors can be confirmed on the basis of dissociation constant (KD) values calculated from the sensorgrams of the interaction or on the basis of the degree of increase in each sensorgram after the action of the antibody sample over the level before the action.

Specifically, the binding activity of the FcγR-binding site against the Fcγ receptors can be measured by ELISA, FACS (fluorescence activated cell sorting), or any of other approaches such as ALPHAScreen® (amplified luminescent proximity homogeneous assay screen) bead-based proximity assay or the BiaCore™ surface plasmon resonance (SPR) method (Proc. Natl. Acad. Sci. USA (2006) 103 (11), 4005-4010).

The ALPHAScreen® bead-based proximity assay method is carried out by the ALPHA® bead-based proximity assay technology using two types of beads (donor and acceptor) on the basis of the following principle: luminescence signals are detected only when these two beads are located in proximity through the biological interaction between a molecule bound with the donor bead and a molecule bound with the acceptor bead. A laser-excited photosensitizer in the donor bead converts ambient oxygen to singlet oxygen in an excited state. The singlet oxygen diffuses around the donor bead and reaches the acceptor bead located in proximity thereto to thereby cause chemiluminescent reaction in the bead, which finally emits light. In the absence of the interaction between the molecule bound with the donor bead and the molecule bound with the acceptor bead, singlet oxygen produced by the donor bead does not reach the acceptor bead. Thus, no chemiluminescent reaction occurs.

For example, a biotin-labeled polypeptide to be tested is bound to streptavidin on the donor bead, while a glutathione S transferase (GST)-tagged Fcγ receptor is bound to the acceptor bead. In the absence of a competing polypeptide, the polypeptide to be tested interacts with the Fcγ receptor to generate signals of 520 to 620 nm. An untagged polypeptide competes with the polypeptide to be tested for the interaction with the Fcγ receptor. Decrease in fluorescence caused as a result of the competition can be quantified to thereby determine relative binding activity. The polypeptide biotinylation using sulfo-NHS-biotin or the like is known in the art. The Fcγ receptor can be tagged with GST by an appropriately adopted method which involves, for example: fusing a polynucleotide encoding the Fcγ receptor in flame with a polynucleotide encoding GST; and allowing the resulting fusion gene to be expressed by cells or the like carrying vectors capable of expression thereof to express the GST-tagged Fcγ receptor, which is then purified using a glutathione column. The obtained signals are preferably analyzed using, for example, software GRAPHPAD PRISM (GraphPad Software, Inc., San Diego) adapted to a one-site competition model based on nonlinear regression analysis.

In this context, the tagging is not limited to the GST tagging and may be carried out with any tag such as, but not limited to, a histidine tag, MBP, CBP, a Flag tag, an HA tag, a V5 tag, or a c-myc tag. The binding of the polypeptide to be tested to the donor bead is not limited to the binding using biotin-streptavidin reaction. Particularly, when the polypeptide to be tested comprises Fc as in an antibody or an Fc fusion polypeptide, a possible method involves binding the polypeptide to be tested via an Fc-recognizing protein such as protein A or protein G on the donor bead.

One (ligand) of the substances between which the interaction is to be observed is immobilized on a thin gold film of a sensor chip. The sensor chip is irradiated with light from the back such that total reflection occurs at the interface between the thin gold film and glass. As a result, a site having a drop in reflection intensity (SPR signal) is formed in a portion of reflected light. The other (analyte) of the substances between which the interaction is to be observed is flowed on the surface of the sensor chip and bound to the ligand so that the mass of the immobilized ligand molecule is increased to change the refractive index of the solvent on the sensor chip surface. This change in the refractive index shifts the position of the SPR signal (on the contrary, the dissociation of the bound molecules gets the signal back to the original position). The BiaCore™ surface plasmon resonance system plots on the ordinate the amount of the shift, i.e., change in mass on the sensor chip surface, and displays time-dependent change in mass as assay data (sensorgram). The binding amount of the analyte to the ligand captured on the sensor chip surface (amount of change in response on the sensorgram between before and after the interaction of the analyte) can be determined from the sensorgram. However, since the binding amount also depends on the amount of the ligand, the comparison must be performed under conditions where substantially the same amounts of the ligand are used. Kinetics, i.e., an association rate constant (ka) and a dissociation rate constant (kd), can be determined from the curve of the sensorgram, while affinity (KD) can be determined from the ratio between these constants. Inhibition assay is also preferably used in the BiaCore™ surface plasmon resonance method. Examples of the inhibition assay are described in Proc. Natl. Acad. Sci. USA (2006) 103 (11), 4005-4010.

In the present invention, the Fc region dimer or the polypeptide comprising the Fc region dimer preferably has 80% or higher affinity (KD) for FcγRIa and 50% or higher affinity (KD) for other receptors, compared with natural IgG, for having binding activity against FcγR or maintaining the binding activity against FcγR by the alteration of an amino acid sequence. The Fc region dimer having such affinity (KD) or the polypeptide comprising the Fc region dimer can maintain the interaction with FcγR.

Whether the Fc region dimer of the present invention or the polypeptide comprising the Fc region dimer does "not bind to an antigen and FcγR at the same time" can be confirmed by confirming its binding activity against each of the desired antigen and FcγR, then binding in advance either of the antigen or FcγR to the Fc region dimer having this binding activity or the polypeptide comprising the Fc region dimer, and then determining the presence or absence of its binding activity against the other molecule according to the method mentioned above.

Alternatively, this can be confirmed by assaying the inhibition of its binding to either of the antigen or FcγR immobilized on an ELISA plate or a sensor chip by the addition of the other molecule into the solution.

The phrase "FcγR-binding site has higher binding activity against FcγR than that of naturally occurring IgG1" according to the present invention means that the FcγR-binding site binds with substantially stronger binding activity to FcγR than that of naturally occurring IgG1, when the assay was conducted under conditions where Fc region dimers having FcγR-binding sites to be compared or polypeptides comprising the dimers are used in substantially the same amounts.

For example, the KD value ratio between dissociation constant KD values measured by the assay method mentioned above (the KD value of naturally occurring IgG1/the KD value of the Fc region dimer or the polypeptide comprising the dimer) is preferably 1.1 or higher, 1.2 or higher, 1.3 or higher, 1.5 or higher, 1.8 or higher, 2 or higher, or 3 or higher, more preferably 5 or higher, 10 or higher, 100 or higher, 250 or higher, or 1000 or higher. In the present specification, the KD value ratio is also referred to as a KD ratio. In the dissociation constant KD values measured by the assay method mentioned above, the KD value of the Fc region dimer or the polypeptide comprising the dimer is reduced by preferably 1 pM or more, more preferably 10 pM, 100 pM, 1 nM or more, 2 nM or more, 3 nM or more, 5 nM or more, 10 nM or more, 20 nM or more, 50 nM or more, 100 nM or more, or 1 μM or more, compared with the naturally occurring IgG1.

In the dissociation constant KD values measured by the assay method mentioned above, the KD value of the Fc region dimer or the polypeptide comprising the dimer is preferably 5 μM or lower, more preferably 3 μM or lower, 1 μM or lower, 0.5 μM or lower, 0.1 μM or lower, 0.01 μM or lower, 1 nM or lower, 0.1 nM or lower, 0.001 nM or lower, or 1 pM or lower.

In the present invention, amino acid alteration(s) may be introduced to the amino acid sequence of the first Fc region and/or the second Fc region constituting the Fc region dimer, in order to enhance the binding activity of the FcγR-binding site in the Fc region dimer against the Fcγ receptor. The amino acid mutation to be introduced is not particularly limited by its type or range.

When the Fcγ receptor is FcγRIIIa, at least one or more amino acid mutation(s) selected from the group consisting of amino acid mutations described in Table 2 herein (which are alterations wherein a heterodimerized antibody with the mutation(s) introduced in one H chain has FcγRIIIa-binding activity of 50% or higher affinity (KD) compared with natural IgG) may be introduced to the amino acid sequence of the first polypeptide and/or the second polypeptide constituting the Fc region.

TABLE 2

| Name | He/Con 3a |
|---|---|
| L234_01G | 55.8 |
| L234_13S | 68.1 |
| L234_02A | 69.7 |
| L234_14T | 69.8 |
| L234_16H | 76.8 |
| L234_19Q | 77.1 |
| L234_06M | 82.9 |
| L234_05P | 85.1 |
| L234_18N | 88.2 |
| L234_03V | 88.3 |
| L234_07I | 99.5 |
| L234_20W | 103.2 |

TABLE 2-continued

| Name | He/Con 3a |
|---|---|
| L234_10E | 110.6 |
| L234_09D | 112.8 |
| L234_04F | 114.0 |
| L234_15Y | 125.7 |
| L235_01G | 56.7 |
| L235_16H | 57.1 |
| L235_18N | 65.0 |
| L235_13S | 67.2 |
| L235_19Q | 68.1 |
| L235_05P | 68.6 |
| L235_02A | 72.0 |
| L235_14T | 73.2 |
| L235_20W | 73.8 |
| L235_06M | 75.6 |
| L235_04F | 76.4 |
| L235_15Y | 77.8 |
| L235_10E | 85.6 |
| L235_09D | 88.5 |
| L235_07I | 92.8 |
| L235_03V | 94.6 |
| G236_03V | 53.8 |
| G236_07I | 55.6 |
| G236_13S | 60.3 |
| G236_10E | 65.8 |
| G236_09D | 66.2 |
| G236_02A | 77.0 |
| G236_04F | 81.0 |
| G236_15Y | 112.4 |
| G236_20W | 126.1 |
| G237_14T | 50.5 |
| G237_03V | 51.3 |
| P238_19Q | 52.7 |
| P238_15Y | 61.0 |
| P238_08L | 71.3 |
| P238_10E | 98.9 |
| P238_09D | 100.0 |
| S239_19Q | 53.8 |
| S239_02A | 70.9 |
| S239_01G | 72.0 |
| S239_03V | 72.4 |
| S239_06M | 73.9 |
| S239_07I | 75.0 |
| S239_08L | 90.0 |
| S239_14T | 93.0 |
| S239_18N | 103.8 |
| S239_09D | 156.4 |
| S239_10E | 171.4 |
| V266_02A | 56.8 |
| V266_06M | 84.9 |
| V266_07I | 112.9 |
| V266_08L | 116.7 |
| S267_18N | 52.0 |
| S267_01G | 53.3 |
| S267_19Q | 64.3 |
| S267_06M | 65.3 |
| S267_10E | 90.9 |
| S267_02A | 148.8 |
| S267_09D | 178.9 |
| H268_05P | 75.6 |
| H268_08L | 75.9 |
| H268_12R | 76.0 |
| H268_06M | 79.5 |
| H268_11K | 81.6 |
| H268_20W | 82.0 |
| H268_07I | 84.1 |
| H268_14T | 90.3 |
| H268_03V | 91.4 |
| H268_01G | 95.7 |
| H268_04F | 96.0 |
| H268_15Y | 96.5 |
| H268_18N | 103.0 |
| H268_19Q | 113.0 |
| H268_13S | 120.6 |
| H268_02A | 120.9 |
| H268_10E | 184.1 |
| H268_09D | 195.2 |
| E269_16H | 50.7 |
| E269_15Y | 51.5 |

TABLE 2-continued

| Name | He/Con 3a |
|---|---|
| E269_08L | 51.5 |
| E269_07I | 55.3 |
| E269_03V | 56.0 |
| E269_18N | 57.2 |
| E269_06M | 57.9 |
| E269_14T | 59.7 |
| E269_01G | 61.6 |
| E269_13S | 62.1 |
| E269_19Q | 64.3 |
| E269_02A | 68.0 |
| E269_09D | 105.7 |
| D270_02A | 50.5 |
| D270_18N | 51.2 |
| D270_13S | 51.4 |
| D270_03V | 54.6 |
| D270_14T | 55.4 |
| D270_06M | 60.0 |
| D270_07I | 63.1 |
| D270_08L | 65.1 |
| D270_19Q | 74.2 |
| D270_10E | 111.8 |
| P271_14T | 59.2 |
| P271_15Y | 62.7 |
| P271_04F | 65.6 |
| P271_16H | 70.3 |
| P271_03V | 73.5 |
| P271_06M | 74.0 |
| P271_08L | 74.5 |
| P271_20W | 77.8 |
| P271_13S | 79.8 |
| P271_07I | 80.2 |
| P271_02A | 83.7 |
| P271_19Q | 84.6 |
| P271_12R | 87.6 |
| P271_11K | 92.5 |
| P271_18N | 94.0 |
| P271_09D | 97.7 |
| P271_10E | 98.2 |
| P271_01G | 118.8 |
| Q295_12R | 73.2 |
| Q295_05P | 74.4 |
| Q295_04F | 75.1 |
| Q295_01G | 76.6 |
| Q295_16H | 80.2 |
| Q295_15Y | 81.5 |
| Q295_11K | 81.8 |
| Q295_09D | 85.6 |
| Q295_18N | 85.7 |
| Q295_03V | 86.2 |
| Q295_13S | 90.4 |
| Q295_06M | 100.2 |
| Q295_07I | 100.7 |
| Q295_10E | 105.1 |
| Q295_02A | 110.8 |
| Q295_08L | 119.5 |
| Q295_14T | 120.4 |
| Y296_01G | 51.3 |
| Y296_11K | 53.3 |
| Y296_13S | 58.1 |
| Y296_14T | 60.7 |
| Y296_02A | 66.3 |
| Y296_12R | 66.5 |
| Y296_18N | 67.9 |
| Y296_16H | 69.1 |
| Y296_03V | 69.1 |
| Y296_19Q | 71.4 |
| Y296_08L | 72.4 |
| Y296_06M | 74.6 |
| Y296_07I | 75.8 |
| Y296_10E | 76.8 |
| Y296_04F | 79.5 |
| Y296_09D | 89.0 |
| Y296_20W | 127.0 |
| S298_11K | 50.0 |
| S298_18N | 51.4 |
| S298_12R | 52.1 |
| S298_09D | 62.7 |
| S298_08L | 69.2 |

TABLE 2-continued

| Name | He/Con 3a |
|---|---|
| S298_19Q | 70.6 |
| S298_16H | 71.9 |
| S298_01G | 74.9 |
| S298_04F | 77.6 |
| S298_15Y | 80.6 |
| S298_06M | 87.2 |
| S298_07I | 90.7 |
| S298_03V | 102.8 |
| S298_14T | 105.9 |
| S298_02A | 150.6 |
| Y300_11K | 63.7 |
| Y300_13S | 80.3 |
| Y300_03V | 83.8 |
| Y300_02A | 88.1 |
| Y300_01G | 88.6 |
| Y300_14T | 92.8 |
| Y300_18N | 96.0 |
| Y300_04F | 100.1 |
| Y300_20W | 100.8 |
| Y300_16H | 101.8 |
| Y300_07I | 103.3 |
| Y300_09D | 103.7 |
| Y300_19Q | 104.6 |
| Y300_06M | 106.5 |
| Y300_10E | 113.2 |
| Y300_08L | 113.9 |
| S324_05P | 72.3 |
| S324_11K | 90.2 |
| S324_08L | 95.5 |
| S324_19Q | 96.2 |
| S324_12R | 98.1 |
| S324_04F | 99.3 |
| S324_07I | 100.6 |
| S324_03V | 101.4 |
| S324_18N | 103.4 |
| S324_10E | 107.8 |
| S324_09D | 109.7 |
| S324_15Y | 110.1 |
| S324_20W | 110.6 |
| S324_14T | 112.0 |
| S324_16H | 112.7 |
| S324_02A | 113.0 |
| S324_01G | 114.0 |
| S324_06M | 124.5 |
| N325_09D | 53.0 |
| N325_16H | 68.0 |
| N325_13S | 71.9 |
| K326_20W | 93.7 |
| K326_12R | 101.4 |
| K326_16H | 106.2 |
| K326_04F | 113.6 |
| K326_01G | 114.1 |
| K326_05P | 117.2 |
| K326_19Q | 117.4 |
| K326_13S | 118.0 |
| K326_15Y | 124.0 |
| K326_08L | 126.1 |
| K326_06M | 126.8 |
| K326_02A | 129.9 |
| K326_18N | 134.2 |
| K326_03V | 134.9 |
| K326_10E | 137.5 |
| K326_14T | 139.7 |
| K326_09D | 147.6 |
| K326_07I | 153.1 |
| A327_20W | 52.6 |
| A327_06M | 54.0 |
| A327_19Q | 54.0 |
| A327_05P | 61.9 |
| A327_18N | 62.8 |
| A327_13S | 66.7 |
| A327_10E | 70.5 |
| A327_01G | 74.4 |
| A327_09D | 86.0 |
| L328_18N | 51.1 |
| L328_10E | 54.9 |
| L328_16H | 55.9 |
| L328_15Y | 70.2 |

TABLE 2-continued

| Name | He/Con 3a |
|---|---|
| L328_13S | 73.7 |
| L328_14T | 77.4 |
| L328_06M | 80.8 |
| L328_03V | 80.9 |
| L328_02A | 81.3 |
| L328_04F | 81.5 |
| L328_19Q | 83.4 |
| L328_07I | 86.4 |
| P329_09D | 52.5 |
| P329_10E | 52.7 |
| P329_02A | 55.2 |
| A330_09D | 56.4 |
| A330_18N | 67.3 |
| A330_12R | 77.3 |
| A330_10E | 82.8 |
| A330_14T | 85.8 |
| A330_19Q | 86.3 |
| A330_01G | 87.3 |
| A330_11K | 91.8 |
| A330_03V | 98.8 |
| A330_07I | 100.9 |
| A330_20W | 102.0 |
| A330_16H | 102.0 |
| A330_08L | 121.8 |
| A330_15Y | 122.3 |
| A330_06M | 138.6 |
| A330_04F | 144.0 |
| A330_05P | 151.9 |
| P331_07I | 60.4 |
| P331_11K | 61.8 |
| P331_12R | 64.8 |
| P331_08L | 66.0 |
| P331_03V | 66.9 |
| P331_18N | 67.1 |
| P331_14T | 67.8 |
| P331_06M | 68.4 |
| P331_10E | 68.7 |
| P331_04F | 70.7 |
| P331_09D | 71.6 |
| P331_20W | 71.9 |
| P331_16H | 73.4 |
| P331_19Q | 73.9 |
| P331_15Y | 74.9 |
| P331_13S | 80.9 |
| P331_02A | 82.5 |
| I332_05P | 56.3 |
| I332_08L | 76.0 |
| I332_12R | 78.1 |
| I332_18N | 84.9 |
| I332_03V | 85.2 |
| I332_16H | 89.0 |
| I332_04F | 89.3 |
| I332_15Y | 92.4 |
| I332_06M | 92.5 |
| I332_13S | 95.6 |
| I332_19Q | 101.0 |
| I332_01G | 101.3 |
| I332_02A | 102.7 |
| I332_14T | 109.6 |
| I332_20W | 115.9 |
| I332_09D | 189.0 |
| I332_10E | 212.9 |
| E333_18N | 76.2 |
| E333_12R | 92.2 |
| E333_11K | 97.7 |
| E333_14T | 100.1 |
| E333_07I | 100.1 |
| E333_06M | 100.4 |
| E333_05P | 100.5 |
| E333_01G | 101.1 |
| E333_15Y | 101.2 |
| E333_19Q | 101.3 |
| E333_08L | 101.5 |
| E333_20W | 103.8 |
| E333_04F | 104.1 |
| E333_13S | 105.7 |
| E333_16H | 106.0 |
| E333_03V | 106.0 |

TABLE 2-continued

| Name | He/Con 3a |
|---|---|
| E333_02A | 108.5 |
| E333_09D | 115.4 |
| K334_12R | 93.5 |
| K334_01G | 124.9 |
| K334_20W | 131.5 |
| K334_05P | 137.6 |
| K334_16H | 137.6 |
| K334_19Q | 140.1 |
| K334_18N | 140.2 |
| K334_15Y | 145.0 |
| K334_14T | 145.6 |
| K334_08L | 147.5 |
| K334_06M | 148.8 |
| K334_13S | 149.5 |
| K334_02A | 151.5 |
| K334_04F | 151.9 |
| K334_03V | 153.9 |
| K334_07I | 155.6 |
| K334_09D | 164.4 |
| K334_10E | 185.9 |
| T335_02A | 90.9 |
| T335_11K | 91.7 |
| T335_04F | 91.7 |
| T335_12R | 93.1 |
| T335_18N | 94.4 |
| T335_01G | 95.1 |
| T335_03V | 96.3 |
| T335_06M | 97.0 |
| T335_20W | 97.3 |
| T335_19Q | 97.7 |
| T335_08L | 97.8 |
| T335_16H | 99.3 |
| T335_15Y | 99.7 |
| T335_05P | 100.2 |
| T335_13S | 100.4 |
| T335_10E | 102.1 |
| T335_07I | 102.5 |
| T335_09D | 102.9 |
| T335_14T | 103.6 |
| I336_15Y | 83.4 |
| I336_19Q | 88.4 |
| I336_12R | 88.8 |
| I336_16H | 92.8 |
| I336_04F | 93.2 |
| I336_11K | 94.4 |
| I336_01G | 94.6 |
| I336_13S | 97.1 |
| I336_07I | 98.5 |
| I336_18N | 99.4 |
| I336_09D | 101.5 |
| I336_08L | 101.6 |
| I336_14T | 103.4 |
| 1336_06M | 104.1 |
| I336_02A | 106.0 |
| I336_03V | 107.3 |
| I336_10E | 114.1 |
| S337_11K | 80.1 |
| S337_03V | 87.1 |
| S337_07I | 88.3 |
| S337_06M | 89.7 |
| S337_08L | 90.2 |
| S337_19Q | 91.2 |
| S337_02A | 92.4 |
| S337_12R | 92.7 |
| S337_20W | 93.8 |
| S337_14T | 94.0 |
| S337_04F | 94.4 |
| S337_15Y | 94.9 |
| S337_01G | 95.2 |
| S337_18N | 96.9 |
| S337_10E | 97.8 |
| S337_16H | 100.3 |
| S337_09D | 102.3 |

He/Con represents a value determined according to the expression: FcγRIIIa-binding activity of a heterodimerized antibody GpH7-A5/GpH7-B3 variant/GpL16-k0 comprising a mutated H chain (GpH7-B3 variant) as one H chain/FcγRIIIa-binding activity of a heterodimerized antibody GpH7-A5/GpH7-B3/GpL16-k0 (SEQ ID NOs: 3, 4, and 5) comprising unmutated GpH7-B3×100. The name of each GpH7-B3 variant is indicated by A_B wherein A represents the EU numbering position of a residue to be altered plus one-letter code of information about the type of the amino acid; and B represents information about an amino acid after substitution. For example, a B3_variant obtained by the substitution of Leu at EU numbering position 234 by Gly is designated as L234_01G. As for the information about an amino acid after substitution, a numerical value unique to the amino acid is described before its one-letter code for the sake of convenience. Specifically, the following symbols are used: 01G for Gly, 02A for Ala, 03V for Val, 04F for Phe, 05P for Pro, 06M for Met, 07I for Ile, 08L for Leu, 09D for Asp, 10E for Glu, 11K for Lys, 12R for Arg, 13S for Ser, 14T for Thr, 15Y for Tyr, 16H for His, 18N for Asn, 19Q for Gln, and 20W for Trp.

For obtaining further stronger binding activity, at least one or more amino acid mutation(s) selected from the group consisting of amino acid mutations described in Table 3 herein (which are alterations wherein a heterodimerized antibody with the mutation(s) introduced in one H chain has FcγRIa-binding activity of 80% or higher affinity (KD) compared with natural IgG and binding activity of 50% or higher affinity (KD) against each of the receptors FcγRIIa, FcγRIIb, and FcγRIIIa compared with natural IgG) may be introduced to the amino acid sequence of the first polypeptide and/or the second polypeptide constituting the Fc region.

TABLE 3

| Name | He/Con 1a | He/Con 2aR | He/Con 2aH | He/Con 2b | He/Con 3a |
|---|---|---|---|---|---|
| L234_03V | 107.8 | 99.0 | 94.4 | 83.4 | 88.3 |
| L234_06M | 107.1 | 108.6 | 96.4 | 89.6 | 82.9 |
| L234_07I | 106.3 | 110.4 | 101.0 | 92.3 | 99.5 |
| L234_04F | 104.3 | 120.9 | 133.2 | 113.9 | 114.0 |
| L234_10E | 103.7 | 130.3 | 98.2 | 134.2 | 110.6 |
| L234_15Y | 103.3 | 113.3 | 133.7 | 109.9 | 125.7 |
| L234_05P | 103.2 | 104.1 | 104.0 | 83.2 | 85.1 |
| L234_20W | 101.8 | 125.2 | 126.2 | 130.6 | 103.2 |
| L234_14T | 101.8 | 90.0 | 86.8 | 71.4 | 69.8 |
| L234_09D | 101.0 | 142.3 | 100.0 | 171.7 | 112.8 |
| L234_02A | 100.7 | 92.5 | 90.1 | 74.1 | 69.7 |
| L234_13S | 100.0 | 82.6 | 89.4 | 67.7 | 68.1 |
| L234_01G | 99.2 | 72.4 | 84.1 | 57.8 | 55.8 |
| L234_19Q | 98.8 | 87.2 | 88.1 | 68.9 | 77.1 |
| L234_18N | 97.3 | 98.0 | 100.2 | 92.0 | 88.2 |
| L234_16H | 97.0 | 83.5 | 97.1 | 67.8 | 76.8 |
| L235_07I | 102.8 | 102.1 | 99.5 | 100.1 | 92.8 |
| L235_06M | 101.2 | 106.2 | 96.3 | 92.4 | 75.6 |
| L235_15Y | 100.3 | 150.3 | 135.1 | 170.3 | 77.8 |
| L235_04F | 100.2 | 132.0 | 123.0 | 135.3 | 76.4 |
| L235_05P | 97.8 | 74.6 | 64.2 | 62.4 | 68.6 |
| L235_03V | 97.8 | 83.4 | 94.9 | 75.8 | 94.6 |
| L235_10E | 96.9 | 98.7 | 80.0 | 90.8 | 85.6 |
| L235_20W | 95.9 | 152.1 | 130.9 | 168.2 | 73.8 |
| L235_02A | 95.2 | 86.6 | 77.6 | 72.0 | 72.0 |
| L235_18N | 95.2 | 77.3 | 73.5 | 62.7 | 65.0 |
| L235_13S | 93.5 | 75.9 | 73.5 | 55.0 | 67.2 |
| L235_16H | 92.7 | 110.2 | 99.8 | 87.8 | 57.1 |
| L235_14T | 91.6 | 70.6 | 79.5 | 53.4 | 73.2 |
| L235_09D | 87.6 | 117.0 | 84.3 | 121.3 | 88.5 |
| G236_20W | 103.9 | 77.3 | 152.8 | 60.7 | 126.1 |
| G236_02A | 99.1 | 144.8 | 144.9 | 100.7 | 77.0 |
| G236_13S | 96.0 | 135.3 | 140.5 | 100.9 | 60.3 |
| G236_09D | 95.5 | 105.3 | 93.5 | 174.3 | 66.2 |
| G236_10E | 92.6 | 124.0 | 115.8 | 114.9 | 65.8 |
| P238_10E | 104.7 | 142.5 | 74.6 | 235.2 | 98.9 |
| P238_08L | 104.1 | 131.5 | 81.8 | 207.4 | 71.3 |

TABLE 3-continued

| Name | He/Con 1a | He/Con 2aR | He/Con 2aH | He/Con 2b | He/Con 3a |
|---|---|---|---|---|---|
| P238_15Y | 104.1 | 147.1 | 57.8 | 220.9 | 61.0 |
| P238_19Q | 100.7 | 97.8 | 54.5 | 111.7 | 52.7 |
| P238_09D | 99.0 | 139.5 | 84.7 | 224.0 | 100.0 |
| S239_10E | 108.5 | 127.0 | 108.3 | 183.1 | 171.4 |
| S239_01G | 104.5 | 120.4 | 93.8 | 146.2 | 72.0 |
| S239_18N | 104.3 | 104.2 | 91.1 | 120.7 | 103.8 |
| S239_14T | 104.2 | 97.4 | 95.9 | 98.6 | 93.0 |
| S239_09D | 104.1 | 128.6 | 110.7 | 208.6 | 156.4 |
| S239_19Q | 103.7 | 79.8 | 80.0 | 87.3 | 53.8 |
| S239_08L | 102.9 | 114.4 | 101.3 | 142.2 | 90.0 |
| S239_02A | 102.7 | 89.8 | 89.9 | 91.6 | 70.9 |
| S239_06M | 102.1 | 94.7 | 95.4 | 102.3 | 73.9 |
| S239_07I | 100.8 | 95.9 | 88.5 | 108.3 | 75.0 |
| S239_03V | 98.9 | 94.1 | 88.0 | 109.9 | 72.4 |
| V266_06M | 96.5 | 161.2 | 84.8 | 264.0 | 84.9 |
| V266_07I | 96.1 | 129.4 | 106.7 | 160.1 | 112.9 |
| V266_08L | 94.9 | 152.4 | 105.6 | 248.3 | 116.7 |
| V266_02A | 93.8 | 88.8 | 69.7 | 85.1 | 56.8 |
| S267_09D | 106.2 | 186.1 | 106.6 | 326.2 | 178.9 |
| S267_02A | 105.3 | 167.0 | 121.1 | 255.7 | 148.8 |
| S267_10E | 102.4 | 187.8 | 103.4 | 398.5 | 90.9 |
| S267_01G | 99.9 | 121.4 | 72.1 | 109.9 | 53.3 |
| S267_19Q | 99.2 | 145.4 | 61.9 | 228.5 | 64.3 |
| H268_14T | 108.5 | 100.2 | 93.5 | 90.3 | 90.3 |
| H268_10E | 107.4 | 158.9 | 125.7 | 242.2 | 184.1 |
| H268_09D | 106.0 | 160.6 | 134.0 | 251.2 | 195.2 |
| H268_13S | 105.7 | 137.0 | 113.6 | 167.7 | 120.6 |
| H268_05P | 105.5 | 113.5 | 82.7 | 122.0 | 75.6 |
| H268_02A | 105.2 | 143.2 | 115.0 | 175.0 | 120.9 |
| H268_18N | 104.4 | 138.1 | 113.3 | 164.2 | 103.0 |
| H268_07I | 104.3 | 101.8 | 91.2 | 93.4 | 84.1 |
| H268_19Q | 104.3 | 128.0 | 103.5 | 139.6 | 113.0 |
| H268_08L | 103.9 | 91.4 | 85.9 | 71.2 | 75.9 |
| H268_15Y | 103.8 | 117.9 | 113.2 | 111.7 | 96.5 |
| H268_01G | 103.7 | 133.5 | 100.3 | 150.9 | 95.7 |
| H268_20W | 103.4 | 121.5 | 96.9 | 117.1 | 82.0 |
| H268_04F | 102.8 | 105.1 | 112.2 | 94.2 | 96.0 |
| H268_12R | 102.7 | 112.6 | 90.9 | 94.3 | 76.0 |
| H268_03V | 102.6 | 116.8 | 100.3 | 119.7 | 91.4 |
| H268_11K | 102.4 | 108.0 | 89.8 | 87.2 | 81.6 |
| H268_06M | 101.3 | 87.2 | 85.8 | 69.0 | 79.5 |
| E269_09D | 103.2 | 113.2 | 104.9 | 110.1 | 105.7 |
| E269_14T | 102.5 | 71.0 | 70.3 | 53.2 | 59.7 |
| E269_02A | 101.0 | 70.2 | 78.7 | 52.4 | 68.0 |
| E269_01G | 101.0 | 70.3 | 72.3 | 54.1 | 61.6 |
| E269_13S | 99.8 | 65.8 | 70.7 | 50.2 | 62.1 |
| D270_10E | 103.6 | 85.7 | 110.6 | 72.5 | 111.8 |
| D270_08L | 93.2 | 62.8 | 81.8 | 50.8 | 65.1 |
| D270_14T | 89.5 | 72.2 | 81.3 | 54.8 | 55.4 |
| P271_01G | 103.1 | 142.7 | 122.7 | 216.7 | 118.8 |
| P271_02A | 101.9 | 93.9 | 88.4 | 98.7 | 83.7 |
| P271_18N | 101.6 | 97.7 | 94.5 | 104.6 | 94.0 |
| P271_19Q | 101.5 | 95.1 | 90.7 | 99.3 | 84.6 |
| P271_15Y | 101.3 | 70.0 | 74.0 | 58.6 | 62.7 |
| P271_10E | 101.1 | 101.6 | 72.4 | 122.5 | 98.2 |
| P271_11K | 101.1 | 97.3 | 100.3 | 101.2 | 92.5 |
| P271_20W | 100.9 | 76.6 | 88.7 | 65.1 | 77.8 |
| P271_06M | 100.8 | 87.3 | 87.7 | 87.0 | 74.0 |
| P271_07I | 100.8 | 88.0 | 94.1 | 86.1 | 80.2 |
| P271_12R | 100.8 | 95.8 | 100.3 | 96.9 | 87.6 |
| P271_13S | 100.7 | 93.5 | 83.3 | 98.2 | 79.8 |
| P271_03V | 100.7 | 85.8 | 85.4 | 83.8 | 73.5 |
| P271_14T | 100.6 | 94.7 | 69.8 | 107.0 | 59.2 |
| P271_08L | 100.6 | 102.8 | 99.4 | 115.2 | 74.5 |
| P271_16H | 100.5 | 79.0 | 76.4 | 76.2 | 70.3 |
| P271_09D | 100.5 | 108.7 | 80.4 | 134.7 | 97.7 |
| P271_04F | 100.2 | 75.2 | 77.1 | 66.7 | 65.6 |
| Q295_08L | 102.9 | 117.6 | 128.3 | 133.9 | 119.5 |
| Q295_02A | 102.6 | 91.5 | 101.1 | 89.4 | 110.8 |
| Q295_06M | 102.5 | 100.7 | 111.0 | 101.4 | 100.2 |
| Q295_03V | 102.4 | 90.3 | 105.5 | 84.9 | 86.2 |
| Q295_05P | 101.8 | 86.6 | 118.5 | 75.7 | 74.4 |
| Q295_10E | 101.4 | 100.6 | 112.0 | 106.4 | 105.1 |
| Q295_07I | 101.3 | 97.3 | 117.3 | 94.5 | 100.7 |
| Q295_14T | 101.0 | 79.2 | 86.2 | 74.9 | 120.4 |
| Q295_16H | 100.8 | 80.5 | 90.1 | 70.3 | 80.2 |
| Q295_18N | 100.8 | 81.7 | 87.8 | 72.8 | 85.7 |

TABLE 3-continued

| Name | He/Con 1a | He/Con 2aR | He/Con 2aH | He/Con 2b | He/Con 3a |
|---|---|---|---|---|---|
| Q295_04F | 100.6 | 82.8 | 87.4 | 72.6 | 75.1 |
| Q295_13S | 100.3 | 73.0 | 79.5 | 63.8 | 90.4 |
| Q295_15Y | 100.1 | 82.0 | 89.3 | 73.3 | 81.5 |
| Q295_11K | 99.7 | 88.1 | 102.5 | 79.0 | 81.8 |
| Q295_12R | 98.8 | 82.2 | 96.4 | 73.1 | 73.2 |
| Q295_09D | 98.5 | 68.7 | 62.6 | 68.1 | 85.6 |
| Q295_01G | 96.1 | 60.3 | 62.5 | 51.6 | 76.6 |
| Y296_19Q | 108.2 | 97.9 | 94.3 | 90.5 | 71.4 |
| Y296_20W | 107.4 | 105.0 | 95.4 | 104.7 | 127.0 |
| Y296_12R | 103.1 | 95.3 | 89.1 | 80.5 | 66.5 |
| Y296_09D | 102.7 | 101.2 | 101.7 | 100.3 | 89.0 |
| Y296_16H | 102.6 | 100.1 | 101.3 | 93.5 | 69.1 |
| Y296_10E | 102.5 | 98.2 | 94.0 | 99.4 | 76.8 |
| Y296_18N | 102.4 | 99.6 | 101.4 | 92.8 | 67.9 |
| Y296_13S | 101.9 | 97.5 | 96.1 | 87.5 | 58.1 |
| Y296_14T | 101.9 | 98.6 | 97.2 | 89.4 | 60.7 |
| Y296_11K | 101.5 | 90.3 | 83.7 | 73.8 | 53.3 |
| Y296_07I | 101.1 | 96.7 | 92.7 | 85.5 | 75.8 |
| Y296_04F | 100.9 | 104.7 | 97.8 | 100.6 | 79.5 |
| Y296_06M | 100.8 | 96.8 | 94.2 | 89.0 | 74.6 |
| Y296_03V | 100.8 | 92.0 | 86.9 | 80.4 | 69.1 |
| Y296_08L | 100.7 | 93.7 | 86.9 | 83.5 | 72.4 |
| Y296_02A | 99.8 | 93.0 | 89.1 | 83.1 | 66.3 |
| Y296_01G | 99.4 | 91.6 | 91.6 | 80.4 | 51.3 |
| S298_06M | 111.0 | 103.7 | 95.8 | 103.2 | 87.2 |
| S298_03V | 106.4 | 82.5 | 83.2 | 65.4 | 102.8 |
| S298_19Q | 106.1 | 90.9 | 88.9 | 74.3 | 70.6 |
| S298_12R | 106.1 | 81.6 | 67.4 | 58.6 | 52.1 |
| S298_11K | 105.9 | 91.0 | 63.9 | 62.2 | 50.0 |
| S298_04F | 105.6 | 80.4 | 75.5 | 66.3 | 77.6 |
| S298_16H | 105.4 | 84.7 | 80.2 | 64.4 | 71.9 |
| S298_15Y | 104.0 | 75.7 | 71.2 | 62.2 | 80.6 |
| S298_14T | 103.8 | 94.2 | 96.2 | 79.0 | 105.9 |
| S298_07I | 103.7 | 86.2 | 84.9 | 71.5 | 90.7 |
| S298_08L | 103.5 | 100.3 | 83.0 | 110.0 | 69.2 |
| S298_02A | 103.4 | 87.2 | 74.3 | 74.4 | 150.6 |
| S298_01G | 100.5 | 94.5 | 71.4 | 81.2 | 74.9 |
| Y300_03V | 110.3 | 96.8 | 108.7 | 96.5 | 83.8 |
| Y300_01G | 109.5 | 66.6 | 82.6 | 63.2 | 88.6 |
| Y300_10E | 107.9 | 127.1 | 107.9 | 174.8 | 113.2 |
| Y300_08L | 106.7 | 96.9 | 120.0 | 96.1 | 113.9 |
| Y300_19Q | 106.2 | 118.8 | 106.6 | 141.5 | 104.6 |
| Y300_09D | 106.1 | 105.1 | 100.8 | 121.7 | 103.7 |
| Y300_20W | 106.0 | 104.0 | 102.6 | 109.9 | 100.8 |
| Y300_02A | 105.9 | 92.9 | 103.7 | 90.5 | 88.1 |
| Y300_06M | 105.8 | 105.1 | 116.3 | 110.1 | 106.5 |
| Y300_14T | 105.4 | 78.6 | 104.4 | 72.7 | 92.8 |
| Y300_13S | 104.8 | 72.4 | 97.8 | 70.4 | 80.3 |
| Y300_16H | 104.6 | 102.8 | 105.1 | 113.7 | 101.8 |
| Y300_04F | 102.3 | 103.3 | 103.3 | 106.2 | 100.1 |
| Y300_07I | 101.7 | 90.9 | 120.3 | 97.4 | 103.3 |
| Y300_11K | 100.9 | 73.1 | 74.2 | 67.4 | 63.7 |
| Y300_18N | 100.9 | 96.2 | 101.0 | 92.7 | 96.0 |
| S324_14T | 114.1 | 93.9 | 107.4 | 115.4 | 112.0 |
| S324_18N | 108.9 | 100.7 | 108.6 | 105.9 | 103.4 |
| S324_20W | 107.8 | 105.6 | 114.4 | 114.3 | 110.6 |
| S324_15Y | 107.4 | 107.1 | 113.5 | 115.3 | 110.1 |
| S324_16H | 106.3 | 105.0 | 113.2 | 109.1 | 112.7 |
| S324_19Q | 105.9 | 86.8 | 106.5 | 87.2 | 96.2 |
| S324_06M | 104.2 | 117.9 | 121.9 | 125.6 | 124.5 |
| S324_04F | 102.7 | 99.6 | 105.6 | 99.9 | 99.3 |
| S324_10E | 98.9 | 99.0 | 114.0 | 101.1 | 107.8 |
| S324_05P | 97.8 | 94.6 | 57.8 | 106.1 | 72.3 |
| S324_03V | 97.7 | 112.6 | 108.2 | 127.8 | 101.4 |
| S324_09D | 97.7 | 102.0 | 117.3 | 112.0 | 109.7 |
| S324_08L | 97.3 | 109.5 | 106.1 | 117.1 | 95.5 |
| S324_02A | 96.9 | 99.9 | 113.7 | 102.3 | 113.0 |
| S324_11K | 96.3 | 91.0 | 102.3 | 89.6 | 90.2 |
| S324_07I | 96.2 | 108.9 | 107.2 | 125.1 | 100.6 |
| S324_12R | 95.9 | 84.0 | 107.1 | 82.4 | 98.1 |
| S324_01G | 93.2 | 94.4 | 109.6 | 106.0 | 114.0 |
| N325_09D | 105.0 | 111.1 | 55.3 | 139.2 | 53.0 |
| N325_13S | 101.7 | 137.3 | 83.0 | 198.5 | 71.9 |
| K326_15Y | 111.2 | 130.7 | 102.3 | 178.6 | 124.0 |
| K326_18N | 110.4 | 110.5 | 113.0 | 118.4 | 134.2 |
| K326_14T | 109.3 | 128.3 | 119.2 | 167.5 | 139.7 |
| K326_10E | 109.0 | 141.6 | 106.0 | 224.2 | 137.5 |

TABLE 3-continued

| Name | He/Con 1a | He/Con 2aR | He/Con 2aH | He/Con 2b | He/Con 3a |
|---|---|---|---|---|---|
| K326_09D | 108.6 | 141.7 | 114.9 | 216.1 | 147.6 |
| K326_16H | 108.6 | 114.9 | 101.9 | 133.0 | 106.2 |
| K326_20W | 108.4 | 125.3 | 86.7 | 166.4 | 93.7 |
| K326_06M | 107.7 | 132.1 | 107.6 | 184.7 | 126.8 |
| K326_19Q | 107.5 | 123.8 | 105.6 | 156.1 | 117.4 |
| K326_04F | 107.0 | 129.4 | 101.0 | 173.8 | 113.6 |
| K326_03V | 107.0 | 134.8 | 101.0 | 196.5 | 134.9 |
| K326_02A | 106.8 | 124.6 | 109.9 | 156.0 | 129.9 |
| K326_05P | 106.3 | 118.5 | 102.9 | 140.7 | 117.2 |
| K326_01G | 106.1 | 107.9 | 104.6 | 119.2 | 114.1 |
| K326_07I | 105.7 | 140.8 | 104.3 | 222.8 | 153.1 |
| K326_13S | 105.5 | 119.0 | 110.3 | 139.0 | 118.0 |
| K326_08L | 105.3 | 131.1 | 96.5 | 197.9 | 126.1 |
| K326_12R | 105.2 | 98.6 | 104.7 | 100.0 | 101.4 |
| A327_10E | 105.8 | 141.7 | 108.1 | 175.1 | 70.5 |
| A327_06M | 105.7 | 80.0 | 89.3 | 74.1 | 54.0 |
| A327_09D | 105.3 | 159.4 | 124.0 | 213.9 | 86.0 |
| A327_13S | 104.8 | 98.6 | 84.4 | 99.0 | 66.7 |
| A327_05P | 101.7 | 80.6 | 67.9 | 86.3 | 61.9 |
| A327_01G | 101.4 | 126.4 | 115.1 | 143.9 | 74.4 |
| A327_18N | 100.1 | 114.4 | 79.0 | 140.9 | 62.8 |
| A327_20W | 100.0 | 95.9 | 76.6 | 98.2 | 52.6 |
| A327_19Q | 98.5 | 77.7 | 79.6 | 67.5 | 54.0 |
| L328_15Y | 104.0 | 174.4 | 106.5 | 240.4 | 70.2 |
| L328_10E | 103.7 | 135.6 | 65.7 | 214.6 | 54.9 |
| L328_19Q | 103.5 | 114.9 | 102.7 | 130.7 | 83.4 |
| L328_03V | 103.4 | 149.6 | 115.8 | 156.6 | 80.9 |
| L328_14T | 102.8 | 152.9 | 137.5 | 176.0 | 77.4 |
| L328_07I | 101.8 | 159.9 | 111.2 | 199.7 | 86.4 |
| L328_13S | 101.4 | 150.1 | 145.8 | 185.9 | 73.7 |
| L328_18N | 101.1 | 76.4 | 80.6 | 100.7 | 51.1 |
| L328_06M | 101.0 | 148.5 | 122.5 | 176.4 | 80.8 |
| L328_02A | 100.9 | 150.2 | 154.2 | 180.0 | 81.3 |
| L328_04F | 100.2 | 177.4 | 84.9 | 272.7 | 81.5 |
| L328_16H | 98.5 | 106.2 | 84.5 | 100.4 | 55.9 |
| P329_10E | 81.4 | 72.7 | 57.6 | 59.5 | 52.7 |
| P329_09D | 80.1 | 76.0 | 57.1 | 60.4 | 52.5 |
| A330_09D | 112.1 | 79.5 | 67.8 | 62.8 | 56.4 |
| A330_20W | 111.1 | 97.6 | 93.8 | 86.0 | 102.0 |
| A330_10E | 110.9 | 97.2 | 87.7 | 79.2 | 82.8 |
| A330_08L | 110.4 | 99.7 | 94.7 | 79.6 | 121.8 |
| A330_18N | 110.0 | 91.0 | 88.3 | 71.9 | 67.3 |
| A330_04F | 109.5 | 112.2 | 103.7 | 104.8 | 144.0 |
| A330_16H | 109.2 | 111.3 | 109.7 | 99.0 | 102.0 |
| A330_01G | 109.2 | 122.2 | 107.0 | 116.9 | 87.3 |
| A330_03V | 109.0 | 84.0 | 86.1 | 59.2 | 98.8 |
| A330_19Q | 108.7 | 116.9 | 110.5 | 102.6 | 86.3 |
| A330_07I | 108.7 | 96.0 | 94.4 | 75.8 | 100.9 |
| A330_14T | 108.5 | 107.1 | 102.1 | 87.9 | 85.8 |
| A330_15Y | 108.4 | 114.3 | 106.3 | 107.2 | 122.3 |
| A330_06M | 108.0 | 107.2 | 101.3 | 90.9 | 138.6 |
| A330_11K | 106.8 | 123.5 | 118.3 | 107.3 | 91.8 |
| A330_05P | 104.8 | 128.9 | 92.6 | 154.4 | 151.9 |
| A330_12R | 102.8 | 116.1 | 116.5 | 95.8 | 77.3 |
| P331_09D | 109.2 | 101.4 | 93.6 | 104.5 | 71.6 |
| P331_15Y | 108.9 | 111.5 | 89.0 | 126.8 | 74.9 |
| P331_04F | 108.3 | 109.7 | 87.7 | 122.5 | 70.7 |
| P331_10E | 107.8 | 112.4 | 90.1 | 128.0 | 68.7 |
| P331_13S | 107.7 | 103.8 | 94.0 | 107.3 | 80.9 |
| P331_19Q | 107.5 | 96.1 | 91.6 | 94.0 | 73.9 |
| P331_20W | 107.3 | 108.9 | 85.8 | 123.2 | 71.9 |
| P331_18N | 106.4 | 103.8 | 87.2 | 109.9 | 67.1 |
| P331_06M | 106.3 | 105.1 | 88.1 | 112.7 | 68.4 |
| P331_07I | 106.0 | 109.0 | 80.1 | 126.9 | 60.4 |
| P331_08L | 104.9 | 100.9 | 85.9 | 106.1 | 66.0 |
| P331_16H | 104.8 | 113.1 | 87.5 | 128.5 | 73.4 |
| P331_02A | 104.7 | 105.1 | 93.9 | 110.3 | 82.5 |
| P331_03V | 104.4 | 113.5 | 85.4 | 131.5 | 66.9 |
| P331_14T | 102.4 | 103.5 | 86.5 | 110.6 | 67.8 |
| P331_12R | 100.5 | 88.7 | 84.3 | 85.0 | 64.8 |
| P331_11K | 100.2 | 94.6 | 83.7 | 93.9 | 61.8 |
| I332_10E | 109.3 | 113.2 | 112.1 | 157.8 | 212.9 |
| I332_04F | 106.2 | 104.1 | 107.8 | 115.2 | 89.3 |
| I332_09D | 106.0 | 117.9 | 121.9 | 162.9 | 189.0 |
| I332_06M | 104.7 | 108.0 | 113.6 | 116.1 | 92.5 |
| I332_20W | 104.4 | 116.9 | 115.1 | 102.1 | 115.9 |
| I332_08L | 104.2 | 91.0 | 94.9 | 91.3 | 76.0 |

TABLE 3-continued

| Name | He/Con 1a | He/Con 2aR | He/Con 2aH | He/Con 2b | He/Con 3a |
|---|---|---|---|---|---|
| I332_14T | 104.2 | 104.2 | 118.9 | 117.9 | 109.6 |
| I332_19Q | 103.2 | 95.1 | 111.8 | 104.5 | 101.0 |
| I332_12R | 102.5 | 73.5 | 103.9 | 60.9 | 78.1 |
| I332_01G | 102.2 | 92.2 | 102.0 | 96.6 | 101.3 |
| I332_15Y | 100.7 | 108.7 | 119.0 | 112.2 | 92.4 |
| I332_16H | 100.5 | 97.6 | 113.1 | 103.1 | 89.0 |
| I332_03V | 100.5 | 87.0 | 108.4 | 89.5 | 85.2 |
| I332_02A | 100.2 | 96.9 | 115.2 | 114.5 | 102.7 |
| I332_18N | 99.3 | 98.3 | 113.9 | 99.6 | 84.9 |
| I332_05P | 99.2 | 80.5 | 69.9 | 83.7 | 56.3 |
| I332_13S | 97.3 | 97.9 | 113.3 | 109.1 | 95.6 |
| E333_03V | 99.4 | 135.3 | 112.2 | 120.2 | 106.0 |
| E333_09D | 98.0 | 140.6 | 118.6 | 121.7 | 115.4 |
| E333_02A | 97.7 | 128.5 | 114.7 | 108.2 | 108.5 |
| E333_13S | 97.6 | 125.3 | 115.4 | 105.6 | 105.7 |
| E333_01G | 97.2 | 126.6 | 112.1 | 105.1 | 101.1 |
| E333_04F | 96.9 | 139.2 | 116.5 | 122.1 | 104.1 |
| E333_05P | 96.9 | 142.9 | 111.6 | 126.1 | 100.5 |
| E333_08L | 96.8 | 140.5 | 116.5 | 122.6 | 101.5 |
| E333_12R | 96.7 | 127.1 | 109.8 | 103.8 | 92.2 |
| E333_06M | 96.7 | 132.0 | 110.1 | 110.3 | 100.4 |
| E333_14T | 96.7 | 134.8 | 115.2 | 111.2 | 100.1 |
| E333_11K | 96.6 | 128.1 | 112.5 | 104.0 | 97.7 |
| E333_07I | 96.5 | 142.4 | 113.0 | 124.1 | 100.1 |
| E333_15Y | 95.8 | 137.3 | 114.5 | 121.8 | 101.2 |
| E333_16H | 95.4 | 118.7 | 113.5 | 107.6 | 106.0 |
| E333_20W | 93.9 | 132.3 | 106.2 | 115.6 | 103.8 |
| E333_19Q | 93.7 | 130.4 | 112.9 | 110.3 | 101.3 |
| E333_18N | 91.4 | 117.9 | 110.3 | 98.2 | 76.2 |
| K334_10E | 103.9 | 144.1 | 112.7 | 147.9 | 185.9 |
| K334_09D | 100.8 | 127.0 | 95.6 | 122.3 | 164.4 |
| K334_19Q | 100.4 | 148.8 | 116.2 | 141.0 | 140.1 |
| K334_02A | 100.2 | 143.0 | 111.3 | 138.8 | 151.5 |
| K334_20W | 99.9 | 142.9 | 112.0 | 134.0 | 131.5 |
| K334_04F | 99.6 | 150.5 | 121.2 | 143.1 | 151.9 |
| K334_16H | 99.3 | 149.2 | 119.2 | 145.6 | 137.6 |
| K334_13S | 99.3 | 148.7 | 116.5 | 143.2 | 149.5 |
| K334_14T | 99.2 | 152.6 | 118.4 | 148.9 | 145.6 |
| K334_15Y | 99.1 | 147.9 | 121.6 | 141.0 | 145.0 |
| K334_03V | 99.1 | 159.9 | 125.5 | 160.9 | 153.9 |
| K334_08L | 99.1 | 144.9 | 119.6 | 137.4 | 147.5 |
| K334_18N | 99.0 | 152.4 | 114.4 | 148.2 | 140.2 |
| K334_06M | 99.0 | 144.2 | 120.6 | 140.8 | 148.8 |
| K334_07I | 98.7 | 155.2 | 126.3 | 153.7 | 155.6 |
| K334_05P | 98.7 | 140.6 | 112.0 | 135.6 | 137.6 |
| K334_12R | 98.2 | 150.8 | 114.4 | 143.5 | 93.5 |
| K334_01G | 98.0 | 127.1 | 92.5 | 119.4 | 124.9 |
| T335_08L | 118.2 | 113.9 | 109.4 | 113.6 | 97.8 |
| T335_12R | 116.4 | 105.7 | 103.3 | 100.4 | 93.1 |
| T335_11K | 114.3 | 105.3 | 102.8 | 99.4 | 91.7 |
| T335_07I | 112.6 | 115.2 | 111.6 | 115.9 | 102.5 |
| T335_10E | 112.2 | 117.3 | 111.5 | 118.5 | 102.1 |
| T335_09D | 110.8 | 115.9 | 110.8 | 118.4 | 102.9 |
| T335_15Y | 110.6 | 117.4 | 110.1 | 118.2 | 99.7 |
| T335_06M | 110.1 | 110.4 | 106.4 | 108.6 | 97.0 |
| T335_14T | 109.9 | 115.8 | 111.8 | 116.5 | 103.6 |
| T335_05P | 109.7 | 109.3 | 111.5 | 109.1 | 100.2 |
| T335_20W | 109.5 | 114.6 | 108.6 | 113.5 | 97.3 |
| T335_18N | 109.1 | 112.1 | 106.9 | 111.0 | 94.4 |
| T335_16H | 109.0 | 114.1 | 109.1 | 111.9 | 99.3 |
| T335_04F | 108.3 | 113.4 | 106.8 | 112.4 | 91.7 |
| T335_19Q | 108.3 | 111.8 | 106.8 | 109.4 | 97.7 |
| T335_13S | 108.1 | 115.5 | 109.9 | 111.1 | 100.4 |
| T335_03V | 107.7 | 112.3 | 106.7 | 109.3 | 96.3 |
| T335_01G | 107.7 | 109.5 | 106.8 | 105.6 | 95.1 |
| T335_02A | 106.6 | 108.0 | 104.4 | 102.7 | 90.9 |
| I336_01G | 112.1 | 104.1 | 100.5 | 98.4 | 94.6 |
| I336_06M | 111.6 | 112.3 | 109.9 | 110.8 | 104.1 |
| I336_18N | 111.2 | 109.8 | 106.7 | 106.7 | 99.4 |
| I336_10E | 111.2 | 103.8 | 105.2 | 98.2 | 114.1 |
| I336_08L | 110.8 | 116.2 | 109.3 | 117.4 | 101.6 |
| I336_02A | 109.3 | 100.2 | 102.4 | 92.8 | 106.0 |
| I336_04F | 108.8 | 105.1 | 98.3 | 99.6 | 93.2 |
| I336_11K | 108.8 | 104.4 | 103.4 | 98.7 | 94.4 |
| I336_03V | 108.5 | 104.1 | 105.8 | 98.7 | 107.3 |
| I336_14T | 107.8 | 102.1 | 103.2 | 97.8 | 103.4 |
| I336_07I | 107.7 | 114.2 | 108.5 | 113.0 | 98.5 |

TABLE 3-continued

| Name | He/Con 1a | He/Con 2aR | He/Con 2aH | He/Con 2b | He/Con 3a |
|---|---|---|---|---|---|
| I336_09D | 106.9 | 104.4 | 100.4 | 100.7 | 101.5 |
| I336_19Q | 106.8 | 70.9 | 76.4 | 63.6 | 88.4 |
| I336_15Y | 106.1 | 83.1 | 84.6 | 74.5 | 83.4 |
| I336_13S | 105.7 | 97.4 | 101.0 | 91.5 | 97.1 |
| I336_12R | 105.2 | 104.4 | 103.5 | 100.6 | 88.8 |
| I336_16H | 104.5 | 99.1 | 97.4 | 93.8 | 92.8 |
| S337_06M | 103.6 | 107.1 | 103.7 | 105.5 | 89.7 |
| S337_03V | 103.4 | 108.0 | 104.0 | 107.8 | 87.1 |
| S337_01G | 103.3 | 101.2 | 98.7 | 100.2 | 95.2 |
| S337_10E | 103.1 | 113.7 | 108.7 | 116.9 | 97.8 |
| S337_04F | 102.9 | 106.5 | 105.1 | 106.6 | 94.4 |
| S337_12R | 102.6 | 109.2 | 105.3 | 108.4 | 92.7 |
| S337_02A | 102.5 | 107.0 | 103.1 | 106.0 | 92.4 |
| S337_09D | 102.4 | 116.9 | 113.7 | 123.9 | 102.3 |
| S337_18N | 102.1 | 108.5 | 105.9 | 112.6 | 96.9 |
| S337_08L | 102.1 | 109.4 | 106.4 | 109.2 | 90.2 |
| S337_07I | 102.0 | 110.9 | 107.0 | 113.4 | 88.3 |
| S337_14T | 101.8 | 112.0 | 109.7 | 114.0 | 94.0 |
| S337_20W | 101.6 | 112.5 | 108.2 | 118.6 | 93.8 |
| S337_16H | 101.4 | 110.6 | 107.6 | 114.0 | 100.3 |
| S337_19Q | 101.4 | 107.6 | 104.1 | 108.7 | 91.2 |
| S337_11K | 100.8 | 104.8 | 101.7 | 102.8 | 80.1 |
| S337_15Y | 100.6 | 107.4 | 105.6 | 109.2 | 94.9 |

As the combination of the positions of amino acids to be altered, for example, amino acids selected from the group consisting of Leu at EU numbering position 234, Leu at EU numbering position 235, Gly at EU numbering position 236, Ser at EU numbering position 239, His at EU numbering position 268, Asp at EU numbering position 270, Ser at EU numbering position 298, Lys at EU numbering position 326, Ala at EU numbering position 330, Ile at EU numbering position 332, and Lys at EU numbering position 334 can be altered in combination to enhance the binding activity against the Fcγ receptor. Specific examples thereof include amino acid alterations selected from the group consisting of the substitution of an amino acid L at EU numbering position 234 by Y, the substitution of an amino acid L at EU numbering position 235 by Y or Q, the substitution of an amino acid G at EU numbering position 236 by W, the substitution of an amino acid S at EU numbering position 239 by D or M, the substitution of an amino acid H at EU numbering position 268 by D, the substitution of an amino acid D at EU numbering position 270 by E, the substitution of an amino acid S at EU numbering position 298 by A, the substitution of an amino acid K at EU numbering position 326 by D, the substitution of an amino acid A at EU numbering position 330 by L or M, the substitution of an amino acid I at EU numbering position 332 by E, and the substitution of an amino acid K at EU numbering position 334 by E. For the Fc region heterodimer, its binding activity against the Fcγ receptor can be enhanced by introducing in combination amino acid alterations selected from the group consisting of the substitution of an amino acid L at EU numbering position 234 by Y, the substitution of an amino acid L at EU numbering position 235 by Y or Q, the substitution of an amino acid G at EU numbering position 236 by W, the substitution of an amino acid S at EU numbering position 239 by M, the substitution of an amino acid H at EU numbering position 268 by D, the substitution of an amino acid D at EU numbering position 270 by E, and the substitution of an amino acid S at EU numbering position 298 by A to the amino acid sequence of either one of the Fc regions and introducing in combination at least one or more amino acid alterations selected from the group consisting of the substitution of an amino acid S at EU numbering position 239 by D, the substitution of an amino acid D at EU numbering position 270 by E, the substitution of an amino acid K at EU numbering position 326 by D, the substitution of an amino acid A at EU numbering position 330 by L or M, the substitution of an amino acid I at EU numbering position 332 by E, and the substitution of an amino acid K at EU numbering position 334 by E to the amino acid sequence of the other Fc region.

More specifically, the binding activity of the Fc region dimer against the Fcγ receptor can be enhanced by using, for example, an Fc region dimer in which either one of the Fc regions has amino acid alterations in any of the combinations (i) to (iii), and the other Fc region has amino acid alterations in any of the combinations (iv) to (vi):

(i) the substitution of an amino acid L at EU numbering position 234 by Y, the substitution of an amino acid G at EU numbering position 236 by W, and the substitution of an amino acid S at EU numbering position 298 by A;

(ii) the substitution of an amino acid L at EU numbering position 234 by Y, the substitution of an amino acid L at EU numbering position 235 by Y, the substitution of an amino acid G at EU numbering position 236 by W, the substitution of an amino acid H at EU numbering position 268 by D, and the substitution of an amino acid S at EU numbering position 298 by A; and (iii) the substitution of an amino acid L at EU numbering position 234 by Y, the substitution of an amino acid L at EU numbering position 235 by Q, the substitution of an amino acid G at EU numbering position 236 by W, the substitution of an amino acid S at EU numbering position 239 by M, the substitution of an amino acid H at EU numbering position 268 by D, the substitution of an amino acid D at EU numbering position 270 by E, and the substitution of an amino acid S at EU numbering position 298 by A; and (iv) the substitution of an amino acid S at EU numbering position 239 by D, the substitution of an amino acid A at EU numbering position 330 by L, and the substitution of an amino acid I at EU numbering position 332 by E;

(v) the substitution of an amino acid K at EU numbering position 326 by D, the substitution of an amino acid A at EU numbering position 330 by M, and the substitution of an amino acid K at EU numbering position 334 by E; and (vi) the substitution of an amino acid D at EU numbering position 270 by E, the substitution of an amino acid K at EU numbering position 326 by D, the substitution of an amino acid A at EU numbering position 330 by M, and the substitution of an amino acid K at EU numbering position 334 by E.

In the present specification, the physicochemical stability of a polypeptide means, for example, the thermodynamic stability of the polypeptide. The thermodynamic stability of the polypeptide can be confirmed, for example, with the Tm value of the CH2 regions as an index. The Tm value can be measured by CD (circular dichroism), DSC (differential scanning calorimetry), or DSF (differential scanning fluorimetry).

CD involves observing change in mean residue molar ellipticity (θ) with a rise in temperature to calculate Tm values. Examples of a measurement instrument include a circular dichroism dispersion meter (JASCO Corp.). CD spectra are measured at one appropriate wavelength (e.g., 208 nm or 222 nm) while the temperature is raised. As a result, the θ value is increased at a certain temperature and kept constant at temperatures over the certain temperature. In this context, Tm is defined as a temperature that assumes the value of the midpoint between low θ temperature and high θ temperature. A protein solution prepared with, for example, a citrate, tris, or phosphate solution may be used in the assay and can be used at a concentration of a few hundred of ug/mL in the assay.

DSC involves observing change in heat capacity with a rise in temperature to calculate Tm values. Examples of a measurement instrument include MicroCal VP-DSC and MicroCal Capillary DSC (both from DKSH Japan K.K.). Assay cells are filled with a protein solution or a buffer solution. The difference in temperature between the cell containing the protein solution and the cell containing the buffer solution is measured while the temperature is raised. As a result, the reaction is changed to endothermic reaction at a certain temperature. Tm is defined as this temperature. A protein solution prepared with, for example, a citrate buffer solution, TBS, PBS, or a histidine buffer solution may be used in the assay and can be used at a concentration of tens to a few hundred of ug/mL in the assay.

DSF involves observing the exposure of a hydrophobic residue with a rise in temperature using a fluorescent reagent (e.g., SYPRO Orange) capable of specifically binding to the hydrophobic residue to calculate Tm values. A protein solution is mixed with the fluorescent reagent at an appropriate ratio. The fluorescence intensity is measured using an RT-PCR apparatus while the temperature is raised. As a result, increase in the fluorescence intensity is observed at a certain temperature. Tm is defined as this temperature. Examples of a measurement instrument include Rotor-Gene Q (Qiagen N.V.) and CFX96 real-time PCR analysis system (Bio-Rad Laboratories, Inc.). A protein solution prepared with, for example, PBS or a histidine buffer solution may be used in the assay and can be used at a concentration of tens to a few hundred of ug/mL in the assay.

In the present specification, the physical stability of a polypeptide is preferably 50° C. or higher, more preferably 55° C. or higher, further preferably 60° C. or higher, in terms of the Tm value of the CH2 regions in the Fc region determined, for example, on the basis of any of the assay methods mentioned above.

Particularly, for enhancing the binding activity of the FcγR-binding site in the Fc region dimer against FcγRIIIa, at least one or more amino acid alteration(s) selected from the group consisting of amino acid alterations described in Tables 4-1 to 4-4 herein (lists of altered forms having alterations wherein a heterodimerized antibody with the mutation(s) introduced in one H chain has FcγRIIIa-binding activity of 50% or higher affinity (KD) compared with natural IgG and corresponding homodimerized antibodies have Tm of 60° C. or higher) may be introduced to the amino acid sequence of the first Fc region and/or the second Fc region constituting the Fc region dimer.

TABLE 4

| Name | He/Con 3a | Tm[° C.] |
|---|---|---|
| L234_01G | 55.8 | 69.5 |
| L234_13S | 68.1 | 69.3 |
| L234_02A | 69.7 | 68.8 |
| L234_14T | 69.8 | 69.2 |
| L234_16H | 76.8 | 69.0 |
| L234_19Q | 77.1 | 69.4 |
| L234_06M | 82.9 | 68.9 |
| L234_05P | 85.1 | 68.9 |
| L234_18N | 88.2 | 69.1 |

TABLE 4-continued

| Name | He/Con 3a | Tm[° C.] |
|---|---|---|
| L234_03V | 88.3 | 69.7 |
| L234_07I | 99.5 | 69.1 |
| L234_20W | 103.2 | 68.9 |
| L234_10E | 110.6 | 67.1 |
| L234_09D | 112.8 | 67.1 |
| L234_04F | 114.0 | 68.5 |
| L234_15Y | 125.7 | 69.0 |
| L235_01G | 56.7 | 69.0 |
| L235_16H | 57.1 | 68.0 |
| L235_18N | 65.0 | 68.1 |
| L235_13S | 67.2 | 68.9 |
| L235_19Q | 68.1 | 67.5 |
| L235_05P | 68.6 | 68.9 |
| L235_02A | 72.0 | 68.8 |
| L235_14T | 73.2 | 68.4 |
| L235_20W | 73.8 | 67.9 |
| L235_06M | 75.6 | 69.0 |
| L235_04F | 76.4 | 68.9 |
| L235_15Y | 77.8 | 68.8 |
| L235_10E | 85.6 | 66.9 |
| L235_09D | 88.5 | 66.7 |
| L235_07I | 92.8 | 69.1 |
| L235_03V | 94.6 | 69.2 |
| G236_03V | 53.8 | 67.9 |
| G236_07I | 55.6 | 65.6 |
| G236_10E | 65.8 | 65.9 |
| G236_09D | 66.2 | 66.2 |
| G236_02A | 77.0 | 68.4 |
| G236_04F | 81.0 | 67.8 |
| G236_15Y | 112.4 | 67.4 |
| G236_20W | 126.1 | 64.8 |
| G237_14T | 50.5 | 67.5 |
| G237_03V | 51.3 | 67.4 |
| P238_19Q | 52.7 | 62.3 |
| P238_15Y | 61.0 | 65.5 |
| P238_08L | 71.3 | 67.4 |
| P238_10E | 98.9 | 60.5 |
| P238_09D | 100.0 | 60.8 |
| S239_19Q | 53.8 | 71.2 |
| S239_02A | 70.9 | 67.2 |
| 3239_01G | 72.0 | 64.9 |
| S239_03V | 72.4 | 67.7 |
| S239_06M | 73.9 | 68.4 |
| S239_07I | 75.0 | 67.3 |
| S239_08L | 90.0 | 67.6 |
| S239_14T | 93.0 | 68.2 |
| S239_18N | 103.8 | 67.5 |
| S239_09D | 156.4 | 65.0 |
| S239_10E | 171.4 | 66.0 |
| V266_02A | 56.8 | 63.0 |
| V266_06M | 84.9 | 64.8 |
| V266_07I | 112.9 | 69.1 |
| V266_08L | 116.7 | 69.7 |
| S267_18N | 52.0 | 66.6 |
| S267_01G | 53.3 | 67.2 |
| S267_19Q | 64.3 | 66.8 |
| S267_06M | 65.3 | 66.4 |
| S267_10E | 90.9 | 64.1 |
| S267_02A | 148.8 | 66.7 |
| S267_09D | 178.9 | 65.4 |
| H268_05P | 75.6 | 69.9 |
| H268_08L | 75.9 | 69.9 |
| H268_12R | 76.0 | 69.2 |
| H268_06M | 79.5 | 70.0 |
| H268_11K | 81.6 | 70.4 |
| H268_20W | 82.0 | 68.5 |
| H268_07I | 84.1 | 69.6 |
| H268_14T | 90.3 | 68.1 |
| H268_03V | 91.4 | 68.1 |
| H268_01G | 95.7 | 67.5 |
| H268_04F | 96.0 | 69.6 |
| H268_15Y | 96.5 | 68.5 |
| H268_18N | 103.0 | 66.8 |
| H268_19Q | 113.0 | 68.7 |
| H268_13S | 120.6 | 67.8 |
| H268_02A | 120.9 | 68.5 |
| H268_10E | 184.1 | 67.6 |
| H268_09D | 195.2 | 67.1 |

TABLE 4-continued

| Name | He/Con 3a | Tm[° C.] |
|---|---|---|
| E269_16H | 50.7 | 68.6 |
| E269_15Y | 51.5 | 67.9 |
| E269_08L | 51.5 | 67.7 |
| E269_07I | 55.3 | 67.7 |
| E269_03V | 56.0 | 68.2 |
| E269_18N | 57.2 | 67.8 |
| E269_06M | 57.9 | 68.0 |
| E269_14T | 59.7 | 68.1 |
| E269_01G | 61.6 | 66.7 |
| E269_13S | 62.1 | 68.7 |
| E269_19Q | 64.3 | 65.9 |
| E269_02A | 68.0 | 68.6 |
| E269_09D | 105.7 | 68.6 |
| D270_02A | 50.5 | 70.0 |
| D270_18N | 51.2 | 70.2 |
| D270_13S | 51.4 | 67.8 |
| D270_03V | 54.6 | 67.5 |
| D270_14T | 55.4 | 68.6 |
| D270_06M | 60.0 | 69.2 |
| D270_07I | 63.1 | 67.4 |
| D270_08L | 65.1 | 67.9 |
| D270_19Q | 74.2 | 68.4 |
| D270_10E | 111.8 | 69.3 |
| P271_14T | 59.2 | 67.0 |
| P271_15Y | 62.7 | 67.2 |
| P271_04F | 65.6 | 66.7 |
| P271_16H | 70.3 | 66.5 |
| P271_03V | 73.5 | 66.2 |
| P271_06M | 74.0 | 66.7 |
| P271_08L | 74.5 | 66.4 |
| P271_20W | 77.8 | 67.3 |
| P271_13S | 79.8 | 67.1 |
| P271_07I | 80.2 | 66.1 |
| P271_02A | 83.7 | 67.0 |
| P271_19Q | 84.6 | 66.5 |
| P271_12R | 87.6 | 65.1 |
| P271_11K | 92.5 | 65.2 |
| P271_18N | 94.0 | 66.2 |
| P271_09D | 97.7 | 68.4 |
| P271_10E | 98.2 | 67.9 |
| P271_01G | 118.8 | 68.0 |
| Q295_12R | 73.2 | 63.9 |
| Q295_05P | 74.4 | 64.3 |
| Q295_04F | 75.1 | 67.8 |
| Q295_01G | 76.6 | 63.8 |
| Q295_16H | 80.2 | 65.5 |
| Q295_15Y | 81.5 | 66.1 |
| Q295_11K | 81.8 | 64.0 |
| Q295_09D | 85.6 | 62.7 |
| Q295_18N | 85.7 | 65.9 |
| Q295_03V | 86.2 | 67.8 |
| Q295_13S | 90.4 | 65.5 |
| Q295_06M | 100.2 | 70.8 |
| Q295_07I | 100.7 | 66.5 |
| Q295_10E | 105.1 | 64.9 |
| Q295_02A | 110.8 | 66.5 |
| Q295_08L | 119.5 | 69.8 |
| Q295_14T | 120.4 | 65.9 |
| Y296_01G | 51.3 | 70.9 |
| Y296_11K | 53.3 | 67.0 |
| Y296_13S | 58.1 | 70.6 |
| Y296_14T | 60.7 | 68.3 |
| Y296_02A | 66.3 | 67.0 |
| Y296_12R | 66.5 | 67.3 |
| Y296_18N | 67.9 | 69.9 |
| Y296_16H | 69.1 | 67.3 |
| Y296_03V | 69.1 | 66.7 |
| Y296_19Q | 71.4 | 70.8 |
| Y296_08L | 72.4 | 66.9 |
| Y296_06M | 74.6 | 65.7 |
| Y296_07I | 75.8 | 65.9 |
| Y296_10E | 76.8 | 69.0 |
| Y296_04F | 79.5 | 69.0 |
| Y296_09D | 89.0 | 69.6 |
| Y296_20W | 127.0 | 66.7 |
| S298_11K | 50.0 | 66.5 |
| S298_18N | 51.4 | 67.2 |
| S298_12R | 52.1 | 66.8 |

TABLE 4-continued

| Name | He/Con 3a | Tm[° C.] |
|---|---|---|
| S298_09D | 62.7 | 67.4 |
| S298_08L | 69.2 | 65.5 |
| S298_19Q | 70.6 | 66.5 |
| S298_16H | 71.9 | 65.1 |
| S298_01G | 74.9 | 72.0 |
| S298_04F | 77.6 | 68.7 |
| S298_15Y | 80.6 | 65.7 |
| S298_06M | 87.2 | 69.7 |
| S298_07I | 90.7 | 64.3 |
| S298_03V | 102.8 | 65.0 |
| S298_14T | 105.9 | 66.1 |
| S298_02A | 150.6 | 68.1 |
| Y300_11K | 63.7 | 66.0 |
| Y300_13S | 80.3 | 64.5 |
| Y300_03V | 83.8 | 63.6 |
| Y300_02A | 88.1 | 66.2 |
| Y300_01G | 88.6 | 68.5 |
| Y300_14T | 92.8 | 63.7 |
| Y300_18N | 96.0 | 63.0 |
| Y300_04F | 100.1 | 62.8 |
| Y300_20W | 100.8 | 67.5 |
| Y300_16H | 101.8 | 63.7 |
| Y300_07I | 103.3 | 60.5 |
| Y300_09D | 103.7 | 68.4 |
| Y300_19Q | 104.6 | 63.0 |
| Y300_06M | 106.5 | 61.9 |
| Y300_10E | 113.2 | 68.6 |
| Y300_08L | 113.9 | 60.6 |
| S324_11K | 90.2 | 68.2 |
| S324_08L | 95.5 | 67.4 |
| S324_19Q | 96.2 | 67.2 |
| S324_12R | 98.1 | 68.8 |
| S324_04F | 99.3 | 69.0 |
| S324_07I | 100.6 | 68.4 |
| S324_03V | 101.4 | 66.3 |
| S324_18N | 103.4 | 69.7 |
| S324_10E | 107.8 | 66.9 |
| S324_09D | 109.7 | 66.2 |
| S324_15Y | 110.1 | 68.6 |
| S324_14T | 112.0 | 67.1 |
| S324_16H | 112.7 | 69.3 |
| S324_02A | 113.0 | 66.3 |
| S324_01G | 114.0 | 65.4 |
| S324_06M | 124.5 | 66.1 |
| N325_09D | 53.0 | 63.1 |
| N325_16H | 68.0 | 71.3 |
| N325_13S | 71.9 | 71.0 |
| K326_20W | 93.7 | 65.5 |
| K326_12R | 101.4 | 68.8 |
| K326_16H | 106.2 | 66.7 |
| K326_04F | 113.6 | 65.3 |
| K326_01G | 114.1 | 69.6 |
| K326_05P | 117.2 | 68.4 |
| K326_19Q | 117.4 | 67.9 |
| K326_13S | 118.0 | 69.8 |
| K326_15Y | 124.0 | 65.7 |
| K326_08L | 126.1 | 67.1 |
| K326_06M | 126.8 | 66.6 |
| K326_02A | 129.9 | 69.2 |
| K326_18N | 134.2 | 68.9 |
| K326_03V | 134.9 | 66.5 |
| K326_10E | 137.5 | 68.0 |
| K326_14T | 139.7 | 64.1 |
| K326_09D | 147.6 | 68.0 |
| K326_07I | 153.1 | 66.1 |
| A327_20W | 52.6 | 67.3 |
| A327_06M | 54.0 | 69.0 |
| A327_19Q | 54.0 | 68.0 |
| A327_05P | 61.9 | 62.1 |
| A327_18N | 62.8 | 68.2 |
| A327_13S | 66.7 | 61.4 |
| A327_10E | 70.5 | 65.4 |
| A327_09D | 86.0 | 65.7 |
| L328_18N | 51.1 | 63.1 |
| L328_16H | 55.9 | 64.2 |
| L328_15Y | 70.2 | 65.5 |
| L328_13S | 73.7 | 64.5 |
| L328_14T | 77.4 | 64.9 |

TABLE 4-continued

| Name | He/Con 3a | Tm[° C.] |
|---|---|---|
| L328_06M | 80.8 | 67.7 |
| L328_03V | 80.9 | 64.9 |
| L328_02A | 81.3 | 65.0 |
| L328_04F | 81.5 | 67.2 |
| L328_19Q | 83.4 | 62.8 |
| L328_07I | 86.4 | 66.0 |
| P329_09D | 52.5 | 66.3 |
| P329_10E | 52.7 | 66.7 |
| P329_02A | 55.2 | 68.7 |
| A330_09D | 56.4 | 65.9 |
| A330_18N | 67.3 | 68.2 |
| A330_12R | 77.3 | 67.9 |
| A330_10E | 82.8 | 67.2 |
| A330_14T | 85.8 | 67.9 |
| A330_19Q | 86.3 | 67.4 |
| A330_01G | 87.3 | 67.0 |
| A330_11K | 91.8 | 68.2 |
| A330_03V | 98.8 | 68.5 |
| A330_07I | 100.9 | 68.2 |
| A330_20W | 102.0 | 67.9 |
| A330_16H | 102.0 | 69.5 |
| A330_08L | 121.8 | 66.9 |
| A330_15Y | 122.3 | 69.0 |
| A330_06M | 138.6 | 68.2 |
| A330_04F | 144.0 | 67.3 |
| P331_07I | 60.4 | 62.8 |
| P331_11K | 61.8 | 60.6 |
| P331_08L | 66.0 | 60.6 |
| P331_03V | 66.9 | 64.1 |
| P331_18N | 67.1 | 61.7 |
| P331_14T | 67.8 | 63.9 |
| P331_06M | 68.4 | 62.0 |
| P331_10E | 68.7 | 63.4 |
| P331_04F | 70.7 | 63.0 |
| P331_09D | 71.6 | 64.1 |
| P331_20W | 71.9 | 61.8 |
| P331_16H | 73.4 | 63.0 |
| P331_19Q | 73.9 | 62.7 |
| P331_15Y | 74.9 | 63.2 |
| P331_13S | 80.9 | 65.8 |
| P331_02A | 82.5 | 66.0 |
| I332_03V | 85.2 | 67.8 |
| I332_16H | 89.0 | 60.6 |
| I332_04F | 89.3 | 61.9 |
| I332_06M | 92.5 | 65.0 |
| I332_13S | 95.6 | 60.9 |
| I332_19Q | 101.0 | 62.8 |
| I332_02A | 102.7 | 63.2 |
| I332_14T | 109.6 | 63.1 |
| I332_10E | 212.9 | 60.1 |
| E333_18N | 76.2 | 63.3 |
| E333_12R | 92.2 | 65.6 |
| E333_11K | 97.7 | 63.0 |
| E333_14T | 100.1 | 66.0 |
| E333_07I | 100.1 | 67.3 |
| E333_06M | 100.4 | 65.9 |
| E333_01G | 101.1 | 61.5 |
| E333_15Y | 101.2 | 66.6 |
| E333_19Q | 101.3 | 68.4 |
| E333_08L | 101.5 | 66.0 |
| E333_20W | 103.8 | 64.0 |
| E333_04F | 104.1 | 65.9 |
| E333_13S | 105.7 | 65.9 |
| E333_16H | 106.0 | 60.8 |
| E333_03V | 106.0 | 68.4 |
| E333_02A | 108.5 | 65.5 |
| K334_01G | 124.9 | 64.2 |
| K334_05P | 137.6 | 62.0 |
| K334_16H | 137.6 | 62.8 |
| K334_19Q | 140.1 | 67.1 |
| K334_18N | 140.2 | 65.4 |
| K334_15Y | 145.0 | 65.9 |
| K334_14T | 145.6 | 65.7 |
| K334_08L | 147.5 | 66.2 |
| K334_13S | 149.5 | 66.1 |
| K334_02A | 151.5 | 65.8 |
| K334_04F | 151.9 | 65.9 |
| K334_03V | 153.9 | 67.0 |

TABLE 4-continued

| Name | He/Con 3a | Tm[° C.] |
|---|---|---|
| K334_07I | 155.6 | 67.3 |
| K334_09D | 164.4 | 65.6 |
| K334_10E | 185.9 | 63.6 |
| T335_02A | 90.9 | 65.8 |
| T335_11K | 91.7 | 67.0 |
| T335_04F | 91.7 | 64.6 |
| T335_12R | 93.1 | 67.0 |
| T335_18N | 94.4 | 63.8 |
| T335_01G | 95.1 | 63.2 |
| T335_03V | 96.3 | 68.4 |
| T335_06M | 97.0 | 66.2 |
| T335_20W | 97.3 | 65.0 |
| T335_19Q | 97.7 | 64.9 |
| T335_08L | 97.8 | 64.9 |
| T335_16H | 99.3 | 64.3 |
| T335_15Y | 99.7 | 64.7 |
| T335_13S | 100.4 | 67.6 |
| T335_10E | 102.1 | 62.9 |
| T335_07I | 102.5 | 67.0 |
| T335_09D | 102.9 | 61.2 |
| T335_14T | 103.6 | 68.0 |
| I336_07I | 98.5 | 67.9 |
| I336_18N | 99.4 | 62.0 |
| I336_08L | 101.6 | 64.8 |
| I336_14T | 103.4 | 64.1 |
| I336_06M | 104.1 | 61.7 |
| I336_02A | 106.0 | 61.8 |
| I336_03V | 107.3 | 67.2 |
| S337_11K | 80.1 | 67.3 |
| S337_03V | 87.1 | 65.3 |
| S337_07I | 88.3 | 63.3 |
| S337_06M | 89.7 | 66.4 |
| S337_08L | 90.2 | 62.6 |
| S337_19Q | 91.2 | 66.9 |
| S337_02A | 92.4 | 67.0 |
| S337_12R | 92.7 | 68.1 |
| S337_20W | 93.8 | 64.4 |
| S337_14T | 94.0 | 67.3 |
| S337_04F | 94.4 | 65.9 |
| S337_15Y | 94.9 | 65.5 |
| S337_01G | 95.2 | 64.9 |
| S337_18N | 96.9 | 64.1 |
| S337_10E | 97.8 | 62.1 |
| S337_16H | 100.3 | 66.6 |

In the present invention, examples of the combination of the first Fc region and the second Fc region with the introduced amino acid alteration(s) can include, but not particularly limited to, combinations of different types and/or the same types of polypeptides selected from polypeptides described in SEQ ID NOs: 2 to 4, 6 to 43, and 45 to 48. Preferred examples thereof can include combinations of polypeptides including the first Fc region and the second Fc region described in Examples of the present application (combinations of two antibody H chains and one antibody L chain).

The polypeptide of the present invention may be an antigen-binding molecule. In the present invention, the antibody-binding molecule is not particularly limited by its type. Preferred examples thereof can include antibodies, multispecific antibodies, and Fc fusion molecules such as peptide-Fc fusion proteins and scaffold-Fc fusion proteins.

Furthermore, an antibody is provided as the polypeptide of the present invention. In the present invention, the term "antibody" is used in the broadest sense and also includes any antibody such as monoclonal antibodies (including whole monoclonal antibodies), polyclonal antibodies, antibody variants, antibody fragments, multispecific antibodies (e.g., bispecific antibodies), chimeric antibodies, and humanized antibodies as long as the antibody exhibits the desired biological activity.

The antibody of the present invention is not limited by the type of its antigen, its origin, etc. and may be any antibody. Examples of the origin of the antibody can include, but not particularly limited to, human antibodies, mouse antibodies, rat antibodies, and rabbit antibodies.

The antibody can be prepared by a method well known to those skilled in the art. For example, the monoclonal antibodies may be produced by a hybridoma method (Kohler and Milstein, Nature 256: 495 (1975)) or a recombination method (U.S. Pat. No. 4,816,567). Alternatively, the monoclonal antibodies may be isolated from phage-displayed antibody libraries (Clackson et al., Nature 352: 624-628 (1991); and Marks et al., J. Mol. Biol. 222: 581-597 (1991)). Also, the monoclonal antibodies may be isolated from single B cell clones (N. Biotechnol. 28 (5): 253-457 (2011)).

The humanized antibodies are also called reshaped human antibodies. Specifically, for example, a humanized antibody consisting of a non-human animal (e.g., mouse) antibody CDR-grafted human antibody is known in the art. General gene recombination approaches are also known for obtaining the humanized antibodies. Specifically, for example, overlap extension PCR is known in the art as a method for grafting mouse antibody CDRs to human FRs.

A DNA encoding an antibody variable region comprising three CDRs and four FRs linked and a human antibody constant region-encoding DNA can be inserted into expression vectors such that these DNAs are fused in frame to prepare vectors for humanized antibody expression. These vectors having the inserts are transferred to hosts to establish recombinant cells. Then, the recombinant cells are cultured for the expression of the humanized antibody-encoding DNA to produce the humanized antibodies into the cultures of the cultured cells (see European Patent Publication No. EP 239400 and International Publication No. WO1996/002576).

If necessary, FR amino acid residue(s) may be substituted such that the CDRs of the reshaped human antibody form an appropriate antigen-binding site. For example, the amino acid sequence of FR can be mutated by the application of the PCR method used in the mouse CDR grafting to the human FRs.

The desired human antibody can be obtained by DNA immunization using transgenic animals having all repertoires of human antibody genes (see International Publication Nos. WO1993/012227, WO1992/003918, WO1994/002602, WO1994/025585, WO1996/034096, and WO1996/033735) as immunized animals.

In addition, a technique of obtaining human antibodies by panning using human antibody libraries is also known. For example, human antibody V regions are expressed as a single-chain antibody (scFv) on the surface of phages by a phage display method. A phage expressing antigen-binding scFv can be selected. The gene of the selected phage can be analyzed to determine DNA sequences encoding the V regions of the antigen-binding human antibody. After the determination of the DNA sequence of the antigen-binding scFv, the V region sequences can be fused in frame with the sequences of the desired human antibody C regions and then inserted to appropriate expression vectors to prepare expression vectors. The expression vectors are transferred to the preferred expression cells as exemplified above. The human antibody-encoding genes are expressed by the cells to obtain the human antibodies. These methods are already known in the art (see International Publication Nos. WO1992/001047, WO1992/020791, WO1993/006213, WO1993/011236, WO1993/019172, WO1995/001438, and WO1995/015388).

The variable regions constituting the antibody of the present invention can be variable regions that recognize an arbitrary antigen.

In the present invention, the "antigen" refers to a first antigen defined as an antigen binding to a region (e.g., variable region) other than the Fc region and a second antigen defined as an antigen binding to the Fc region. In the present specification, the antigen is not particularly limited and may be any antigen. Examples of the antigen include 17-IA, 4-1BB, 4Dc, 6-keto-PGF1a, 8-iso-PGF2a, 8-oxo-dG, A1 adenosine receptor, A33, ACE, ACE-2, activin, activin A, activin AB, activin B, activin C, activin RIA, activin RIA ALK-2, activin RIB ALK-4, activin RIIA, activin RIIB, ADAM, ADAM10, ADAM12, ADAM15, ADAM17/TACE, ADAM8, ADAM9, ADAMTS, ADAMTS4, ADAMTS5, addressin, adiponectin, ADP-ribosyl cyclase-1, aFGF, AGE, ALCAM, ALK, ALK-1, ALK-7, allergen, α1-antichymotrypsin, α1-antitrypsin, α-synuclein, α-V/β-1 antagonist, aminin, amylin, amyloid β, amyloid immunoglobulin heavy chain variable region, amyloid immunoglobulin light chain variable region, androgen, ANG, angiotensinogen, angiopoietin ligand-2, anti-Id, antithrombin III, anthrax, APAF-1, APE, APJ, apo-A1, apo-serum amyloid A, apo-SAA, APP, APRIL, AR, ARC, ART, artemin, ASPARTIC, atrial natriuretic factor, atrial natriuretic peptide, atrial natriuretic peptide A, atrial natriuretic peptide B, atrial natriuretic peptide C, av/b3 integrin, Ax1, B7-1, B7-2, B7-H, BACE, BACE-1, *Bacillus anthracis* protective antigen, Bad, BAFF, BAFF-R, Bag-1, BAK, Bax, BCA-1, BCAM, Bcl, BCMA, BDNF, b-ECGF, β-2-microglobulin, β lactamase, bFGF, BID, Bik, BIM, BLC, BL-CAM, BLK, B-lymphocyte stimulator (BLyS), BMP, BMP-2 (BMP-2a), BMP-3 (osteogenin), BMP-4 (BMP-2b), BMP-5, BMP-6 (Vgr-1), BMP-7 (OP-1), BMP-8 (BMP-8a), BMPR, BMPR-IA (ALK-3), BMPR-IB (ALK-6), BMPR-II (BRK-3), BMP, BOK, bombesin, bone-derived neurotrophic factor, bovine growth hormone, BPDE, BPDE-DNA, BRK-2, BTC, B-lymphocyte cell adhesion molecule, C10, C1 inhibitor, C1q, C3, C3a, C4, C5, C5a (complement 5a), CA125, CAD-8, cadherin-3, calcitonin, cAMP, carbonate dehydratase-IX, carcinoembryonic antigen (CEA), carcinoma-associated antigen, cardiotrophin-1, cathepsin A, cathepsin B, cathepsin C/DPPI, cathepsin D, cathepsin E, cathepsin H, cathepsin L, cathepsin O, cathepsin S, cathepsin V, cathepsin X/Z/P, CBL, CCI, CCK2, CCL, CCL1/I-309, CCL11/eotaxin, CCL12/MCP-5, CCL13/MCP-4, CCL14/HCC-1, CCL15/HCC-2, CCL16/HCC-4, CCL17/TARC, CCL18/PARC, CCL19/ELC, CCL2/MCP-1, CCL20/MIP-3-α, CCL21/SLC, CCL22/MDC, CCL23/MPIF-1, CCL24/eotaxin-2, CCL25/TECK, CCL26/eotaxin-3, CCL27/CTACK, CCL28/MEC, CCL3/M1P-1-α, CCL3L1/LD-78-β, CCL4/MIP-1-β, CCL5/RANTES, CCL6/C10, CCL7/MCP-3, CCL8/MCP-2, CCL9/10/MTP-1-γ, CCR, CCR1, CCR10, CCR2, CCR3, CCR4, CCR5, CCR6, CCR7, CCR8, CCR9, CD1, CD10, CD105, CD11a, CD11b, CD11c, CD123, CD13, CD137, CD138, CD14, CD140a, CD146, CD147, CD148, CD15, CD152, CD16, CD164, CD18, CD19, CD2, CD20, CD21, CD22, CD23, CD25, CD26, CD27L, CD28, CD29, CD3, CD30, CD30L, CD32, CD33 (p67 protein), CD34, CD37, CD38, CD3E, CD4, CD40, CD40L, CD44, CD45, CD46, CD49a, CD49b, CD5, CD51, CD52, CD54, CD55, CD56, CD6, CD61, CD64, CD66e, CD7, CD70, CD74, CD8, CD80 (B7-1), CD89, CD95, CD105, CD158a, CEA, CEACAM5, CFTR, cGMP, CGRP receptor, CINC, CKb8-1, claudin 18, CLC, *Clostridium botulinum* toxin, *Clostridium difficile* toxin, *Clostridium perfringens* toxin, c-Met, CMV, CMV UL, CNTF, CNTN-1, complement factor 3 (C3), complement factor D, corticosteroid-binding globulin, colony-stimulating factor-1 receptor, COX, C-Ret, CRG-2, CRTH2, CT-1, CTACK, CTGF, CTLA-4, CX3CL1/fractalkine, CX3CR1, CXCL, CXCL1/Gro-α, CXCL10, CXCL11/I-TAC, CXCL12/SDF-1-α/β, CXCL13/BCA-1, CXCL14/BRAK, CXCL15/Lungkine, CXCL16, CXCL16, CXCL2/Gro-β CXCL3/Gro-γ, CXCL3, CXCL4/PF4, CXCL5/ENA-78, CXCL6/GCP-2, CXCL7/NAP-2, CXCL8/IL-8, CXCL9/Mig, CXCLlO/IP-10, CXCR, CXCR1, CXCR2, CXCR3, CXCR4, CXCR5, CXCR6, cystatin C, cytokeratin tumor-associated antigen, DAN, DCC, DcR3, DC-SIGN, decay accelerating factor, delta-like protein ligand 4, des(1-3)-IGF-1 (brain IGF-1), Dhh, DHICA oxidase, Dickkopf-1, digoxin, dipeptidyl peptidase IV, DK1, DNAM-1, Dnase, Dpp, DPPIV/CD26, Dtk, ECAD, EDA, EDA-A1, EDA-A2, EDAR, EGF, EGFR (ErbB-1), EGF-like domain-containing protein 7, elastase, elastin, EMA, EMMPRIN, ENA, ENA-78, endosialin, endothelin receptor, endotoxin, enkephalinase, eNOS, Eot, eotaxin, eotaxin-2, eotaxin-1, EpCAM, ephrin B2/EphB4, Epha2 tyrosine kinase receptor, epithelial growth factor receptor (EGFR), ErbB2 receptor, ErbB3 tyrosine kinase receptor, ERCC, EREG, erythropoietin (EPO), erythropoietin receptor, E-selectin, ET-1, exodus-2, RSV F protein, F10, F11, F12, F13, F5, F9, factor Ia, factor IX, factor Xa, factor VII, factor VIII, factor VIIIc, Fas, FcaR, Fc-epsilon RI, FcγIIb, FcγRI, FcγRIIa, FcγRIIIa, FcγRIIIb, FcRn, FEN-1, ferritin, FGF, FGF-19, FGF-2, FGF-2 receptor, FGF-3, FGF-8, FGF-acidic, FGF-basic, FGFR, FGFR-3, fibrin, fibroblast activation protein (FAP), fibroblast growth factor, fibroblast growth factor-10, fibronectin, FL, FLIP, Flt-3, FLT3 ligand, folate receptor, follicle-stimulating hormone (FSH), fractalkine (CX3C), free heavy chain, free light chain, FZD1, FZD10, FZD2, FZD3, FZD4, FZD5, FZD6, FZD7, FZD8, FZD9, G250, Gas 6, GCP-2, GCSF, G-CSF, G-CSF receptor, GD2, GD3, GDF, GDF-1, GDF-15 (MIC-1), GDF-3 (Vgr-2), GDF-5 (BMP-14/CDMP-1), GDF-6 (BMP-13/CDMP-2), GDF-7 (BMP-12/CDMP-3), GDF-8 (myostatin), GDF-9, GDNF, gelsolin, GFAP, GF-CSF, GFR-α1, GFR-α2, GFR-α3, GF-β1, gH envelope glycoprotein, GITR, glucagon, glucagon receptor, glucagon-like peptide 1 receptor, Glut 4, glutamate carboxypeptidase II, glycoprotein hormone receptor, glycoprotein 11b/111a (GP 11b/111a), glypican-3, GM-CSF, GM-CSF receptor, gp130, gp140, gp72, granulocyte-CSF (G-CSF), GRO/MGSA, growth hormone-releasing factor, GRO-β, GRO-γ, *H. pylori*, hapten (NP-cap or NIP-cap), HB-EGF, HCC, HCC 1, HCMV gB envelope glycoprotein, HCMV UL, hematopoietic growth factor (HGF), Hep B gp120, heparanase, heparin cofactor II, hepatic growth factor, *Bacillus anthracis* protective antigen, hepatitis C virus E2 glycoprotein, hepatitis E, hepcidin, Her1, Her2/neu (ErbB-2), Her3 (ErbB-3), Her4 (ErbB-4), herpes simplex virus (HSV) gB glycoprotein, HGF, HGFA, high-molecular-weight melanoma-associated antigen (HMW-MAA), HIV envelope proteins (e.g., GP120), HIV MIB gp 120 V3 loop, HLA, HLA-DR, HM1.24, HMFG PEM, HMGB-1, HRG, Hrk, HSP47, Hsp90, HSV gD glycoprotein, human heart myosin, human cytomegalovirus (HCMV), human growth hormone (hGH), human serum albumin, human tissue plasminogen activator (t-PA), huntingtin, HVEM, IAP, ICAM, ICAM-1, ICAM-3, ICE, ICOS, IFN-α, IFN-0, IFN-γ, IgA, IgA receptor, IgE, IGF, IGF-binding protein, IGF-1, IGF-1 R, IGF-2, IGFBP, IGFR, IL, IL-1, IL-10, IL-10 receptor, IL-11, IL-11 receptor, IL-12, IL-12 receptor, IL-13, IL-13 receptor, IL-15, IL-15 receptor, IL-16, IL-16 receptor, IL-17, IL-17 receptor, IL-18 (IGIF), IL-18 receptor, IL-1α, IL-1β, IL-1 receptor, IL-2, IL-2 receptor, IL-20, IL-20 receptor, IL-21, IL-21 receptor, IL-23, IL-23 receptor, IL-2 receptor, IL-3, IL-3 receptor, IL-31, IL-31 receptor, IL-3 receptor, IL-4, IL-4 receptor, IL-5, IL-5 receptor, IL-6, IL-6 receptor, IL-7, IL-7 receptor, IL-8, IL-8 receptor, IL-9, IL-9 receptor, immunoglobulin immune complex, immunoglobulin, INF-α, INF-α receptor, INF-β, INF-β receptor, INF-γ, INF-γ receptor, type I IFN, type I IFN receptor, influenza, inhibin, inhibin α, inhibin β, iNOS, insulin, insulin A chain, insulin B chain, insulin-like growth factor 1, insulin-like growth factor 2, insulin-like growth factor-binding protein, integrin, integrin α2, integrin α3, integrin α4, integrin α4/β1, integrin α-V/β-3, integrin α-V/β-6, integrin α4/β7, integrin α5/β1, integrin α5/β3, integrin α5/β6, integrin α-δ(αV), integrin α-θ, integrin β1, integrin β2, integrin β3 (GPIIb-IIIa), IP-10, I-TAC, JE, kallikrein, kallikrein 11, kallikrein 12, kallikrein 14, kallikrein 15, kallikrein 2, kallikrein 5, kallikrein 6, kallikrein L1, kallikrein L2, kallikrein L3, kallikrein L4, kallistatin, KC, KDR, keratinocyte growth factor (KGF), keratinocyte growth factor-2 (KGF-2), KGF, killer immunoglobulin-like receptor, kit ligand (KL), Kit tyrosine kinase, laminin 5, LAMP, LAPP (amylin or islet amyloid polypeptide), LAP (TGF-1), latency-associated peptide, latent TGF-1, latent TGF-1 bp1, LBP, LDGF, LDL, LDL receptor, LECT2, lefty, leptin, luteinizing hormone (LH), Lewis-Y antigen, Lewis-Y-related antigen, LFA-1, LFA-3, LFA-3 receptor, Lfo, LIF, LIGHT, lipoprotein, LIX, LKN, Lptn, L-selectin, LT-a, LT-b, LTB4, LTBP-1, lung surfactant, luteinizing hormone, lymphotactin, lymphotoxin β receptor, lysosphingolipid receptor, Mac-1, macrophage-CSF (M-CSF), MAdCAM, MAG, MAP2, MARC, maspin, MCAM, MCK-2, MCP, MCP-1, MCP-2, MCP-3, MCP-4, MCP-I (MCAF), M-CSF, MDC, MDC (67 a.a.), MDC (69 a.a.), megsin, Mer, MET tyrosine kinase receptor family, metalloprotease, membrane glycoprotein OX2, mesothelin, MGDF receptor, MGMT, MHC (HLA-DR), microbial protein, MIF, MIG, MIP, MIP-1α, MIP-1β, MIP-3α, MIP-3β, MIP-4, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, monocyte attractant protein, monocyte colony inhibitory factor, mouse gonadotropin-associated peptide, MPIF, Mpo, MSK, MSP, MUC-16, MTJC18, mucin (Mud), mullerian-inhibiting factor, Mug, MuSK, myelin-associated glycoprotein, myeloid progenitor inhibitory factor-1 (MPIF-I), NAIP, Nanobody, NAP, NAP-2, NCA 90, NCAD, N-cadherin, NCAM, neprilysin, neural cell adhesion molecule, neroserpin, nerve growth factor (NGF), neurotrophin-3, neurotrophin-4, neurotrophin-6, neuropilin 1, neurturin, NGF-β, NGFR, NKG20, N-methionyl human growth hormone, nNOS, NO, Nogo-A, Nogo receptor, hepatitis C virus-derived nonstructural protein 3 (NS3), NOS, Npn, NRG-3, NT, NT-3, NT-4, NTN, OB, OGG1, oncostatin M, OP-2, OPG, OPN, OSM, OSM receptor, osteoinductive factor, osteopontin, OX40L, OX40R, oxidized LDL, p150, p95, PADPr, parathyroid hormone, PARC, PARP, PBR, PBSF, PCAD, P-cadherin, PCNA, PCSK9, PDGF, PDGF receptor, PDGF-AA, PDGF-AB, PDGF-BB, PDGF-D, PDK-1, PECAM, PEDF, PEM, PF-4, PGE, PGF, PGI2, PGJ2, PIGF, PIN, PLA2, placental growth factor, placental alkaline phosphatase (PLAP), placental lactogen, plasminogen activator inhibitor-1, platelet-growth factor, plgR, PLP, different sizes of polyglycol chains (e.g., PEG-20, PEG-30, and PEG40), PP14, prekallikrein, prion protein, procalcitonin, programmed cell death protein 1, proinsulin, prolactin, proprotein convertase PC9, prorelaxin, prostate-specific membrane antigen (PSMA), protein A, protein C, protein D, protein S, protein Z, PS, PSA, PSCA, PsmAr, PTEN, PTHrp, Ptk, PTN, P-selectin glycoprotein ligand-1, R51, RAGE, RANK, RANKL, RANTES, relaxin, relaxin A chain, relaxin B chain, renin, respiratory syncytial virus (RSV) F, Ret, reticulon 4, rheumatoid factor, RLI P76, RPA2, RPK-1, RSK, RSV Fgp, S100, RON-8, SCF/KL, SCGF, sclerostin, SDF-1, SDF1 α, SDF1 β, SERINE, serum amyloid P, serum albumin, sFRP-3, Shh, Shiga-like toxin II, SIGIRR, SK-1, SLAM, SLPI, SMAC, SMDF, SMOH, SOD, SPARC, sphingosine-1-phosphate receptor 1, staphylococcal lipoteichoic acid, Stat, STEAP, STEAP-II, stem cell factor (SCF), streptokinase, superoxide dismutase, syndecan-1, TACE, TACI, TAG-72 (tumor-associated glycoprotein-72), TARC, TB, TCA-3, T cell receptor α/β, TdT, TECK, TEM1, TEM5, TEM7, TEM8, tenascin, TERT, testicular PLAP-like alkaline phosphatase, TfR, TGF, TGF-α, TGF-β, TGF-β pan specific, TGF-β RII, TGF-β RIIb, TGF-β RIII, TGF-β R1 (ALK-5), TGF-β1, TGF-β2, TGF-β3, TGF-β4, TGF-β5, TGF-I, thrombin, thrombopoietin (TPO), thymic stromal lymphoprotein receptor, thymus Ck-1, thyroid stimulating hormone (TSH), thyroxine, thyroxine-binding globulin, Tie, TIMP, TIQ, tissue factor, tissue factor protease inhibitor, tissue factor protein, TMEFF2, Tmpo, TMPRSS2, TNF receptor I, TNF receptor II, TNF-α, TNF-β, TNF-β2, TNFc, TNF-RI, TNF-RII, TNFRSF10A (TRAIL R1 Apo-2/DR4), TNFRSF10B (TRAIL R2 DR5/KILLER/TRICK-2A/TRICK-B), TNFRSF10C (TRAIL R3 DcR1/LIT/TRID), TNFRSF10D (TRAIL R4 DcR2/TRUNDD), TNFRSF11A (RANK ODF R/TRANCE R), TNFRSF11B (OPG OCIF/TR1), TNFRSF12 (TWEAK R FN14), TNFRSF12A, TNFRSF13B (TACI), TNFRSF13C (BAFF R), TNFRSF14 (HVEM ATAR/HveA/LIGHT R/TR2), TNFRSF16 (NGFR p75NTR), TNFRSF17 (BCMA), TNFRSF18 (GITR AITR), TNFRSF19 (TROY TAJ/TRADE), TNFRSF19L (RELT), TNFRSF1A (TNF R1 CD120a/p55-60), TNFRSF1B (TNF RII CD120b/p75-80), TNFRSF21 (DR6), TNFRSF22 (DcTRAIL R2 TNFRH2), TNFRSF25 (DR3 Apo-3/LARD/TR-3/TRAMP/WSL-1), TNFRSF26 (TNFRH3), TNFRSF3 (LTbR TNF RIII/TNFC R), TNFRSF4 (OX40 ACT35/TXGP1 R), TNFRSF5 (CD40 p50), TNFRSF6 (Fas Apo-1/APT1/CD95), TNFRSF6B (DcR3 M68/TR6), TNFRSF7 (CD27), TNFRSF8 (CD30), TNFRSF9 (4-1 BB CD137/ILA), TNFRST23 (DcTRAIL R1 TNFRH1), TNFSF10 (TRAIL Apo-2 ligand/TL2), TNFSF11 (TRANCE/RANK ligand ODF/OPG ligand), TNFSF12 (TWEAK Apo-3 ligand/DR3 ligand), TNFSF13 (APRIL TALL2), TNFSF13B (BAFF BLYS/TALL1/THANK/TNFSF20), TNFSF14 (LIGHT HVEM ligand/LTg), TNFSF15 (TL1A/VEGI), TNFSF18 (GITR ligand AITR ligand/TL6), TNFSF1A (TNF-a Conectin/DIF/TNFSF2), TNFSF1B (TNF-b LTa/TNFSF1), TNFSF3 (LTb TNFC/p33), TNFSF4 (OX40 ligand gp34/TXGP1), TNFSF5 (CD40 ligand CD154/gp39/HIGM1/IMD3/TRAP), TNFSF6 (Fas ligand Apo-ligand/APT1 ligand), TNFSF7 (CD27 ligand CD70), TNFSF8 (CD30 ligand CD153), TNFSF9 (4-1 BB ligand CD137 ligand), TNF-α, TNF-β, TNIL-I, toxic metabolite, TP-1, t-PA, Tpo, TRAIL, TRAIL R, TRAIL-R1, TRAIL-R2, TRANCE, transferrin receptor, transforming growth factor (TGF) (e.g., TGF-α and TGF-β), transmembrane glycoprotein NMB, transthyretin, TRF, Trk, TROP-2, trophoblast glycoprotein, TSG, TSLP, tumor necrosis factor (TNF), tumor-associated antigen CA 125, tumor-associated antigen exhibiting Lewis Y-related carbohydrate, TWEAK, TXB2, Ung, uPAR, uPAR-1, urokinase, VAP-1, vascular endothelial growth factor (VEGF), vaspin, VCAM, VCAM-1, VECAD, VE-cadherin, VE-cadherin-2, VEFGR-1 (flt-1), VEFGR-2, VEGF receptor (VEGFR), VEGFR-3 (flt-4), VEGI, VIM, viral antigen, vitamin B12 receptor, vitronectin receptor, VLA, VLA-1, VLA-4, VNR integrin, von Willebrand factor (vWF), WIF-1, WNT1, WNT10A, WNT10B, WNT11, WNT16, WNT2, WNT2B/13, WNT3, WNT3A, WNT4, WNT5A, WNT5B, WNT6, WNT7A, WNT7B, WNT8A, WNT8B, WNT9A, WNT9B, XCL1, XCL2/SCM-1-β, XCL1/lymphotactin, XCR1, XEDAR, XIAP, and XPD. Preferably, the first antigen is, for example, an antigen specific for a tumor cell. Specific examples thereof include EpCAM, EREG, and GPC3. Preferably, the second antigen is, for example, an immunocyte surface molecule (T cell surface molecule, NK cell surface molecule, antigen-displaying cell surface molecule (CD3, TCR, NKG2D, CD137, OX40, GITR, CD40, TLR1 to TLR10, C type lectin, etc.), or an antigen expressed not only on tumor cells, tumor vessels, stromal cells, and the like but on normal tissues (integrin, tissue factor, VEGFR, PDGFR, EGFR, IGFR, MET chemokine receptor, heparan sulfate proteoglycan, CD44, fibronectin, DR5, TNFRSF, etc.). Specific examples thereof include CD3 and integrin.

The alteration of one or more amino acid residue(s) is acceptable for the amino acid sequence constituting each variable region as long as its antigen-binding activity is maintained. In the case of altering the amino acid sequence of the variable region, the alteration site or the number of the amino acid to be altered is not particularly limited. For example, amino acid(s) present in CDRs and/or FRs can be appropriately altered. The variable region with the altered amino acid(s) preferably maintains its binding activity and preferably has, but not particularly limited to, for example, 50% or higher, more preferably 80% or higher, further preferably 100% or higher binding activity, compared with that before the alteration. Alternatively, the binding activity of the variable region may be increased by amino acid alteration and may be, for example, 2 times, 5 times, or 10 times the binding activity before the alteration. In the antibody of the present invention, the alteration of an amino acid sequence can be at least one of the substitution, addition, deletion, insertion, and modification of amino acid residue(s).

For example, the modification of N-terminal glutamine of the variable region to pyroglutamic acid by pyroglutamylation is a modification well known to those skilled in the art. Thus, the antibody of the present invention having glutamine at the N terminus of its heavy chain may contain a variable region with this N-terminal glutamine modified to pyroglutamic acid.

The variable regions of the antibody of the present invention may have an arbitrary sequence and may be variable regions of an antibody of any origin, including mouse antibodies, rat antibodies, rabbit antibodies, goat antibodies, camel antibodies, humanized antibodies obtained by the humanization of these nonhuman antibodies, and human antibodies. The "humanized antibodies" are also called reshaped human antibodies and obtained by grafting CDRs (complementarity determining regions) of a non-human mammal-derived antibody, for example, a mouse antibody to human antibody CDRs. Methods for identifying CDRs are known in the art (Kabat et al., Sequence of Proteins of Immunological Interest (1987), National Institute of Health, Bethesda, Md.; and Chothia et al., Nature (1989) 342: 877). General gene recombination approaches therefor are also known in the art (see European Patent Application Publication No. EP 125023 and WO 96/02576). Alternatively, various amino acid substitutions may be introduced to the variable regions of these antibodies in order to improve their antigen binding, pharmacokinetics, stability, or antigenicity. The variable regions of the antibody of the present invention may have the pH dependence of its binding to an antigen and be thereby capable of repetitively binding to the antigen (WO/2009/125825).

The alteration of a variable region is carried out for the purpose of, for example, enhancing binding activity, improving specificity, reducing pI, conferring pH-dependent antigen-binding properties, improving the thermal stability of binding, improving solubility, improving stability against chemical modification, improving heterogeneity derived from a sugar chain, avoiding a T cell epitope identified by use of in silico prediction or in vitro T cell-based assay for reduction in immunogenicity, or introducing a T cell epitope for activating regulatory T cells (mAbs 3: 243-247, 2011).

Alternatively, the polypeptide of the present invention may be an Fc fusion protein molecule comprising the Fc region bound with an additional protein, a biologically active peptide, or the like (peptide-Fc fusion protein) or an Fc fusion protein molecule comprising the Fc region bound with an extracellular matrix or the like constituted by collagen or a polymer (e.g., polylactic acid) (scaffold-Fc fusion protein).

Examples of the additional protein or the biologically active peptide include, but not limited to, receptors, adhesion molecules, ligands, and enzymes.

Preferred examples of the Fc fusion protein molecule of the present invention include proteins comprising the Fc domain fused with a target-binding receptor protein and specifically include TNFR-Fc fusion proteins, IL1R-Fc fusion proteins, VEGFR-Fc fusion proteins, and CTLA4-Fc fusion proteins (Nat Med. 2003 January; 9 (1): 47-52, and BioDrugs. 2006; 20 (3): 151-60). The protein to be fused with the polypeptide of the present invention may be any molecule capable of binding to a target molecule. Examples thereof include scFv molecules (WO2005/037989), single-domain antibody molecules (WO2004/058821 and WO2003/002609), and antibody-like molecules (Current Opinion in Biotechnology 2006, 17: 653-658, Current Opinion in Biotechnology 2007, 18: 1-10, Current Opinion in Structural Biology 1997, 7: 463-469, and Protein Science 2006, 15: 14-27), for example, DARPins (WO2002/020565), Affibody (WO1995/001937), Avimer (WO2004/044011 and WO2005/040229), and Adnectin (WO2002/032925). Alternatively, the antibody and the Fc fusion protein molecule may be multispecific antibodies, such as bispecific antibodies, which bind to plural types of target molecules or epitopes.

The antibody of the present invention also includes modified forms of the antibody. Examples of the modified forms of the antibody can include antibodies conjugated with various molecules such as polyethylene glycol (PEG) or cytotoxic substances. Such modified forms of the antibody can be obtained by the chemical modification of the antibody of the present invention. The antibody modification method has already been established in the art.

In addition, the antibody of the present invention may be a bispecific antibody. The bispecific antibody refers to an antibody having, in one antibody molecule, variable regions that recognize different epitopes. The epitopes may be present in different molecules or may be present in the same molecule.

The polypeptide of the present invention can be produced by a method generally known to those skilled in the art. For example, the antibody can be prepared by the following method, though the method for preparing the antibody of the present invention is not limited thereto. Many combinations of host cells and expression vectors are known in the art for antibody preparation by the transfer of isolated polypeptide-encoding genes into appropriate hosts. All of these expression systems can be applied to the isolation of the antigen-binding molecule of the present invention. In the case of using eukaryotic cells as the host cells, animal, plant, or fungus cells can be appropriately used. Specifically, examples of the animal cells can include the following cells:

(1) mammalian cells such as CHO (Chinese hamster ovary cell line), COS (monkey kidney cell line), myeloma cells (Sp2/O, NS0, etc.), BHK (baby hamster kidney cell line), HEK293 (human embryonic kidney cell line with sheared adenovirus (Ad)5 DNA), PER.C6 cell (human embryonic retinal cell line transformed with the Adenovirus Type 5 (Ad5) E1A and E1B genes), Hela, and Vero (Current Protocols in Protein Science (May, 2001, Unit 5.9, Table 5.9.1));
(2) amphibian cells such as *Xenopus* oocytes; and
(3) insect cells such as sf9, sf21, and Tn5.

DNAs encoding heavy chains of the antibody, which are DNAs encoding heavy chains with one or more amino acid residue(s) in their Fc region substituted by the different amino acid(s) of interest, and DNAs encoding light chains of the antibody are expressed. The DNAs encoding heavy chains with one or more amino acid residue(s) in their Fc region substituted by the different amino acid(s) of interest can be obtained, for example, by obtaining the Fc region sequences of DNAs encoding naturally occurring heavy chains and appropriately introducing a substitution such that a codon encoding the particular amino acid in the Fc region encodes the different amino acid of interest.

Alternatively, a DNA encoding a protein in which one or more amino acid residue(s) in the Fc region of naturally occurring heavy chains is substituted by the different amino acid(s) of interest may be designed in advance and chemically synthesized to obtain the DNAs encoding heavy chains with one or more amino acid residue(s) in their Fc region substituted by the different amino acid(s) of interest. The amino acid substitution site and the type of the substitution are not particularly limited. Instead of the substitution, deletion, addition, insertion, or modification, or a combination thereof may be used.

The DNAs encoding heavy chains with one or more amino acid residue(s) in their Fc region substituted by the different amino acid(s) of interest can each be produced as separate partial DNAs. Examples of the combination of the partial DNAs include, but not limited to: the combination of a variable region-encoding DNA and a constant region-encoding DNA; and the combination of a Fab region-encoding DNA and an Fc region-encoding DNA. Likewise, the light chain-encoding DNA can also be produced as separate partial DNAs.

These DNAs can be expressed by the following exemplary method: for example, a heavy chain variable region-encoding DNA, together with a heavy chain constant region-encoding DNA, is incorporated into an expression vector to construct a heavy chain expression vector. Likewise, a light chain variable region-encoding DNA, together with a light chain constant region-encoding DNA, is incorporated into an expression vector to construct a light chain expression vector. These heavy and light chain genes may be incorporated into a single vector.

The DNA encoding the antibody of interest is incorporated into expression vectors so as to be expressed under the control of expression control regions, for example, an enhancer and a promoter. Next, host cells can be transformed with the resulting expression vectors and allowed to express antibodies. In this case, appropriate hosts and expression vectors can be used in combination.

Examples of the vectors include M13 series vectors, pUC series vectors, pBR322, pBluescript, and pCR-Script. In addition to these vectors, for example, pGEM-T, pDIRECT, or pT7 can also be used for the purpose of cDNA subcloning and excision.

Particularly, expression vectors are useful for using the vectors for the purpose of producing the antibody of the present invention. For example, when the host is *E. coli* such as JM109, DH5α, HB101, or XL1-Blue, the expression vectors indispensably have a promoter that permits efficient expression in *E. coli*, for example, lacZ promoter (Ward et al., Nature (1989) 341, 544-546; and FASEB J. (1992) 6, 2422-2427, which are incorporated herein by reference in their entirety), araB promoter (Better et al., Science (1988) 240, 1041-1043, which is incorporated herein by reference in its entirety), or T7 promoter. Examples of such vectors include the vectors mentioned above as well as pGEX-5X-1 (manufactured by Pharmacia), "QIAexpress system" (manufactured by Qiagen N.V.), pEGFP, and pET (in this case, the host is preferably BL21 expressing T7 RNA polymerase).

The vectors may contain a signal sequence for polypeptide secretion. In the case of production in the periplasm of *E. coli*, pelB signal sequence (Lei, S. P. et al J. Bacteriol. (1987) 169, 4397, which is incorporated herein by reference in its entirety) can be used as the signal sequence for polypeptide secretion. The vectors can be transferred to the host cells using, for example, a Lipofectin method, a calcium, phosphate method, or a DEAE-dextran method.

In addition to the expression vectors for *E. coli*, examples of the vectors for producing the polypeptide of the present invention include mammal-derived expression vectors (e.g., pcDNA3 (manufactured by Invitrogen Corp.), pEGF-BOS (Nucleic Acids. Res. 1990, 18 (17), p. 5322, which is incorporated herein by reference in its entirety), pEF, and pCDM8), insect cell-derived expression vectors (e.g., "Bac-to-BAC baculovirus expression system" (manufactured by GIBCO BRL), and pBacPAK8), plant-derived expression vectors (e.g., pMH1 and pMH2), animal virus-derived expression vectors (e.g., pHSV, pMV, and pAdexLcw), retrovirus-derived expression vectors (e.g., pZIPneo), yeast-derived expression vectors (e.g., "*Pichia* Expression Kit" (manufactured by Invitrogen Corp.), pNV11, and SP-Q01), and *Bacillus subtilis*-derived expression vectors (e.g., pPL608 and pKTH50).

For the purpose of expression in animal cells such as CHO cells, COS cells, NIH3T3 cells, or HEK293 cells, the vectors indispensably have a promoter necessary for intracellular expression, for example, SV40 promoter (Mulligan et al., Nature (1979) 277, 108, which is incorporated herein by reference in its entirety), MMTV-LTR promoter, EF1α promoter (Mizushima et al., Nucleic Acids Res. (1990) 18, 5322, which is incorporated herein by reference in its entirety), CAG promoter (Gene. (1991) 108, 193, which is incorporated herein by reference in its entirety), or CMV promoter and, more preferably, have a gene for screening for transformed cells (e.g., a drug resistance gene that can work as a marker by a drug (neomycin, G418, etc.)). Examples of the vectors having such properties include pMAM, pDR2, pBK-RSV, pBK-CMV, pOPRSV, and pOP13. In addition, EBNA1 protein may be coexpressed therewith for the purpose of increasing the number of gene copies. In this case, vectors having a replication origin OriP are used (Biotechnol Bioeng. 2001 Oct. 20; 75 (2): 197-203., and Biotechnol Bioeng. 2005 Sep. 20; 91 (6): 670-7).

An exemplary method intended to stably express the gene and increase the number of intracellular gene copies involves transforming CHO cells deficient in nucleic acid synthesis pathway with vectors having a DHFR gene serving as a complement thereto (e.g., pCHOI) and using methotrexate (MTX) in the gene amplification. An exemplary method intended to transiently express the gene involves using COS cells having an SV40 T antigen gene on their chromosomes to transform the cells with vectors having a replication origin of SV40 (pcD, etc.). Also, a replication origin derived from polyomavirus, adenovirus, bovine papillomavirus (BPV), or the like may be used. For increasing the number of gene copies in the host cell system, the expression vectors can contain a selection marker such as an aminoglycoside phosphoryl transferase (APH) gene, a thymidine kinase (TK) gene, an *E. coli* xanthine guanine phosphoribosyltransferase (Ecogpt) gene, or a dihydrofolate reductase (dhfr) gene.

The antibody can be recovered, for example, by culturing the transformed cells and then separating the antibody from within the molecule-transformed cells or from the culture solution thereof. The antibody can be separated and purified by appropriately using in combination methods such as centrifugation, ammonium sulfate fractionation, salting out, ultrafiltration, C1q, FcRn, protein A, and protein G columns, affinity chromatography, ion-exchanged chromatography, and gel filtration chromatography.

The technique that can be used in the association for the heterodimer or the polypeptide comprising the heterodimer as mentioned above, such as the knobs-into-holes technology (WO1996/027011, Ridgway J B et al., Protein Engineering (1996) 9, 617-621, and Merchant A M et al. Nature Biotechnology (1998) 16, 677-681) or the technique of suppressing the unintended association between H chains by the introduction of electric charge repulsion (WO2006/106905), can be applied to a method for efficiently preparing the bispecific antibody.

The present invention further provides a method for producing the polypeptide comprising the Fc region dimer according to the present invention, the method comprising the step of preparing a polypeptide library comprising Fc region dimers having diverse amino acid sequences in their Fc regions.

Examples thereof can include a production method comprising the following steps:

(i) preparing a peptide library consisting of peptides or polypeptides containing CH2 domains having diverse amino acid sequences;

(ii) selecting a CH2 domain-containing peptide or polypeptide from the prepared library, wherein the CH2 domain-containing peptide or polypeptide has binding activity against each of FcγR and an antigen, but does not bind to the FcγR and the antigen at the same time;

(iii) culturing a host cell containing a nucleic acid encoding a polypeptide comprising an Fc region dimer having the same CH2 domains as those of the peptide or the polypeptide selected in step (ii) to express the intended polypeptide comprising an Fc region dimer; and (iv) recovering the polypeptide comprising an Fc region dimer from cultures of the host cell.

In this production method, step (ii) may further comprise the following step:

(v) selecting a CH2 domain-containing peptide or polypeptide whose CH2 domains have a thermal denaturation temperature of 50° C. or higher.

In the present invention, the thermal denaturation temperature of the CH2 domains is preferably equal to or higher than 40° C., which is the body temperature of an organism. The thermal denaturation temperature of the CH2 domains is more preferably 50° C. or higher, further preferably 60° C. or higher, from the viewpoint of thermal stability after administration into an organism.

The CH2 domain-containing peptide or polypeptide used in the above step (i) is not particularly limited as long as the peptide or the polypeptide contains antibody CH2 domains. The CH2 domain-containing peptide or polypeptide may be an Fc region dimer or may be a polypeptide comprising the Fc region dimer. The CH2 domain-containing peptide or polypeptide may be a heterodimer comprising two CH2 domains (first CH2 domain and second CH2 domain) differing in their amino acid sequences or may be a homodimer comprising the same CH2 domains.

The "peptides or polypeptides containing CH2 domains having diverse amino acid sequences" can be obtained by altering the amino acid sequences of the peptides or the polypeptides. Particularly preferably, the CH2 domains have diversified amino acid sequences. The sites to be diversified are more preferably sites that do not reduce binding activity against FcγR and/or sites that do not decrease the thermal denaturation temperature of the CH2 domains. When the CH2 domain-containing peptide or polypeptide is an Fc region dimer or a polypeptide comprising the Fc region dimer, its amino acid sequence may be diversified such that the Fc region dimer is a heterodimer, or may be diversified such that the Fc region dimer is a homodimer.

Particularly, for obtaining the CH2 domain-containing peptide or polypeptide having binding activity against the desired antigen, the amino acid to be altered preferably resides in the amino acid sequence of a loop region in a CH2 domain. Specifically, in the case of diversifying, for example, the amino acid sequence of an Fc region originated from human IgG1, at least one amino acid selected from EU numbering positions 231 to 239, EU numbering positions 265 to 271, EU numbering positions 295 to 300, and EU numbering positions 324 to 332 is preferably altered. When the Fc region dimer used is a heterodimer, at least one amino acid selected from EU numbering positions 265 to 271 and EU numbering positions 295 to 300 of the first Fc region and EU numbering positions 265 to 271 and EU numbering positions 324 to 332 of the second Fc region is preferably altered. In the present invention, the diversification of an amino acid sequence may be achieved by the random insertion of, to the region mentioned above, a peptide previously known to have binding activity against the desired antigen to prepare a peptide library comprising Fc region dimers having diverse amino acid sequences in their Fc regions, or may be achieved by the insertion of an appropriate length of amino acids to the region mentioned above to prepare a library with increased diversity. For the insertion of amino acids, the number of the amino acids to be inserted is preferably 3 to 9.

For obtaining the CH2 domain-containing peptide or polypeptide having binding activity against FcγR, the amino acid to be altered is preferably at least one amino acid residue selected from EU numbering positions 226 to 447, for example, in the case of diversifying the amino acid sequence of an Fc region originated from human IgG1. More specifically, at least one amino acid residue selected from EU numbering positions 234 to 239, 265 to 271, 295, 296, 298, 300, 324 to 337, 356, 435, and 439 in the amino acid sequence of a human IgG1 constant region is preferably altered.

More specifically, at least one amino acid residue selected from EU numbering positions 234 to 239, 265 to 271, 295, 296, 298, 300, 324, and 325 to 337 in the amino acid sequence of a human IgG1 constant region is more preferably altered.

The polypeptide comprising the Fc region dimer according to the present invention may be prepared using an Fc region dimer previously known to have binding activity against FcγR, such as an IgG Fc region dimer, or an Fc region dimer with the amino acid alteration(s) introduced for enhancing binding activity against FcγR. In such a case, the amino acid sequence of a site that is not involved in FcγR binding may be diversified to select an Fc region dimer whose Fc region has binding activity against each of the desired antigen and FcγR, but does not bind to the antigen and the FcγR at the same time, or a polypeptide comprising the Fc region dimer.

Whether the CH2 domain-containing peptide or polypeptide has binding activity against an antigen or FcγR or whether this peptide or polypeptide does not bind to the antigen and the FcγR at the same time can also be confirmed according to the method for confirming whether the Fc region dimer or the polypeptide comprising the Fc region dimer has binding activity against an antigen or FcγR or whether the Fc region dimer or the polypeptide comprising the Fc region dimer does not bind to the antigen and the FcγR at the same time as mentioned above.

The present invention further includes a polypeptide produced by the production method.

The amino acid mutation introduced by the method according to the present invention is not particularly limited by its type or range.

The present invention further provides a nucleic acid encoding the antibody Fc region dimer comprising an antigen-binding site and an FcγR-binding site, wherein the Fc region dimer does not bind to an antigen and FcγR at the same time, or the polypeptide comprising the Fc region dimer. The nucleic acid of the present invention may be in any form including DNA and RNA.

The present invention further provides a vector comprising the nucleic acid of the present invention. The type of the vector can be appropriately selected by those skilled in the art according to host cells to which the vector is transferred. For example, any of the vectors mentioned above can be used.

The present invention further relates to a host cell transformed with the vector of the present invention. The host cell can be appropriately selected by those skilled in the art. For example, any of the host cells mentioned above can be used.

The present invention also provides a pharmaceutical composition comprising the polypeptide of the present invention. The pharmaceutical composition of the present invention can be formulated according to a method known in the art by using an antibody or an Fc fusion protein molecule, which is the polypeptide of the present invention, and further supplementing the antibody or the molecule with a pharmaceutically acceptable carrier. For example, the pharmaceutical composition can be used in the form of a parenteral injection of an aseptic solution or suspension with water or any other pharmaceutically acceptable solution. For example, the pharmaceutical composition may be formulated with the antibody or the molecule mixed in a unit dosage form required for generally accepted pharmaceutical practice, in appropriate combination with pharmacologically acceptable carriers or media, specifically, sterilized water, physiological saline, plant oil, an emulsifier, a suspending agent, a surfactant, a stabilizer, a flavoring agent, an excipient, a vehicle, a preservative, a binder, etc. Specific examples of the carrier can include light anhydrous silicic acid, lactose, crystalline cellulose, mannitol, starch, carmellose calcium, carmellose sodium, hydroxypropylcellulose, hydroxypropylmethylcellulose, polyvinyl acetal diethylaminoacetate, polyvinylpyrrolidone, gelatin, medium-chain fatty acid triglyceride, polyoxyethylene hydrogenated castor oil 60, saccharide, carboxymethylcellulose, cornstarch, and inorganic salts. The amount of the active ingredient in such a preparation is determined such that an appropriate dose within the prescribed range can be achieved.

An aseptic composition for injection can be formulated according to conventional pharmaceutical practice using a vehicle such as injectable distilled water. Examples of aqueous solutions for injection include physiological saline, isotonic solutions containing glucose and other adjuvants, for example, D-sorbitol, D-mannose, D-mannitol, and sodium chloride. These solutions may be used in combination with an appropriate solubilizer, for example, an alcohol (specifically, ethanol) or a polyalcohol (e.g., propylene glycol and polyethylene glycol), or a nonionic surfactant, for example, polysorbate 80(TM) or HCO-50.

Examples of oily solutions include sesame oil and soybean oil. These solutions may be used in combination with benzyl benzoate or benzyl alcohol as a solubilizer. The solutions may be further mixed with a buffer (e.g., a phosphate buffer solution and a sodium acetate buffer solution), a soothing agent (e.g., procaine hydrochloride), a stabilizer (e.g., benzyl alcohol and phenol), and an antioxidant. The injection solutions thus prepared are usually charged into appropriate ampules. The pharmaceutical composition of the present invention is preferably administered parenterally. Specific examples of its dosage forms include injections, intranasal administration agents, transpulmonary administration agents, and percutaneous administration agents. Examples of the injections include intravenous injection, intramuscular injection, intraperitoneal injection, and subcutaneous injection, through which the pharmaceutical composition can be administered systemically or locally.

Also, the administration method can be appropriately selected depending on the age, symptoms, etc. of a patient. The dose of a pharmaceutical composition containing the polypeptide or a polynucleotide encoding the polypeptide can be selected within a range of, for example, 0.0001 to 1000 mg/kg of body weight per dose. Alternatively, the dose can be selected within a range of, for example, 0.001 to 100000 mg/body of a patient, though the dose is not necessarily limited to these numeric values. Although the dose and the administration method vary depending on the weight, age, symptoms, etc. of a patient, those skilled in the art can appropriately select the dose and the method.

The three-letter codes and corresponding one-letter codes of amino acids used herein are defined as follows: alanine: Ala and A, arginine: Arg and R, asparagine: Asn and N, aspartic acid: Asp and D, cysteine: Cys and C, glutamine: Gln and Q, glutamic acid: Glu and E, glycine: Gly and G, histidine: His and H, isoleucine: Ile and I, leucine: Leu and L, lysine: Lys and K, methionine: Met and M, phenylalanine: Phe and F, proline: Pro and P, serine: Ser and S, threonine: Thr and T, tryptophan: Trp and W, tyrosine: Tyr and Y, and valine: Val and V.

All references cited herein are incorporated herein by reference in their entirety.

The present invention will be further illustrated with reference to Examples below. However, the present invention is not intended to be limited by Examples below.

EXAMPLES

[Example 1] Concept of Altered Immunoglobulin Constant Regions (IgG Fc Region) that Bind to Each of FcγR and Antigen, but do not Binds to FcγR and Antigen at the Same Time Naturally occurring immunoglobulin binds to an antigen via its variable regions and binds to a receptor (e.g., FcγR, FcRn, FcαR, or FcεR) or a complement via its constant regions. FcRn, a binding molecule that interacts with the Fc region of IgG, binds by one molecule to each of antibody heavy chains and as such, reportedly binds by two molecules to one molecule of the IgG antibody. Unlike FcRn, etc., FcγR binds, as shown in FIG. 1, interacts with antibody hinge regions and CH2 domains and binds only by one molecule to one molecule of the IgG antibody (J. Bio. Chem., (20001) 276, 16469-16477).

Figure 2:
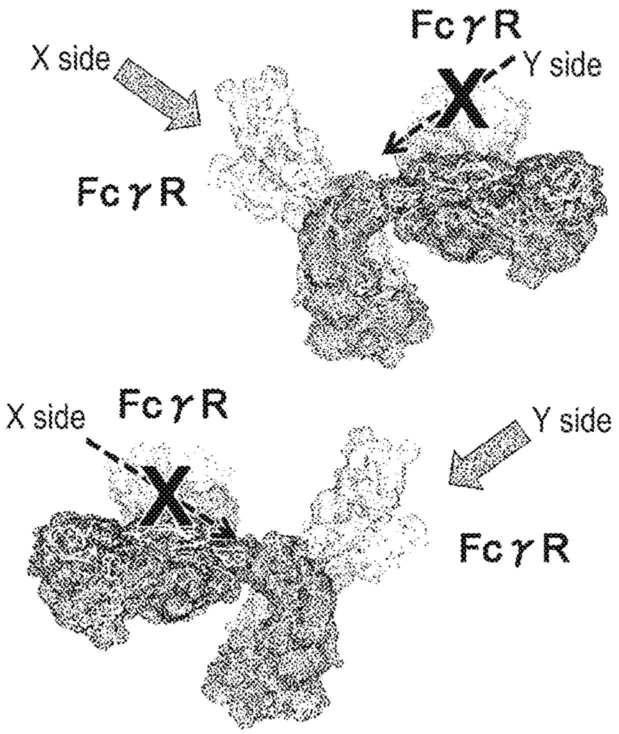
FIG. 2 is a diagram showing that two FcγR molecules cannot bind to an IgG molecule. When the first FcγR molecule binds to an IgG molecule from the X side, Fab falls over toward the Y side to hinder the second FcγR molecule from binding to the IgG molecule from the Y side. Likewise, when the first FcγR molecule binds to an IgG molecule from the Y side, Fab falls over toward the X side to hinder the second FcγR molecule from binding to the IgG molecule from the X side.

Only one FcγR molecule binds to one molecule of the IgG antibody, probably because one FcγR molecule binds to the Fc region of one IgG antibody molecule and thereby changes the structure of the IgG antibody to hinder the second FcγR molecule from binding to the Fc region. Specifically, as shown in FIG. 1, the N terminus of the hinge region of the IgG antibody is oriented opposite to the binding site of FcγR bound from the X side. When the position of the Fab region is predicted from the N-terminal main chain structure of the hinge region, the Fab region takes a structure where Fab is more inclined than usual (structure where Fab is located closer to the Fc region) as shown in FIG. 2 to hinder the second FcγR molecule from coming close to the Fc region from the Y side. As a result, the second FcγR molecule may no longer bind to the Fc region.

The IgG antibody is naturally controlled so as not to be able to bind to two FcγR molecules because its binding to two FcγR molecules at the same time causes the cross-linking reaction between these two FcγR molecules. For example, two molecules of activating FcγR, when cross-linked, transduce activating FcγR ITAM signals, resulting in the possible IgG antibody-mediated activation of immunocytes. This is not favorable for biological reaction. The IgG antibody is therefore designed so as to be able to bind to only one FcγR molecule. Consequently, two or more molecules of activating FcγR are cross-linked only in the presence of an antigen to activate immunocytes.

On the other hand, when the IgG antibody binds to a first antigen via its variable regions (Fab), this IgG antibody can also bind to one FcγR molecule via its Fc region at the same time therewith. In this case, cross-link occurs between the first antigen and FcγR. Depending on the antigen, the cross-link between the antigen and FcγR may not be favorable. This is because, for example, the antigen cross-linked with FcγR may cause immune activation such as cytokine release (J. Immunol. (1999) August 1, 163 (3), 1246-52). In such a case, the Fc region can lose its binding activity against FcγR by the introduction of alteration to prevent the cross-linking reaction between the first antigen and FcγR (Advanced Drug Delivery Reviews (2006) 58, 640-656).

A conventional naturally occurring IgG antibody can merely bind to the first antigen via its variable regions (Fab). The advanced technique of preparing bispecific antibodies can now confer binding activity against the second antigen by improving the naturally occurring IgG antibody (MAbs. (2012) March 1, 4 (2)). Specifically, use of an Fc region having binding activity against each of the first antigen and the second antigen and binding activity against FcγR enables the preparation of an improved antibody that causes the cross-linking reaction between the first antigen and the FcγR, the cross-linking reaction between the second antigen and the FcγR, and the cross-linking reaction between the first antigen and the second antigen. On the other hand, use of an Fc region with reduced binding activity against FcγR also enables the preparation of an improved antibody that causes the cross-linking reaction only between the first antigen and the second antigen while preventing both of the cross-linking reaction between the first antigen and the FcγR and the cross-linking reaction between the second antigen and the FcγR.

Figure 3:
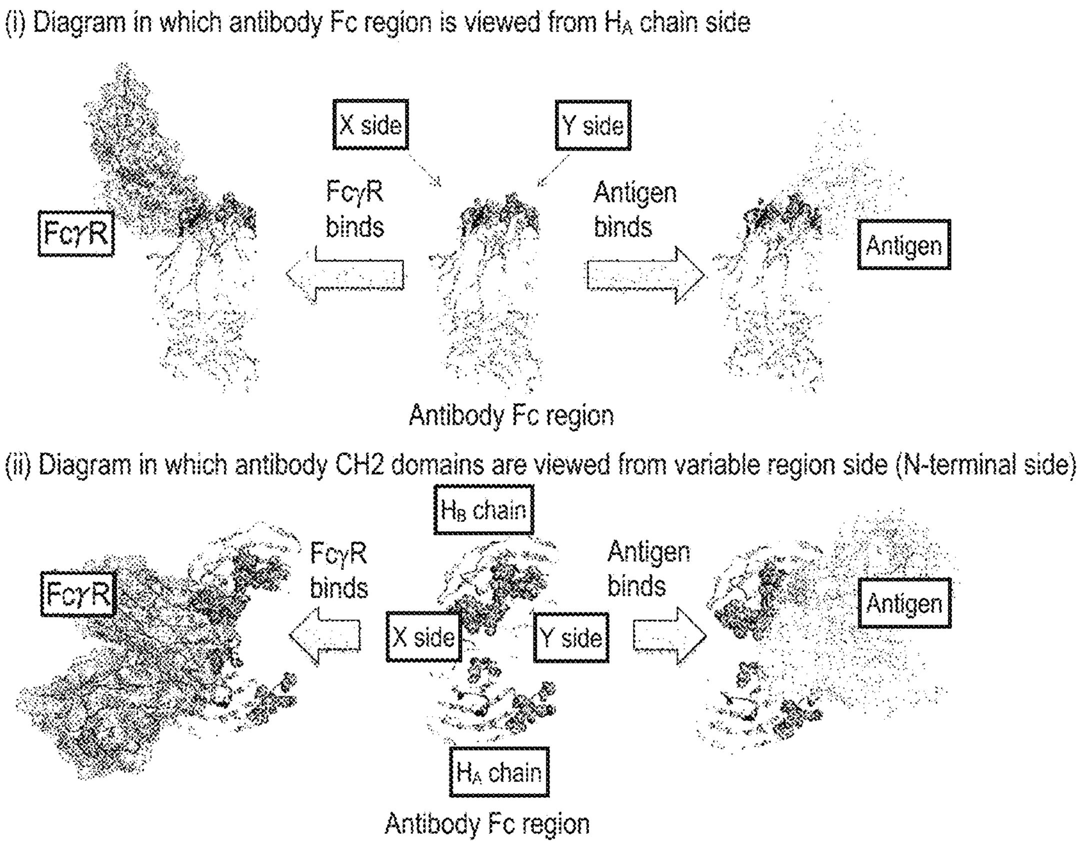
FIG. 3 is a pair of diagrams (diagram (i) and diagram (ii)) showing the concept of dual binding Fc to which FcγR binds from the X side and a second antigen binds from the Y side. Diagram (i) shows the structure of an antibody-FcγR complex viewed from the HA chain side. Diagram (ii) shows the structure of an antibody-FcγR complex viewed from the HA chain side, from above (N-terminal side).
Figure 4:
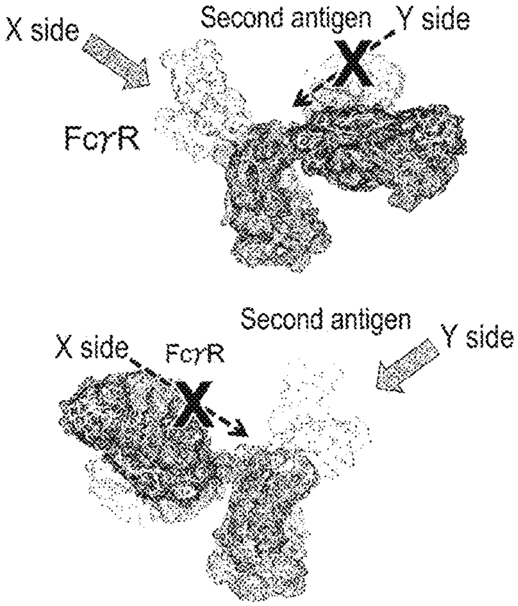
FIG. 4 is a diagram showing that FcγR and a second antigen cannot bind at the same time to an IgG molecule having dual binding Fc. When FcγR binds to an IgG molecule from the X side, Fab falls over toward the Y side to hinder the second antigen from binding to the IgG molecule from the Y side. Likewise, when the second antigen binds to an IgG molecule from the Y side, Fab falls over toward the X side to hinder the FcγR from binding to the IgG molecule from the X side.
Figure 5:
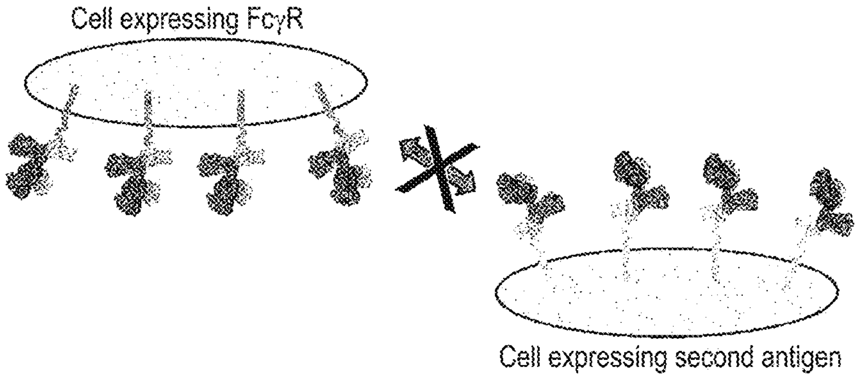
FIG. 5 is a diagram showing that cross-linking reaction does not occur between FcγR and a second antigen because the FcγR and the second antigen cannot bind at the same time.

The previous methods, however, cannot prepare an improved antibody that causes the cross-linking reaction between the first antigen and the FcγR and the cross-linking reaction between the first antigen and the second antigen, while preventing the cross-linking reaction between the second antigen and the FcγR. Accordingly, the present inventors assumed that the disability of the Fc region to bind to two FcγR molecules at the same time can be used in a method for achieving such controlled cross-linking reactions. Specifically, one possible approach was dual binding Fc that has binding activity based on its variable regions (Fab) against the first antigen and binds to one FcγR molecule on the X side (X surface) of the Fc region and to one second antigen molecule on the improved Y side (Y surface) of the Fc region (FIG. 3). The H chain shown on the left side in FIG. 1 is referred to as an $H_A$ chain, while the H chain shown on the right side is referred to as an $H_B$ chain. FIG. 3 shows the structure of an antibody-FcγR complex viewed from the $H_A$ chain side and the structure of the complex viewed from above (N-terminal side). The FcγR-binding surface is located on the X side, while the second antigen-binding surface is located on the Y side. Just as the Fc region cannot bind to two FcγR molecules at the same time, the improved antibody provided with the property of binding to the second antigen on the Y side probably changes its structure upon binding to the second antigen on the Y side, as shown in FIG. 4, to inhibit the binding to FcγR on the X side. Likewise, the binding of this improved antibody to the second antigen on the Y side is probably inhibited by the binding to FcγR on the X side. Thus, the improved antibody having such properties of dual binding Fc cannot bind to the FcγR and the second antigen at the same time and as such, is unlikely to cause the cross-linking reaction between the FcγR and the second antigen (FIG. 5). By contrast, the first antigen, which binds to the variable regions (Fab), presumably undergoes cross-linking reaction with FcγR (FIG. 6) and also undergoes cross-linking reaction with the second antigen (FIG. 7).

Figure 6:
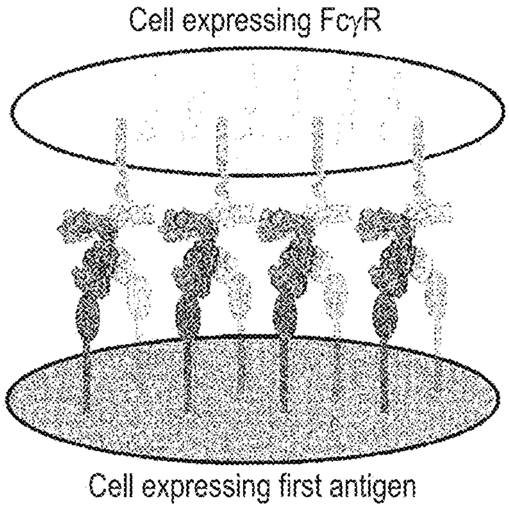
FIG. 6 is a diagram showing that cross-linking reaction occurs between a first antigen binding to variable regions (Fab) and FcγR.
Figure 7:
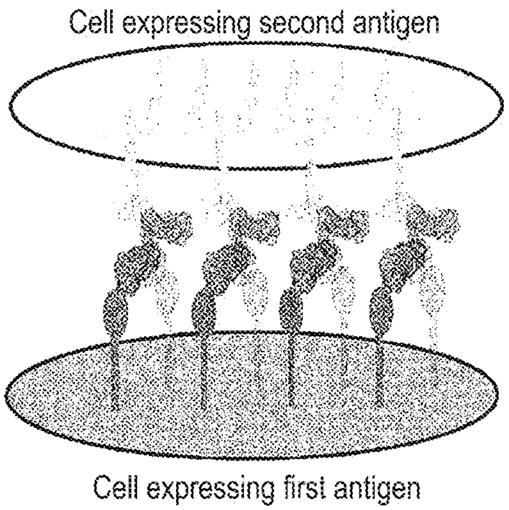
FIG. 7 is a diagram showing that cross-linking reaction occurs between a first antigen and a second antigen.

Briefly, if an Fc region can be improved as dual binding Fc to confer the following properties, an antibody having the effects as shown in FIGS. 5 to 7 can be developed:

1. having strong binding activity against FcγR on the X side;
2. having binding activity against an antigen of interest (second antigen) on the Y side; and
3. not binding to the FcγR and the antigen (which binds to the Y side) at the same time.

[Example 2] Concept of Enhanced Binding Activity Against FcγR on X Side

As described in Example 1, the dual binding Fc refers to a molecule that binds to FcγR on the X side and to the second antigen on the Y side, but does not binds to the FcγR and the second antigen at the same time. In the case of introducing amino acid alteration to the Fc region for binding to the second antigen, the amino acid alteration is usually introduced to both of two H chains. This introduction of the alteration to both of the H chains alters amino acids not only on the Y side of interest but on the X side. As a result of introducing the alteration to the X side, interaction with FcγR on the X side might be reduced. Thus, the dual binding Fc requires introducing alteration for enhancing the interaction with FcγR to the X side and introducing alteration for enhancing the interaction with an antigen to the Y side.

Since a conventional antibody is a homodimer, FcγR is capable of binding thereto both from the X side and from the Y side. In this respect, which of the surfaces is contacted with the receptor is not distinguishable. Thus, only the binding of the antibody on the X side remains, if its binding activity against FcγR is completely lost, for example, due to alteration on the Y side. The resulting antibody is presumed to have half the chance of binding to FcγR, compared with naturally occurring IgG, and have lower binding activity. However, the interaction of the antibody with FcγR on the X side enhanced by the amino acid alteration of the Fc region can probably secure sufficient FcγR binding, even if the Y side does not contribute to the binding. In such a state, the concept of the dual binding Fc can be achieved, provided that binding activity against the antigen of interest can be conferred to the Y side.

The interaction with FcγR on the X side of such an antibody molecule binding to the antigen on the Y side can be kept at a level equivalent to or higher than that of a naturally occurring IgG antibody (which means that binding activity against FcγR is maintained) or the binding activity against each FcγR can be enhanced (optimized) by a method which involves introducing amino acid alteration to enhance the interaction with FcγR. The previously reported amino acid alteration to enhance the interaction with FcγR is symmetrically introduced such that the same alterations are added to two heavy chains constituting the Fc region (WO2006/019447 and WO2000/042072).

Figure 8:
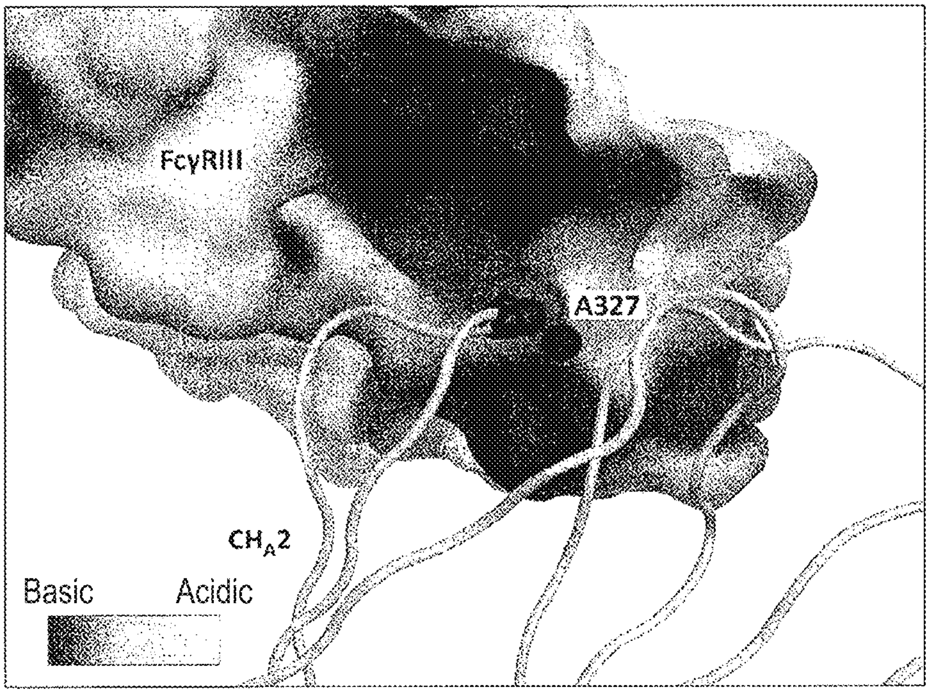
FIG. 8 is a pair of diagrams (diagram (A) and diagram (B)) showing that FcγR is recognized via the respective CH2 domains of two antibody heavy chains, whereas these heavy chains differ in their amino acids interacting with FcγR. Diagram (A) shows that Ala 327 (EU numbering) in the $H_A$ chain interacts with a partner residue in FcγRIII that has the property of being basic (as opposed to acidic). Diagram (B) shows that Ala 327 (EU numbering) in the $H_B$ chain interacts with a partner residue in FcγRIII that is acidic.
Figure 8:
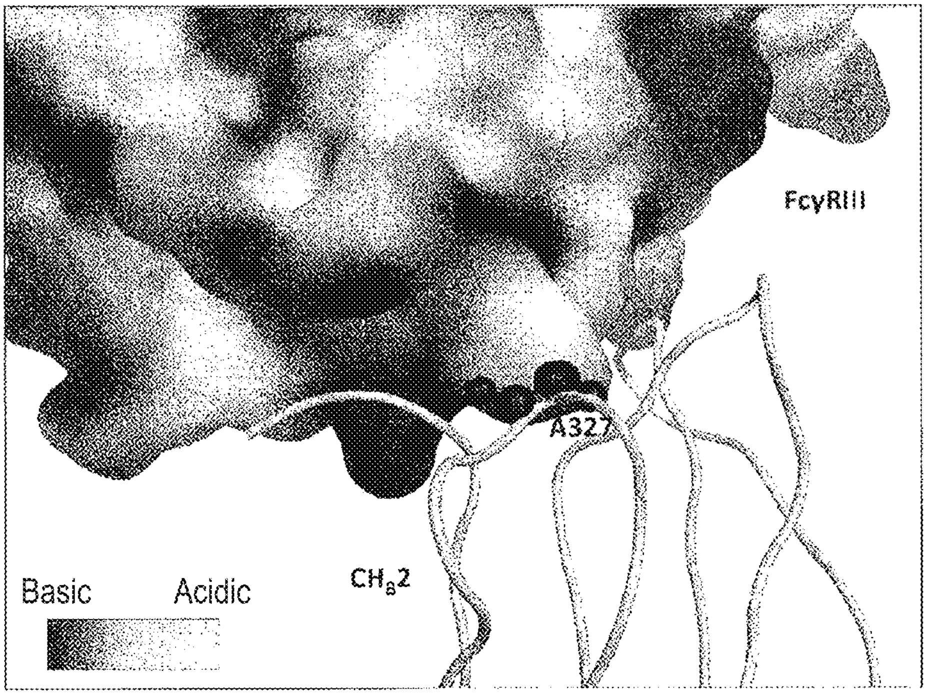

Meanwhile, the antibody recognizes FcγR via the CH2 domains of its two heavy chains, which however differ in their amino acids that interact with FcγR. This means that the CH2 domains asymmetrically interact in the interaction of the antibody with FcγR. For example, Ala 327 (EU numbering) interacts with FcγR in each of the $H_A$ chain and the $H_B$ chain, but differs in the properties of partner residues that interact with these H chains (FIG. 8). Ala 327 (EU numbering) in the $H_A$ chain hydrophobically interacts with Trp 87 (EU numbering) and Trp 110 (EU numbering) of FcγRIII, whereas this residue in the HE chain interacts with His 131 (EU numbering) of FcγRIII. For this reason, the substitution of Ala 327 (EU numbering) by a highly hydrophobic amino acid such as Trp is effective for improving the binding activity of the $H_A$ chain against FcγR, but might reduce the binding activity of the $H_B$ chain against FcγR.

This suggests that the asymmetric effects of each H chain on FcγR should be taken into consideration for optimizing the interaction of the IgG Fc region with FcγR on the X side by means of amino acid alteration. However, considering the asymmetric interaction of the IgG Fc region with FcγR, the introduction of different alterations to the H chains may be more likely to precisely optimize the interaction between IgG and FcγR. Specifically, it appeared that a heterodimerized antibody, which is an antibody with H chains altered differently to optimize the interaction of the Fc region with FcγR, could be used to enhance (optimize) the interaction with FcγR on the X side, compared with a homodimerized antibody, which is an antibody with identically altered H chains carried out by the conventional technique. Use of the heterodimerized antibody having the enhanced interaction with FcγR on the X side probably enables the development of dual binding Fc that has strong binding activity against FcγR on the X side and has binding activity against the antigen of interest on the Y side, but does not bind to the FcγR and the antigen (which binds to the Y side) at the same time.

[Example 3] Enhanced Binding Activity of Heterodimerized Antibody Against FcγR on X Side (3-1) Proof of Concept of Enhanced Binding Activity of Heterodimerized Antibody Against FcγR on X Side A study was conducted on whether use of a heterodimerized antibody was able to enhance (optimize) the binding activity against FcγR on the X side.

Heretofore, alteration that enhances binding activity against FcγR has been searched for by using a homodimerized antibody with the same alterations introduced in both H chains of an antibody. As mentioned in Example 2, however, the same alterations introduced in both H chains enhance the binding activity of one H chain against FcγR, but might inhibit the FcγR binding of the other H chain, due to the asymmetric interaction between the antibody and FcγR. The homodimerized antibody with such alterations introduced in both H chains does not always have the enhanced binding activity against FcγR, whereas a heterodimerized antibody with only one H chain altered may have the enhanced binding activity against FcγR. In other words, this alteration can be found to enhance the interaction with FcγR on the X side, but not always enhance the interaction with FcγR on the Y side. Such alteration can be regarded as alteration that enhances binding activity on the X side.

Figure 9:
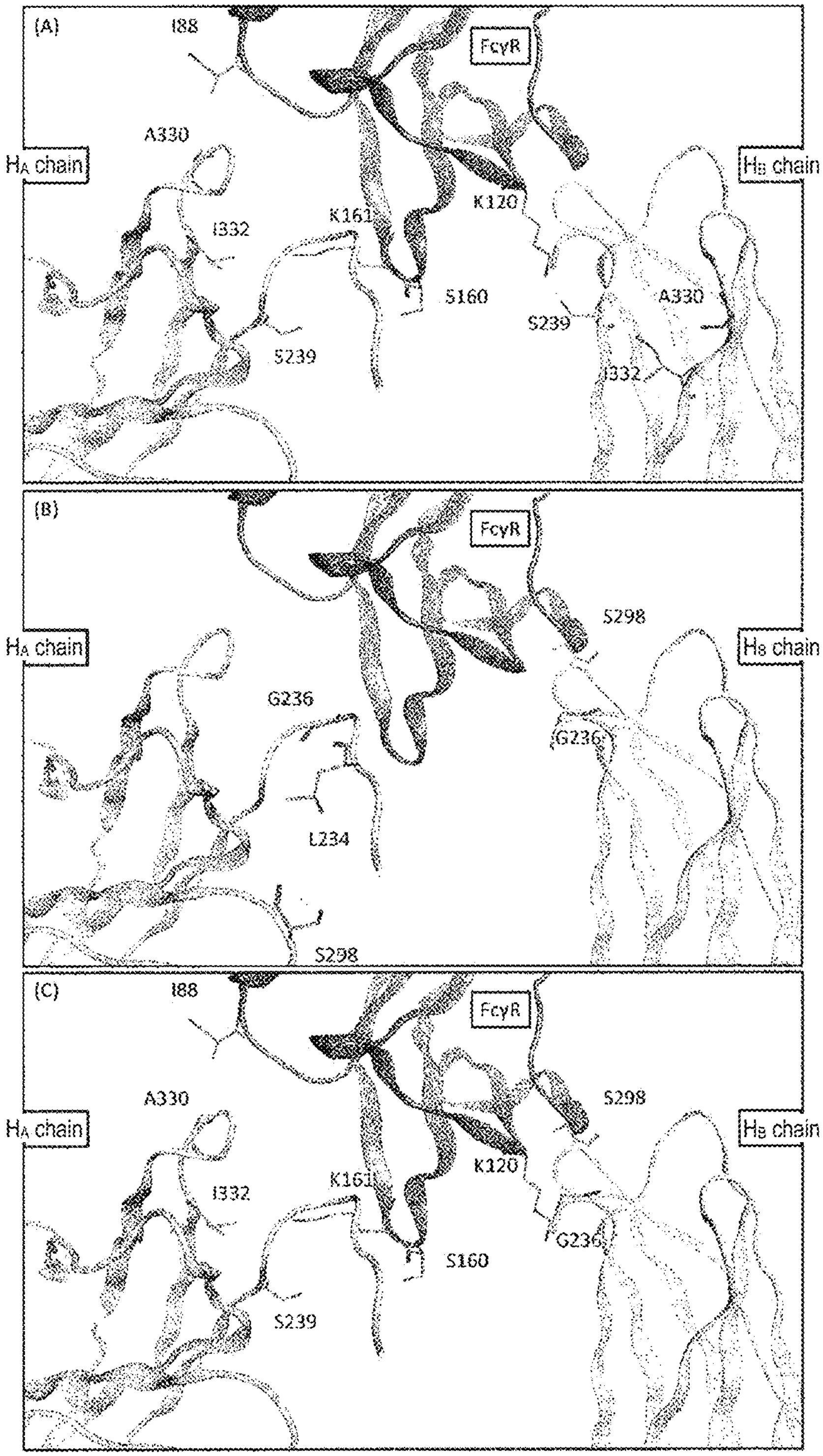
FIG. 9 is a diagram showing the interaction of each of (A) residues S239, A330, and I332, (B) residues L234, G236, and S298, and (C) residues S239, A330, and I332 of the $H_A$ chain and G236 and S298 of the $H_B$ chain in the antibody Fc region with FcγRIII (PDB database: 1T89).

Specifically, in the case of an antibody with introduced S239D, I332E, and A330L alterations, its three-dimensional structure suggests that the altered residues of S239D, I332E, and A330L in the $H_A$ chain are all involved in enhancing the interaction with FcγR, whereas these residues, except for S239D, in the $H_B$ chain does not contact with FcγR, probably making no contribution to the enhanced binding activity against FcγR on the X side (FIG. 9). Considering the asymmetric property of the interaction between the Fc region and FcγR, each alteration introduced by the conventional antibody alteration technique seems to be insufficient for optimizing the interaction between the antibody and FcγR due to its disability to secure sufficient interaction with FcγR on the X side and on the Y side. For example, in the case of the S239D, I332E, and A330L alterations, alteration(s) that enhance the interaction with FcγRIIIa from the $H_B$ chain side may be introduced instead of these alterations to the $H_B$ chain to further enhance the binding activity against FcγRIIIa on the X side.

The three-dimensional structure of the Fc-FcγRIIIa complex suggests that in contrast to S239D, I332E, or A330L, S298 interacts only in the $H_B$ chain (FIG. 9) with FcγR (JBC, 276: 16469-16477, 2001). This may indicate that the introduction of an alteration to S298 allows the amino acid residue substituted therefore to also interact with FcγRIIIa on the $H_B$ chain side. Thus, S239D, A330L, and I332E are introduced to one H chain, while L234Y, G236W, and S298A are introduced to the other H chain. All the residues thus altered can interact with FcγR at the same time. As a result, the interaction with FcγR may be further enhanced.

In order to test this hypothesis, S239D, A330L, and I332E were introduced to one H chain, and L234Y, G236W, and S298A were introduced to the other H chain to prepare a heterodimerized antibody. In addition, homodimerized antibodies (conventional technique) based on each altered H chain and heterodimerized antibodies comprising each altered H chain and a naturally occurring IgG1 constant region were prepared. The antibodies thus prepared were compared in terms of binding activity against FcγR. The conventional idea assumes that if a certain alteration enhances binding activity against FcγR, the homodimerized antibody must always be superior in this respect to the heterodimerized antibody. Depending on the type of the alteration, however, the heterodimerized antibody is supposed to exhibit stronger binding activity against FcγR than that of the homodimerized antibody, provided that antibody Fc asymmetrically recognizes FcγR.

An anti-glypican 3 antibody variable region comprising CDRs of pH7 of an anti-glypican 3 antibody having improved kinetics in plasma as disclosed in WO2009/041062 was used as the variable region of an antibody H chain and designated as GpH7 (SEQ ID NO: 1). Antibody H chain constant regions shown below were used in combination with GpH7. In this context, a sequence corresponding to an antibody H chain having constant regions designated as H1 and the variable region GpH7 is designated as GpH7-H1. The alteration of an amino acid is represented by, for example, D356K. The first alphabet (which corresponds to D in D356K) means an alphabet that represents the one-letter code of the amino acid residue before the alteration. The number (which corresponds to 356 in D356K) following the alphabet means the EU numbering position of this altered residue. The last alphabet (which corresponds to K in D356K) means an alphabet that represents the one-letter code of an amino acid residue after the alteration. GpH7-G1d (SEQ ID NO: 2) derived from IgG1 having the variable region GpH7 by the deletion of C-terminal Gly and Lys, GpH7-A5 (SEQ ID NO: 3) derived from GpH7-G1d by the introduction of D356K and H435R mutations, and GpH7-B3 (SEQ ID NO: 4) derived from GpH7-G1d by the introduction of a K439E mutation were prepared according to the method of Reference Example 1. The D356K and K439E mutations introduced in the respective H chains were introduced for the purpose of efficiently forming heterodimerized forms based on each H chain in the production of a heterodimerized antibody consisting of two H chains (WO2006/106905). The H435R alteration hampers binding to protein A and was introduced for the purpose of efficiently separating heterodimerized forms from homodimerized forms (WO/2011/078332). Likewise, GpL16-k0 (SEQ ID NO: 5), which is the L chain of the anti-glypican 3 antibody having improved kinetics in plasma as disclosed in WO2009/041062, was used as an antibody L chain.

A mutation for proving the concept of the heterodimerized antibody was introduced to GpH7-A5 and GpH7-B3 as parent polypeptides to prepare altered forms, which were then used in evaluation. Prepared expression vectors were used in the transfection of FreeStyle 293 cells (Invitrogen Corp.) according to the method of Reference Example 1. The expressed antibodies were purified according to the method of Reference Example 1. An expression vector having a gene insert of the antibody L chain GpL16-k0 and an expression vector having a gene insert of one type of antibody H chain sequence were used for the expression of a homodimerized antibody. An expression vector having a gene insert of the antibody L chain GpL16-k0, as in the homodimerized antibody, and an expression vector having a gene insert of a sequence further altered from GpH7-A5 with the introduced D356K alteration as one antibody H chain were used for the expression of a heterodimerized antibody. In addition, an expression vector having a gene insert of a sequence further altered from GpH7-B3 with the introduced K439E alteration as another antibody H chain was used to permit efficient expression of the heterodimerized antibody. Each antibody obtained by purification after the expression is represented by, for example, GpH7-H1/GpH7-H2/GpL16-k0 wherein GpH7-H1 is used for one of the expression vectors corresponding to the antibody H chains used in the heterodimerized antibody expression; GpH7-H2 is used as another antibody H chain; and GpL16-k0 is used for the expression vector corresponding to the antibody L chain. In this respect, the sequence with the introduced D356K and H435R alterations was set to H1, while the sequence with the introduced K439E alteration was set to H2.

Next, expression vectors having a gene insert of GpH7-A57 (SEQ ID NO: 6) derived from GpH7-A5 by the introduction of all of S239D, A330L, and I332E, GpH7-B78 (SEQ ID NO: 7) derived from GpH7-B3 by the introduction of these alterations, GpH7-TA7 (SEQ ID NO: 8) derived from GpH7-A5 by the introduction of all of L234Y, G236W, and S298A, or GpH7-TA45 (SEQ ID NO: 9) derived from GpH7-B3 by the introduction of these alterations were prepared according to the method of Reference Example 1. These expression vectors and GpH7-A5, GpH7-B3, and GpL16-k0 were used in the expression and preparation of heterodimeric GpH7-TA7/GpH7-B78/GpL16-k0 with L234Y, G236W, and S298A introduced in one H chain and S239D, A330L, and I332E introduced in the other H chain, GpH7-TA7/GpH7-B3/GpL16-k0 with only L234Y, G236W, and S298A introduced in one H chain, GpH7-TA7/GpH7-TA45/GpL16-k0 with L234Y, G236W, and S298A introduced in both H chains, GpH7-A5/GpH7-B78/GpL16-k0 with only S239D, A330L, and I332E introduced in one H chain, and GpH7-A57/GpH7-B78/GpL16-k0 with S239D, A330L, and I332E introduced in both H chains according to the method of Reference Example 1. The prepared antibodies were compared in terms of binding activity against FcγRIIIa using, as an index, KD against FcγRIIIa measured according to the method of Reference Example 2. The results of testing effects brought about by the combination of L234Y, G236W, and S298A as well as S239D, A330L, and I332E are summarized in Table 5.

TABLE 5

| Sample | SEQ ID NO | H1 | Mutation position | | | H2 | Mutation position | | | KD[M] | KD ratio1 | KD ratio2 |
|---|---|---|---|---|---|---|---|---|---|---|---|---|
| GpH7-G1d/GpL16-k0 | SEQ ID NO: 2, 5 | G1d | | | | G1d | | | | 1.2E−06 | 1 | |
| GpH7-A5/GpH7-B3/GpL16-k0 | SEQ ID NO: 3, 4, 5 | A5 | — | — | — | B3 | — | — | — | 1.6E−06 | 0.75 | 1 |

TABLE 5-continued

| Sample | SEQ ID NO | H1 | Mutation position | | | H2 | Mutation position | | | KD[M] | KD ratio1 | KD ratio2 |
|---|---|---|---|---|---|---|---|---|---|---|---|---|
| GpH7-TA7/GpH7-B3/GpL16-k0 | SEQ ID NO: 8, 4, 5 | TA7 | L234Y | G236W | S298A | B3 | — | — | — | 3.2E−07 | 3.8 | 5.1 |
| GpH7-A5/GpH7-B78/GpL16-k0 | SEQ ID NO: 3, 7, 5 | A5 | — | — | — | B78 | S239D | A330L | I332E | 5.4E−08 | 23 | 30 |
| GpH7-A57/GpH7-B78/GpL16-k0 | SEQ ID NO: 6, 7, 5 | A57 | S237D | A330L | I332E | B78 | S239D | A330L | I332E | 6.2E−09 | 199 | 263 |
| GpH7-TA7/GpH7-TA45/GpL16-k0 | SEQ ID NO: 8, 9, 5 | TA7 | L234Y | G236W | S298A | TA45 | L234Y | G236W | S298A | 3.3E−06 | 0.37 | 0.49 |
| GpH7-TA7/GpH7-B78/GpL16-k0 | SEQ ID NO: 8, 7, 5 | TA7 | L234Y | G236W | S298A | B78 | S239D | A330L | I332E | 4.7E−09 | 261 | 347 |

The column "Sample" represents an antibody name. The columns "H1" and "H2" represent the names of the H chain constant regions of each antibody. The column "Mutation position" represents mutations different from those in GpH7-A5/GpH7-B3/GpL16-k0 ("–" denotes no particular mutation). KD ratio 1 is defined as a value determined by dividing the KD of GpH7-G1d/GpL16-k0 against FcγRIIIa by the KD of each antibody. KD ratio 2 is defined as a value determined by dividing the KD of GpH7-A5/GpH7-B3/GpL16-k0 against FcγRIIIa by the KD of each antibody. SEQ ID NOs of amino acid sequences corresponding to the H and L chains of each antibody are also shown in the table.

In light of the results shown in Table 5, first, D356K/H435R and K439E introduced for the heterodimerized antibody preparation were each tested for the influence of introduction to one H chain on the interaction with FcγR. The naturally occurring IgG1 GpH7-G1d/GpL16-k0 was compared with GpH7-A5/GpH7-B3/GpL16-k0 having D356K/H435R and K439E respectively introduced to the H chains. As a result, this altered form varied by 0.75 times in binding activity against FcγRIIIa, and no large difference was observed. This indicated that the D356K, H435R, and K439E alterations had no influence on binding activity against FcγR.

In light of the results of Table 5, next, each heterodimerized antibody was tested for its potential to enhance (optimize) the interaction with FcγR.

The homodimerized antibody prepared using the conventional technique was tested for the effects of each alteration. The homodimerized antibody GpH7-A57/GpH7-B78/GpL16-k0 with S239D, A330L, and I332E introduced in both H chains had FcγRIIIa-binding activity approximately 260 times stronger than that of GpH7-A5/GpH7-B3/GpL16-k0, whereas the homodimerized antibody GpH7-TA7/GpH7-TA45/GpL16-k0 with L234Y, G236W, and S298A introduced in both H chains had FcγRIIIa-binding activity 0.49 times weaker than that of GpH7-A5/GpH7-B3/GpL16-k0. These results demonstrated that only the alteration group of S239D, A330L, and I332E is effective for enhancing the binding activity of the homodimerized antibody against FcγRIIIa.

Each heterodimerized antibody with each alteration group introduced in one H chain was tested for the effects of this alteration group. The heterodimerized antibody GpH7-A5/GpH7-B78/GpL16-k0 with S239D, A330L, and I332E introduced in one H chain had FcγRIIIa-binding activity 30 times stronger than that of GpH7-A5/GpH7-B3/GpL16-k0. The heterodimerized antibody GpH7-TA7/GpH7-B3/GpL16-k0 with L234Y, G236W, and S298A introduced in one H chain had FcγRIIIa-binding activity 5.1 times stronger than that of GpH7-A5/GpH7-B3/GpL16-k0. These results demonstrated that the alteration group of S239D, A330L, and I332E is more effective for enhancing the binding activity against FcγRIIIa.

Each alteration group was tested for the difference in its effects between the homodimerized antibody and the heterodimerized antibody. The alteration group of S239D, A330L, and I332E enhanced FcγRIIIa-binding activity by 30 times in the heterodimerized antibody compared with GpH7-A5/GpH7-B3/GpL16-k0 and enhanced the binding activity by approximately 260 times in the homodimerized antibody, demonstrating that this alteration group introduced in the homodimerized antibody further enhances the binding activity against FcγRIIIa. On the other hand, the alteration group of L234Y, G236W, and S298A enhanced FcγRIIIa-binding activity by 5.1 times in the heterodimerized antibody compared with GpH7-A5/GpH7-B3/GpL16-k0 and however, attenuated the binding activity to 0.49 times in the homodimerized antibody. These results show that the alteration group of L234Y, G236W, and S298A is found effective for enhancing the binding activity against FcγRIIIa only in the heterodimerized antibody.

The results described above showed that: only the alteration group of S239D, A330L, and I332E is effective for enhancing the FcγRIIIa binding of the homodimerized antibody; and the alteration group of S239D, A330L, and I332E is more effective for enhancing even the FcγRIIIa binding of the heterodimerized antibody. In view of the possible combination of the alteration group of S239D, A330L, and I332E and the alteration group of L234Y, G236W, and S298A from these results, the homodimerized antibody GpH7-A57/GpH7-B78/GpL16-k0 prepared by the introduction of only the alteration group of S239D, A330L, and I332E, which highly enhances FcγRIIIa binding both in the heterodimerized antibody and in the homodimerized antibody, to both H chains is predicted to be most effective for enhancing the FcγRIIIa binding, on the basis of the conventional idea. Nonetheless, the heterodimerized antibody GpH7-TA7/GpH7-B78/GpL16-k0 with S239D, A330L, and I332E introduced in one H chain and L234Y, G236W, and S298A introduced in the other H chain had FcγRIIIa-binding activity approximately 350 times stronger than that of GpH7-A5/GpH7-B3/GpL16-k0, showing a higher binding activity-enhancing effect than that of the homodimerized antibody with S239D, A330L, and I332E introduced in both H chains. This result seemed to support the hypothesis that all the alterations in the alteration group of S239D, A330L, and I332E and the alteration group of L234Y, G236W, and S298A respectively introduced to different H chains could enhance the FcγRIIIa-binding activity of each of the $H_A$ chain and the H3 chain and exert higher effects than those of the alteration group of S239D, A330L, and I332E introduced in both H chains.

The results described above demonstrated that use of the heterodimerized antibody can further optimize the asymmetric interaction between the Fc region and FcγRIIIa and can design an Fc region having higher binding activity, compared with use of the conventional homodimerized antibody. Specifically, the adoption of such alteration groups was shown to be able to enhance (optimize) the interaction of a dual binding Fc molecule with FcγR on the X side. Furthermore, the homodimerized antibody with the alteration group of L234Y, G236W, and S298A introduced in both chains interacted with FcγR at an attenuated level, showing that the alteration group of L234Y, G236W, and S298A enhances binding activity against FcγR on the X side, but is ineffective from the viewpoint of enhancing the interaction with FcγR on the Y side, without participating in the binding to FcγR on the Y side. In this respect, the Y side can be utilized in interaction with an antigen. It therefore appeared that the heterodimerized antibody with different alterations introduced in the first H chain and the second H chain could be applied to dual binding Fc.

(3-2) Regarding ADCC Activity of Heterodimerized Antibody Having Enhanced Binding Activity Against FcγRIIIa As discussed in the preceding paragraph, use of the heterodimerized antibody was able to enhance the interaction with FcγR on the X side and successfully achieved the stronger binding activity against FcγRIIIa than that of the altered form developed by the conventional homodimerized antibody technique. Antibodies induce NK cells via FcγRIIIa, exerting antibody-dependent cytotoxic activity against cells expressing target antigens. In order to confirm that not only the binding activity against FcγRIIIa but ADCC activity was also enhanced in the heterodimerized antibody, ADCC activity was measured according to the method of Reference Example 3 as to the heterodimerized antibodies having the enhanced binding activity against FcγRIIIa, the homodimerized antibodies, and the naturally occurring IgG1 described in Table 5. The results are shown in FIG. 10.

Figure 10:
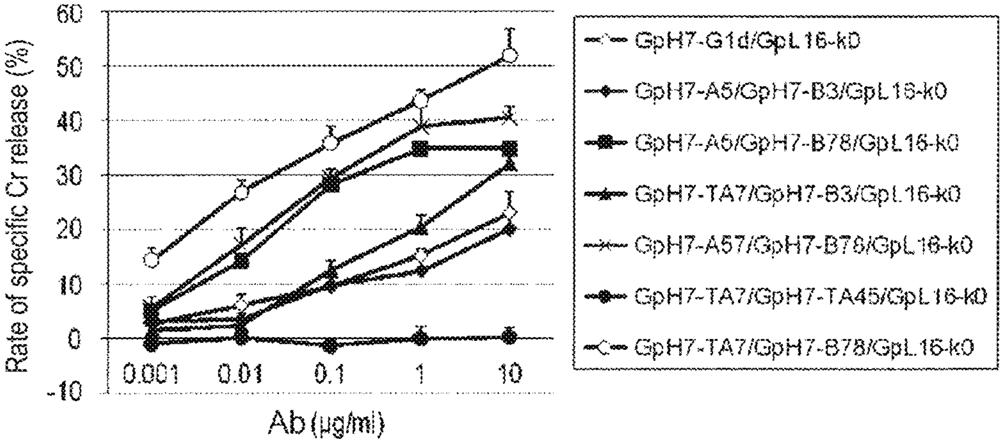
FIG. 10 is a diagram showing the ADCC activity of each antibody that exhibits enhanced binding activity against FcγR on the X side by a heterodimer YWA-DLE variant.

As seen from the results of FIG. 10, no large difference in ADCC activity was observed between the naturally occurring IgG1, GpH7-G1d/GpL16-k0, and GpH7-A5/GpH7-B3/GpL16-k0 with D356K/H435R and K439E respectively introduced to the H chains. This indicated that the D356K, H435R, and K439E alterations had no influence on ADCC activity.

Next, the conventional homodimerized antibody in which the same alterations for enhancing binding activity against FcγRIIIa were introduced in both H chains of the antibody was tested for whether its binding activity-enhancing effect exhibited similar tendency toward ADCC activity. GpH7-TA7/GpH7-TA45/GpL16-k0 with L234Y, G236W, and S298A introduced in both H chains was compared with GpH7-A57/GpH7-B78/GpL16-k0 with S239D, A330L, and I332E introduced in both H chains. As for binding activity against FcγRIIIa, the binding activity was significantly enhanced in GpH7-A57/GpH7-B78/GpL16-k0 compared with GpH7-A5/GpH7-B3/GpL16-k0, whereas the binding activity was reduced in GpH7-TA7/GpH7-TA45/GpL16-k0 compared with GpH7-A5/GpH7-B3/GpL16-k0. Also as for ADCC activity, the activity was increased in GpH7-A57/GpH7-B78/GpL16-k0 compared with GpH7-A5/GpH7-B3/GpL16-k0, whereas the activity was decreased in GpH7-TA7/GpH7-TA45/GpL16-k0 compared with GpH7-A5/GpH7-B3/GpL16-k0. Thus, the correlation of the strength of binding activity against FcγRIIIa with the strength of ADCC activity was observed in the homodimerized antibody.

Next, each heterodimerized antibody in which the alterations for enhancing binding activity against FcγRIIIa were introduced only in one H chain of the antibody was tested for whether its binding activity-enhancing effect exhibited similar tendency toward ADCC activity. GpH7-TA7/GpH7-B3/GpL16-k0 with L234Y, G236W, and S298A introduced in one H chain was compared with GpH7-A5/GpH7-B78/GpL16-k0 with S239D, A330L, and I332E introduced in one H chain. The binding activity against FcγRIIIa was enhanced in both of GpH7-A5/GpH7-B78/GpL16-k0 and GpH7-TA7/GpH7-B3/GpL16-k0 compared with GpH7-A5/GpH7-B3/GpL16-k0, while similar tendency was also observed in the ADCC activity. In addition, GpH7-A5/GpH7-B78/GpL16-k0 had FcγRIIIa-binding activity stronger than that of GpH7-TA7/GpH7-B3/GpL16-k0 and also maintained similar tendency toward ADCC activity, showing the correlation of the strength of binding activity against FcγRIIIa with the strength of ADCC activity in the heterodimerized antibody, as in the homodimerized antibody.

Next, the alteration group of L234Y, G236W, and S298A and the alteration group of S239D, A330L, and I332E were each tested for whether the binding activity of each heterodimerized antibody or homodimerized antibody against FcγRIIIa was observed to correlate with an ADCC activity-enhancing effect. First, the heterodimerized antibody GpH7-A5/GpH7-B78/GpL16-k0 with the alteration group of S239D, A330L, and I332E introduced only in one H chain was compared with the homodimerized antibody GpH7-A57/GpH7-B78/GpL16-k0 with this alteration group introduced in both H chains. As for binding activity against FcγRIIIa, the homodimerized antibody was more effective for enhancing the binding activity than the heterodimerized antibody. As for ADCC activity, no difference was confirmed between these antibodies. Next, the heterodimerized antibody GpH7-TA7/GpH7-B3/GpL16-k0 with the alteration group of L234Y, G236W, and S298A introduced only in one H chain was compared with the homodimerized antibody GpH7-TA7/GpH7-TA45/GpL16-k0 with this alteration group introduced in both H chains. As for binding activity against FcγRIIIa, the binding activity was enhanced in the heterodimerized antibody compared with GpH7-A5/GpH7-B3/GpL16-k0, whereas the binding activity was attenuated in the homodimerized antibody compared with GpH7-A5/GpH7-B3/GpL16-k0. Similar tendency was also observed in the ADCC activity. Hence, the effect of enhancing FcγRIIIa-binding activity only in one direction by the alteration group of L234Y, G236W, and S298A was presumably reflected in ADCC activity. These results indicated that the strength of binding activity against FcγRIIIa correlated with the strength of ADCC activity in a heterodimerized antibody with a certain alteration group introduced only in one H chain and a homodimerized antibody with this alteration group introduced in both H chains.

Next, the heterodimerized antibody GpH7-TA7/GpH7-B78/GpL16-k0 with L234Y, G236W, and S298A introduced in one H chain and S239D, A330L, and I332E introduced in the other H chain was compared with the homodimerized antibody GpH7-A57/GpH7-B78/GpL16-k0 with S239D, A330L, and I332E introduced in both H chains. The binding activity against FcγRIIIa was significantly enhanced in both of the heterodimerized antibody and the homodimerized antibody compared with GpH7-A5/GpH7-B3/GpL16-k0, while similar tendency was also observed in the ADCC activity. In addition, GpH7-TA7/GpH7-B78/GpL16-k0 exhibited FcγRIIIa-binding activity stronger than that of GpH7-A57/GpH7-B78/GpL16-k0 and also exhibited ADCC activity stronger than that of GpH7-A57/GpH7-B78/GpL16-k0.

As mentioned above, when the alteration group of L234Y, G236W, and S298A and the alteration group of S239D, A330L, and I332E were each introduced to one H chain or introduced to both H chains, the latter alteration group of S239D, A330L, and I332E was observed to be more effective for enhancing ADCC activity. However, the alteration group of L234Y, G236W, and S298A and the alteration group of S239D, A330L, and I332E respectively introduced to different H chains were shown to be more effective for enhancing ADCC activity, compared with the case where the alteration group of S239D, A330L, and I332E having the high effect of enhancing the ADCC activity of each of the heterodimerized antibody and the homodimerized antibody was added to both H chains.

The results described above demonstrated that the correlation of the strength of binding activity against FcγRIIIa with the strength of ADCC activity as observed in the homodimerized antibody of the conventional technique is similarly observed both in the comparison between the heterodimerized antibodies and in the comparison between the heterodimerized antibody and the homodimerized antibody. This demonstrated that the heterodimerized antibody technique capable of enhancing (optimizing) the interaction with FcγR on the X side can be used to develop an antibody superior in ADCC activity to the conventional technique. As in the paragraph (3-1), the ADCC activity was reduced in the homodimerized antibody with L234Y, G236W, and S298A introduced in both chains, confirming that the Y side was not used in the interaction with FcγR. In this respect, the Y side can be utilized in interaction with an antigen. It therefore appeared that the heterodimerized antibody with different alterations introduced in the first H chain and the second H chain could be applied to dual binding Fc.

(3-3) Thermal Stability Evaluation of Heterodimerized Antibody Having Enhanced Binding Activity Against FcγRIIIa Antibodies, when developed as drugs, are required to have in vivo stability in organisms and preservation stability and therefore, also expected to have high physicochemical stability. For example, in the case of introducing the S239D, A330L, and I332E alterations to both chains of an antibody as mentioned above, these introduced alterations have been reported to render the antibody Fc region unstable thermodynamically, and such reduction in thermal stability complicates development as a drug (Molecular Immunol. (2008) 45, 1872-1882). For enhancing the usefulness of an antibody drug and the ease of development thereof, it is also important to maintain its physicochemical stability, while enhancing the binding activity against FcγR. The homodimerized antibody, which has such alterations introduced in both H chains, contains two alteration sites per antibody molecule as a result of introducing one type of alteration. The heterodimerized antibody, however, can contain merely one alteration site per antibody molecule even by the introduction of one type of alteration, because the presence or absence of the alteration to be introduced can be selected for each H chain. As discussed in the preceding paragraphs, depending on the type of the alteration, its introduction to one H chain may suffice for the effect of enhancing binding activity against FcγRIIIa. If a certain alteration has the effect of reducing the physicochemical stability of the antibody, the introduction of this alteration only to one H chain confers the effect of enhancing binding activity against FcγRIIIa, but can probably minimize the physicochemical destabilization of the antibody.

In order to test this theory, the heterodimerized antibody GpH7-TA7/GpH7-B78/GpL16-k0 with the alteration group of L234Y, G236W, and S298A introduced in one H chain and the alteration group of S239D, A330L, and I332E introduced in the other H chain, the heterodimerized antibody GpH7-TA7/GpH7-B3/GpL16-k0 with only the alteration group of L234Y, G236W, and S298A introduced in one H chain, the homodimerized antibody GpH7-TA7/GpH7-TA45/GpL16-k0 with this alteration group introduced in both H chains, the heterodimerized antibody GpH7-A5/GpH7-B78/GpL16-k0 with only the alteration group of S239D, A330L, and I332E introduced in one H chain, and the homodimerized antibody GpH7-A57/GpH7-B78/GpL16-k0 with this alteration group introduced in both H chains, as used in the preceding paragraphs, were prepared according to the method of Reference Example 1. Thermal stability was compared among these antibodies in terms of the thermal denaturation temperature (hereinafter, referred to as Tm) of the altered CH2 domain(s) by thermal shift assay according to the method of Reference Example 4 to study the influence of the combination of L234Y, G236W, and S298A as well as S239D, A330L, and I332E on Tm (Table 6). In the description below, Tm refers to the thermal denaturation temperature of CH2 domains, unless otherwise specified.

TABLE 6

| Sample | SEQ ID NO | H1 | Mutation position in CH2 region | | | H2 | Mutation position in CH2 region | | | Tm [° C.] | ΔTm [° C.] |
|---|---|---|---|---|---|---|---|---|---|---|---|
| GpH7-G1d/GpL16-k0 | SEQ ID NO: 2, 5 | G1d | | | | G1d | | | | 69 | 1 |
| GpH7-A5/GpH7-B3/GpL16-k0 | SEQ ID NO: 3, 4, 5 | A5 | — | — | — | B3 | — | — | — | 68 | 0 |
| GpH7-TA7/GpH7-B3/GpL16-k0 | SEQ ID NO: 8, 4, 5 | TA7 | L234Y | G236W | S298A | B3 | — | — | — | 68 | 0 |
| GpH7-A5/GpH7-B78/GpL16-k0 | SEQ ID NO: 3, 7, 5 | A5 | — | — | — | B78 | S239D | A330L | I332E | 60 | −8 |
| GpH7-A57/GpH7-B78/GpL16-k0 | SEQ ID NO: 6, 7, 5 | A57 | S239D | A330L | I332E | B78 | S239D | A330L | I332E | 48 | −20 |

TABLE 6-continued

| Sample | SEQ ID NO | H1 | Mutation position in CH2 region | | | H2 | Mutation position in CH2 region | | | Tm [° C.] | ΔTm [° C.] |
|---|---|---|---|---|---|---|---|---|---|---|---|
| GpH7-TA7/GpH7-TA45/GpL16-k0 | SEQ ID NO: 8, 9, 5 | TA7 | L234Y | G236W | S298A | TA45 | L234Y | G236W | S298A | 68 | 0 |
| GpH7-TA7/GpH7-B78/GpL16-k0 | SEQ ID NO: 8, 7, 5 | TA7 | L234Y | G236W | S298A | B78 | S239D | A330L | I332E | 59 | −9 |

The column "Sample" represents an antibody name. The columns "H1" and "H2" represent the names of the H chain constant regions of each antibody. The column "Mutation position" represents mutations different from those in GpH7-G1d/GpL16-k0 ("−" denotes no particular mutation). The column "Tm" represents the Tm of each antibody. The column "ΔTm" represents the difference of the Tm of each antibody from the Tm of GpH7-A5/GpH7-B3/GpL16-k0. SEQ ID NOs of amino acid sequences corresponding to the H and L chains of each antibody are also shown in the table.

GpH7-A5/GpH7-B3/GpL16-k0 with the introduced D356K/H435R and K439E alterations enhancing the efficiency of heterodimerized antibody formation was compared with the naturally occurring IgG1 GpH7-G1d/GpL16-k0. As a result, the Tm of the CH2 domains was decreased by 1° C.

The homodimerized antibody of the conventional technique was tested for the effects of each alteration group. The homodimerized antibody GpH7-A57/GpH7-B78/GpL16-k0 with S239D, A330L, and I332E introduced in both H chains had Tm 20° C. lower than that of GpH7-A5/GpH7-B3/GpL16-k0 and exhibited significantly reduced stability. By contrast, no reduction in Tm was observed in the homodimerized antibody GpH7-TA7/GpH7-TA45/GpL16-k0 with the alteration group of L234Y, G236W, and S298A introduced in both H chains, indicating that the alteration group of L234Y, G236W, and S298A had no effect of reducing Tm by itself in the homodimerized antibody.

Each heterodimerized antibody with each alteration group introduced only in one H chain was tested for the effects of this alteration group. The heterodimerized antibody GpH7-A5/GpH7-B78/GpL16-k0 with S239D, A330L, and I332E introduced in one H chain had Tm 8° C. lower than that of GpH7-A5/GpH7-B3/GpL16-k0, while no reduction in Tm was observed in the heterodimerized antibody GpH7-TA7/GpH7-B3/GpL16-k0 with L234Y, G236W, and S298A introduced in one H chain. These results indicated that the alteration group of L234Y, G236W, and S298A also had no effect of reducing Tm by itself in the heterodimerized antibody.

GpH7-A57/GpH7-B78/GpL16-k0 with S239D, A330L, and I332E introduced in both H chains had Tm 21° C. lower than that of the naturally occurring IgG1, whereas GpH7-A5/GpH7-B78/GpL16-k0 having the S239D, A330L, and I332E alterations only in one H chain had Tm of 60° C. and maintained Tm at least 10° C. higher than that of the homodimerized antibody. From the results of Table 5, the homodimerized antibody containing S239D, A330L, and I332E was confirmed to have FcγRIIIa-binding activity approximately 9 times stronger than that of the corresponding heterodimerized antibody. The introduction of S239D, A330L, and I332E to both H chains largely enhances the binding activity against FcγRIIIa, but significantly reduces Tm.

Next, GpH7-TA7/GpH7-TA45/GpL16-k0 with L234Y, G236W, and S298A introduced in both H chains had Tm only 1° C. lower than that of the naturally occurring antibody. This was presumably due to the influence of D356K/H435R and K439E used for preparing the heterodimerized antibody as discussed above, rather than due to reduction in Tm caused by L234Y, G236W, and S298A. This was also consistent with the results showing that Tm was also decreased merely by 1° C. in GpH7-TA7/GpH7-B3/GpL16-k0 with L234Y, G236W, and S298A introduced in one H chain.

Finally, GpH7-TA7/GpH7-B78/GpL16-k0 having L234Y, G236W, and S298A in one H chain and S239D, A330L, and I332E in the other H chain had Tm 10° C. lower than that of the naturally occurring antibody and had Tm almost equal to that of GpH7-A5/GpH7-B78/GpL16-k0 having S239D, A330L, and I332E in one H chain. From the results of Table 5, however, GpH7-TA7/GpH7-B78/GpL16-k0 was confirmed to have FcγRIIIa-binding activity at least 10 times stronger than that of GpH7-A5/GpH7-B78/GpL16-k0.

The results described above demonstrated that use of the heterodimerized antibody GpH7-TA7/GpH7-B78/GpL16-k0 having L234Y, G236W, and S298A in one H chain and S239D, A330L, and I332E in the other H chain can enhance binding activity against FcγRIIIa and furthermore, can also improve Tm by 10° C. or more, compared with the homodimerized antibody GpH7-A57/GpH7-B78/GpL16-k0 having S239D, A330L, and I332E. This shows that the heterodimerized antibody can not only enhance binding activity against FcγR but can improve stability, compared with the conventional homodimerized antibody; thus the heterodimerized antibody can be technically more valuable as an antibody drug than the homodimerized antibody. The dual binding Fc comprises a first H chain and a second H chain altered differently and as such, is a molecule that can have not only the enhanced (optimized) binding activity against FcγR but the improved stability, compared with the homodimerized antibody, as in the antibodies mentioned above.

(3-4-1) Creation of Heterodimerized Antibody H240-Kn061/H240-H1071/L73-k0 Having Enhanced Binding Activity Against FcγRIIIa The preceding paragraphs showed that the heterodimerized antibody can not only have the enhanced (or optimized) interaction with FcγR but is superior in thermal stability, compared with the homodimerized antibody of the conventional technique. The preceding paragraphs further showed that the altered form having the enhanced binding activity against FcγRIIIa also has the enhanced ADCC activity. Accordingly, an antibody exhibiting the further optimized interaction with FcγR was created.

Here, an anti-epiregulin (EREG) antibody was used. H240 (SEQ ID NO: 10) was used as the sequence of the H chain variable region of the anti-EREG antibody, while L73-k0 (SEQ ID NO: 11) was used as the sequence of an L chain comprising variable and constant regions. Also, the heterodimerization technique used was the knobs-into-holes technology. The knobs-into-holes technology involves substituting an amino acid side chain present in the CH3 region of one H chain by a larger side chain (knob), substituting its counterpart amino acid side chain present in the CH3 region of the other H chain by a smaller side chain (hole), and placing the knob into the hole to promote the heterodimerization of the H chains. This technique is capable of efficiently producing the heterodimerized antibody of interest (Nature, (1994) 372, 379-383).

Specifically, H240-Kn033 (SEQ ID NO: 13) derived from H240-G1d (SEQ ID NO: 12) by the introduction of Y349C and T366W alterations to its constant region, and H240-H1033 (SEQ ID NO: 14) derived from H240-G1d by the introduction of D356C, T366S, L368A, and Y407V alterations to its constant region were prepared according to the method of Reference Example 1.

Preparation of Antibody for Comparison

An afucosylated antibody reported to enhance binding activity against FcγRIIIa (Glycobiol. (2006) Vol. 17 no. 1 pp. 104-118, etc.) was prepared for comparison. The functions of a fucose transporter are inhibited in cells in which the expression of fucose transporter genes on both homologous chromosomes is artificially suppressed. These cells can be used to obtain a fucose-deficient antibody (WO2006/067913, etc.). Alternatively, cells forced to express beta-1,4-N-acetylglucosaminyltransferase III and Golgi alpha-mannosidase II may be allowed to produce an antibody which is a fucose-deficient antibody (Ferrara et al., Biotechnol. Bioeng. (2006) 93 (5), 851-861). H240-G1d (SEQ ID NO: 12) and L73-k0 (SEQ ID NO: 11) were coexpressed by these approaches generally known to those skilled in the art to obtain an H240-afucosyl_G1d/L73-k0, which was an afucosylated form of the antibody H240-G1d/L73-k0.

Next, an altered form containing S239D, A330L, and I332E reported to enhance binding activity against FcγRIIIa was prepared for use as a subject to be compared with heterodimerized antibodies prepared in this paragraph. Specifically, H240-Kn032 (SEQ ID NO: 15) and H240-H1032 (SEQ ID NO: 16) derived from H240-Kn033 (SEQ ID NO: 13) and H240-H1033 (SEQ ID NO: 14), respectively, by the introduction of S239D, A330L, and I332E were prepared according to the method of Reference Example 1. H240-Kn032, H240-H1032, and L73-k0 were coexpressed to produce a homodimerized antibody H240-Kn032/H240-H1032/L73-k0 according to the method of Reference Example 1.

Preparation of antibody exhibiting enhanced interaction with FcγR An antibody exhibiting the enhanced interaction with FcγR was prepared. Specifically, L234Y, L235Y, G236W, H268D, and S298A were introduced to H240-Kn033 (SEQ ID NO: 13) to prepare H240-Kn061 (SEQ ID NO: 17) according to the method of Reference Example 1. K326D, A330M, and K334E were introduced to H240-H1033 (SEQ ID NO: 14) to prepare H240-H1071 (SEQ ID NO: 18) according to the method of Reference Example 1.

In order to further confirm whether the heterodimerized antibody H240-Kn061/H240-H1071/L73-k0 had the feature that the heterodimerized antibody had stronger binding activity against FcγR than that of homodimerized antibodies based on each H chain, H240-H1134 (SEQ ID NO: 19) with L234Y/L235Y/G236W/H268D/S298A introduced in H240-H1033, and H240-Kn132 (SEQ ID NO: 20) with K326D/A330M/K334E introduced in H240-Kn033 were prepared according to the method of Reference Example 1. Their expression vectors were used in the expression of a homodimerized antibody H240-Kn061/H240-H1134/L73-k0 having L234Y/L235Y/G236W/H268D/S298A in both H chains and the expression of a homodimerized antibody H240-Kn132/H240-H1071/L73-k0 having K326D/A330M/K334E in both H chains according to the method of Reference Example 1.

Also, H240-Kn033 (SEQ ID NO: 13), H240-H1033 (SEQ ID NO: 14), and L73-k0 (SEQ ID NO: 11) were coexpressed to produce a control H240-Kn033/H240-H1033/L73-k0 according to the method of Reference Example 1.

These antibodies were evaluated for their binding activity against each FcγR according to the method of Reference Example 2.

TABLE 7

| Sample | FcγRIa KD (M) | FcγRIIa(R) KD (M) | FcγRIIa(H) KD (M) | FcγRIIb KD (M) | FcγRIIIa(F) KD (M) | FcγRIIIa(V) KD (M) |
|---|---|---|---|---|---|---|
| H240-G1d/L73-k0 (H240-G1d/H240-G1d/L73-k0) | 2.3E−10 | 8.8E−07 | 6.6E−07 | 6.0E−06 | 1.4E−06 | 3.1E−07 |
| H240-Kn033/H240-HI033/L73-k0 | 2.5E−10 | 1.0E−06 | 9.3E−07 | 4.1E−06 | 2.6E−06 | 3.9E−07 |
| H240-Kn032/H240-HI032/L73-k0 | 7.3E−11 | 3.4E−07 | 6.9E−07 | 6.2E−07 | 9.1E−09 | 3.1E−09 |
| H240-afucosyl_G1d/L73-k0 | 4.3E−10 | 4.9E−07 | 7.8E−07 | 2.6E−06 | 7.8E−08 | 6.9E−09 |
| H240-Kn061/H240-HI071/L73-k0 | 1.4E−10 | 3.5E−07 | 2.8E−07 | 1.2E−06 | 5.1E−09 | 1.8E−09 |
| H240-Kn061/H240-HI134/L73-k0 | | | | | 6.6E−07 | 8.6E−08 |
| H240-Kn132/H240-HI071/L73-k0 | | | | | 7.7E−08 | 1.6E−08 |

As seen from the results of Table 7, the heterodimerized antibody H240-Kn061/H240-H1071/L73-k0 had stronger binding activity, particularly, against FcγRIIIa F or FcγRIIIa V, than that of H240-Kn033/H240-H1033/L73-k0. Since the heterodimerized antibody H240-Kn061/H240-H1071/L73-k0 is an altered form derived from H240-Kn033/H240-H1033/L73-k0 by the introduction of L234Y/L235Y/G236W/H268D/S298A and K326D/A330M/K334E, these introduced alterations can be regarded as enhancing the binding activity of the altered form against FcγR.

As seen from the results of Table 7, the heterodimerized antibody H240-Kn061/H240-H1071/L73-k0 had stronger binding activity against FcγRIIIa F and FcγRIIIa V than that of H240-afucosyl_G1d/L73-k0 and H240-Kn032/H240-H1032/L73-k0 prepared by the application of the existing technique of enhancing ADCC activity. These results demonstrated that the heterodimerized antibody is more effective for enhancing binding to FcγRIIIa than the technique of enhancing ADCC activity by means of the conventional homodimerized antibody and the technique of enhancing ADCC activity by means of afucosylation.

In addition, in terms of FcγRIIa binding activity considered important for enhanced ADCP activity, the heterodimerized antibody had stronger binding activity against FcγRIIa H than that of both of the antibodies and had FcγRIIa R-binding activity which was stronger than that of H240-afucosyl_G1d/L73-k0 and was equivalent to that of H240-Kn032/H240-H1032/L73-k0.

(3-4-2) Discussion on Whether H240-Kn061/H240-H1071/L73-k0 has Feature of Heterodimerized Antibody Discussion was made on whether H240-Kn061/H240-H1071/L73-k0 had the feature of the heterodimerized antibody. From the results of Table 7, the heterodimerized antibody H240-Kn061/H240-H1071/L73-k0 having L234Y/L235Y/G236W/H268D/S298A in one H chain and K326D/A330M/K334E in the other H chain was confirmed to have stronger binding activity against FcγRIIIa F and FcγRIIIa V than that of both of the homodimerized antibody H240-Kn061/H240-H1134/L73-k0 having L234Y/L235Y/G236W/H268D/S298A in both H chains and the homodimerized antibody H240-Kn132/H240-H1071/L73-k0 having K326D/A330M/K334E in both H chains. This demonstrated that H240-Kn061/H240-H1071/L73-k0 has the feature that the heterodimerized antibody has stronger binding activity against FcγR than that of homodimerized antibodies based on each H chain. In short, H240-Kn061/H240-H1071/L73-k0 exhibits the enhanced binding activity against FcγR in one direction (on the X side) and as such, can serve as a dual binding Fc molecule using the Y side as a second antigen-binding site.

(3-5) Further Improvement in Heterodimerized Antibody H240-Kn061/H240-H1071/L73-k0

With the aim of further optimizing the interaction with FcγR, H240-Kn125 (SEQ ID NO: 21) with Y235Q, S239M, and D270E introduced in H240-Kn061, and H240-H1076 (SEQ ID NO: 22) with D270E introduced in H240-H1071 were prepared according to the method of Reference Example 1. H240-H1076 as one H chain, L73-k0 as an L chain, and H240-Kn125 as the other H chain were combined to prepare H240-Kn125/H240-H1076/L73-k0 according to the method of Reference Example 1. The prepared antibody was evaluated for its binding activity against each FcγR according to the method of Reference Example 2, together with the naturally occurring IgG1 H240-G1d/L73-k0, H240-Kn033/H240-H1033/L73-k0 derived therefrom by the knobs-into-holes technology, the afucosylated antibody H240-afucosyl_G1d/L73-k0 prepared by the existing technique of enhancing ADCC activity, and the homodimerized antibody H240-Kn032/H240-H1032/L73-k0 with the ADCC activity-enhancing alterations S239D/A330L/I332E introduced in both H chains. The results are summarized in Table 8.

TABLE 8

| Sample | FcγRIa KD (M) | FcγRIIa(R) KD (M) | FcγRIIa(H) KD (M) | FcγRIIb KD (M) | FcγRIIIa(F) KD (M) | FcγRIIIa(V) KD (M) |
|---|---|---|---|---|---|---|
| H240-G1d/L73-k0 (H240-G1d/H240-G1d/L73-k0) | 2.3E−10 | 8.8E−07 | 6.6E−07 | 6.0E−06 | 1.4E−06 | 3.1E−07 |
| H240-Kn033/H240-HI033/L73-k0 | 2.5E−10 | 1.0E−06 | 9.3E−07 | 4.1E−06 | 2.6E−06 | 3.9E−07 |
| H240-Kn032/H240-HI032/L73-k0 | 7.3E−11 | 3.4E−07 | 6.9E−07 | 6.2E−07 | 9.1E−09 | 3.1E−09 |
| H240-afucosyl_G1d/L73-k0 | 4.3E−10 | 4.9E−07 | 7.8E−07 | 2.6E−08 | 7.8E−08 | 6.9E−09 |
| H240-Kn061/H240-HI071/L73-k0 | 1.4E−10 | 3.5E−07 | 2.8E−07 | 1.2E−06 | 5.1E−09 | 1.8E−09 |
| H240-Kn125/H240-HI075/L73-k0 | 2.4E−10 | 3.8E−07 | 1.9E−07 | 4.2E−08 | 1.2E−09 | 3.7E−10 |

H240-Kn125/H240-H1076/L73-k0 had stronger binding activity against FcγRIIIa F and FcγRIIIa V, which play important role in ADCC activity, than that of H240-Kn061/H240-H1071/L73-k, while maintaining its binding activity against FcγRIIb (inhibitory FcγR) at a level equivalent to that of the naturally occurring IgG1. This antibody had stronger binding activity against FcγRIIa H, one allotype of FcγRIIa, weaker binding activity against FcγRIIb, and stronger binding activity against both allotypes of FcγRIIIa, compared with the afucosylated antibody H240-afucosyl_G1d/L73-k0 prepared by the existing technique of enhancing ADCC activity and the homodimerized antibody H240-Kn032/H240-H1032/L73-k0 with the ADCC activity-enhancing alterations S239D/A330L/I332E introduced in both H chains. From these results, H240-Kn125/H240-H1076/L73-k0 can be expected to enhance ADCP activity and ADCC activity more than the afucosylated antibody and the homodimerized antibody prepared by the application of the existing ADCC activity-enhancing alterations and in addition, can be expected to attenuate immunosuppressive effects.

Figure 12:
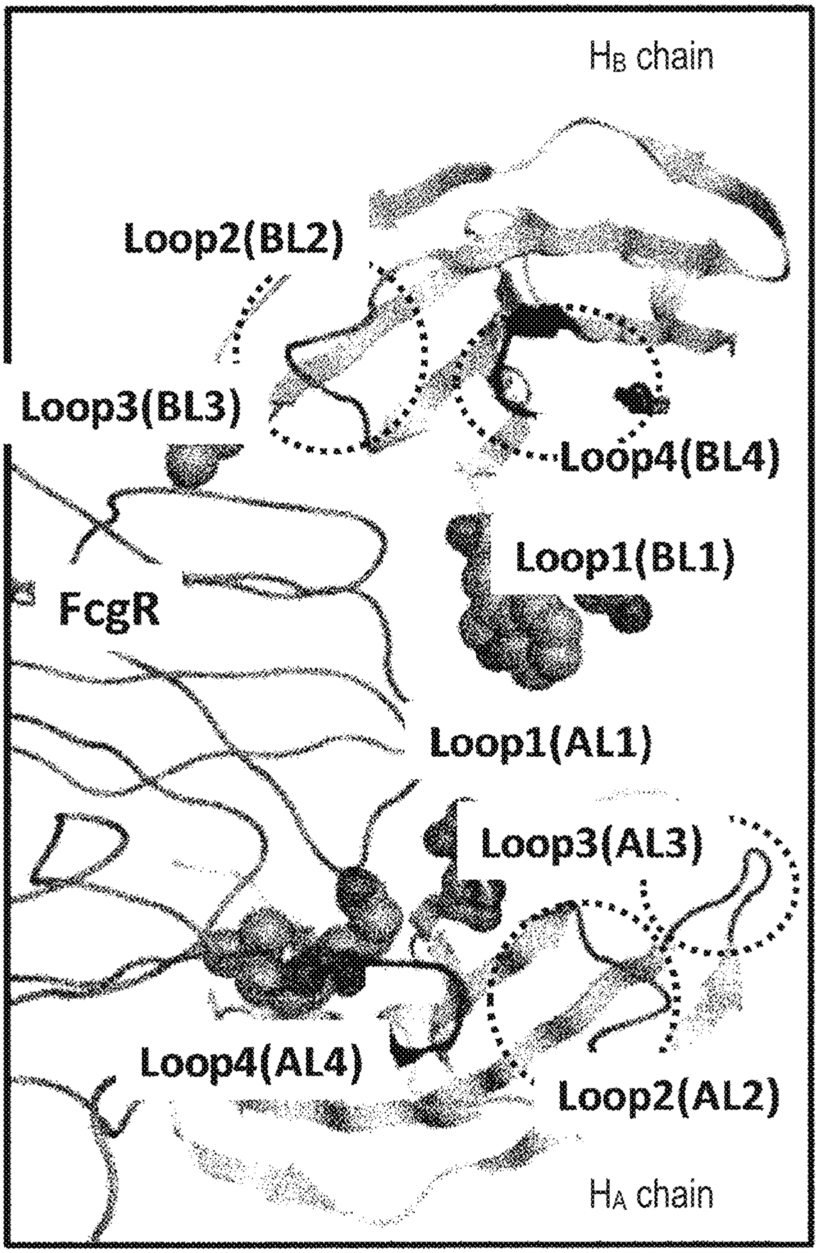
FIG. 12 is a diagram showing loop regions on the Y side that are made into a library.

[Example 4] Design of Library for Obtaining Fc Region Binding to Antigen on Y Side An exemplary method for obtaining an Fc region that binds to the antigen of interest on the Y side while maintaining its binding activity against FcγR on the X side involves screening a molecular population (referred to as a library) of Fc regions having diverse amino acid sequences. Possible regions made into a library to confer binding activity against the antigen on the Y side were loops AL2, AL3, BL2, and BL4 shown in FIG. 12. Specifically, as shown in FIGS. 11 and 12, the possible loops made into a library were an $H_A$ chain loop AL2 from EU numbering positions 265 to 271, an $H_A$ chain loop AL3 from EU numbering positions 295 to 300, an $H_B$ chain loop BL2 from EU numbering positions 265 to 271, and an $H_B$ chain loop BL4 from EU numbering positions 324 to 332. These regions are not much involved in the binding to FcγR on the X side. Nonetheless, the binding to FcγR on the X side may be very difficult to maintain, if these loops are made into a complete library such that various amino acids appear therein. Thus, for a library in which random amino acids appear in these loops, it is very difficult to obtain a molecule that maintains binding activity against FcγR on the X side at a level at least equivalent to that of naturally occurring IgG, has thermal stability against use as a drug, and has binding activity against the antigen of interest on the Y side.

Accordingly, first, an amino acid that was able to secure the binding activity against FcγR and secure Tm equal to or higher than 60° C. was identified by screening as an amino acid other than a natural amino acid at each residue in each of the loop regions shown in FIG. 12, i.e., Loop 1 (EU numbering positions 234 to 239), Loop 2 (EU numbering positions 265 to 271), Loop 3 (EU numbering positions 295 to 300), and Loop 4 (EU numbering positions 324 to 332).

The thermal stability was evaluated using homodimerized antibodies having H chains containing an altered amino acid at each residue. As discussed in Example 3, antibodies with amino acid alterations added to both H chains (homodimerized antibodies) have lower thermal stability than that of antibodies with the amino acid alterations added to either one H chain (heterodimerized antibodies). For the library molecules, such an amino acid is introduced to at least either one H chain. Nevertheless, an amino acid having higher stability can be selected, because the thermal stability is evaluated using the homodimerized antibodies.

On the other hand, the binding activity against FcγR was evaluated using heterodimerized antibodies having an H chain containing an altered amino acid at each residue and a natural IgG1 H chain. As discussed in Example 3, alterations useful for heterodimerized antibodies, such as L234Y, G236W, and S298A introduced in the antibody carried out in Example 3, were judged as reducing activity in homodimerized antibodies by evaluation using the homodimerized antibody of the conventional technique. Thus, evaluation using heterodimerized antibodies seemed to be appropriate for screening for an amino acid that would secure or enhance the interaction of a heterodimerized antibody with FcγR.

Specifically, amino acid alterations for use in the library were identified by the following screening method: in GpH7-B3 (SEQ ID NO: 4) prepared in Example 2, Leu at EU numbering position 234, Leu at EU numbering position 235, Gly at EU numbering position 236, Gly at EU numbering position 237, Pro at EU numbering position 238, Ser at EU numbering position 239, Asp at EU numbering position 265, Val at EU numbering position 266, Ser at EU numbering position 267, His at EU numbering position 268, Glu at EU numbering position 269, Asp at EU numbering position 270, Pro at EU numbering position 271, Gln at EU numbering position 295, Tyr at EU numbering position 296, Ser at EU numbering position 298, Tyr at EU numbering position 300, Ser at EU numbering position 324, Asn at EU numbering position 325, Lys at EU numbering position 326, Ala at EU numbering position 327, Leu at EU numbering position 328, Pro at EU numbering position 329, Ala at EU numbering position 330, Pro at EU numbering position 331, Ile at EU numbering position 332, Glu at EU numbering position 333, Lys at EU numbering position 334, Thr at EU numbering position 335, Ile at EU numbering position 336, and Ser at EU numbering position 337 were each substituted by 18 types of amino acids except for the original amino acid and cysteine to prepare GpH7-B3 variants. The name of each GpH7-B3 variant is indicated by A_B wherein A represents the EU numbering position of a residue to be altered plus one-letter code of information about the type of the amino acid; and B represents information about an amino acid after substitution. For example, a B3_variant obtained by the substitution of Leu at EU numbering position 234 by Gly is designated as L234_01G. As for the information about an amino acid after substitution, a numerical value unique to the amino acid is described before its one-letter code for the sake of convenience. Specifically, the following symbols are used: 01G for Gly, 02A for Ala, 03V for Val, 04F for Phe, 05P for Pro, 06M for Met, 071 for Ile, 08L for Leu, 09D for Asp, 10E for Glu, 11K for Lys, 12R for Arg, 13S for Ser, 14T for Thr, 15Y for Tyr, 16H for His, 18N for Asn, 19Q for Gln, and 20W for Trp.

Each homodimerized antibody with both H chains mutated was prepared according to the following procedures: each GpH7-B3 variant as an H chain and GpL16-k0 (SEQ ID NO: 5) as an L chain were used in antibody expression to prepare antibodies according to the method of Reference Example 1. The thus-prepared homodimerized antibody with both H chains mutated is referred to as Ho Ab.

Each heterodimerized antibody with only one H chain mutated was prepared according to the following procedures: each GpH7-B3 variant as one H chain, GpH7-A5 (SEQ ID NO: 3) as the other H chain, and GpL16-k0 (SEQ ID NO: 5) as an L chain were used in antibody expression to prepare antibodies according to the method of Reference Example 1. The thus-prepared heterodimerized antibody with only one H chain mutated is referred to as He Ab.

An antibody GpH7-B3/GpL16-k0 was prepared as a homodimerized antibody control using GpH7-B3 (SEQ ID NO: 4) as an H chain and GpL16-k0 (SEQ ID NO: 5) as an L chain according to the method of Reference Example 1. This antibody serving as a homodimerized antibody control is referred to as HoCon Ab. As studied in Example 3, HoCon Ab does not largely vary in binding activity against each FcγR from naturally occurring IgG1.

An antibody GpH7-A5/GpH7-B3/GpL16-k0 was prepared as a heterodimerized antibody control using GpH7-A5 (SEQ ID NO: 3) as one H chain, GpH7-B3 (SEQ ID NO: 4) as the other H chain, and GpL16-k0 (SEQ ID NO: 5) as an L chain according to the method of Reference Example 1. This antibody serving as a heterodimerized antibody control is referred to as HeCon Ab. As studied in Example 3, HeCon Ab does not largely vary in binding activity against each FcγR from naturally occurring IgG1.

The prepared Ho Ab and HoCon Ab were used to evaluate the thermal stability of CH2 domains by the method shown in Reference Example 4. Also, the prepared He Ab and HeCon Ab were used to determine binding activity against FcγRIa, FcγRIIa(R), FcγRIIa(H), FcγRIIb, and FcγRIIIa according to the method of Reference Example 2. The assay results about each FcγR were plotted according to the following method: He/Con were defined as a value determined according to the expression: Binding activity of He Ab against each FcγR/Binding activity of HeCon Ab against the FcγR×100. As discussed in Example 2, FcγR binding on the X side and FcγR binding on the Y side are not distinguishable from each other for the naturally occurring IgG. Accordingly, a heterodimerized molecule in screening was regarded as maintaining its binding activity against FcγR, when the molecule had interaction with FcγRI 80% higher than that of the control and interaction with each of the receptors FcγRIIa, FcγRIIb, and FcγRIIIa 50% higher than that of the control Table 9 shows amino acids that secure binding activity against FcγR and Tm equal to or higher than 60° C. and are acceptable at each position of each loop. In the design of a library for obtaining a molecule having binding activity against the antigen on the Y side, the library is designed such that these acceptable amino acids, instead of 20 types of amino acids, appear at each position of each loop. A population contained in the resulting library is more likely to have high binding activity against FcγR and high Tm.

TABLE 9

| Name | He/Con 1a | He/Con 2aR | He/Con 2aH | He/Con 2b | He/Con 3a | Tm [° C.] |
|---|---|---|---|---|---|---|
| L234_01G | 99.2 | 72.4 | 84.1 | 57.8 | 55.8 | 69.5 |
| L234_13S | 100.0 | 82.6 | 89.4 | 67.7 | 68.1 | 69.3 |
| L234_02A | 100.7 | 92.5 | 90.1 | 74.1 | 69.7 | 68.8 |
| L234_14T | 101.8 | 90.0 | 86.8 | 71.4 | 69.8 | 69.2 |
| L234_16H | 97.0 | 83.5 | 97.1 | 67.8 | 76.8 | 69.0 |
| L234_19Q | 98.8 | 87.2 | 88.1 | 68.9 | 77.1 | 69.4 |
| L234_06M | 107.1 | 108.6 | 96.4 | 89.6 | 82.9 | 68.9 |
| L234_05P | 103.2 | 104.1 | 104.0 | 83.2 | 85.1 | 68.9 |
| L234_18N | 97.3 | 98.0 | 100.2 | 92.0 | 88.2 | 69.1 |
| L234_03V | 107.8 | 99.0 | 94.4 | 83.4 | 88.3 | 69.7 |
| L234_07I | 106.3 | 110.4 | 101.0 | 92.3 | 99.5 | 69.1 |
| L234_20W | 101.8 | 125.2 | 126.2 | 130.6 | 103.2 | 68.9 |
| L234_10E | 103.7 | 130.3 | 98.2 | 134.2 | 110.6 | 67.1 |
| L234_09D | 101.0 | 142.3 | 100.0 | 171.7 | 112.8 | 67.1 |
| L234_04F | 104.3 | 120.9 | 133.2 | 113.9 | 114.0 | 68.5 |
| L234_15Y | 103.3 | 113.3 | 133.7 | 109.9 | 125.7 | 69.0 |

TABLE 9-continued

| Name | He/Con 1a | He/Con 2aR | He/Con 2aH | He/Con 2b | He/Con 3a | Tm [° C.] |
|---|---|---|---|---|---|---|
| L235_16H | 92.7 | 110.2 | 99.8 | 87.8 | 57.1 | 68.0 |
| L235_18N | 95.2 | 77.3 | 73.5 | 62.7 | 65.0 | 68.1 |
| L235_13S | 93.5 | 75.9 | 73.5 | 55.0 | 67.2 | 68.9 |
| L235_05P | 97.8 | 74.6 | 64.2 | 62.4 | 68.6 | 68.9 |
| L235_02A | 95.2 | 86.6 | 77.6 | 72.0 | 72.0 | 68.8 |
| L235_14T | 91.6 | 70.6 | 79.5 | 53.4 | 73.2 | 68.4 |
| L235_20W | 95.9 | 152.1 | 130.9 | 168.2 | 73.8 | 67.9 |
| L235_06M | 101.2 | 106.2 | 96.3 | 92.4 | 75.6 | 69.0 |
| L235_04F | 100.2 | 132.0 | 123.0 | 135.3 | 76.4 | 68.9 |
| L235_15Y | 100.3 | 150.3 | 135.1 | 170.3 | 77.8 | 68.8 |
| L235_10E | 96.9 | 98.7 | 80.0 | 90.8 | 85.6 | 66.9 |
| L235_09D | 87.6 | 117.0 | 84.3 | 121.3 | 88.5 | 66.7 |
| L235_07I | 102.8 | 102.1 | 99.5 | 100.1 | 92.8 | 69.1 |
| L235_03V | 97.8 | 83.4 | 94.9 | 75.8 | 94.6 | 69.2 |
| G236_10E | 92.6 | 124.0 | 115.8 | 114.9 | 65.8 | 65.9 |
| G236_09D | 95.5 | 105.3 | 93.5 | 174.3 | 66.2 | 66.2 |
| G236_02A | 99.1 | 144.8 | 144.9 | 100.7 | 77.0 | 68.4 |
| G236_20W | 103.9 | 77.3 | 152.8 | 60.7 | 126.1 | 64.8 |
| P238_19Q | 100.7 | 97.8 | 54.5 | 111.7 | 52.7 | 62.3 |
| P238_15Y | 104.1 | 147.1 | 57.8 | 220.9 | 61.0 | 65.5 |
| P238_08L | 104.1 | 131.5 | 81.8 | 207.4 | 71.3 | 67.4 |
| P238_10E | 104.7 | 142.5 | 74.6 | 235.2 | 98.9 | 60.5 |
| P238_09D | 99.0 | 139.5 | 84.7 | 224.0 | 100.0 | 60.8 |
| S239_19Q | 103.7 | 79.8 | 80.0 | 87.3 | 53.8 | 71.2 |
| S239_02A | 102.7 | 89.8 | 89.9 | 91.6 | 70.9 | 67.2 |
| S239_01G | 104.5 | 120.4 | 93.8 | 146.2 | 72.0 | 64.9 |
| S239_03V | 98.9 | 94.1 | 88.0 | 109.9 | 72.4 | 67.7 |
| S239_06M | 102.1 | 94.7 | 95.4 | 102.3 | 73.9 | 68.4 |
| S239_07I | 100.8 | 95.9 | 88.5 | 108.3 | 75.0 | 67.3 |
| S239_08L | 102.9 | 114.4 | 101.3 | 142.2 | 90.0 | 67.6 |
| S239_14T | 104.2 | 97.4 | 95.9 | 98.6 | 93.0 | 68.2 |
| S239_18N | 104.3 | 104.2 | 91.1 | 120.7 | 103.8 | 67.5 |
| S239_09D | 104.1 | 128.6 | 110.7 | 208.6 | 156.4 | 65.0 |
| S239_10E | 108.5 | 127.0 | 108.3 | 183.1 | 171.4 | 66.0 |
| V266_02A | 93.8 | 88.8 | 69.7 | 85.1 | 56.8 | 63.0 |
| V266_06M | 96.5 | 161.2 | 84.8 | 264.0 | 84.9 | 64.8 |
| V266_07I | 96.1 | 129.4 | 106.7 | 160.1 | 112.9 | 69.1 |
| V266_08L | 94.9 | 152.4 | 105.6 | 248.3 | 116.7 | 69.7 |
| S267_01G | 99.9 | 121.4 | 72.1 | 109.9 | 53.3 | 67.2 |
| S267_19Q | 99.2 | 145.4 | 61.9 | 228.5 | 64.3 | 66.8 |
| S267_10E | 102.4 | 187.8 | 103.4 | 398.5 | 90.9 | 64.1 |
| S267_02A | 105.3 | 167.0 | 121.1 | 255.7 | 148.8 | 66.7 |
| S267_09D | 106.2 | 186.1 | 106.6 | 326.2 | 178.9 | 65.4 |
| H268_05P | 105.5 | 113.5 | 82.7 | 122.0 | 75.6 | 69.9 |
| H268_08L | 103.9 | 91.4 | 85.9 | 71.2 | 75.9 | 69.9 |
| H268_12R | 102.7 | 112.6 | 90.9 | 94.3 | 76.0 | 69.2 |
| H268_06M | 101.3 | 67.2 | 85.8 | 69.0 | 79.5 | 70.0 |
| H268_11K | 102.4 | 108.0 | 89.8 | 87.2 | 81.6 | 70.4 |
| H268_20W | 103.4 | 121.5 | 96.9 | 117.1 | 82.0 | 68.5 |
| H268_07I | 104.3 | 101.8 | 91.2 | 93.4 | 84.1 | 69.6 |
| H268_14T | 108.5 | 100.2 | 93.5 | 90.3 | 90.3 | 68.1 |
| H268_03V | 102.6 | 116.8 | 100.3 | 119.7 | 91.4 | 68.1 |
| H268_01G | 103.7 | 133.5 | 100.3 | 150.9 | 95.7 | 67.5 |
| H268_04F | 102.8 | 105.1 | 112.2 | 94.2 | 96.0 | 69.6 |
| H268_15Y | 103.8 | 117.9 | 113.2 | 111.7 | 96.5 | 68.5 |
| H268_18N | 104.4 | 138.1 | 113.3 | 164.2 | 103.0 | 66.8 |
| H268_19Q | 104.3 | 128.0 | 103.5 | 139.6 | 113.0 | 68.7 |
| H268_13S | 105.7 | 137.0 | 113.6 | 167.7 | 120.6 | 67.8 |
| H268_02A | 105.2 | 143.2 | 115.0 | 175.0 | 120.9 | 68.5 |
| H268_10E | 107.4 | 158.9 | 125.7 | 242.2 | 184.1 | 67.6 |
| H268_09D | 106.0 | 160.6 | 134.0 | 251.2 | 195.2 | 67.1 |
| E269_14T | 102.5 | 71.0 | 70.3 | 53.2 | 59.7 | 68.1 |
| E269_01G | 101.0 | 70.3 | 72.3 | 54.1 | 61.6 | 66.7 |
| E269_13S | 99.8 | 65.8 | 70.7 | 50.2 | 62.1 | 68.7 |
| E269_02A | 101.0 | 70.2 | 78.7 | 52.4 | 68.0 | 68.6 |
| E269_09D | 103.2 | 113.2 | 104.9 | 110.1 | 105.7 | 68.6 |
| D270_14T | 89.5 | 72.2 | 81.3 | 54.8 | 55.4 | 68.6 |
| D270_08L | 93.2 | 62.8 | 81.8 | 50.8 | 65.1 | 67.9 |
| D270_10E | 103.6 | 85.7 | 110.6 | 72.5 | 111.8 | 69.3 |
| P271_14T | 100.6 | 94.7 | 69.8 | 107.0 | 59.2 | 67.0 |
| P271_15Y | 101.3 | 70.0 | 74.0 | 58.6 | 62.7 | 67.2 |
| P271_04F | 100.2 | 75.2 | 77.1 | 66.7 | 65.6 | 66.7 |
| P271_16H | 100.5 | 79.0 | 76.4 | 76.2 | 70.3 | 66.5 |
| P271_03V | 100.7 | 85.8 | 85.4 | 83.8 | 73.5 | 66.2 |
| P271_06M | 100.8 | 87.3 | 87.7 | 87.0 | 74.0 | 66.7 |
| P271_08L | 100.6 | 102.8 | 99.4 | 115.2 | 74.5 | 66.4 |
| P271_20W | 100.9 | 76.6 | 88.7 | 65.1 | 77.8 | 67.3 |

TABLE 9-continued

| Name | He/Con 1a | He/Con 2aR | He/Con 2aH | He/Con 2b | He/Con 3a | Tm [° C.] |
|---|---|---|---|---|---|---|
| P271_13S | 100.7 | 93.5 | 83.3 | 98.2 | 79.8 | 67.1 |
| P271_07I | 100.8 | 88.0 | 94.1 | 86.1 | 80.2 | 66.1 |
| P271_02A | 101.9 | 93.9 | 88.4 | 98.7 | 83.7 | 67.0 |
| P271_19Q | 101.5 | 95.1 | 90.7 | 99.3 | 84.6 | 66.5 |
| P271_12R | 100.8 | 95.8 | 100.3 | 96.9 | 87.6 | 65.1 |
| P271_11K | 101.1 | 97.3 | 100.3 | 101.2 | 92.5 | 65.2 |
| P271_18N | 101.6 | 97.7 | 94.5 | 104.6 | 94.0 | 66.2 |
| P271_09D | 100.5 | 108.7 | 80.4 | 134.7 | 97.7 | 68.4 |
| P271_10E | 101.1 | 101.6 | 72.4 | 122.5 | 98.2 | 67.9 |
| P271_01G | 103.1 | 142.7 | 122.7 | 216.7 | 118.8 | 68.0 |
| Q295_12R | 98.8 | 82.2 | 96.4 | 73.1 | 73.2 | 63.9 |
| Q295_05P | 101.8 | 86.6 | 118.5 | 75.7 | 74.4 | 64.3 |
| Q295_04F | 100.6 | 82.8 | 87.4 | 72.6 | 75.1 | 67.8 |
| Q295_01G | 96.1 | 60.3 | 62.5 | 51.6 | 76.6 | 63.8 |
| Q295_16H | 100.8 | 80.5 | 90.1 | 70.3 | 80.2 | 65.5 |
| Q295_15Y | 100.1 | 82.0 | 89.3 | 73.3 | 81.5 | 66.1 |
| Q295_11K | 99.7 | 88.1 | 102.5 | 79.0 | 81.8 | 64.0 |
| Q295_09D | 98.5 | 68.7 | 62.6 | 68.1 | 85.6 | 62.7 |
| Q295_18N | 100.8 | 81.7 | 87.8 | 72.8 | 85.7 | 65.9 |
| Q295_03V | 102.4 | 90.3 | 105.5 | 84.9 | 86.2 | 67.8 |
| Q295_13S | 100.3 | 73.0 | 79.5 | 63.8 | 90.4 | 65.5 |
| Q295_06M | 102.5 | 100.7 | 111.0 | 101.4 | 100.2 | 70.8 |
| Q295_07I | 101.3 | 97.3 | 117.3 | 94.5 | 100.7 | 66.5 |
| Q295_10E | 101.4 | 100.6 | 112.0 | 106.4 | 105.1 | 64.9 |
| Q295_02A | 102.6 | 91.5 | 101.1 | 89.4 | 110.8 | 66.5 |
| Q295_08L | 102.9 | 117.6 | 128.3 | 133.9 | 119.5 | 69.8 |
| Q295_14T | 101.0 | 79.2 | 86.2 | 74.9 | 120.4 | 65.9 |
| Y296_01G | 99.4 | 91.6 | 91.6 | 80.4 | 51.3 | 70.9 |
| Y296_11K | 101.5 | 90.3 | 83.7 | 73.8 | 53.3 | 67.0 |
| Y296_13S | 101.9 | 97.5 | 96.1 | 87.5 | 58.1 | 70.6 |
| Y296_14T | 101.9 | 98.6 | 97.2 | 89.4 | 60.7 | 68.3 |
| Y296_02A | 99.8 | 93.0 | 89.1 | 83.1 | 66.3 | 67.0 |
| Y296_12R | 103.1 | 95.3 | 89.1 | 80.5 | 66.5 | 67.3 |
| Y296_18N | 102.4 | 99.6 | 101.4 | 92.8 | 67.9 | 69.9 |
| Y296_16H | 102.6 | 100.1 | 101.3 | 93.5 | 69.1 | 67.3 |
| Y296_03V | 100.8 | 92.0 | 86.9 | 80.4 | 69.1 | 66.7 |
| Y296_19Q | 108.2 | 97.9 | 94.3 | 90.5 | 71.4 | 70.8 |
| Y296_08L | 100.7 | 93.7 | 86.9 | 83.5 | 72.4 | 66.9 |
| Y296_06M | 100.8 | 96.8 | 94.2 | 89.0 | 74.6 | 65.7 |
| Y296_07I | 101.1 | 96.7 | 92.7 | 85.5 | 75.8 | 65.9 |
| Y296_10E | 102.5 | 98.2 | 94.0 | 99.4 | 76.8 | 69.0 |
| Y296_04F | 100.9 | 104.7 | 97.8 | 100.6 | 79.5 | 69.0 |
| Y296_09D | 102.7 | 101.2 | 101.7 | 100.3 | 89.0 | 69.6 |
| Y296_20W | 107.4 | 105.0 | 95.4 | 104.7 | 127.0 | 66.7 |
| S298_11K | 105.9 | 91.0 | 63.9 | 62.2 | 50.0 | 66.5 |
| S298_12R | 106.1 | 81.6 | 67.4 | 58.6 | 52.1 | 66.8 |
| S298_08L | 103.5 | 100.3 | 83.0 | 110.0 | 69.2 | 65.5 |
| S298_19Q | 106.1 | 90.9 | 88.9 | 74.3 | 70.6 | 66.5 |
| S298_16H | 105.4 | 84.7 | 80.2 | 64.4 | 71.9 | 65.1 |
| S298_01G | 100.5 | 94.5 | 71.4 | 81.2 | 74.9 | 72.0 |
| S298_04F | 105.6 | 80.4 | 75.5 | 66.3 | 77.6 | 68.7 |
| S298_15Y | 104.0 | 75.7 | 71.2 | 62.2 | 80.6 | 65.7 |
| S298_06M | 111.0 | 103.7 | 95.8 | 103.2 | 87.2 | 69.7 |
| S298_07I | 103.7 | 86.2 | 84.9 | 71.5 | 90.7 | 64.3 |
| S298_03V | 106.4 | 82.5 | 83.2 | 65.4 | 102.8 | 65.0 |
| S298_14T | 103.8 | 94.2 | 96.2 | 79.0 | 105.9 | 66.1 |
| S298_02A | 103.4 | 87.2 | 74.3 | 74.4 | 150.6 | 68.1 |
| Y300_11K | 100.9 | 73.1 | 74.2 | 67.4 | 63.7 | 66.0 |
| Y300_13S | 104.8 | 72.4 | 97.8 | 70.4 | 80.3 | 64.5 |
| Y300_03V | 110.3 | 96.8 | 108.7 | 96.5 | 83.8 | 63.6 |
| Y300_02A | 105.9 | 92.9 | 103.7 | 90.5 | 88.1 | 66.2 |
| Y300_01G | 109.5 | 66.6 | 82.6 | 63.2 | 88.6 | 68.5 |
| Y300_14T | 105.4 | 78.6 | 104.4 | 72.7 | 92.8 | 63.7 |
| Y300_18N | 100.9 | 96.2 | 101.0 | 92.7 | 96.0 | 63.0 |
| Y300_04F | 102.3 | 103.3 | 103.3 | 106.2 | 100.1 | 62.8 |
| Y300_20W | 106.0 | 104.0 | 102.6 | 109.9 | 100.8 | 67.5 |
| Y300_16H | 104.6 | 102.8 | 105.1 | 113.7 | 101.8 | 63.7 |
| Y300_07I | 101.7 | 90.9 | 120.3 | 97.4 | 103.3 | 60.5 |
| Y300_09D | 106.1 | 105.1 | 100.8 | 121.7 | 103.7 | 68.4 |
| Y300_19Q | 106.2 | 118.8 | 106.6 | 141.5 | 104.6 | 63.0 |
| Y300_06M | 105.8 | 105.1 | 116.3 | 110.1 | 106.5 | 61.9 |
| Y300_10E | 107.9 | 127.1 | 107.9 | 174.8 | 113.2 | 68.6 |
| Y300_08L | 106.7 | 96.9 | 120.0 | 96.1 | 113.9 | 60.6 |
| S324_11K | 96.3 | 91.0 | 102.3 | 89.6 | 90.2 | 68.2 |
| S324_08L | 97.3 | 109.5 | 106.1 | 117.1 | 95.5 | 67.4 |
| S324_19Q | 105.9 | 86.8 | 106.5 | 87.2 | 96.2 | 67.2 |
| S324_12R | 95.9 | 84.0 | 107.1 | 82.4 | 98.1 | 68.8 |

TABLE 9-continued

| Name | He/Con 1a | He/Con 2aR | He/Con 2aH | He/Con 2b | He/Con 3a | Tm [° C.] |
|---|---|---|---|---|---|---|
| S324_04F | 102.7 | 99.6 | 105.6 | 99.9 | 99.3 | 69.0 |
| S324_07I | 96.2 | 108.9 | 107.2 | 125.1 | 100.6 | 68.4 |
| S324_03V | 97.7 | 112.6 | 108.2 | 127.8 | 101.4 | 66.3 |
| S324_18N | 108.9 | 100.7 | 108.6 | 105.9 | 103.4 | 69.7 |
| S324_10E | 98.9 | 99.0 | 114.0 | 101.1 | 107.8 | 66.9 |
| S324_09D | 97.7 | 102.0 | 117.3 | 112.0 | 109.7 | 66.2 |
| S324_15Y | 107.4 | 107.1 | 113.5 | 115.3 | 110.1 | 68.6 |
| S324_14T | 114.1 | 93.9 | 107.4 | 115.4 | 112.0 | 67.1 |
| S324_16H | 106.3 | 105.0 | 113.2 | 109.1 | 112.7 | 69.3 |
| S324_02A | 96.9 | 99.9 | 113.7 | 102.3 | 113.0 | 66.3 |
| S324_01G | 93.2 | 94.4 | 109.6 | 106.0 | 114.0 | 65.4 |
| S324_06M | 104.2 | 117.9 | 121.9 | 125.6 | 124.5 | 66.1 |
| N325_09D | 105.0 | 111.1 | 55.3 | 139.2 | 53.0 | 63.1 |
| N325_16H | 99.9 | 85.3 | 50.0 | 78.5 | 68.0 | 71.3 |
| N325_13S | 101.7 | 137.3 | 83.0 | 198.5 | 71.9 | 71.0 |
| K326_20W | 108.4 | 125.3 | 86.7 | 166.4 | 93.7 | 65.5 |
| K326_12R | 105.2 | 98.6 | 104.7 | 100.0 | 101.4 | 68.8 |
| K326_16H | 108.6 | 114.9 | 101.9 | 133.0 | 106.2 | 66.7 |
| K326_04F | 107.0 | 129.4 | 101.0 | 173.8 | 113.6 | 65.3 |
| K326_01G | 106.1 | 107.9 | 104.6 | 119.2 | 114.1 | 69.6 |
| K326_05P | 106.3 | 118.5 | 102.9 | 140.7 | 117.2 | 68.4 |
| K326_19Q | 107.5 | 123.8 | 105.6 | 156.1 | 117.4 | 67.9 |
| K326_13S | 105.5 | 119.0 | 110.3 | 139.0 | 118.0 | 69.8 |
| K326_15Y | 111.2 | 130.7 | 102.3 | 178.6 | 124.0 | 65.7 |
| K326_08L | 105.3 | 131.1 | 96.5 | 197.9 | 126.1 | 67.1 |
| K326_06M | 107.7 | 132.1 | 107.6 | 184.7 | 126.8 | 66.6 |
| K326_02A | 106.8 | 124.6 | 109.9 | 156.0 | 129.9 | 69.2 |
| K326_18N | 110.4 | 110.5 | 113.0 | 118.4 | 134.2 | 68.9 |
| K326_03V | 107.0 | 134.8 | 101.0 | 196.5 | 134.9 | 66.5 |
| K326_10E | 109.0 | 141.6 | 106.0 | 224.2 | 137.5 | 68.0 |
| K326_14T | 109.3 | 128.3 | 119.2 | 167.5 | 139.7 | 64.1 |
| K326_09D | 108.6 | 141.7 | 114.9 | 216.1 | 147.6 | 68.0 |
| K326_07I | 105.7 | 140.8 | 104.3 | 222.8 | 153.1 | 66.1 |
| A327_20W | 100.0 | 95.9 | 76.6 | 98.2 | 52.6 | 67.3 |
| A327_06M | 105.7 | 80.0 | 89.3 | 74.1 | 54.0 | 69.0 |
| A327_19Q | 98.5 | 77.7 | 79.6 | 67.5 | 54.0 | 68.0 |
| A327_05P | 101.7 | 80.6 | 67.9 | 86.3 | 61.9 | 62.1 |
| A327_18N | 100.1 | 114.4 | 79.0 | 140.9 | 62.8 | 68.2 |
| A327_13S | 104.8 | 98.6 | 84.4 | 99.0 | 66.7 | 61.4 |
| A327_10E | 105.8 | 141.7 | 108.1 | 175.1 | 70.5 | 65.4 |
| A327_09D | 105.3 | 159.4 | 124.0 | 213.9 | 86.0 | 65.7 |
| L328_18N | 101.1 | 76.4 | 80.6 | 100.7 | 51.1 | 63.1 |
| L328_16H | 98.5 | 106.2 | 84.5 | 100.4 | 55.9 | 64.2 |
| L328_15Y | 104.0 | 174.4 | 106.5 | 240.4 | 70.2 | 65.5 |
| L328_13S | 101.4 | 150.1 | 145.8 | 185.9 | 73.7 | 64.5 |
| L328_14T | 102.8 | 152.9 | 137.5 | 176.0 | 77.4 | 64.9 |
| L328_06M | 101.0 | 148.5 | 122.5 | 176.4 | 80.8 | 67.7 |
| L328_03V | 103.4 | 149.6 | 115.8 | 156.6 | 80.9 | 64.9 |
| L328_02A | 100.9 | 150.2 | 154.2 | 180.0 | 81.3 | 65.0 |
| L328_04F | 100.2 | 177.4 | 84.9 | 272.7 | 81.5 | 67.2 |
| L328_19Q | 103.5 | 114.9 | 102.7 | 130.7 | 83.4 | 62.8 |
| L328_07I | 101.8 | 159.9 | 111.2 | 199.7 | 86.4 | 66.0 |
| P329_09D | 80.1 | 76.0 | 57.1 | 60.4 | 52.5 | 66.3 |
| P329_10E | 81.4 | 72.7 | 57.6 | 59.5 | 52.7 | 66.7 |
| A330_09D | 112.1 | 79.5 | 67.8 | 62.8 | 56.4 | 65.9 |
| A330_18N | 110.0 | 91.0 | 88.3 | 71.9 | 67.3 | 68.2 |
| A330_12R | 102.8 | 116.1 | 116.5 | 95.8 | 77.3 | 67.9 |
| A330_10E | 110.9 | 97.2 | 87.7 | 79.2 | 82.8 | 67.2 |
| A330_14T | 108.5 | 107.1 | 102.1 | 87.9 | 85.8 | 67.9 |
| A330_19Q | 108.7 | 116.9 | 110.5 | 102.6 | 86.3 | 67.4 |
| A330_01G | 109.2 | 122.2 | 107.0 | 116.9 | 87.3 | 67.0 |
| A330_11K | 106.8 | 123.5 | 118.3 | 107.3 | 91.8 | 68.2 |
| A330_03V | 109.0 | 84.0 | 86.1 | 59.2 | 98.8 | 68.5 |
| A330_07I | 108.7 | 96.0 | 94.4 | 75.8 | 100.9 | 68.2 |
| A330_20W | 111.1 | 97.6 | 93.8 | 86.0 | 102.0 | 67.9 |
| A330_16H | 109.2 | 111.3 | 109.7 | 99.0 | 102.0 | 69.5 |
| A330_08L | 110.4 | 99.7 | 94.7 | 79.6 | 121.8 | 66.9 |
| A330_15Y | 108.4 | 114.3 | 106.3 | 107.2 | 122.3 | 69.0 |
| A330_06M | 108.0 | 107.2 | 101.3 | 90.9 | 138.6 | 68.2 |
| A330_04F | 109.5 | 112.2 | 103.7 | 104.8 | 144.0 | 67.3 |
| P331_07I | 106.0 | 109.0 | 80.1 | 126.9 | 60.4 | 62.8 |
| P331_11K | 100.2 | 94.6 | 83.7 | 93.9 | 61.8 | 60.6 |
| P331_08L | 104.9 | 100.9 | 85.9 | 106.1 | 66.0 | 60.6 |
| P331_03V | 104.4 | 113.5 | 85.4 | 131.5 | 66.9 | 64.1 |
| P331_18N | 106.4 | 103.8 | 87.2 | 109.9 | 67.1 | 61.7 |
| P331_14T | 102.4 | 103.5 | 86.5 | 110.6 | 67.8 | 63.9 |
| P331_06M | 106.3 | 105.1 | 88.1 | 112.7 | 68.4 | 62.0 |

TABLE 9-continued

| Name | He/Con 1a | He/Con 2aR | He/Con 2aH | He/Con 2b | He/Con 3a | Tm [° C.] |
|---|---|---|---|---|---|---|
| P331_10E | 107.8 | 112.4 | 90.1 | 128.0 | 68.7 | 63.4 |
| P331_04F | 108.3 | 109.7 | 87.7 | 122.5 | 70.7 | 63.0 |
| P331_09D | 109.2 | 101.4 | 93.6 | 104.5 | 71.6 | 64.1 |
| P331_20W | 107.3 | 108.9 | 85.8 | 123.2 | 71.9 | 61.8 |
| P331_16H | 104.8 | 113.1 | 87.5 | 128.5 | 73.4 | 63.0 |
| P331_19Q | 107.5 | 96.1 | 91.6 | 94.0 | 73.9 | 62.7 |
| P331_I5Y | 108.9 | 111.5 | 89.0 | 126.8 | 74.9 | 63.2 |
| P331_13S | 107.7 | 103.8 | 94.0 | 107.3 | 80.9 | 65.8 |
| P331_02A | 104.7 | 105.1 | 93.9 | 110.3 | 82.5 | 66.0 |
| I332_03V | 100.5 | 87.0 | 108.4 | 89.5 | 85.2 | 67.8 |
| I332_16H | 100.5 | 97.6 | 113.1 | 103.1 | 89.0 | 60.6 |
| I332_04F | 106.2 | 104.1 | 107.8 | 115.2 | 89.3 | 61.9 |
| I332_06M | 104.7 | 108.0 | 113.6 | 116.1 | 92.5 | 65.0 |
| I332_13S | 97.3 | 97.9 | 113.3 | 109.1 | 95.6 | 60.9 |
| I332_19Q | 103.2 | 95.1 | 111.8 | 104.5 | 101.0 | 62.8 |
| I332_02A | 100.2 | 96.9 | 115.2 | 114.5 | 102.7 | 63.2 |
| I332_14T | 104.2 | 104.2 | 118.9 | 117.9 | 109.6 | 63.1 |
| I332_10E | 109.3 | 113.2 | 112.1 | 157.8 | 212.9 | 60.1 |
| E333_18N | 91.4 | 117.9 | 110.3 | 98.2 | 76.2 | 63.3 |
| E333_12R | 96.7 | 127.1 | 109.8 | 103.8 | 92.2 | 65.6 |
| E333_11K | 96.6 | 128.1 | 112.5 | 104.0 | 97.7 | 63.0 |
| E333_14T | 96.7 | 134.8 | 115.2 | 111.2 | 100.1 | 66.0 |
| E333_07I | 96.5 | 142.4 | 113.0 | 124.1 | 100.1 | 67.3 |
| E333_06M | 96.7 | 132.0 | 110.1 | 110.3 | 100.4 | 65.9 |
| E333_01G | 97.2 | 126.6 | 112.1 | 105.1 | 101.1 | 61.5 |
| E333_15Y | 95.8 | 137.3 | 114.5 | 121.8 | 101.2 | 66.6 |
| E333_19Q | 93.7 | 130.4 | 112.9 | 110.3 | 101.3 | 68.4 |
| E333_08L | 96.8 | 140.5 | 116.5 | 122.6 | 101.5 | 66.0 |
| E333_20W | 93.9 | 132.3 | 106.2 | 115.6 | 103.8 | 64.0 |
| E333_04F | 96.9 | 139.2 | 116.5 | 122.1 | 104.1 | 65.9 |
| E333_13S | 97.6 | 125.3 | 115.4 | 105.6 | 105.7 | 65.9 |
| E333_16H | 95.4 | 118.7 | 113.5 | 107.6 | 106.0 | 60.8 |
| E333_03V | 99.4 | 135.3 | 112.2 | 120.2 | 106.0 | 68.4 |
| E333_02A | 97.7 | 128.5 | 114.7 | 108.2 | 108.5 | 65.5 |
| K334_01G | 98.0 | 127.1 | 92.5 | 119.4 | 124.9 | 64.2 |
| K334_05P | 98.7 | 140.6 | 112.0 | 135.6 | 137.6 | 62.0 |
| K334_16H | 99.3 | 149.2 | 119.2 | 145.6 | 137.6 | 62.8 |
| K334_19Q | 100.4 | 148.8 | 116.2 | 141.0 | 140.1 | 67.1 |
| K334_18N | 99.0 | 152.4 | 114.4 | 148.2 | 140.2 | 65.4 |
| K334_15Y | 99.1 | 147.9 | 121.6 | 141.0 | 145.0 | 65.9 |
| K334_14T | 99.2 | 152.6 | 118.4 | 148.9 | 145.6 | 65.7 |
| K334_08L | 99.1 | 144.9 | 119.6 | 137.4 | 147.5 | 66.2 |
| K334_13S | 99.3 | 148.7 | 116.5 | 143.2 | 149.5 | 66.1 |
| K334_02A | 100.2 | 143.0 | 111.3 | 138.8 | 151.5 | 65.8 |
| K334_04F | 99.6 | 150.5 | 121.2 | 143.1 | 151.9 | 65.9 |
| K334_03V | 99.1 | 159.9 | 125.5 | 160.9 | 153.9 | 67.0 |
| K334_07I | 98.7 | 155.2 | 126.3 | 153.7 | 155.6 | 67.3 |
| K334_09D | 100.8 | 127.0 | 95.6 | 122.3 | 164.4 | 65.6 |
| K334_10E | 103.9 | 144.1 | 112.7 | 147.9 | 185.9 | 63.6 |
| T335_02A | 106.6 | 108.0 | 104.4 | 102.7 | 90.9 | 65.8 |
| T335_11K | 114.3 | 105.3 | 102.8 | 99.4 | 91.7 | 67.0 |
| T335_04F | 108.3 | 113.4 | 106.8 | 112.4 | 91.7 | 64.6 |
| T335_12R | 116.4 | 105.7 | 103.3 | 100.4 | 93.1 | 67.0 |
| T335_18N | 109.1 | 112.1 | 106.9 | 111.0 | 94.4 | 63.8 |
| T335_01G | 107.7 | 109.5 | 106.8 | 105.6 | 95.1 | 63.2 |
| T335_03V | 107.7 | 112.3 | 106.7 | 109.3 | 96.3 | 68.4 |
| T335_06M | 110.1 | 110.4 | 106.4 | 108.6 | 97.0 | 66.2 |
| T335_20W | 109.5 | 114.6 | 108.6 | 113.5 | 97.3 | 65.0 |
| T335_19Q | 108.3 | 111.8 | 106.8 | 109.4 | 97.7 | 64.9 |
| T335_08L | 118.2 | 113.9 | 109.4 | 113.6 | 97.8 | 64.9 |
| T335_16H | 109.0 | 114.1 | 109.1 | 111.9 | 99.3 | 64.3 |
| T335_15Y | 110.6 | 117.4 | 110.1 | 118.2 | 99.7 | 64.7 |
| T335_13S | 108.1 | 115.5 | 109.9 | 111.1 | 100.4 | 67.6 |
| T335_10E | 112.2 | 117.3 | 111.5 | 118.5 | 102.1 | 62.9 |
| T335_07I | 112.6 | 115.2 | 111.6 | 115.9 | 102.5 | 67.0 |
| T335_09D | 110.8 | 115.9 | 110.8 | 118.4 | 102.9 | 61.2 |
| T335_14T | 109.9 | 115.8 | 111.8 | 116.5 | 103.6 | 68.0 |
| I336_07I | 107.7 | 114.2 | 108.5 | 113.0 | 98.5 | 67.9 |
| I336_18N | 111.2 | 109.8 | 106.7 | 106.7 | 99.4 | 62.0 |
| I336_08L | 110.8 | 116.2 | 109.3 | 117.4 | 101.6 | 64.8 |
| I336_14T | 107.8 | 102.1 | 103.2 | 97.8 | 103.4 | 64.1 |
| I336_06M | 111.6 | 112.3 | 109.9 | 110.8 | 104.1 | 61.7 |
| I336_02A | 109.3 | 100.2 | 102.4 | 92.8 | 106.0 | 61.8 |
| I336_03V | 108.5 | 104.1 | 105.8 | 98.7 | 107.3 | 67.2 |
| S337_11K | 100.8 | 104.8 | 101.7 | 102.8 | 80.1 | 67.3 |
| S337_03V | 103.4 | 108.0 | 104.0 | 107.8 | 87.1 | 65.3 |
| S337_07I | 102.0 | 110.9 | 107.0 | 113.4 | 88.3 | 63.3 |

TABLE 9-continued

| Name | He/Con 1a | He/Con 2aR | He/Con 2aH | He/Con 2b | He/Con 3a | Tm [° C.] |
|---|---|---|---|---|---|---|
| S337_06M | 103.6 | 107.1 | 103.7 | 105.5 | 89.7 | 66.4 |
| S337_08L | 102.1 | 109.4 | 106.4 | 109.2 | 90.2 | 62.6 |
| S337_19Q | 101.4 | 107.6 | 104.1 | 108.7 | 91.2 | 66.9 |
| S337_02A | 102.5 | 107.0 | 103.1 | 106.0 | 92.4 | 67.0 |
| S337_12R | 102.6 | 109.2 | 105.3 | 108.4 | 92.7 | 68.1 |
| S337_20W | 101.6 | 112.5 | 108.2 | 118.6 | 93.8 | 64.4 |
| S337_14T | 101.8 | 112.0 | 109.7 | 114.0 | 94.0 | 67.3 |
| S337_04F | 102.9 | 106.5 | 105.1 | 106.6 | 94.4 | 65.9 |
| S337_15Y | 100.6 | 107.4 | 105.6 | 109.2 | 94.9 | 65.5 |
| S337_01G | 103.3 | 101.2 | 98.7 | 100.2 | 95.2 | 64.9 |
| S337_18N | 102.1 | 108.5 | 105.9 | 112.6 | 96.9 | 64.1 |
| S337_10E | 103.1 | 113.7 | 108.7 | 116.9 | 97.8 | 62.1 |
| S337_16H | 101.4 | 110.6 | 107.6 | 114.0 | 100.3 | 66.6 |

Figure 13:
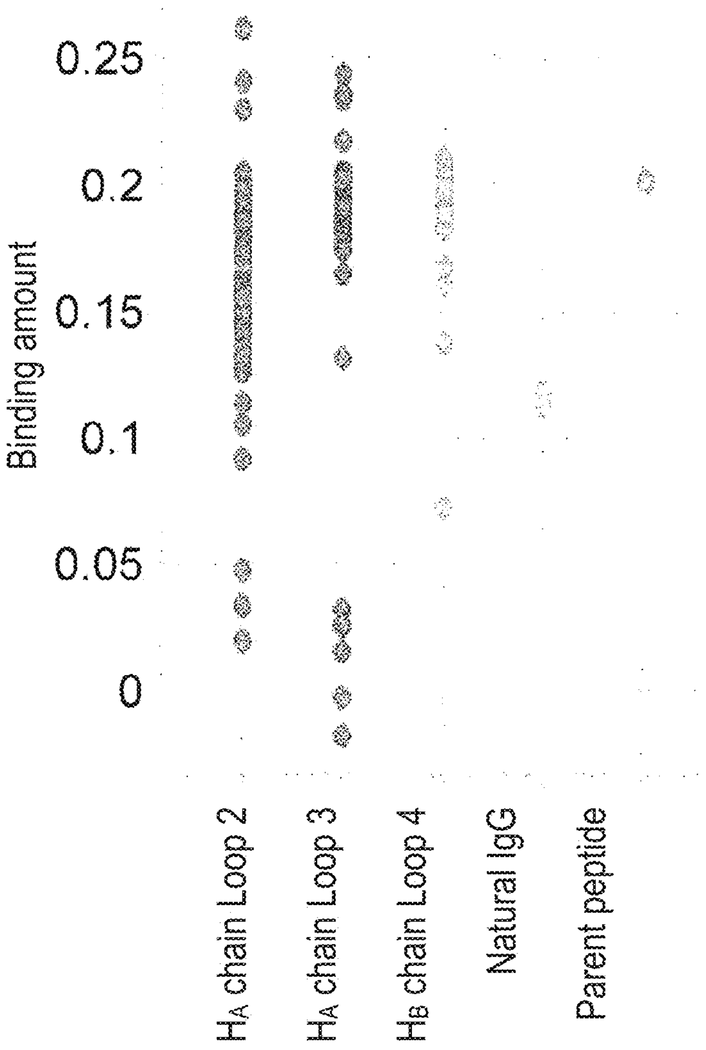
FIG. 13 is a diagram showing results of comparing the FcγRIIIa-binding activity of arbitrary clones selected from an antibody library, wherein each loop of H240-Kn071/H240-H1076/L73 was made into the library, with that of naturally occurring IgG1 (H240-G1d/H240-G1d/L73) and a parent peptide (H240-Kn071/H240-H1076/L73).
Figure 14:
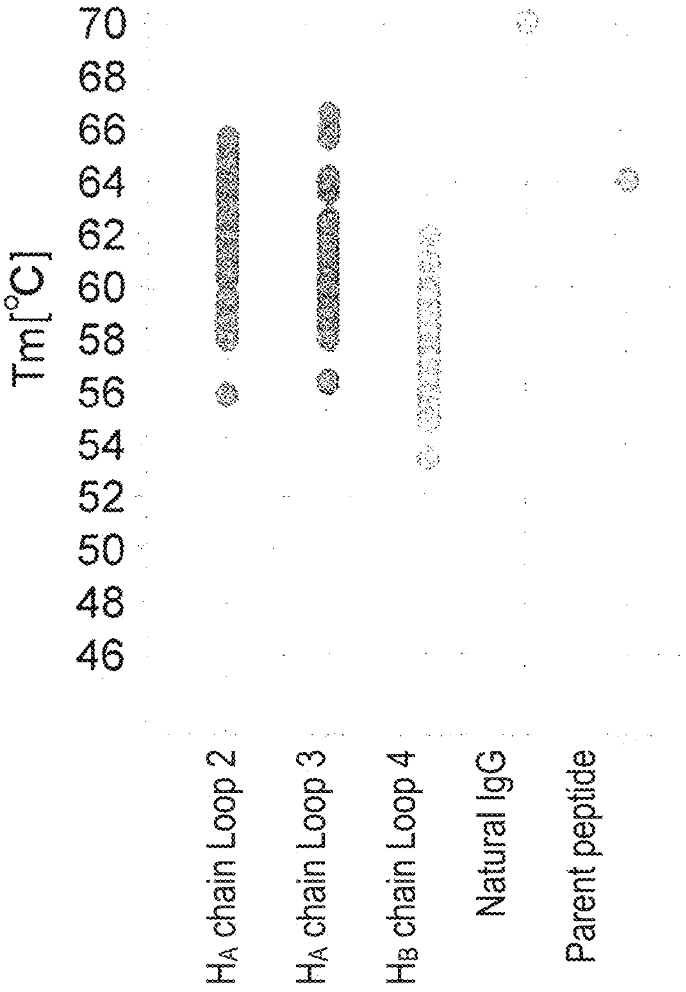
FIG. 14 is a diagram showing results of comparing the thermal denaturation temperatures [° C.] of CH2 domains of arbitrary clones selected from an antibody library, wherein each loop of H240-Kn071/H240-H1076/L73 was made into the library, with those of naturally occurring IgG1 (H240-G1d/H240-G1d/L73) and a parent peptide (H240-Kn071/H240-H1076/L73).

Of the loop regions in the parent peptide H240-Kn061/H240-H1071/L73 obtained in Example 3, particularly, AL2, AL3, BL2, and BL4 were presumed to participate in binding on the Y side, from the structure shown in FIG. 12. Constant regions in which the amino acids shown in Table 9 appeared at random in AL2, AL3, and BL4 presumed to particularly largely participate in the binding were prepared by the method shown in Reference Example 1 to prepare antibody molecules. The prepared molecules were evaluated for their binding activity against FcγR and thermal stability of the CH2 domains according to Reference Examples 2 and 4, respectively. The binding activity against FcγR was evaluated by comparison with a binding amount at the binding phase of the parent peptide or the naturally occurring IgG1. Since the antibody concentration and the antigen (FcγR) concentration used in the evaluation were each kept constant, the binding activity of each antibody against FcγR can be determined by the comparison of a binding amount at the binding phase. In short, each antibody can be regarded as maintaining its binding activity against FcγR, when its binding amount is not reduced compared with the parent peptide or the naturally occurring IgG1 used. The results are shown in FIG. 13. Many altered forms were found to also maintain binding activity against FcγR at a level equal to or higher than that of the naturally occurring IgG1. In addition, the thermal denaturation temperature of CH2 domains was compared between each antibody and the parent peptide or the naturally occurring IgG1. The results are shown in FIG. 14. As a result, the thermal denaturation temperature of each antibody was not drastically reduced compared with the naturally occurring IgG1 or the parent peptide. Particularly, all of the samples had a thermal denaturation temperature at least 10° C. higher than the body temperature (40° C.) of organisms. Thus, the molecules contained in the library can be expected to be sufficiently stable even in vivo. These results suggested that the library containing the amino acids selected in Table 9 for each region is useful for obtaining a molecule that maintains the interaction with FcγR on the X side and interacts with the second antigen on the Y side, while maintaining the stability of the CH2 regions.

[Example 5] Extension of Loop for Obtaining Fc Region Binding to Antigen on Y Side A shown in Example 4, the library was designed in which the acceptable amino acids appeared in the loops AL2 ($H_A$ chain Loop 2), AL3 ($H_A$ chain Loop 3), BL2 ($H_B$ chain Loop 2), and BL4 ($H_B$ chain Loop 4) shown in FIG. 12. In the case of obtaining a scaffold protein molecule binding to an arbitrary antigen, a method is known, which involves preparing a library using a loop derived, by alteration to a larger length (extension), from the loop of a natural protein used in the scaffold (Peds (2010), 23 (4), 289-297). The advantages of such a longer loop are that: amino acid sequence diversity can be increased; and a long loop, such as antibody heavy chain CDR3, permits diverse confirmations; thus, a molecule binding to an arbitrary antigen can be obtained easily. A consideration for extending the loop of the existing scaffold protein is merely whether the resulting molecule maintains thermal stability. For dual binding Fc, however, it is a very important consideration whether the molecule can maintain thermal stability as well as binding activity against FcγR on the X side. In the case of homodimerized antibodies having extended loops in both H chains as usually performed, the extended loop regions are thought to reduce thermal stability and interaction with FcγR, despite that these regions make no contribution to antigen binding on the Y side. Thus, the loop needs to be extended in either one chain, not in both chains.

Figures 1, 15:
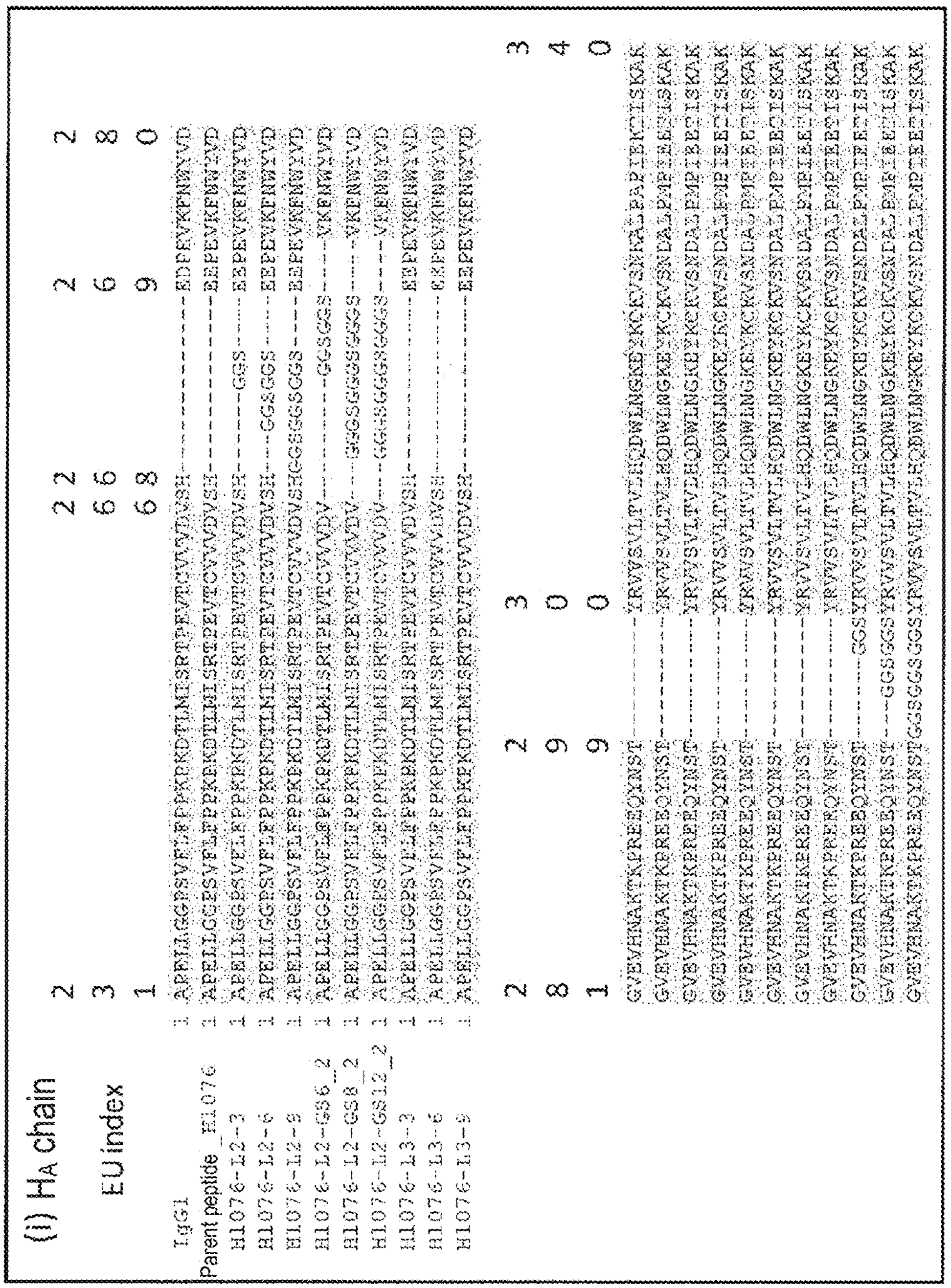
Figures 2, 15:
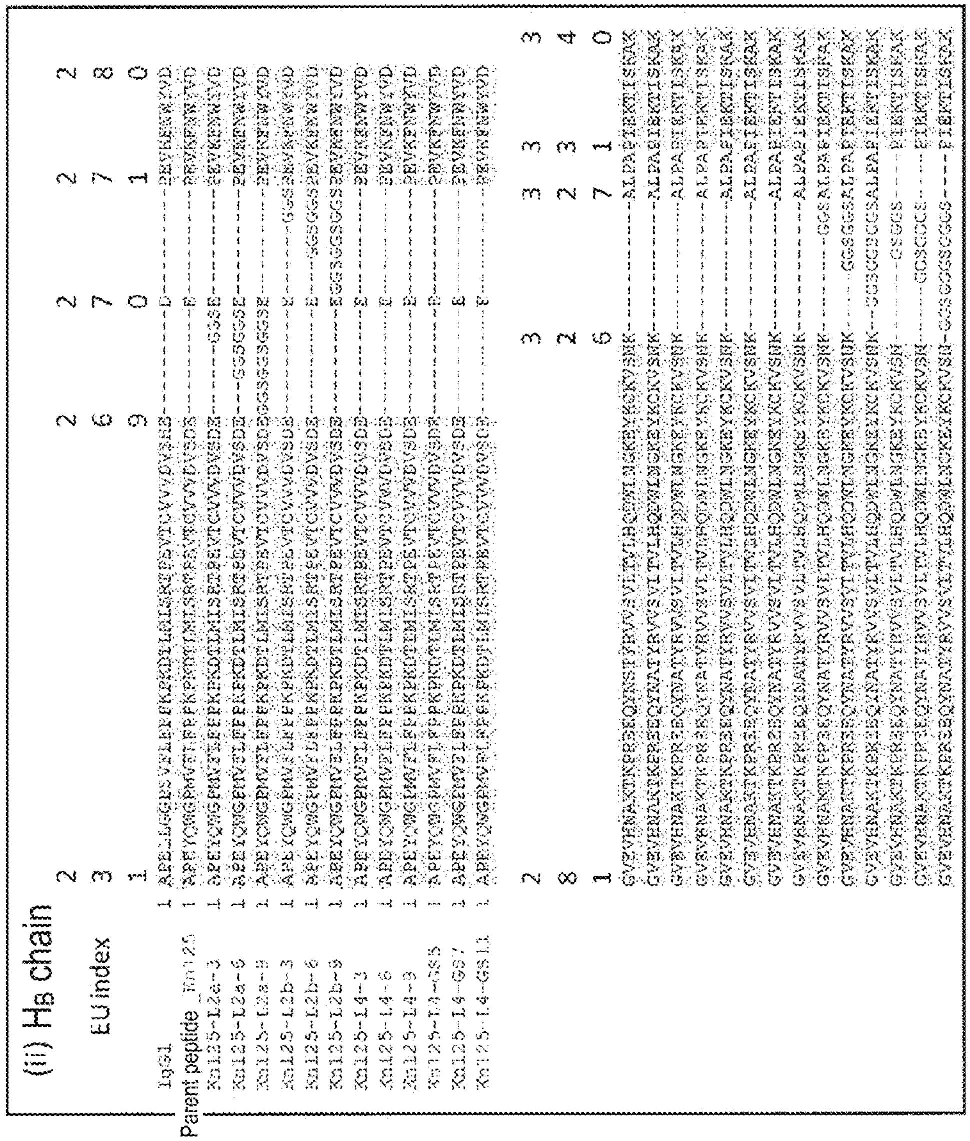

Accordingly, a study was conducted on whether the loop of the parent peptide H240-Kn125/H240-H1076/L73 could be extended without significantly impairing its thermal stability and binding activity against FcγR on the X side. Each peptide chain of 3 to 9 amino acids constituted by glycine and serine as shown in FIG. 15 was incorporated to each loop region shown in FIG. 12 to prepare antibody molecules. The prepared antibody molecules were evaluated for their thermal denaturation temperatures (Tm) with binding activity against FcγR and stability as indexes. Each heterodimerized antibody having an altered $H_A$ chain of the parent peptide H240-H1076 was prepared using the altered form of the $H_A$ chain and H240-Kn125 (SEQ ID NO: 21) as H chains and L73-k0 (SEQ ID NO: 11) as an L chain. Likewise, each heterodimerized antibody having an altered $H_B$ chain of the parent peptide H240-Kn125 was prepared using the altered form of the $H_B$ chain and H240-H1076 (SEQ ID NO: 22) as H chains and L73-k0 (SEQ ID NO: 11) as an L chain.

The molecules with the incorporated peptide chains were prepared and expressed according to the method described in Reference Example 1. The thermal denaturation temperatures of the obtained molecules were measured by the method described in Reference Example 4. Their binding activity against FcγR was evaluated by the method described in Reference Example 2.

Table 10 shows the results of evaluating the binding activity against FcγR and measuring the thermal denaturation temperatures. Even the molecules with the longest peptide chain (9 amino acids) inserted in each of the loops AL2, AL3, BL2, and BL4 maintained the binding activity against FcγR and also had a sufficiently high thermal denaturation temperature. These results demonstrated that a peptide chain is inserted to the first H chain or the second H chain of the Fc region to extend the loop in the heterodimerized antibody, whereby the peptide chain can be extended without impairing binding activity against FcγR and the stability of the Fc region. Although the peptide constituted by Gly and Ser to extend the loop was inserted in this test, a peptide comprising arbitrary amino acids may be inserted.

TABLE 10

| Antibody | First H chain SEQ ID NO | Second H chain SEQ ID NO | L chain SEQ ID NO | FcγRIIIaV KD[M] | Tm [° C.] |
|---|---|---|---|---|---|
| HI076/Kn125 | SEQ ID NO: 22 | SEQ ID NO: 21 | SEQ ID NO: 11 | 4.70E−10 | 63.40 |
| HI076-L2-GS6 | SEQ ID NO: 23 | SEQ ID NO: 21 | SEQ ID NO: 11 | 2.80E−09 | 59.92 |
| HI076-L2-GS8 | SEQ ID NO: 24 | SEQ ID NO: 21 | SEQ ID NO: 11 | 5.00E−09 | 60.60 |
| HI076-L2-GS12 | SEQ ID NO: 25 | SEQ ID NO: 21 | SEQ ID NO: 11 | 2.80E−09 | 60.40 |
| HI076-L2-3 | SEQ ID NO: 26 | SEQ ID NO: 21 | SEQ ID NO: 11 | 2.30E−09 | 61.08 |
| HI076-L2-6 | SEQ ID NO: 27 | SEQ ID NO: 21 | SEQ ID NO: 11 | 1.90E−09 | 60.68 |
| HI076-L2-9 | SEQ ID NO: 28 | SEQ ID NO: 21 | SEQ ID NO: 11 | 2.40E−09 | 60.68 |
| HI076-L3-3 | SEQ ID NO: 29 | SEQ ID NO: 21 | SEQ ID NO: 11 | 2.90E−09 | 60.12 |
| HI076-L3-6 | SEQ ID NO: 30 | SEQ ID NO: 21 | SEQ ID NO: 11 | 7.20E−09 | 59.80 |
| HI076-L3-9 | SEQ ID NO: 31 | SEQ ID NO: 21 | SEQ ID NO: 11 | 7.30E−09 | 59.60 |
| Kn125-L4-GS5 | SEQ ID NO: 22 | SEQ ID NO: 32 | SEQ ID NO: 11 | 1.80E−09 | 61.72 |
| Kn125-L4-GS7 | SEQ ID NO: 22 | SEQ ID NO: 33 | SEQ ID NO: 11 | 2.00E−09 | 60.72 |
| Kn125-L4-GS11 | SEQ ID NO: 22 | SEQ ID NO: 34 | SEQ ID NO: 11 | 1.50E−09 | 59.48 |
| Kn125-L2a-3 | SEQ ID NO: 22 | SEQ ID NO: 35 | SEQ ID NO: 11 | 1.00E−08 | 61.80 |
| Kn125-L2a-6 | SEQ ID NO: 22 | SEQ ID NO: 36 | SEQ ID NO: 11 | 9.20E−09 | 61.00 |
| Kn125-L2a-9 | SEQ ID NO: 22 | SEQ ID NO: 37 | SEQ ID NO: 11 | 1.10E−08 | 60.68 |
| Kn125-L2b-3 | SEQ ID NO: 22 | SEQ ID NO: 38 | SEQ ID NO: 11 | 7.80E−09 | 61.28 |
| Kn125-L2b-6 | SEQ ID NO: 22 | SEQ ID NO: 39 | SEQ ID NO: 11 | 6.30E−09 | 60.32 |
| Kn125-L2b-9 | SEQ ID NO: 22 | SEQ ID NO: 40 | SEQ ID NO: 11 | 7.00E−09 | 60.28 |
| Kn125-L4-3 | SEQ ID NO: 22 | SEQ ID NO: 41 | SEQ ID NO: 11 | 6.90E−09 | 60.40 |
| Kn125-L4-6 | SEQ ID NO: 22 | SEQ ID NO: 42 | SEQ ID NO: 11 | 1.70E−09 | 59.28 |
| Kn125-L4-9 | SEQ ID NO: 22 | SEQ ID NO: 43 | SEQ ID NO: 11 | 1.70E−09 | 58.88 |
| IgG1 | SEQ ID NO: 44 | SEQ ID NO: 44 | SEQ ID NO: 11 | 3.40E−07 | 70.00 |

These studies indicated that the library containing the amino acids selected in Example 4 and the library containing peptide chains extended within the regions concerted shown in this Example can be used as a library for obtaining an improved antibody as dual binding Fc that has strong binding activity against FcγR on the X side and binding activity against the antigen of interest (second antigen) on the Y side, but does not bind to the FcγR and the Y-side binding antigen (second antigen) at the same time. The library designed in Examples 4 and 5 can be used to obtain improved Fc regions and improved antibodies as shown below. Techniques known in the art, for example, in vitro display methods (e.g., ribosomal display and mRNA display methods), bacteria display methods (e.g., phage display and *E. coli* display methods), and cell display methods (e.g., yeast display and mammalian display methods) can be used (Advanced Drug Delivery Reviews (2006), 58, 1622-1654). According to these methods, the CH2 domains contained in the designed library can be displayed to select a CH2 domain having binding activity against the antigen (second antigen). The gene sequence of the selected CH2 domain is determined, and the CH2 domain of the desired human antibody or Fc region is replaced with this CH2 domain. A clone that has binding activity against FcγR, but does not bind to the antigen (second antigen) and the FcγR at the same time can be selected as to the altered human antibody or Fc region thus obtained. The yeast display and mammalian display methods can display the whole Fc regions or antibody molecules. These regions can therefore be displayed to select an Fc region that has binding activity against the antigen (second antigen) and binding activity against FcγR, but does not bind to the antigen (second antigen) and the FcγR at the same time. In addition to these methods using the library to obtain a CH2 domain having binding activity against the second antigen, an exemplary alternative method employs a peptide previously known to have binding activity against the second antigen. Specifically, the peptide known to have binding activity against the antigen is inserted to each loop region proven alterable from the studies of Examples 4 and 5 to obtain a human antibody or an Fc region having binding activity against the second antigen. The altered human antibody or the altered Fc region thus obtained is confirmed to bind to FcγR and not to bind to the antigen and the FcγR at the same time. In this way, the altered human antibody or the altered Fc region (dual binding Fc) can also be obtained.

[Example 6] Obtainment of Dual Binding Fc Having Fc Region that Binds to Each of FcγR and Antigen, but does not Bind to FcγR and Antigen at the Same Time Integrin avβ3, known as an adhesion molecule, is expressed in many cancer cells and peritumoral blood vessels and as such, is useful as a target molecule in tumor targeting, whereas this molecule is also known to be expressed in various normal cells (Thromb Haemost. 1998 November; 80 (5): 726-34). Thus, binding to FcγR and integrin αvβ3 at the same time might damage normal cells due to potent ADCC activity mediated by NK cells. Accordingly, it was assumed that an anti-EREG antibody molecule can target tumor cells expressing integrin avβ3 without damaging normal cells, if a molecule that does not bind to FcγR and integrin αvβ3 at the same time can be prepared. Thus, a study was conducted to obtain a dual binding Fc molecule capable of binding via its variable regions (Fab) to the first antigen epiregulin (EREG) and binding via its Fc region to FcγR on the X side the second antigen integrin αvβ3 on the Y side, but not capable of binding to the FcγR and the integrin αvβ3 at the same time.

Given that a "molecule that binds via its Fc region to FcγR under integrin αvβ3-free conditions and binds via its Fc region to integrin αvβ3 under FcγR-free conditions" can be shown to be a "molecule that does not bind to integrin αvβ3 in a state bound with FcγR or does not bind to FcγR in a state bound with integrin αvβ3", it can be concluded that an anti-EREG antibody having the properties of dual binding Fc of interest (i.e., the properties of binding to FcγR on the X side and binding to the antigen on the Y side, but not binding to the FcγR and the antigen at the same time) has been developed successfully.

Obtainment of Antibody Having Fc Region Binding to Integrin αvβ3

Methods for obtaining the dual binding Fc molecule include, as mentioned above, a method using libraries and a method using the insertion of a peptide known to have binding activity to proteins. An RGD (Arg-Gly-Asp) peptide is known as a peptide having binding activity against integrin αvβ3. The RGD (Arg-Gly-Asp) peptide was inserted to a loop region of H240-Kn125/H240-H1076/L73 presumably available in antigen binding from the viewpoint of interaction with FcγR and thermal stability in Examples 4 and 5, to prepare molecules (H240-Kn125/H240-H1076-mal/L73; SEQ ID NOs: 21/45/11, and H240-Kn125-mal/H240-H1076/L73; SEQ ID NOs: 46/22/11) according to Reference Example 1. Also, H240-G1dE/H240-G1dE/L73 (SEQ ID NOs: 44/44/11) having constant regions derived from human natural IgG1, and antibodies (H240-Kn125-CD/H240-H1076/L73; SEQ ID NOs: 47/22/11, and (H240-G1d-CD/H240-G1d-CD/L73; SEQ ID NOs: 48/48/11) with the RGD (Arg-Gly-Asp) peptide inserted in antibody CH3 regions reported in J. Biotech, 155, 193-202, 2011 were prepared as controls according to Reference Example 1. These molecules binding to integrin αvβ3 via their CH3 regions are presumably capable of binding to FcγR and integrin αvβ3 at the same time.

Confirmation of Binding of Antibody to Integrin αvβ3

The integrin αvβ3 binding of each molecule with the RGD (Arg-Gly-Asp) peptide inserted in the Fc region was assessed by ELISA (enzyme-Linked immunosorbent assay). Specifically, integrin αvβ3 (R&D Systems, Inc.) diluted to 1 μg/mL with a coating buffer (0.1 M $NaHCO_3$, pH 9.6) was added at a concentration of 100 μL/well to Nunc-Immuno™ MicroWell™ 96 well solid plates (Nunc) to immobilize the integrin αvβ3 to the plates. Each well of the antigen (integrin αvβ3)-immobilized plates was washed three times with 250 μL of a TBS solution containing 0.1 g/L calcium chloride and 0.1 g/L magnesium chloride (referred to as a TBS(+) solution). A TBS solution containing 5% BSA, 0.1 g/L calcium chloride, and 0.1 g/L magnesium chloride (referred to as a blocking solution) was added thereto at a concentration of 250 μL/well, and the plates were incubated at room temperature for 1 hour.

After removal of the blocking solution, each well was washed three times with a TBS(+) solution. An antibody solution prepared at 1, 10, or 100 μg/mL using a TBS(+) solution was added thereto at a concentration of 100 μL/well, and the plates were incubated at room temperature for 1 hour to bind the antibody to the integrin αvβ3.

After removal of the antibody solution, each well was washed three times with a TBS(+) solution. An HRP-labeled, anti-human IgG-recognizing antibody diluted 50000-fold with a blocking solution was added thereto, and the plates were incubated at room temperature for 1 hour.

After removal of the HRP-labeled antibody solution, each well was washed three times with a TBS(+) solution. After sufficient removal of the solution remaining in each well, a TMB solution was added thereto, and the plates were incubated at room temperature for 20 minutes for color development. The reaction was stopped by the addition of 50 μL of a 1 M sulfuric acid solution. The absorbance of the solution whose reaction had been stopped was measured at a wavelength of 450 nm.

Figure 16:
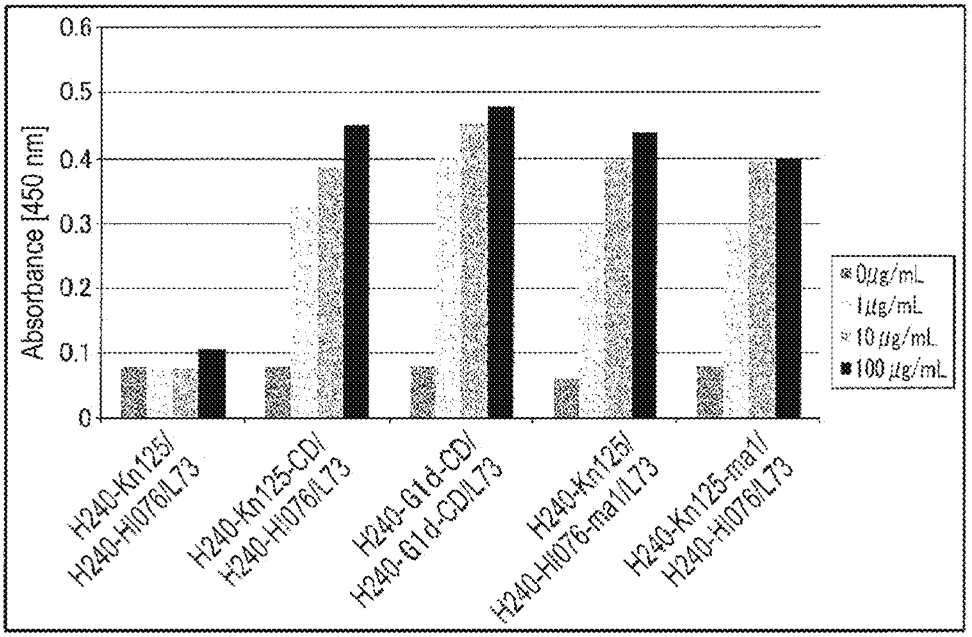
FIG. 16 is a diagram showing results of ELISA by which the binding of an antibody to integrin avβ3 was evaluated.

The results are shown in FIG. 16. The parent antibody H240-Kn125/H240-H1076/L73 exhibited no binding activity against integrin αvβ3, whereas H240-Kn125/H240-H1076-mal/L73, H240-Kn125-mal/H240-H1076/L73, H240-Kn125-CD/H240-H1076/L73, and H240-G1d-CD/H240-G1d-CD/L73 were all observed to bind to integrin αvβ3.

Confirmation of Binding of Antibody to FcγRIIIa

Next, whether the antibodies binding to integrin αvβ3 via their Fc regions, prepared in the preceding paragraph, retained binding activity against FcγR was confirmed by the SPR (surface plasmon resonance) method. Specifically, their interaction with FcγRIIIa was analyzed using BiaCore™ T100 surface plasmon resonance system (GE Healthcare Japan Corp.). The running buffer used was the TBS(+) solution used in the preceding paragraph. The assay temperature was set to 25° C. Protein L was immobilized onto Series S Sensor Chip CM4 (GE Healthcare Japan Corp.) by the amine coupling method to prepare a chip. Each antibody of interest was captured onto the protein L-immobilized chip and allowed to interact with FcγRIIIa diluted with a running buffer. The antibody captured on the chip was washed off through the reaction of 10 mM glycine-HCl (pH 1.5) to regenerate the chip, which was repetitively used.

Each antibody was evaluated for its binding activity against FcγRIIIa with binding activity against FcγRIIIa and dissociation constant for FcγRIIIa as main indexes. The dissociation constant of each antibody for FcγRIIIa was calculated by kinetic analysis on BiaCore™ surface plasmon resonance assay results. Specifically, a sensorgram obtained by assay using BiaCore™ surface plasmon resonance Evaluation Software was globally fit into the 1:1 Langmuir model to calculate an association rate constant ka (L/mol/s) and a dissociation rate constant kd (1/s). From these values, the dissociation constant KD (mol/L) was calculated.

The results are shown in Table 11. From the results shown in Table 11, the antibodies provided with binding activity against integrin αvβ3 were all shown to have stronger binding activity against FcγRIIIa than that of the naturally occurring IgG1 (H240-G1dE/H240-G1dE/L73). In this context, the stronger binding activity than that of the naturally occurring IgG1 means that the dissociation constant KD takes a smaller value than that of the naturally occurring IgG1.

TABLE 11

| Name | SEQ ID NO of first H chain | SEQ ID NO of second H chain | SEQ ID NO of L chain | KD[M] |
|---|---|---|---|---|
| H240-G1dE/H240-G1dE/L73 | SEQ ID NO: 44 | SEQ ID NO: 44 | SEQ ID NO: 11 | 2.9E−07 |
| H240-G1d-CD/H240-G1d-CD/L73 | SEQ ID NO: 48 | SEQ ID NO: 48 | SEQ ID NO: 11 | 3.1E−07 |
| H240-Kn125-CD/H240-HI076/L73 | SEQ ID NO: 22 | SEQ ID NO: 47 | SEQ ID NO: 11 | 8.5E−10 |
| H240-Kn125/H240-HI076-ma1/L73 | SEQ ID NO: 45 | SEQ ID NO: 21 | SEQ ID NO: 11 | 2.1E−09 |
| H240-Kn125-ma1/H240-HI076/L73 | SEQ ID NO: 22 | SEQ ID NO: 46 | SEQ ID NO: 11 | 1.6E−07 |

Confirmation by Competitive ELISA that Fc Region does not Bind to Integrin αvβ3 and FcγRIIIa at Same Time As is evident from the results of the above paragraphs, the obtained molecules had binding activity against integrin αvβ3 and had stronger binding activity against FcγRIIIa than that of the naturally occurring IgG1. Next, the binding of the Fc regions prepared in the above paragraphs to FcγRIIIa and integrin αvβ3 at the same time was assessed.

When a molecule with the RGD (Arg-Gly-Asp) peptide inserted in the Fc region cannot bind to integrin αvβ3 and FcγR at the same time, the amount of the antibody capable of binding to integrin αvβ3 is predicted to be decreased in an FcγR concentration-dependent manner by the addition of FcγR to the antibody solution to be reacted with the integrin αvβ3. The integrin αvβ3 binding of each antibody after addition of FcγR to the antibody solution was assessed by ELISA (enzyme-Linked immunosorbent assay). Specifically, integrin αvβ3 (R&D Systems, Inc.) diluted to 1 μg/mL with a coating buffer (0.1 M $NaHCO_3$, pH 9.6) was added at a concentration of 100 μL/well to Nunc-Immuno™ MicroWell™ 96 well solid plates (Nunc) to immobilize the integrin αvβ3 to the plates. Each well of the antigen (integrin αvβ3)-immobilized plates was washed three times with 250 μL of a TBS solution containing 0.1 g/L calcium chloride and 0.1 g/L magnesium chloride (referred to as a TBS(+) solution). A TBS solution containing 5BSA, 0.1 g/L calcium chloride, and 0.1 g/L magnesium chloride (referred to as a blocking solution) was added thereto at a concentration of 250 μL/well, and the plates were incubated at room temperature for 1 hour.

After removal of the blocking solution, each well was washed three times with a TBS(+) solution. 55 μL of an antibody solution diluted in advance to 2 μg/mL with a TBS(+) solution was mixed with 55 μL of a 0, 2, 20, or 200 μg/mL FcγRIIIa solution to prepare an antibody-FcγR mixed solution, which was then incubated at room temperature for 1 hour. The antibody-FcγR mixed solution was added thereto at a concentration of 100 μL/well, and the plates were incubated at room temperature for 1 hour to bind the antibody to the integrin αvβ3.

After removal of the antibody-FcγR mixed solution, each well was washed three times with a TBS(+) solution. An HRP-labeled, anti-human IgG-recognizing antibody diluted 50000-fold with a blocking solution was added thereto, and the plates were incubated at room temperature for 1 hour.

After removal of the HRP-labeled antibody solution, each well was washed three times with a TBS(+) solution. After sufficient removal of the solution remaining in each well, a TMB solution was added thereto, and the plates were incubated at room temperature for 20 minutes for color development. The reaction was stopped by the addition of 50 μL of a 1 M sulfuric acid solution. The absorbance of the solution whose reaction had been stopped was measured at a wavelength of 450 nm.

Figure 17:
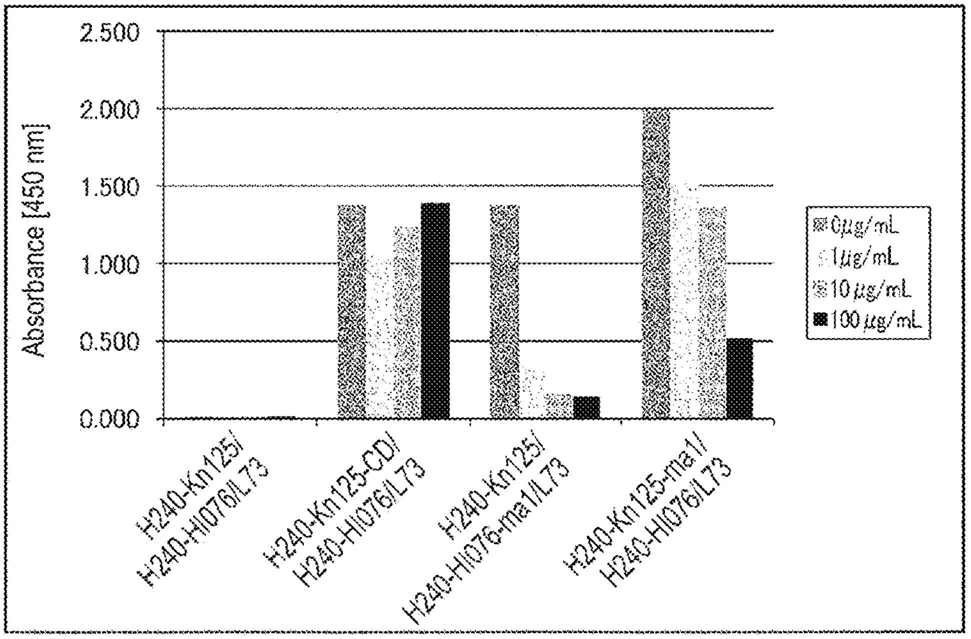
FIG. 17 is a diagram showing results of competitive ELISA by which whether the binding of an antibody to integrin avβ3 was inhibited by FcγRIIIa was evaluated.

The results are shown in FIG. 17. No change was observed in the interaction between integrin αvβ3 and H240-Kn125-CD/H240-H1076/L73 with the RGD (Arg-Gly-Asp) peptide inserted in the CH3 region, even with increase in the concentration of FcγR. By contrast, H240-Kn125/H240-H1076-mal/L73 and H240-Kn125-mal/H240-H1076/L73 both exhibited the FcγR concentration-dependent attenuation of binding to integrin αvβ3. This suggested that H240-Kn125-CD/H240-H1076/L73 binds to integrin αvβ3 at the same time with binding to FcγR, whereas H240-Kn125/H240-H1076-mal/L73 and H240-Kn125-mal/H240-H1076/L73 does not bind to integrin αvβ3 in a state bound with FcγR.

Confirmation by SPR Method that Fc Region does not Bind to Integrin αvβ3 and FcγRIIIa at Same Time The integrin αvβ3 binding of each antibody bound with FcγR was assessed by the SPR method. Specifically, the binding of the FcγRIIIa-bound antibody to integrin αvβ3 was confirmed using a BiaCore™ T200 surface plasmon resonance system (GE Healthcare Japan Corp.). The running buffer used was the TBS(+) solution used in the preceding paragraph. The assay temperature was set to 15° C. An anti-His antibody (anti-penta-His antibody, Qiagen N.V.) was immobilized onto Series S Sensor Chip CM5 (GE Healthcare Japan Corp.) by the amine coupling method to prepare a chip. FcγRIIIa was captured onto the anti-His antibody-immobilized chip. Next, each antibody diluted with a running buffer was allowed to interact therewith. Only the FcγRIIIa-bound antibody was present on the resulting chip. Integrin αvβ3 diluted to 260 nM with a running buffer was allowed to interact with the antibody-captured chip. The antibody captured on the chip was washed off through the reaction of 10 mM glycine-HCl (pH 2.5) to regenerate the chip, which was repetitively used.

The binding activity of each FcγRIIIa-bound antibody against integrin αvβ3 was confirmed on the basis of the shape of a sensorgram.

Figure 18:
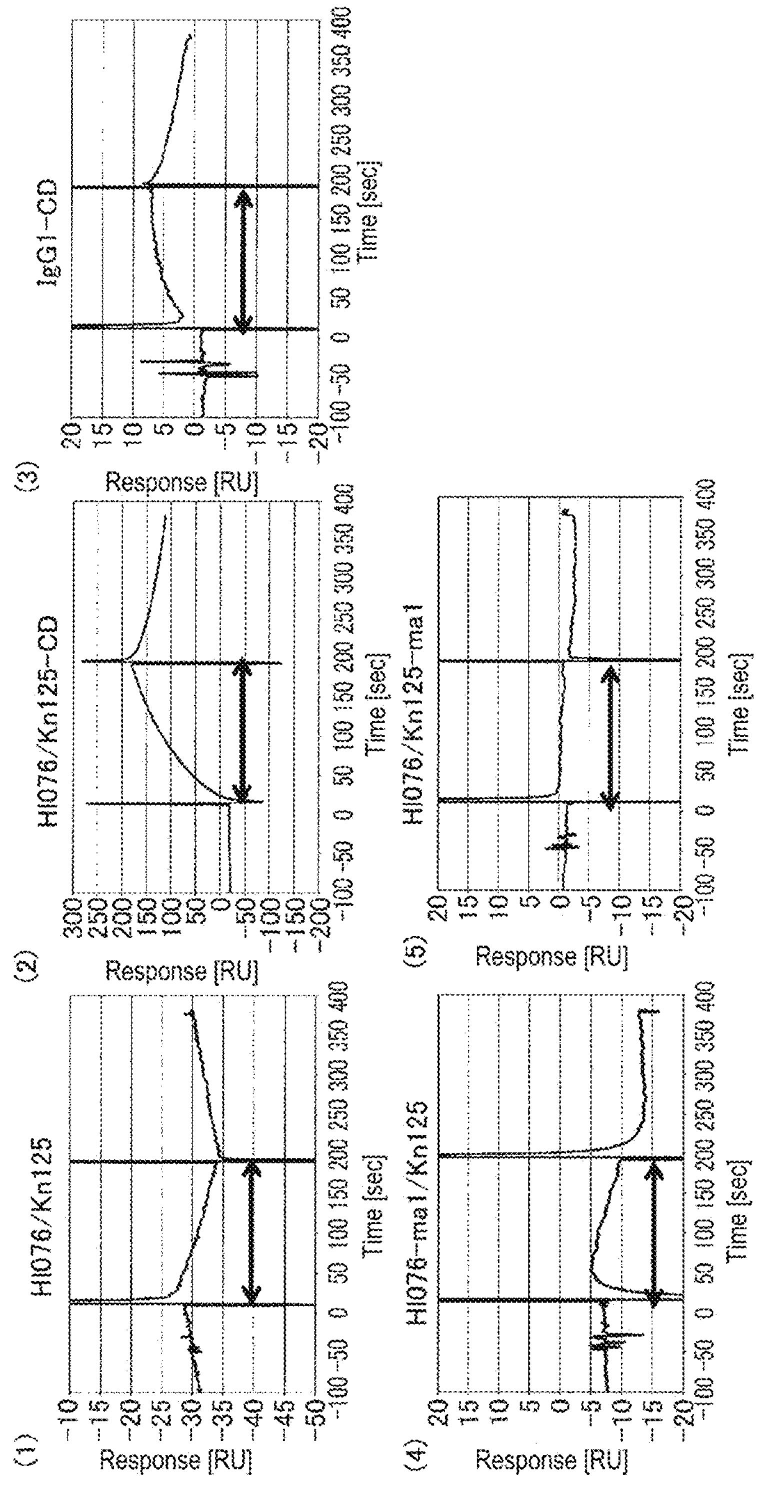
FIG. 18 is a set of diagrams (diagrams (1)-(5)) depicting Biacore™ surface plasmon resonance sensorgrams for evaluating whether an FcγRIIIa-bound antibody could bind to integrin αvβ3. The integrin αvβ3 was allowed to interact therewith in each region indicated by the arrow. These diagrams were drawn by subtracting a sensorgram obtained from the interaction under the condition of 0 nM integrin αvβ3 (baseline) from a sensorgram obtained from the interaction under the condition of 260 nM integrin αvβ3. The time 0 represents before injection of integrin αvβ3. Diagram (1) is a panel showing the assessment of H1076/Kn125. Diagram (2) is a panel showing the assessment of H1076/Kn125-CD. Diagram (3) is a panel showing the assessment of IgG1-CD. Diagram (4) is a panel showing the assessment of H1076-mal/Kn125. Diagram (5) is a panel showing the assessment of H1076/Kn125-mal.

FIG. 18 shows the results of allowing integrin αvβ3 to act on the antibodies bound with FcγRIIIa in advance. The control antibody H240-Kn125-CD/H240-H1076/L73 with the RGD (Arg-Gly-Asp) peptide inserted in the CH3 region was observed to exhibit binding response by the action of integrin αvβ3. By contrast, all of the antibodies such as H240-Kn125/H240-H1076-mal/L73 and H240-Kn125-mal/H240-H1076/L73 exhibited no observable binding response even by the action of integrin αvβ3. These results showed that the antibody bound with FcγRIIIa does not bind to integrin αvβ3, demonstrating that the Fc region does not bind to FcγRIIIa and integrin αvβ3 at the same time.

Discussion on Results of Competitive ELISA and SPR Methods Showing that Fc Region does not Bind to Integrin αvβ3 and FcγRIIIa at Same Time As is evident from the results described above, the developed anti-EREG antibody had the properties of the dual binding Fc molecule binding to FcγRIIIa on the X side and binding to integrin αvβ3 on the Y side, but not binding to the FcγRIIIa and the integrin αvβ3 at the same time. In this Example, the RGD peptide binding to the second antigen integrin αvβ3 was inserted to the loop on the Y side of the variable region-containing antibody binding to the first antigen EREG to successfully obtain a molecule that was provided with the binding activity against the second antigen, but did not bind to the FcγR and the second antigen at the same time. By similar methods, a peptide having binding activity against a protein as illustrated in WO2006036834 can be inserted to the loop selected in Example 4 or 5 to obtain an anti-EREG antibody having binding activity against an arbitrary second antigen. In addition, the library designed in Examples 4 and 5 can presumably be used to develop an anti-EREG antibody having binding activity against an arbitrary second antigen. The variable regions against the first antigen can be obtained by various methods generally known to those skilled in the art. Hence, it was concluded that such libraries can be used to develop antibody molecules that have binding activity against each of an arbitrary first antigen, an arbitrary second antigen, and FcγR, but cannot bind to the second antigen and the FcγR at the same time.

[Example 7] X-Ray Crystal Structure Analysis of Fc(YWA-DLE) and FcγRIIIa Extracellular Region Complex Example 3 showed that the heterodimerized antibody can be used to further optimize the asymmetric interaction of the Fc region with FcγR, compared with the conventional homodimerized antibody used. In Example 3, the heterodimerized antibody with the S239D, A330L, and I332E alterations introduced in one H chain and the L234Y, G236W, and S298A alterations introduced in the other H chain was used as an example showing such optimization. Whether the introduced amino acid alterations were actually involved in the interaction with FcγR as discussed in Example 3 was discussed based on the crystal structure analysis of a heterodimerized antibody and FcγRIIIa (FcγRIIIa extracellular region) complex.

Preparation of Fc Region

The Fc region of the heterodimerized antibody with S239D, A330L, and I332E introduced in one H chain and L234Y, G236W, and S298A introduced in the other H chain are referred to as Fc(YWA-DLE). This Fc(YWA-DLE) is constituted by Fc(DLE) and Fc(YWA). The Fc(YWA-DLE) was prepared as follows: S239D, A330L, and I332E were introduced to H240-Kn033 (SEQ ID NO: 13), while L234Y, G236W, and S298A were introduced to H240-H1033 (SEQ ID NO: 14). In addition, Cys at EU numbering position 220 was substituted by Ser, and sequences from Glu at EU numbering position 236 to the C terminus were set to Fc(DLE) (SEQ ID NO: 53) and Fc(YWA) (SEQ ID NO: 54). Nucleotide sequences encoding Fc(DLE) and Fc(YWA) were incorporated into vectors for expression in animal cells. The prepared vectors were transferred to animal cells to carry out the expression and purification of Fc(YWA-DLE) according to the method of Reference Example 1. Cys at EU numbering position 220 forms a disulfide bond with Cys of the L chain in general IgG1. The L chain is not co-expressed when Fc alone is prepared, and therefore, this residue was substituted with Ser to avoid formation of unnecessary disulfide bonds.

Preparation of FcγRIIIa Extracellular Region

The FcγRIIIa (FcγRIIIa extracellular region) used for the crystal structure analysis was expressed and simply purified according to the method of Reference Example 5. To 4 mg of the obtained FcγRIIIa extracellular region sample, 0.4 mg of endoglycosidase Endo F1 (Protein Science 1996, 5, 2617-2622) expressed and purified from *Escherichia coli* as a glutathione S-transferase fusion protein was added. This was allowed to remain at room temperature for several days under the buffer condition of 0.1 M Bis-Tris (pH 6.5), and the N-linked oligosaccharide was cleaved, leaving N-acetylglucosamine directly bound to Asn. Next, this FcγRIIIa extracellular domain sample subjected to carbohydrate cleavage treatment was concentrated by ultrafiltration with 5000 MWCO, and purified by gel filtration chromatography (Superdex200 10/300) using a column equilibrated with 0.02 M HEPS (pH 7.5) and 0.05 M NaCl.

Purification of Fc(YWA-DLE)/FcγRIIIa Extracellular Region Complex

To the carbohydrate-cleaved FcγRIIIa extracellular region fraction obtained by the above mentioned method, Fc(YWA-DLE) was added so that the molar ratio of the FcγRIIIa extracellular region would be present in slight excess, and after concentration by ultrafiltration with 10,000 MWCO, a fraction of the Fc(YWA-DLE)/FcγRIIIa extracellular region complex was obtained through purification by gel filtration chromatography (Superdex200 10/300) using a column equilibrated in 0.02 M HEPS at pH 7.5 containing 0.05 M NaCl. In addition, this fraction was further applied to an anion-exchanged column (Mono Q 5/50 GL) equilibrated with 0.02 M HEPES (pH 7.5), and eluted by the gradient of NaCl. A plurality of separate peaks were found in the resulting chromatogram. Of them, fractions corresponding to 3 main peaks were separately collected and each sample was used as an Fc(YWA-DLE)/FcγRIIIa extracellular region complex sample for crystallization.

Crystallization of Fc(YWA-DLE) and FcγRIIIa Extracellular Region Complex

Each sample of the Fc(YWA-DLE)/FcγRIIIa extracellular region complex which was purified by the above mentioned method, was concentrated to approximately 10 mg/mL by ultrafiltration with 10,000 MWCO while the buffer was replaced with 0.05 M imidazole (pH 8), and crystallization was carried out by the sitting drop vapor diffusion method. Hydra II Plus One (MATRIX) was used for crystallization; and for a reservoir solution containing 0.1 M MES (pH 7), 15' PEG3350, 0.2 M ammonium acetate, and 0.01 M spermine, a crystallization drop was produced by mixing at a ratio of reservoir solution:crystallization sample=0.2 μL:0.2 μL, and after sealing, this was allowed to remain at 20° C., and thin columnar crystals were successfully obtained.

Measurement of X-Ray Diffraction Data from a Fc(YWA-DLE)/FcγRIIIa Extracellular Region Complex Crystal One of the obtained single crystals of the Fc(YWA-DLE)/FcγRIIIa extracellular region complexes was soaked into a solution containing 0.1 M MES (pH 7), 18% PEG3350, 0.2 M ammonium acetate, 0.01 M spermine, and 20% (v/v) ethylene glycol, then the crystal was fished out of the solution using a pin with a tiny nylon loop attached, and frozen in liquid nitrogen; and then X-ray diffraction data was measured at Spring-8 BL32XU. During the measurement, the crystal was constantly placed in a nitrogen stream at −178° C. to maintain in a frozen state, and a total of 180 diffraction images were collected, with rotating the crystal 1° at a time, using a CCD detector MX-225HE (Rayonix, L.L.C.) attached to the beam line. Determination of cell parameters, indexing of diffraction spots, and diffraction data processing from the obtained diffraction images were performed using the program Xia2 (J. Appl. Cryst. (2010) 43, 186-190), XDS Package (Acta Cryst. (2010) D66, 125-132) and Scala (Acta Cryst. (2006) D62, 72-82); and finally, diffraction intensity data up to a resolution of 2.97 angstroms was successfully obtained. This crystal belonged to the space group $P2_12_12_1$: and had lattice constants a=71.80 angstroms, b=100.91 angstroms, c=123.54 angstroms, α=90°, β=90°, and γ=90°.

X-Ray Crystal Structure Analysis of Fc(YWA-DLE)/FcγRIIIa Extracellular Region Complex To determine the structure of the Fc(YWA-DLE)/FcγRIIIa extracellular region complex, the molecular replacement method using the program Phaser (J. Appl. Cryst. (2007) 40, 658-674) was performed. From the size of the obtained crystal lattice and the molecular weight of the Fc(YMA-DLE)/FcγRIIIa extracellular region complex, the number of complexes in the asymmetric unit was predicted to be one. The structure coordinate of PDB code: 3SGJ, which corresponds to the crystal structure of a known IgG1-Fc/FcγRIIIa extracellular region complex, was used as a search model and the orientation and position of the search model in the crystal lattice was determined based on the rotation and translation functions. When rigid body refinement which independently moves each two CH2 domains and two CH3 domains in the Fc region and the FcγRIIIa extracellular region was performed on the obtained initial structural model, the crystallographic reliability factor R became 43.9% and the Free R value became 43.4% for the diffraction intensity data from 25 to 3.0 angstroms. Furthermore, structural refinement using the program Refmac5 (Acta Cryst. (2011) D67, 355-367), and revision of the model to observe the electron density maps whose coefficient have 2Fo-Fc or Fo-Fc, which are calculated based on the experimentally determined structural factor Fo, the calculated structural factor Fc and the calculated phase using the model, was carried out by the Coot program (Acta Cryst. (2010) D66, 486-501), and model refinement was carried out by repeating these steps. Finally, the crystallographic reliability factor R values and the Free R value of the model containing 4891 non-hydrogen atoms became 21.7% and 26.9% respectively to 18126 diffraction intensity data with a resolution of 25 to 2.97 angstroms.

Figure 19:
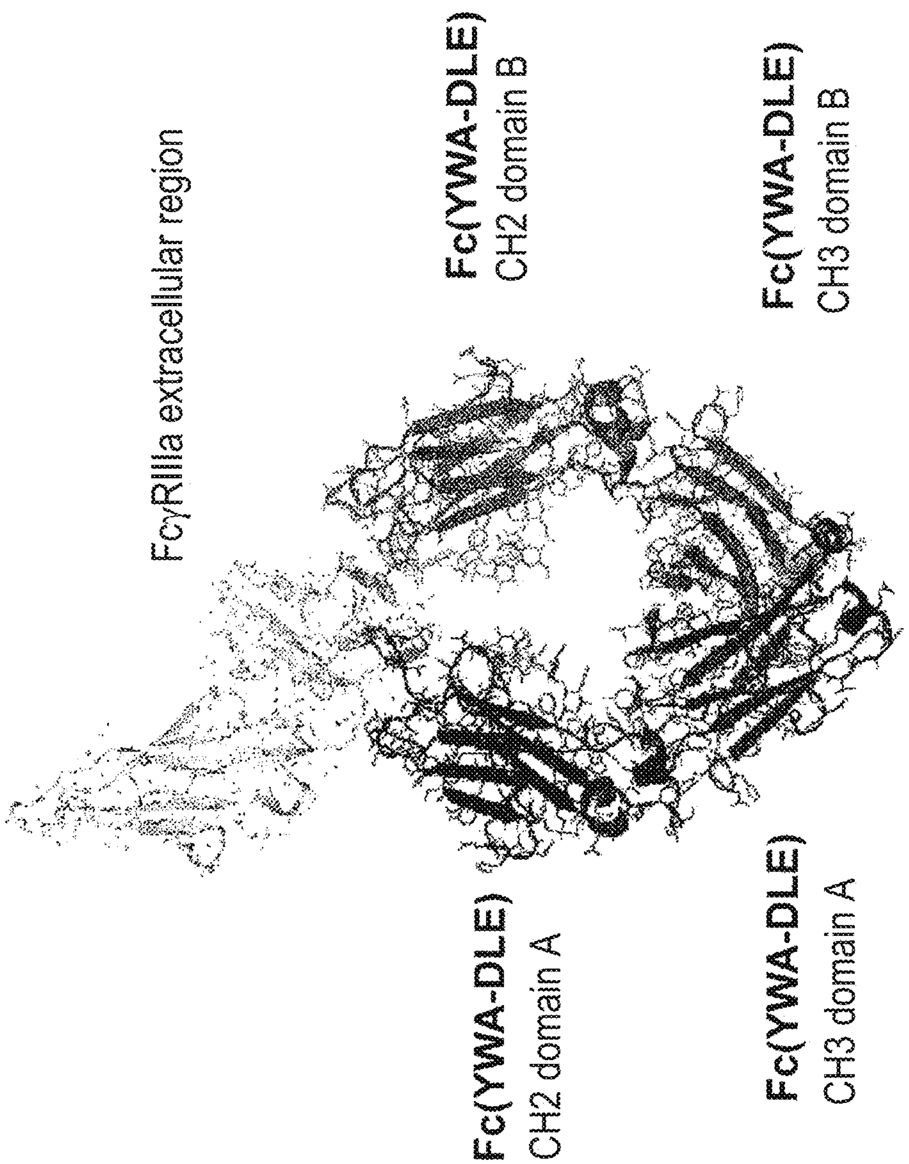
FIG. 19 is a diagram showing the whole crystal structure of an Fc(YWA-DLE) and FcγRIIIa extracellular region complex. FcγRIIIa binds to the CH2 regions of Fc(YWA-DLE).

Discussion on Results of X-Ray Crystal Structure Analysis of Fc(YWA-DLE)/FcγRIIIa Extracellular Region Complex The three-dimensional structure of the Fc(YWA-DLE) and FcγRIIIa extracellular region complex was determined by X-ray crystal structure analysis at 2.97 angstroms resolution. The structural analysis results are shown in FIG. 19. The FcγRIIIa extracellular region was bound between two Fc CH2 domains. This structure was almost the same as the three-dimensional structures (conformations) of the previously analyzed complexes of IgG1-Fc with the extracellular regions of FcγRIIIa (Proc. Natl. Acad. Sci. USA, 2011, 108, 12669-126674) and FcγRIIIb (Nature, 2000, 400, 267-273; and J. Biol. Chem. 2011, 276, 16469-16477). Hereinafter, the position of an amino acid in FcγRIIIa will be described according to the Standard NCBI numbering (Mol Immunol. 2008 April; 45 (7): 1872-82).

Figure 20:
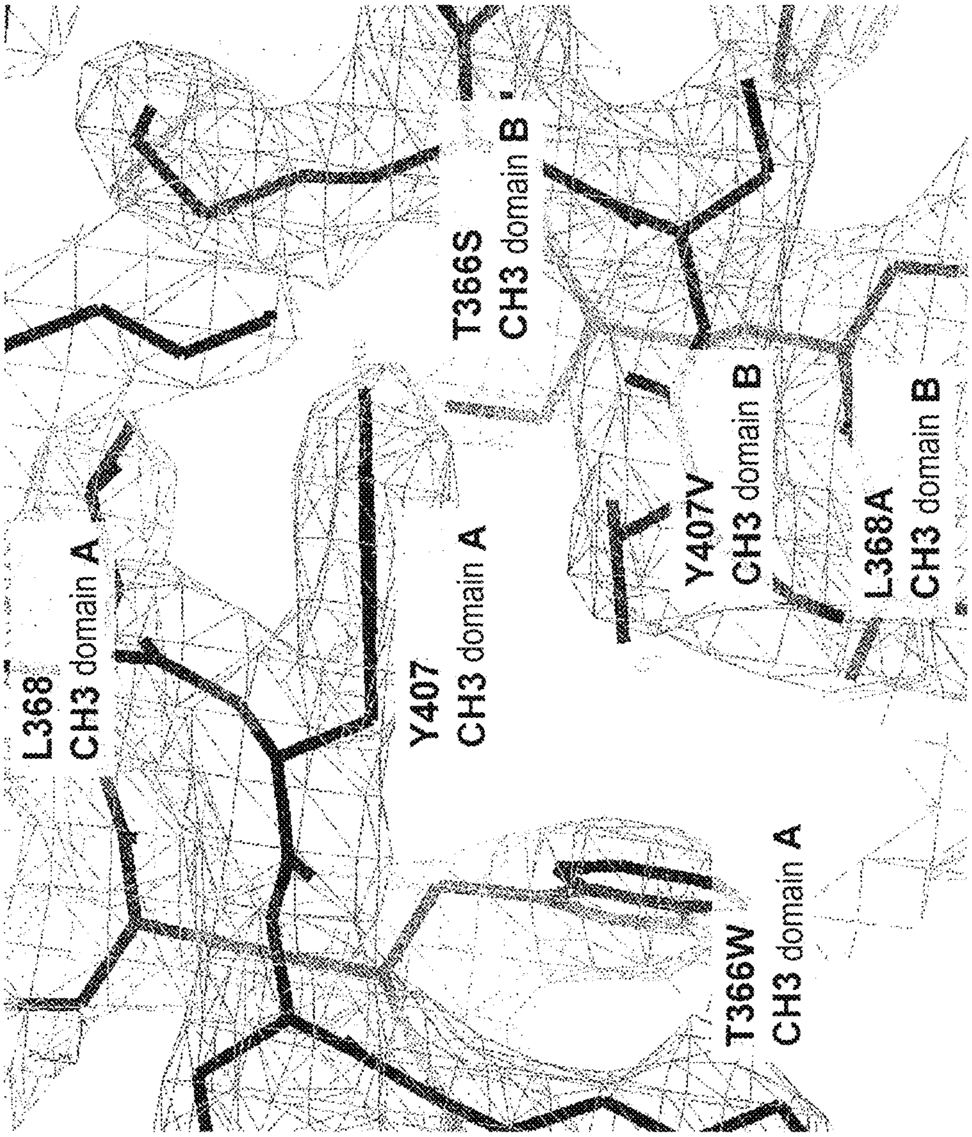
FIG. 20 is a diagram showing the interaction at the interface between knob and hole structures in the crystal structure of the Fc(YWA-DLE)/FcγRIIIa extracellular region complex, together with observed electron density.

For the preparation of Fc(YWA-DLE) in this paragraph, the knobs-into-holes technology (Protein Eng. 1996, 9, 617-621) was used in order to efficiently form the heterodimer. Specifically, a knob structure (T366W) was introduced to the Fc A chain having the S239D, A330L, and I332E substitutions (Fc(DLE)), while a hole structure (T366S, L368A, and Y407V) was introduced to the Fc B chain having the L234Y, G236W, and S298A substitutions (Fc (YWA)). Accordingly, first, to confirm whether the binding between FcγRIIIa and Fc(YWA-DLE) occurred preferentially on one surface (X surface), the electron density of the amino acids constituting the knob structure and the hole structure present in the CH3 interface was checked. If two binding surfaces (X and Y surfaces) coexist for the binding between FcγRIIIa and Fc(YWA-DLE), as in natural IgG, the positions of the chain having the knob structure and the chain having the hole structure become heterogeneous relative to FcγRIIIa in the crystal. As a result, the electron density become obscure because these structures are mixed with each other and the electron density of the knob structure and the hole structure is averaged. FIG. 20 shows the interface between the knob structure and the hole structure, together with their electron density. The electron density of the structures of the knob and hole parts was clearly observed. This means that the CH2 domain in each chain of the heterodimer Fc(YWA-DLE) is bound with FcγRIIIa in the fixed direction, i.e., Fc(YWA-DLE) is bound with FcγRIIIa preferentially on only one surface (only X surface) out of the two FcγRIIIa-binding surfaces (X and Y surfaces).

Figure 21:
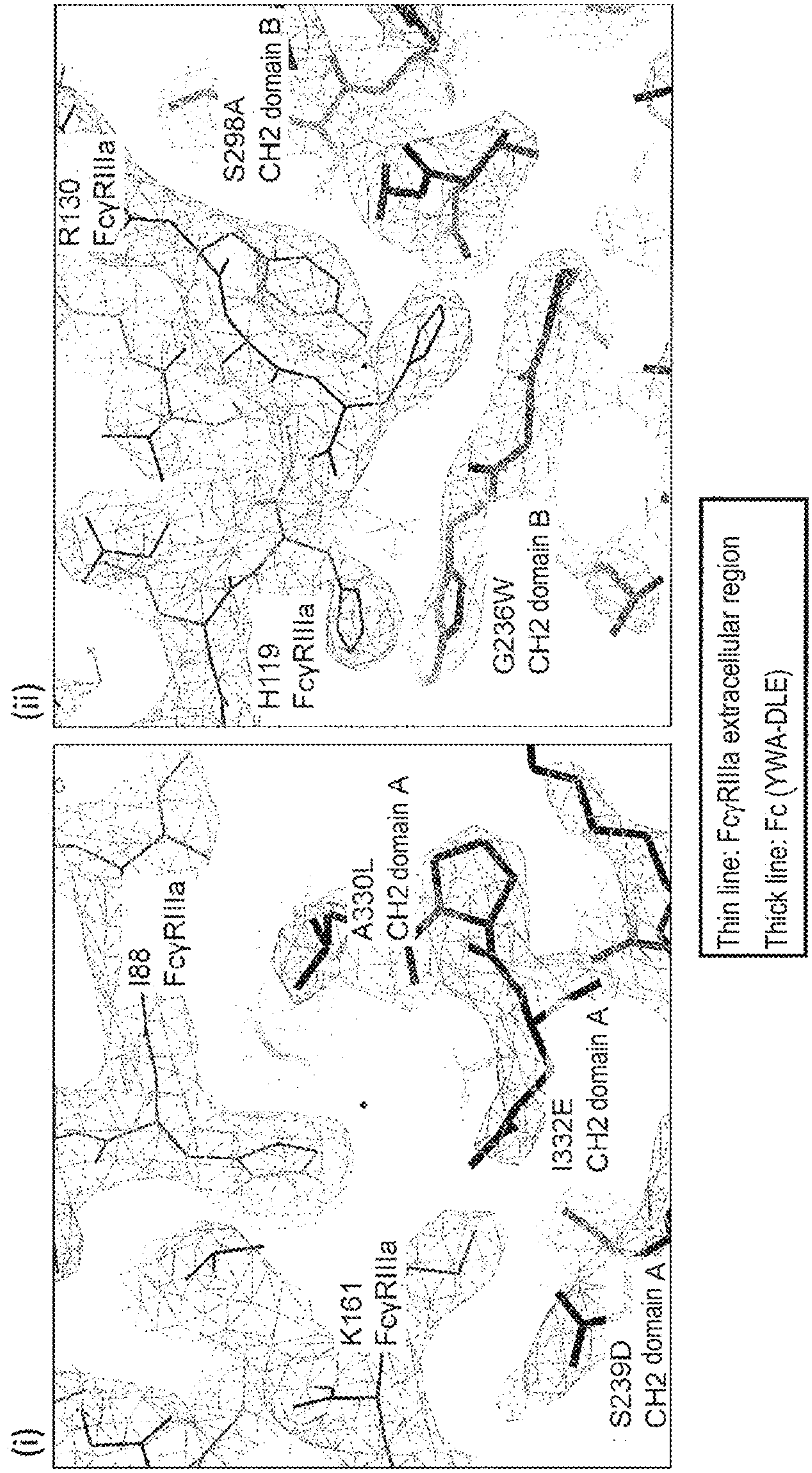
FIG. 21 is a set of diagrams showing the interaction of each heavy chain of Fc(YWA-DLE) with an FcγRIIIa extracellular region complex, together with observed electron density. The thin line represents an FcγRIIIa extracellular region. The thick line represents Fc(YWA-DLE). Diagram(i) shows the interaction of Fc(DLE) having the introduced amino acid substitutions S239D, A330L, and I332E with an FcγRIIIa extracellular region complex. Diagram(ii) shows the interaction of Fc(YWA) having the introduced amino acid substitutions L234Y, G236W, and S298A with an FcγRIIIa extracellular region complex.

Further referring to the FcγRIIIa-binding surfaces in detail, the Fc A chain having the S239D, A330L, and I332E substitutions is bound with FcγRIIIa from the front left side of FIG. 19. As shown in FIG. 21(*i*), the Fc A chain is found to have the enhanced interaction with FcγRIIIa on the binding surface shown in the drawing because of the electrostatic interaction formed between its S239D and I332E and K161 in FcγRIIIa and the hydrophobic interaction formed between its A330L and I88 in FcγRIIIa. On the other hand, the Fc B chain having the L234Y, G236W, and S298A substitutions is bound with FcγRIIIa from the front right side of FIG. 19. As shown in FIG. 21(*ii*), the Fc B chain has the enhanced interaction with FcγRIIIa on the binding surface shown in the drawing because of the π-π stacking formed between its G236W and H119 in FcγRIIIa as well as the van der Waals and hydrophobic interactions formed between its S298A and the R130 main chain of FcγRIIIa. In this context, no electron density was observed as to L234Y.

Thus, the FcγRIIIa-recognizing interaction surface was asymmetrically enhanced by the asymmetric introduction of amino acid substitutions to two Fc chains. As a result, the direction of binding of the Fc region to FcγR was successfully controlled. These results demonstrated that Fc can be altered such that the FcγR binding preferentially occurs on only one surface of FcγR-binding surfaces present in Fc. To adopt such an alteration group, a dual binding Fc molecule can enhance or optimize the interaction with FcγR on the X side (in one direction) shown in FIG. 4. To use the Y side, which does not participate in the interaction with FcγR, it seems to be able to interact with an antigen.

Reference Examples

[Reference Example 1] Preparation of Antibody Expression Vector and Expression and Purification of Antibody Amino acid substitution was carried out by a method generally known to those skilled in the art using QuikChange Site-Directed Mutagenesis Kit (Stratagene Corp.), PCR or In fusion Advantage PCR cloning kit (Takara Bio Inc.), or the like to construct expression vectors. The obtained expression vectors were sequenced by a method generally known to those skilled in the art. The prepared plasmids were transiently transferred to human embryonic kidney cancer cell-derived HEK293H line (Invitrogen Corp.) or FreeStyle 293 cells (Invitrogen Corp.) to express antibodies. Each antibody was purified from the obtained culture supernatant by a method generally known to those skilled in the art using rProtein A Sepharose™ Fast Flow (GE Healthcare Japan Corp.). As for the concentration of the purified antibody, the absorbance was measured at 280 nm using a spectrophotometer, and the antibody concentration was calculated by use of an extinction coefficient calculated from the obtained value by PACE (Protein Science 1995; 4: 2411-2423).

[Reference Example 2] Evaluation of Binding Activity Against FcγR

The antibody of interest was analyzed for its interaction with FcγR using a BiaCore™ T100, BiaCore™ A100, or BiaCore™ 4000 surface plasmon resonance system (GE Healthcare Japan Corp.). The running buffer used was HBS-EP+ (GE Healthcare Japan Corp.). The assay temperature was set to 25° C. The sensor chips used were: a chip prepared by immobilizing antigenic peptides onto Series S Sensor Chip CM5 (GE Healthcare Japan Corp.) by the amine coupling method; a chip prepared by immobilizing antigenic peptides biotinylated in advance onto Series S Sensor Chip SA (certified) (GE Healthcare Japan Corp.) through their interaction; a chip prepared by immobilizing protein L (ACTIGEN, BioVision, Inc.) onto Series S Sensor Chip CM5 (GE Healthcare Japan Corp.); and a chip prepared by immobilizing protein A/G (Thermo Fisher Scientific K.K.) onto Series S Sensor Chip CM5 (GE Healthcare Japan Corp.). The antibody of interest was captured onto any of these chips and allowed to interact with FcγR diluted with a running buffer. The antibody captured on the chip was washed off through the reaction of 10 mM glycine-HCl (pH 1.5) to regenerate the chip, which was repetitively used.

Each antibody was evaluated for its binding activity against FcγR with binding activity against FcγR and dissociation constant for FcγR as main indexes.

The binding activity against FcγR means relative binding activity against the FcγR. The relative binding activity against the FcγR was calculated as the binding activity of each antibody relative to the binding activity of a control sample for each assay defined as 100(%). In this context, the binding activity used was a value determined by dividing the amount of change in sensorgram between before and after the interaction of each captured antibody with FcγR by the amount of the captured antibody. This is because the binding activity against FcγR depends on the amount of the captured antibody.

The dissociation constant of each antibody for FcγR was calculated by kinetic analysis on BiaCore™ surface plasmon resonance assay results. Specifically, a sensorgram obtained by assay using BiaCore™ surface plasmon resonance Evaluation Software was globally fit into the 1:1 Langmuir model to calculate an association rate constant ka (L/mol/s) and a dissociation rate constant kd (1/s). From these values, the dissociation constant KD (mol/L) was calculated.

[Reference Example 3] ADCC Activity of Each Antibody to be Tested Using Human Peripheral Blood Mononuclear Cell as Effector Cell Each altered form having the FcγR-binding activity enhanced by the alteration of either one H chain of an antibody was assayed for its ADCC activity according to the method described below.

Human peripheral blood mononuclear cells (hereinafter, referred to as human PBMCs) were used as effector cells to determine the ADCC activity of each antibody to be tested as follows:

(1) Preparation of Human PBMC Solution

A syringe charged in advance with 200 μl of 1000 units/ml heparin solution (Novo-Heparin 5,000 units for Injection, Novo Nordics A/S) was used to collect 50 ml of peripheral blood from each healthy volunteer (adult man) belonging to Chugai Pharmaceutical Co., Ltd. This peripheral blood was diluted 2-fold with PBS(−) and equally divided into 4 portions, which were then added to Leucosep lymphocyte separation tubes (Greiner bio-one) each charged in advance with 15 ml of Ficoll-Paque PLUS followed by centrifugation. The separation tubes containing the dispensed peripheral blood were centrifuged at a speed of 2150 rpm at room temperature for 10 minutes. Then, the layers of mononuclear cell fractions were separated. The cells contained in each fraction layer were washed once with a Dulbecco's modified Eagle's medium (Sigma-Aldrich Corp.) containing 10FBS (hereinafter, referred to as 10% FBS/D-MEM) and then suspended at their cell density of $5\times10^6$ cells/ml in 10% FBS/D-MEM. This cell suspension was subjected as a human PBMC solution to the subsequent experiments.

(2) Preparation of Target Cell

SK-pca13a (SK-Hep-1 forced to express human glypican 3) was dissociated from a dish, and 1.85 MBq of Cr-51 was added to $3\times10^6$ cells. The cells supplemented with Cr-51 were incubated at 37° C. for 1 hour in a 5% $CO_2$ incubator, then washed once with 10FBS/D-MEM, and suspended at their cell density of $2\times10^5$ cells/ml in 10% FBS/D-MEM. This cell suspension was subjected as target cells to the subsequent experiments.

(3) Chromium Release Test (ADCC Activity)

The ADCC activity was evaluated on the basis of the rate of specific chromium release by the chromium release method. First, an antibody solution prepared at each concentration (0, 0.004, 0.04, 0.4, 4, and 40 μg/ml) was added at a concentration of 50 μl/well to 96-well U-bottom plates. Next, the target cells prepared in the paragraph (2) were inoculated thereto at a concentration of 50 μl/well ($1\times10^4$ cells/well), and the plates were left standing at room temperature for 15 minutes. The human PBMC solution prepared in the paragraph (1) was added thereto at a concentration of 100 μl/well ($5\times10^5$ cells/well), and the plates were left standing at 37° C. for 4 hours in a 5% $CO_2$ incubator and then centrifuged. The radioactivity of 100 μl of the culture supernatant in each well of the plates was measured using a gamma counter. The rate of specific chromium release was determined according to the following expression:

$$\text{Rate of specific chromium release (\%)}=(A-C)\times100/(B-C)$$

In the above expression, A represents the average radioactivity (cpm) of 100 μl of the culture supernatant in each well. B represents the average radioactivity (cpm) of 100 μl of the culture supernatant in each well containing the target cells supplemented with 100 μl of a 2% aqueous NP-40 solution (Nonidet P-40, Nacalai Tesque, Inc.) and 50 μl of 10% FBS/D-MEM medium. C represents the average radioactivity (cpm) of 100 μl of the culture supernatant in each well containing the target cells supplemented with 150 μl of 10% FBS/D-MEM medium. The test was conducted in triplicate. Mean and standard deviation were calculated for the rate of specific chromium release (%) in the test reflecting the ADCC activity of each antibody to be tested.

[Reference Example 4] Tm Evaluation of Altered Antibody by Differential Scanning Fluorimetry In this study, each altered antibody was evaluated for its Tm (thermal denaturation temperature) by differential scanning fluorimetry using Rotor-Gene Q (Qiagen N.V.). This approach has already been reported to show favorable correlation with Tm evaluation using a differential scanning calorimeter widely known as a method for evaluating the thermal stability of antibodies (Journal of Pharmaceutical Science 2010; 4: 1707-1720).

5000×SYPRO orange (Molecular Probes Inc.) was diluted with PBS (Sigma-Aldrich Corp.) and then mixed with each antibody solution to prepare an assay sample. Each sample (20 μL) was loaded in a tube for assay, and the temperature was raised from 30° C. to 99° C. at a heating rate of 240° C./hr. Change in fluorescence with the rise in temperature was detected at 470 nm (excitation wavelength)/555 nm (fluorescence wavelength).

The data was processed using Rotor-Gene Q Series Software (Qiagen N.V.) to calculate the temperature at which fluorescence transition was observed. This value was used as Tm.

[Reference Example 5] Method for Preparing FcγR and Method for Analyzing Interaction Between Altered Antibody and FcγR The extracellular domain of FcγR was prepared by the following method: first, the gene of the FcγR extracellular domain was synthesized by a method generally known to those skilled in the art. For this synthesis, the sequence of each FcγR was prepared on the basis of the information registered in NCBI. Specifically, FcγRI was prepared on the basis of the sequence of NCBI accession #NM_000566.3; FcγRIIa was prepared on the basis of the sequence of NCBI accession #NM_001136219.1; FcγRIIb was prepared on the basis of the sequence of NCBI accession #NM_004001.3; FcγRIIIa was prepared on the basis of the sequence of NCBI accession #NM_001127593.1; and FcγRIIIb was prepared on the basis of the sequence of NCBI accession #NM_000570.3. These sequences were C-terminally tagged with a His tag (HHHHHH) sequence. Also, polymorphism is known about FcγRIIa, FcγRIIIa, and FcγRIIIb. The polymorphic sites were prepared with reference to J. Exp. Med., 1990, 172: 19-25 for FcγRIIa, J. Clin. Invest., 1997, 100 (5): 1059-1070 for FcγRIIIa, and J. Clin. Invest., 1989, 84, 1688-1691 for FcγRIIIb.

Each obtained gene fragment was inserted to vectors for expression in animal cells to prepare expression vectors. The prepared expression vectors were transiently transferred to human embryonic kidney cancer cell-derived FreeStyle 293 cells (Invitrogen Corp.) to express the protein of interest. The obtained culture supernatant was purified by a method generally known to those skilled in the art, i.e., various chromatography techniques. As an example, the purification was carried out by the following 4 steps: cation-exchanged column chromatography (SP Sepharose FF) as step 1, affinity column chromatography (HisTrap HP) as step 2, gel filtration column chromatography (Superdex 200) as step 3, and sterile filtration as step 4. However, for FcγRI, anion-exchanged column chromatography was carried out in step 1 using Q Sepharose FF. The absorbance was measured for each purified protein at 280 nm using a spectrophotometer, and the concentration of the purified protein was calculated by use of an extinction coefficient calculated from the obtained value by a method such as PACE (Protein Science 1995; 4: 2411-2423).

For the FcγRIIIa extracellular domain used in the crystallography, the expression vectors prepared above were transiently transferred to human embryonic kidney cancer cell-derived FreeStyle 293 cells (Invitrogen Corp.) to express the protein of interest in the presence of Kifunensine (final concentration: 10 ug/mL). The expression in the presence of Kifunensine allowed high-mannose-type sugar chains to be added to FcγRIIIa. After culture, the obtained culture supernatant was recovered and then passed through a 0.22-μm filter to obtain a culture supernatant. The obtained culture supernatant was subjected to affinity column chromatography (HisTrap HP) for the His tag and gel filtration column chromatography (Superdex 200). The absorbance was measured for the purified protein at 280 nm using a spectrophotometer, and the concentration of the purified protein was calculated by use of an extinction coefficient calculated from the obtained value by a method such as PACE (Protein Science 1995; 4: 2411-2423).

INDUSTRIAL APPLICABILITY

The present invention enables the preparation of a multispecific binding polypeptide capable of avoiding an adverse reaction that may be caused by its binding to an antigen and FcγR at the same time. Thus, the present invention provides a polypeptide suitable as a drug.

The invention claimed is:

1. A method of treating a tumor in a subject, the method comprising identifying the subject as having a tumor that expresses a first antigen, and administering an antibody comprising an antibody variable region that binds to the first antigen and an Fc region dimer comprising a first IgG1 Fc region and a second IgG1 Fc region, wherein the first and second IgG1 Fc regions each comprise a CH2 domain;

wherein the CH2 domain of either or both of the first and second IgG1 Fc regions comprises an antigen-binding site that binds to a second antigen different from the first antigen;

wherein the antigen-binding site is within loop 2, loop 3, or loop 4 of one of the CH2 domains;

wherein the second antigen is a molecule naturally expressed on an immunocyte or on both a tumor cell and a normal cell, and is not an FcγR;

wherein the Fc region dimer comprises an FcγR-binding site that binds to FcγRIIIa;

wherein the Fc region dimer does not bind to both the second antigen and FcγRIIIa at the same time;

wherein the antibody can treat the tumor (A) by cross-linking a tumor cell and the immunocyte, or (B) by crosslinking a tumor cell and a cell expressing FcγRIIIa, or both (A) and (B);

wherein each of the following EU numbering positions in the first IgG1 Fc region is occupied by the amino acid residue specified for that position:

position 234: Tyr, position 236: Trp, and position 298: Ala; and wherein each of the following EU numbering positions in the second IgG1 Fc region is occupied by the amino acid residue specified for that position:

position 239: Asp, position 330: Leu, and position 332: Glu.

2. The method of claim 1, wherein the second antigen is a molecule naturally expressed on an immunocyte, and is not an FcγR.

3. The method of claim 1, wherein the second antigen is a molecule naturally expressed both on a tumor cell and on a normal cell, and is not an FcγR.

4. The method of claim 1, wherein the second antigen is a T cell surface molecule other than an FcγR.

5. The method of claim 1, wherein the amino acid sequence of the antigen-binding site of the Fc region dimer comprises at least one amino acid residue that differs from the residue present at the corresponding position in SEQ ID NO: 49.

6. The method of claim 5, wherein the at least one amino acid residue is at a position selected from EU numbering positions 231, 232, 233, 234, 235, 236, 237, 238, 239, 265, 266, 267, 268, 269, 270, 271, 295, 296, 297, 298, 299, 300, 324, 325, 326, 327, 328, 329, 330, 331, 332, 333, 334, 335, 336, and 337.

7. The method of claim 1, wherein the antigen-binding site comprises three to twelve amino acid residues located within loop 2, loop 3, or loop 4 of one of the CH2 domains.

8. The method of claim 1, wherein the antigen-binding site comprises one or more amino acid residues inserted between two contiguous EU numbering positions in loop 2, loop 3, or loop 4 of one of the CH2 domains.

9. The method of claim 1, wherein the antigen-binding site comprises one to nine amino acid residues inserted between two contiguous EU numbering positions in loop 2, loop 3, or loop 4 of one of the CH2 domains.

10. The method of claim 1, wherein the antigen-binding site comprises three to nine amino acid residues inserted between two contiguous EU numbering positions in loop 2, loop 3, or loop 4 of one of the CH2 domains.

11. The method of claim 1, wherein the antigen-binding site comprises a peptide that is three to nine amino acid residues in length, wherein the amino acid sequence of the peptide is not present in the amino acid sequence of any of SEQ ID NOs: 49-52.

12. The method of claim 11, wherein the peptide binds the second antigen.

13. The method of claim 1, wherein the FcγR-binding site (i) binds to FcγRIIIa, (ii) has an amino acid sequence that differs from the sequence of the FcγR-binding site of a naturally occurring human IgG that binds to FcγRIIIa, and (iii) binds more strongly to FcγRIIIa than does the naturally occurring human IgG.

14. The method of claim 1, wherein the FcγR-binding site binds more strongly to FcγRIIIa than an FcγR-binding site of a homodimer of SEQ ID NO: 49 binds to FcγRIIIa.

15. The method of claim 1, wherein the amino acid sequence of the FcγR-binding site of the Fc region dimer comprises one or more amino acid residues that differ from the residue present at the corresponding position(s) in each of SEQ ID NOs: 49-52.

16. The method of claim 15, wherein at least one of the one or more amino acid residues is in the CH2 domain of the first IgG1 Fc region, or the CH2 domain of the second IgG1 Fc region, or both.

17. The method of claim 1, wherein the amino acid sequence of the FcγR-binding site of the Fc region dimer is identical to the FcγR-binding site of a naturally occurring human IgG1.

18. The method of claim 1, wherein at least one of the following EU numbering positions in the first IgG1 Fc region is occupied by an amino acid residue specified for that position:

position 235: Tyr or Gln,
position 239: Asp or Met,
position 268: Asp,
position 270: Glu,
position 326: Asp,
position 330: Leu or Met,
position 332: Glu, and
position 334: Glu.

19. The method of claim 1, wherein (a) at least one of the following EU numbering positions in the first IgG1 Fc region is occupied by an amino acid residue specified for that position:

position 235: Tyr or Gln,
position 239: Met,
position 268: Asp, and
position 270: Glu, or (b) at least one of the following EU numbering positions in the second IgG1 Fc region is occupied by an amino acid residue specified for that position:

position 270: Glu,
position 326: Asp, and
position 334: Glu;

or (c) both (a) and (b).

20. The method of claim 1, wherein the first IgG1 Fc region comprises one of the following two sets of amino acid residues at the respective specified EU numbering positions:

set (i):
Tyr at position 234,
Tyr at position 235,
Trp at position 236,
Asp at position 268, and
Ala at position 298;

set (ii):
Tyr at position 234,
Gln at position 235,
Trp at position 236,
Met at position 239,
Asp at position 268,
Glu at position 270, and
Ala at position 298.

21. The method of claim 2, wherein:

the second antigen is a molecule that (1) is naturally expressed on the surface of an immunocyte having cytotoxic activity, and (2) is not an FcγR; and when the antibody binds simultaneously to both the first antigen on the tumor cell and the second antigen on the immunocyte, the antibody crosslinks the tumor cell and the immunocyte; and when the antibody binds simultaneously to both the first antigen on the tumor cell and to FcγRIIIa on a cell that expresses FcγRIIIa, the antibody crosslinks the tumor cell and the cell that expresses FcγRIIIa; and because the antibody does not bind to the second antigen and FcγRIIIa at the same time, the antibody does not crosslink the immunocyte and the cell that expresses FcγRIIIa.

22. The method of claim 1, wherein the amino acid sequences of the first and second IgG1 Fc regions differ from each other at one or more positions, including at least one position selected from EU numbering positions 265, 266, 267, 268, 269, 270, 271, 295, 296, 297, 298, 299, 300, 324, 325, 326, 327, 328, 329, 330, 331, and 332.

23. The method of claim 1, wherein at least one difference between the first and second IgG1 Fc regions is at a position selected from EU numbering positions 234, 235, 236, 239, 268, 270, 298, 326, 330, 332, and 334.

24. The method of claim 2, wherein the second antigen is selected from CD3, TCR, NKG2D, CD137, OX40, GITR, CD40, TLR1 to TLR10 and C type lectin.

25. The method of claim 3, wherein the second antigen is selected from integrin, tissue factor, VEGFR, PDGFR, EGFR, IGFR, MET chemokine receptor, heparan sulfate proteoglycan, CD44, fibronectin, DR5, and TNFRSF.

* * * * *

SEQUENCE LISTING

```
<160> NUMBER OF SEQ ID NOS: 54

<210> SEQ ID NO 1
<211> LENGTH: 115
<212> TYPE: PRT
<213> ORGANISM: Artificial
<220> FEATURE:
<223> OTHER INFORMATION: An artificially synthesized peptide sequence

<400> SEQUENCE: 1

Gln Val Gln Leu Val Gln Ser Gly Ala Glu Val Lys Lys Pro Gly Ala
1               5                   10                  15

Ser Val Thr Val Ser Cys Lys Ala Ser Gly Tyr Thr Phe Thr Asp Tyr
            20                  25                  30

Glu Met His Trp Ile Arg Gln Pro Pro Gly Glu Gly Leu Glu Trp Ile
        35                  40                  45

Gly Ala Ile Asp Pro Lys Thr Gly Asp Thr Ala Tyr Ser Glu Ser Phe
    50                  55                  60

Gln Asp Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser
        115


<210> SEQ ID NO 2
<211> LENGTH: 443
<212> TYPE: PRT
<213> ORGANISM: Artificial
```

```
<220> FEATURE:
<223> OTHER INFORMATION: An artificially synthesized peptide sequence

<400> SEQUENCE: 2

Gln Val Gln Leu Val Gln Ser Gly Ala Glu Val Lys Lys Pro Gly Ala
1               5                   10                  15

Ser Val Thr Val Ser Cys Lys Ala Ser Gly Tyr Thr Phe Thr Asp Tyr
            20                  25                  30

Glu Met His Trp Ile Arg Gln Pro Pro Gly Glu Gly Leu Glu Trp Ile
        35                  40                  45

Gly Ala Ile Asp Pro Lys Thr Gly Asp Thr Ala Tyr Ser Glu Ser Phe
    50                  55                  60

Gln Asp Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400
```

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro
        435                 440

<210> SEQ ID NO 3
<211> LENGTH: 443
<212> TYPE: PRT
<213> ORGANISM: Artificial
<220> FEATURE:
<223> OTHER INFORMATION: An artificially synthesized peptide sequence

<400> SEQUENCE: 3

Gln Val Gln Leu Val Gln Ser Gly Ala Glu Val Lys Lys Pro Gly Ala
1               5                   10                  15

Ser Val Thr Val Ser Cys Lys Ala Ser Gly Tyr Thr Phe Thr Asp Tyr
            20                  25                  30

Glu Met His Trp Ile Arg Gln Pro Pro Gly Glu Gly Leu Glu Trp Ile
        35                  40                  45

Gly Ala Ile Asp Pro Lys Thr Gly Asp Thr Ala Tyr Ser Glu Ser Phe
    50                  55                  60

Gln Asp Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

```
Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Lys Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

Arg Tyr Thr Gln Lys Ser Leu Ser Leu Ser Pro
        435                 440
```

<210> SEQ ID NO 4
<211> LENGTH: 443
<212> TYPE: PRT
<213> ORGANISM: Artificial
<220> FEATURE:
<223> OTHER INFORMATION: An artificially synthesized peptide sequence

<400> SEQUENCE: 4

```
Gln Val Gln Leu Val Gln Ser Gly Ala Glu Val Lys Lys Pro Gly Ala
1               5                   10                  15

Ser Val Thr Val Ser Cys Lys Ala Ser Gly Tyr Thr Phe Thr Asp Tyr
            20                  25                  30

Glu Met His Trp Ile Arg Gln Pro Pro Gly Glu Gly Leu Glu Trp Ile
        35                  40                  45

Gly Ala Ile Asp Pro Lys Thr Gly Asp Thr Ala Tyr Ser Glu Ser Phe
    50                  55                  60

Gln Asp Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240
```

Phe Pro Pro Lys Pro Lys Asp Thr Leu Met Ile Ser Arg Thr Pro Glu
245 250 255

Val Thr Cys Val Val Val Asp Val Ser His Glu Asp Pro Glu Val Lys
260 265 270

Phe Asn Trp Tyr Val Asp Gly Val Glu Val His Asn Ala Lys Thr Lys
275 280 285

Pro Arg Glu Glu Gln Tyr Asn Ser Thr Tyr Arg Val Val Ser Val Leu
290 295 300

Thr Val Leu His Gln Asp Trp Leu Asn Gly Lys Glu Tyr Lys Cys Lys
305 310 315 320

Val Ser Asn Lys Ala Leu Pro Ala Pro Ile Glu Lys Thr Ile Ser Lys
325 330 335

Ala Lys Gly Gln Pro Arg Glu Pro Gln Val Tyr Thr Leu Pro Pro Ser
340 345 350

Arg Asp Glu Leu Thr Lys Asn Gln Val Ser Leu Thr Cys Leu Val Lys
355 360 365

Gly Phe Tyr Pro Ser Asp Ile Ala Val Glu Trp Glu Ser Asn Gly Gln
370 375 380

Pro Glu Asn Asn Tyr Lys Thr Thr Pro Pro Val Leu Asp Ser Asp Gly
385 390 395 400

Ser Phe Phe Leu Tyr Ser Lys Leu Thr Val Asp Lys Ser Arg Trp Gln
405 410 415

Gln Gly Asn Val Phe Ser Cys Ser Val Met His Glu Ala Leu His Asn
420 425 430

His Tyr Thr Gln Glu Ser Leu Ser Leu Ser Pro
435 440

<210> SEQ ID NO 5
<211> LENGTH: 219
<212> TYPE: PRT
<213> ORGANISM: Artificial
<220> FEATURE:
<223> OTHER INFORMATION: An artificially synthesized peptide sequence

<400> SEQUENCE: 5

Asp Ile Val Met Thr Gln Ser Pro Leu Ser Leu Pro Val Thr Pro Gly
1 5 10 15

Glu Pro Ala Ser Ile Ser Cys Gln Ala Ser Glu Ser Leu Val His Ser
20 25 30

Asn Arg Asn Thr Tyr Leu His Trp Tyr Leu Gln Lys Pro Gly Gln Ser
35 40 45

Pro Gln Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Ser Gln Asn
85 90 95

Thr His Val Pro Pro Thr Phe Gly Gln Gly Thr Lys Val Glu Ile Glu
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 6
<211> LENGTH: 443
<212> TYPE: PRT
<213> ORGANISM: Artificial
<220> FEATURE:
<223> OTHER INFORMATION: An artificially synthesized peptide sequence

<400> SEQUENCE: 6

Gln Val Gln Leu Val Gln Ser Gly Ala Glu Val Lys Lys Pro Gly Ala
1 5 10 15

Ser Val Thr Val Ser Cys Lys Ala Ser Gly Tyr Thr Phe Thr Asp Tyr
20 25 30

Glu Met His Trp Ile Arg Gln Pro Pro Gly Glu Gly Leu Glu Trp Ile
35 40 45

Gly Ala Ile Asp Pro Lys Thr Gly Asp Thr Ala Tyr Ser Glu Ser Phe
50 55 60

Gln Asp Arg Val Thr Leu Thr Ala Asp Lys Ser Thr Ser Thr Ala Tyr
65 70 75 80

Met Glu Leu Ser Ser Leu Thr Ser Glu Asp Thr Ala Val Tyr Tyr Cys
85 90 95

Thr Arg Phe Tyr Ser Tyr Thr Tyr Trp Gly Gln Gly Thr Leu Val Thr
100 105 110

Val Ser Ser Ala Ser Thr Lys Gly Pro Ser Val Phe Pro Leu Ala Pro
115 120 125

Ser Ser Lys Ser Thr Ser Gly Gly Thr Ala Ala Leu Gly Cys Leu Val
130 135 140

Lys Asp Tyr Phe Pro Glu Pro Val Thr Val Ser Trp Asn Ser Gly Ala
145 150 155 160

Leu Thr Ser Gly Val His Thr Phe Pro Ala Val Leu Gln Ser Ser Gly
165 170 175

Leu Tyr Ser Leu Ser Ser Val Val Thr Val Pro Ser Ser Ser Leu Gly
180 185 190

Thr Gln Thr Tyr Ile Cys Asn Val Asn His Lys Pro Ser Asn Thr Lys
195 200 205

Val Asp Lys Lys Val Glu Pro Lys Ser Cys Asp Lys Thr His Thr Cys
210 215 220

Pro Pro Cys Pro Ala Pro Glu Leu Leu Gly Gly Pro Asp Val Phe Leu
225 230 235 240

Phe Pro Pro Lys Pro Lys Asp Thr Leu Met Ile Ser Arg Thr Pro Glu
245 250 255

Val Thr Cys Val Val Val Asp Val Ser His Glu Asp Pro Glu Val Lys
260 265 270

Phe Asn Trp Tyr Val Asp Gly Val Glu Val His Asn Ala Lys Thr Lys
275 280 285

Pro Arg Glu Glu Gln Tyr Asn Ser Thr Tyr Arg Val Val Ser Val Leu
290 295 300

Thr Val Leu His Gln Asp Trp Leu Asn Gly Lys Glu Tyr Lys Cys Lys
305 310 315 320

Val Ser Asn Lys Ala Leu Pro Leu Pro Glu Glu Lys Thr Ile Ser Lys
325 330 335

Ala Lys Gly Gln Pro Arg Glu Pro Gln Val Tyr Thr Leu Pro Pro Ser
340 345 350

Arg Lys Glu Leu Thr Lys Asn Gln Val Ser Leu Thr Cys Leu Val Lys
355 360 365

Gly Phe Tyr Pro Ser Asp Ile Ala Val Glu Trp Glu Ser Asn Gly Gln
370 375 380

Pro Glu Asn Asn Tyr Lys Thr Thr Pro Pro Val Leu Asp Ser Asp Gly
385 390 395 400

Ser Phe Phe Leu Tyr Ser Lys Leu Thr Val Asp Lys Ser Arg Trp Gln
405 410 415

Gln Gly Asn Val Phe Ser Cys Ser Val Met His Glu Ala Leu His Asn
420 425 430

Arg Tyr Thr Gln Lys Ser Leu Ser Leu Ser Pro
435 440

<210> SEQ ID NO 7
<211> LENGTH: 443
<212> TYPE: PRT
<213> ORGANISM: Artificial
<220> FEATURE:
<223> OTHER INFORMATION: An artificially synthesized peptide sequence

<400> SEQUENCE: 7

Gln Val Gln Leu Val Gln Ser Gly Ala Glu Val Lys Lys Pro Gly Ala
1 5 10 15

Ser Val Thr Val Ser Cys Lys Ala Ser Gly Tyr Thr Phe Thr Asp Tyr
20 25 30

Glu Met His Trp Ile Arg Gln Pro Pro Gly Glu Gly Leu Glu Trp Ile
35 40 45

Gly Ala Ile Asp Pro Lys Thr Gly Asp Thr Ala Tyr Ser Glu Ser Phe
50 55 60

Gln Asp Arg Val Thr Leu Thr Ala Asp Lys Ser Thr Ser Thr Ala Tyr
65 70 75 80

Met Glu Leu Ser Ser Leu Thr Ser Glu Asp Thr Ala Val Tyr Tyr Cys
85 90 95

Thr Arg Phe Tyr Ser Tyr Thr Tyr Trp Gly Gln Gly Thr Leu Val Thr
100 105 110

Val Ser Ser Ala Ser Thr Lys Gly Pro Ser Val Phe Pro Leu Ala Pro
115 120 125

Ser Ser Lys Ser Thr Ser Gly Gly Thr Ala Ala Leu Gly Cys Leu Val
130 135 140

Lys Asp Tyr Phe Pro Glu Pro Val Thr Val Ser Trp Asn Ser Gly Ala
145 150 155 160

Leu Thr Ser Gly Val His Thr Phe Pro Ala Val Leu Gln Ser Ser Gly
165 170 175

Leu Tyr Ser Leu Ser Ser Val Val Thr Val Pro Ser Ser Ser Leu Gly
180 185 190

Thr Gln Thr Tyr Ile Cys Asn Val Asn His Lys Pro Ser Asn Thr Lys
195 200 205

Val Asp Lys Lys Val Glu Pro Lys Ser Cys Asp Lys Thr His Thr Cys
210 215 220

```
Pro Pro Cys Pro Ala Pro Glu Leu Leu Gly Gly Pro Asp Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Leu Pro Glu Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Glu Ser Leu Ser Leu Ser Pro
        435                 440
```

<210> SEQ ID NO 8
<211> LENGTH: 443
<212> TYPE: PRT
<213> ORGANISM: Artificial
<220> FEATURE:
<223> OTHER INFORMATION: An artificially synthesized peptide sequence

<400> SEQUENCE: 8

```
Gln Val Gln Leu Val Gln Ser Gly Ala Glu Val Lys Lys Pro Gly Ala
1               5                   10                  15

Ser Val Thr Val Ser Cys Lys Ala Ser Gly Tyr Thr Phe Thr Asp Tyr
            20                  25                  30

Glu Met His Trp Ile Arg Gln Pro Pro Gly Glu Gly Leu Glu Trp Ile
        35                  40                  45

Gly Ala Ile Asp Pro Lys Thr Gly Asp Thr Ala Tyr Ser Glu Ser Phe
    50                  55                  60

Gln Asp Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140
```

```
Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Tyr Leu Trp Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ala Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Lys Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

Arg Tyr Thr Gln Lys Ser Leu Ser Leu Ser Pro
        435                 440
```

<210> SEQ ID NO 9
<211> LENGTH: 443
<212> TYPE: PRT
<213> ORGANISM: Artificial
<220> FEATURE:
<223> OTHER INFORMATION: An artificially synthesized peptide sequence

<400> SEQUENCE: 9

```
Gln Val Gln Leu Val Gln Ser Gly Ala Glu Val Lys Lys Pro Gly Ala
1               5                   10                  15

Ser Val Thr Val Ser Cys Lys Ala Ser Gly Tyr Thr Phe Thr Asp Tyr
            20                  25                  30

Glu Met His Trp Ile Arg Gln Pro Pro Gly Glu Gly Leu Glu Trp Ile
        35                  40                  45

Gly Ala Ile Asp Pro Lys Thr Gly Asp Thr Ala Tyr Ser Glu Ser Phe
    50                  55                  60
```

```
Gln Asp Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Tyr Leu Trp Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ala Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Glu Ser Leu Ser Leu Ser Pro
        435                 440
```

<210> SEQ ID NO 10
<211> LENGTH: 116
<212> TYPE: PRT
<213> ORGANISM: Artificial
<220> FEATURE:

<223> OTHER INFORMATION: An artificially synthesized peptide sequence

<400> SEQUENCE: 10

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Lys Gln Thr Lys Tyr Arg Glu Lys Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Arg Glu Phe Asp Tyr Trp Gly Gln Gly Thr Leu Val
            100                 105                 110

Thr Val Ser Ser
        115

<210> SEQ ID NO 11
<211> LENGTH: 213
<212> TYPE: PRT
<213> ORGANISM: Artificial
<220> FEATURE:
<223> OTHER INFORMATION: An artificially synthesized peptide sequence

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile His Lys Tyr
            20                  25                  30

Ile Ala Trp Tyr Gln Gln Lys Pro Gly Gln Ala Pro Arg Leu Leu Ile
        35                  40                  45

Gln Tyr Thr Ser Thr Leu Gln Pro Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Leu Gln Tyr Glu Gln Leu Arg Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 12
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 12

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Lys Gln Thr Lys Tyr Arg Glu Lys Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Arg Glu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

```
Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
        435                 440


<210> SEQ ID NO 13
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 13

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Lys Gln Thr Lys Tyr Arg Glu Lys Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Arg Glu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285
```

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Cys Thr Leu Pro Pro
            340                 345                 350

Ser Arg Asp Glu Leu Thr Lys Asn Gln Val Ser Leu Trp Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
        435                 440

<210> SEQ ID NO 14
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 14

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Lys Gln Thr Lys Tyr Arg Glu Lys Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Arg Glu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

```
Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Cys Glu Leu Thr Lys Asn Gln Val Ser Leu Ser Cys Ala Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
        435                 440
```

<210> SEQ ID NO 15
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 15

```
Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Lys Gln Thr Lys Tyr Arg Glu Lys Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Arg Glu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125
```

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Ser Leu
180 185 190

Gly Thr Gln Thr Tyr Ile Cys Asn Val Asn His Lys Pro Ser Asn Thr
195 200 205

Lys Val Asp Lys Lys Val Glu Pro Lys Ser Cys Asp Lys Thr His Thr
210 215 220

Cys Pro Pro Cys Pro Ala Pro Glu Leu Leu Gly Gly Pro Asp Val Phe
225 230 235 240

Leu Phe Pro Pro Lys Pro Lys Asp Thr Leu Met Ile Ser Arg Thr Pro
245 250 255

Glu Val Thr Cys Val Val Val Asp Val Ser His Glu Asp Pro Glu Val
260 265 270

Lys Phe Asn Trp Tyr Val Asp Gly Val Glu Val His Asn Ala Lys Thr
275 280 285

Lys Pro Arg Glu Glu Gln Tyr Asn Ser Thr Tyr Arg Val Val Ser Val
290 295 300

Leu Thr Val Leu His Gln Asp Trp Leu Asn Gly Lys Glu Tyr Lys Cys
305 310 315 320

Lys Val Ser Asn Lys Ala Leu Pro Leu Pro Glu Glu Lys Thr Ile Ser
325 330 335

Lys Ala Lys Gly Gln Pro Arg Glu Pro Gln Val Cys Thr Leu Pro Pro
340 345 350

Ser Arg Asp Glu Leu Thr Lys Asn Gln Val Ser Leu Trp Cys Leu Val
355 360 365

Lys Gly Phe Tyr Pro Ser Asp Ile Ala Val Glu Trp Glu Ser Asn Gly
370 375 380

Gln Pro Glu Asn Asn Tyr Lys Thr Thr Pro Pro Val Leu Asp Ser Asp
385 390 395 400

Gly Ser Phe Phe Leu Tyr Ser Lys Leu Thr Val Asp Lys Ser Arg Trp
405 410 415

Gln Gln Gly Asn Val Phe Ser Cys Ser Val Met His Glu Ala Leu His
420 425 430

Asn His Tyr Thr Gln Lys Ser Leu Ser Leu Ser Pro
435 440

<210> SEQ ID NO 16
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 16

Gln Asp Gln Leu Val Gln Ser Gly Ala Glu Val Lys Lys Pro Gly Ala
1 5 10 15

Ser Val Lys Val Ser Cys Lys Ala Ser Gly Phe Asn Ile Lys Asp Thr
20 25 30

Tyr Ile Gln Trp Val Arg Gln Ala Pro Gly Gln Gly Leu Glu Trp Met
35 40 45

```
Gly Arg Ile Asp Pro Leu Arg Lys Gln Thr Lys Tyr Arg Glu Lys Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Arg Glu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Asp Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Leu Pro Glu Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Cys Glu Leu Thr Lys Asn Gln Val Ser Leu Ser Cys Ala Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
        435                 440
```

<210> SEQ ID NO 17
<211> LENGTH: 444

<212> TYPE: PRT
<213> ORGANISM: Artificial
<220> FEATURE:
<223> OTHER INFORMATION: An artificially synthesized peptide sequence

<400> SEQUENCE: 17

```
Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Lys Gln Thr Lys Tyr Arg Glu Lys Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Arg Glu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Tyr Tyr Trp Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Asp Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ala Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Cys Thr Leu Pro Pro
            340                 345                 350

Ser Arg Asp Glu Leu Thr Lys Asn Gln Val Ser Leu Trp Cys Leu Val
        355                 360                 365

Lys Gly Phe Tyr Pro Ser Asp Ile Ala Val Glu Trp Glu Ser Asn Gly
    370                 375                 380
```

Gln Pro Glu Asn Asn Tyr Lys Thr Thr Pro Pro Val Leu Asp Ser Asp
385 390 395 400

Gly Ser Phe Phe Leu Tyr Ser Lys Leu Thr Val Asp Lys Ser Arg Trp
405 410 415

Gln Gln Gly Asn Val Phe Ser Cys Ser Val Met His Glu Ala Leu His
420 425 430

Asn His Tyr Thr Gln Lys Ser Leu Ser Leu Ser Pro
435 440

<210> SEQ ID NO 18
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 18

Gln Asp Gln Leu Val Gln Ser Gly Ala Glu Val Lys Lys Pro Gly Ala
1 5 10 15

Ser Val Lys Val Ser Cys Lys Ala Ser Gly Phe Asn Ile Lys Asp Thr
20 25 30

Tyr Ile Gln Trp Val Arg Gln Ala Pro Gly Gln Gly Leu Glu Trp Met
35 40 45

Gly Arg Ile Asp Pro Leu Arg Lys Gln Thr Lys Tyr Arg Glu Lys Phe
50 55 60

Glu Gly Arg Val Thr Ile Thr Ala Asp Thr Ser Thr Asn Thr Ala Tyr
65 70 75 80

Met Glu Leu Ser Ser Leu Arg Ser Glu Asp Thr Ala Val Tyr Tyr Cys
85 90 95

Val Arg Ser Gly Arg Glu Phe Asp Tyr Trp Gly Gln Gly Thr Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Ser Leu
180 185 190

Gly Thr Gln Thr Tyr Ile Cys Asn Val Asn His Lys Pro Ser Asn Thr
195 200 205

Lys Val Asp Lys Lys Val Glu Pro Lys Ser Cys Asp Lys Thr His Thr
210 215 220

Cys Pro Pro Cys Pro Ala Pro Glu Leu Leu Gly Gly Pro Ser Val Phe
225 230 235 240

Leu Phe Pro Pro Lys Pro Lys Asp Thr Leu Met Ile Ser Arg Thr Pro
245 250 255

Glu Val Thr Cys Val Val Val Asp Val Ser His Glu Asp Pro Glu Val
260 265 270

Lys Phe Asn Trp Tyr Val Asp Gly Val Glu Val His Asn Ala Lys Thr
275 280 285

Lys Pro Arg Glu Glu Gln Tyr Asn Ser Thr Tyr Arg Val Val Ser Val
290 295 300

```
Leu Thr Val Leu His Gln Asp Trp Leu Asn Gly Lys Glu Tyr Lys Cys
305                 310                 315                 320

Lys Val Ser Asn Asp Ala Leu Pro Met Pro Ile Glu Glu Thr Ile Ser
                325                 330                 335

Lys Ala Lys Gly Gln Pro Arg Glu Pro Gln Val Tyr Thr Leu Pro Pro
            340                 345                 350

Ser Arg Cys Glu Leu Thr Lys Asn Gln Val Ser Leu Ser Cys Ala Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
        435                 440


<210> SEQ ID NO 19
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 19

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Lys Gln Thr Lys Tyr Arg Glu Lys Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Arg Glu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220
```

-continued

Cys Pro Pro Cys Pro Ala Pro Glu Tyr Tyr Trp Gly Pro Ser Val Phe
225 230 235 240

Leu Phe Pro Pro Lys Pro Lys Asp Thr Leu Met Ile Ser Arg Thr Pro
245 250 255

Glu Val Thr Cys Val Val Val Asp Val Ser Asp Glu Asp Pro Glu Val
260 265 270

Lys Phe Asn Trp Tyr Val Asp Gly Val Glu Val His Asn Ala Lys Thr
275 280 285

Lys Pro Arg Glu Glu Gln Tyr Asn Ala Thr Tyr Arg Val Val Ser Val
290 295 300

Leu Thr Val Leu His Gln Asp Trp Leu Asn Gly Lys Glu Tyr Lys Cys
305 310 315 320

Lys Val Ser Asn Lys Ala Leu Pro Ala Pro Ile Glu Lys Thr Ile Ser
325 330 335

Lys Ala Lys Gly Gln Pro Arg Glu Pro Gln Val Tyr Thr Leu Pro Pro
340 345 350

Ser Arg Cys Glu Leu Thr Lys Asn Gln Val Ser Leu Ser Cys Ala Val
355 360 365

Lys Gly Phe Tyr Pro Ser Asp Ile Ala Val Glu Trp Glu Ser Asn Gly
370 375 380

Gln Pro Glu Asn Asn Tyr Lys Thr Thr Pro Pro Val Leu Asp Ser Asp
385 390 395 400

Gly Ser Phe Phe Leu Val Ser Lys Leu Thr Val Asp Lys Ser Arg Trp
405 410 415

Gln Gln Gly Asn Val Phe Ser Cys Ser Val Met His Glu Ala Leu His
420 425 430

Asn His Tyr Thr Gln Lys Ser Leu Ser Leu Ser Pro
435 440

<210> SEQ ID NO 20
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 20

Gln Asp Gln Leu Val Gln Ser Gly Ala Glu Val Lys Lys Pro Gly Ala
1 5 10 15

Ser Val Lys Val Ser Cys Lys Ala Ser Gly Phe Asn Ile Lys Asp Thr
20 25 30

Tyr Ile Gln Trp Val Arg Gln Ala Pro Gly Gln Gly Leu Glu Trp Met
35 40 45

Gly Arg Ile Asp Pro Leu Arg Lys Gln Thr Lys Tyr Arg Glu Lys Phe
50 55 60

Glu Gly Arg Val Thr Ile Thr Ala Asp Thr Ser Thr Asn Thr Ala Tyr
65 70 75 80

Met Glu Leu Ser Ser Leu Arg Ser Glu Asp Thr Ala Val Tyr Tyr Cys
85 90 95

Val Arg Ser Gly Arg Glu Phe Asp Tyr Trp Gly Gln Gly Thr Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

```
Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Asp Ala Leu Pro Met Pro Ile Glu Glu Thr Ile Ser
                325                 330                 335

Lys Ala Lys Gly Gln Pro Arg Glu Pro Gln Val Cys Thr Leu Pro Pro
            340                 345                 350

Ser Arg Asp Glu Leu Thr Lys Asn Gln Val Ser Leu Trp Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
        435                 440


<210> SEQ ID NO 21
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 21

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Lys Gln Thr Lys Tyr Arg Glu Lys Phe
    50                  55                  60
```

```
Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Arg Glu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Tyr Gln Trp Gly Pro Met Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Asp Glu Glu Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ala Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Cys Thr Leu Pro Pro
            340                 345                 350

Ser Arg Asp Glu Leu Thr Lys Asn Gln Val Ser Leu Trp Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
        435                 440
```

<210> SEQ ID NO 22
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 22

Gln Asp Gln Leu Val Gln Ser Gly Ala Glu Val Lys Lys Pro Gly Ala
1 5 10 15

Ser Val Lys Val Ser Cys Lys Ala Ser Gly Phe Asn Ile Lys Asp Thr
20 25 30

Tyr Ile Gln Trp Val Arg Gln Ala Pro Gly Gln Gly Leu Glu Trp Met
35 40 45

Gly Arg Ile Asp Pro Leu Arg Lys Gln Thr Lys Tyr Arg Glu Lys Phe
50 55 60

Glu Gly Arg Val Thr Ile Thr Ala Asp Thr Ser Thr Asn Thr Ala Tyr
65 70 75 80

Met Glu Leu Ser Ser Leu Arg Ser Glu Asp Thr Ala Val Tyr Tyr Cys
85 90 95

Val Arg Ser Gly Arg Glu Phe Asp Tyr Trp Gly Gln Gly Thr Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Ser Leu
180 185 190

Gly Thr Gln Thr Tyr Ile Cys Asn Val Asn His Lys Pro Ser Asn Thr
195 200 205

Lys Val Asp Lys Lys Val Glu Pro Lys Ser Cys Asp Lys Thr His Thr
210 215 220

Cys Pro Pro Cys Pro Ala Pro Glu Leu Leu Gly Gly Pro Ser Val Phe
225 230 235 240

Leu Phe Pro Pro Lys Pro Lys Asp Thr Leu Met Ile Ser Arg Thr Pro
245 250 255

Glu Val Thr Cys Val Val Val Asp Val Ser His Glu Glu Pro Glu Val
260 265 270

Lys Phe Asn Trp Tyr Val Asp Gly Val Glu Val His Asn Ala Lys Thr
275 280 285

Lys Pro Arg Glu Glu Gln Tyr Asn Ser Thr Tyr Arg Val Val Ser Val
290 295 300

Leu Thr Val Leu His Gln Asp Trp Leu Asn Gly Lys Glu Tyr Lys Cys
305 310 315 320

Lys Val Ser Asn Asp Ala Leu Pro Met Pro Ile Glu Glu Thr Ile Ser
325 330 335

Lys Ala Lys Gly Gln Pro Arg Glu Pro Gln Val Tyr Thr Leu Pro Pro
340 345 350

Ser Arg Cys Glu Leu Thr Lys Asn Gln Val Ser Leu Ser Cys Ala Val
355 360 365

Lys Gly Phe Tyr Pro Ser Asp Ile Ala Val Glu Trp Glu Ser Asn Gly
370 375 380

Gln Pro Glu Asn Asn Tyr Lys Thr Thr Pro Pro Val Leu Asp Ser Asp
385 390 395 400

Gly Ser Phe Phe Leu Val Ser Lys Leu Thr Val Asp Lys Ser Arg Trp

```
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
        435                 440


<210> SEQ ID NO 23
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 23

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Lys Gln Thr Lys Tyr Arg Glu Lys Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Arg Glu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Gly Gly Ser Gly Gly Ser Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Asp Ala Leu Pro Met Pro Ile Glu Glu Thr Ile Ser
```

```
                325                 330                 335

Lys Ala Lys Gly Gln Pro Arg Glu Pro Gln Val Tyr Thr Leu Pro Pro
            340                 345                 350

Ser Arg Cys Glu Leu Thr Lys Asn Gln Val Ser Leu Ser Cys Ala Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
        435                 440


<210> SEQ ID NO 24
<211> LENGTH: 450
<212> TYPE: PRT
<213> ORGANISM: Artificial
<220> FEATURE:
<223> OTHER INFORMATION: An artificially synthesized peptide sequence

<400> SEQUENCE: 24

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Lys Gln Thr Lys Tyr Arg Glu Lys Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Arg Glu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
```

245 250 255

Glu Val Thr Cys Val Val Val Asp Val Gly Gly Gly Ser Gly Gly Gly
260 265 270

Ser Gly Gly Gly Ser Val Lys Phe Asn Trp Tyr Val Asp Gly Val Glu
275 280 285

Val His Asn Ala Lys Thr Lys Pro Arg Glu Glu Gln Tyr Asn Ser Thr
290 295 300

Tyr Arg Val Val Ser Val Leu Thr Val Leu His Gln Asp Trp Leu Asn
305 310 315 320

Gly Lys Glu Tyr Lys Cys Lys Val Ser Asn Asp Ala Leu Pro Met Pro
325 330 335

Ile Glu Glu Thr Ile Ser Lys Ala Lys Gly Gln Pro Arg Glu Pro Gln
340 345 350

Val Tyr Thr Leu Pro Pro Ser Arg Cys Glu Leu Thr Lys Asn Gln Val
355 360 365

Ser Leu Ser Cys Ala Val Lys Gly Phe Tyr Pro Ser Asp Ile Ala Val
370 375 380

Glu Trp Glu Ser Asn Gly Gln Pro Glu Asn Asn Tyr Lys Thr Thr Pro
385 390 395 400

Pro Val Leu Asp Ser Asp Gly Ser Phe Phe Leu Val Ser Lys Leu Thr
405 410 415

Val Asp Lys Ser Arg Trp Gln Gln Gly Asn Val Phe Ser Cys Ser Val
420 425 430

Met His Glu Ala Leu His Asn His Tyr Thr Gln Lys Ser Leu Ser Leu
435 440 445

Ser Pro
450

<210> SEQ ID NO 25
<211> LENGTH: 450
<212> TYPE: PRT
<213> ORGANISM: Artificial
<220> FEATURE:
<223> OTHER INFORMATION: An artificially synthesized peptide sequence

<400> SEQUENCE: 25

Gln Asp Gln Leu Val Gln Ser Gly Ala Glu Val Lys Lys Pro Gly Ala
1 5 10 15

Ser Val Lys Val Ser Cys Lys Ala Ser Gly Phe Asn Ile Lys Asp Thr
20 25 30

Tyr Ile Gln Trp Val Arg Gln Ala Pro Gly Gln Gly Leu Glu Trp Met
35 40 45

Gly Arg Ile Asp Pro Leu Arg Lys Gln Thr Lys Tyr Arg Glu Lys Phe
50 55 60

Glu Gly Arg Val Thr Ile Thr Ala Asp Thr Ser Thr Asn Thr Ala Tyr
65 70 75 80

Met Glu Leu Ser Ser Leu Arg Ser Glu Asp Thr Ala Val Tyr Tyr Cys
85 90 95

Val Arg Ser Gly Arg Glu Phe Asp Tyr Trp Gly Gln Gly Thr Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly 145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Ser Leu
180 185 190

Gly Thr Gln Thr Tyr Ile Cys Asn Val Asn His Lys Pro Ser Asn Thr
195 200 205

Lys Val Asp Lys Lys Val Glu Pro Lys Ser Cys Asp Lys Thr His Thr
210 215 220

Cys Pro Pro Cys Pro Ala Pro Glu Leu Leu Gly Gly Pro Ser Val Phe
225 230 235 240

Leu Phe Pro Pro Lys Pro Lys Asp Thr Leu Met Ile Ser Arg Thr Pro
245 250 255

Glu Val Thr Cys Val Val Val Asp Val Gly Gly Gly Ser Gly Gly Gly
260 265 270

Ser Gly Gly Gly Ser Val Lys Phe Asn Trp Tyr Val Asp Gly Val Glu
275 280 285

Val His Asn Ala Lys Thr Lys Pro Arg Glu Glu Gln Tyr Asn Ser Thr
290 295 300

Tyr Arg Val Val Ser Val Leu Thr Val Leu His Gln Asp Trp Leu Asn
305 310 315 320

Gly Lys Glu Tyr Lys Cys Lys Val Ser Asn Asp Ala Leu Pro Met Pro
325 330 335

Ile Glu Glu Thr Ile Ser Lys Ala Lys Gly Gln Pro Arg Glu Pro Gln
340 345 350

Val Tyr Thr Leu Pro Pro Ser Arg Cys Glu Leu Thr Lys Asn Gln Val
355 360 365

Ser Leu Ser Cys Ala Val Lys Gly Phe Tyr Pro Ser Asp Ile Ala Val
370 375 380

Glu Trp Glu Ser Asn Gly Gln Pro Glu Asn Asn Tyr Lys Thr Thr Pro
385 390 395 400

Pro Val Leu Asp Ser Asp Gly Ser Phe Phe Leu Val Ser Lys Leu Thr
405 410 415

Val Asp Lys Ser Arg Trp Gln Gln Gly Asn Val Phe Ser Cys Ser Val
420 425 430

Met His Glu Ala Leu His Asn His Tyr Thr Gln Lys Ser Leu Ser Leu
435 440 445

Ser Pro
450

<210> SEQ ID NO 26
<211> LENGTH: 447
<212> TYPE: PRT
<213> ORGANISM: Artificial
<220> FEATURE:
<223> OTHER INFORMATION: An artificially synthesized peptide sequence

<400> SEQUENCE: 26

Gln Asp Gln Leu Val Gln Ser Gly Ala Glu Val Lys Lys Pro Gly Ala
1 5 10 15

Ser Val Lys Val Ser Cys Lys Ala Ser Gly Phe Asn Ile Lys Asp Thr
20 25 30

Tyr Ile Gln Trp Val Arg Gln Ala Pro Gly Gln Gly Leu Glu Trp Met
35 40 45

Gly Arg Ile Asp Pro Leu Arg Lys Gln Thr Lys Tyr Arg Glu Lys Phe

```
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Arg Glu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Gly Gly Ser Glu Glu
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Asp Ala Leu Pro Met Pro Ile Glu Glu
                325                 330                 335

Thr Ile Ser Lys Ala Lys Gly Gln Pro Arg Glu Pro Gln Val Tyr Thr
            340                 345                 350

Leu Pro Pro Ser Arg Cys Glu Leu Thr Lys Asn Gln Val Ser Leu Ser
        355                 360                 365

Cys Ala Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445


<210> SEQ ID NO 27
<211> LENGTH: 450
<212> TYPE: PRT
<213> ORGANISM: Artificial
```

```
<220> FEATURE:
<223> OTHER INFORMATION: An artificially synthesized peptide sequence

<400> SEQUENCE: 27

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Lys Gln Thr Lys Tyr Arg Glu Lys Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Arg Glu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Gly Gly Ser Gly Gly
            260                 265                 270

Ser Glu Glu Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Asp Ala Leu Pro Met Pro
                325                 330                 335

Ile Glu Glu Thr Ile Ser Lys Ala Lys Gly Gln Pro Arg Glu Pro Gln
            340                 345                 350

Val Tyr Thr Leu Pro Pro Ser Arg Cys Glu Leu Thr Lys Asn Gln Val
        355                 360                 365

Ser Leu Ser Cys Ala Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400
```

```
Pro Val Leu Asp Ser Asp Gly Ser Phe Phe Leu Val Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro
    450
```

<210> SEQ ID NO 28
<211> LENGTH: 453
<212> TYPE: PRT
<213> ORGANISM: Artificial
<220> FEATURE:
<223> OTHER INFORMATION: An artificially synthesized peptide sequence

<400> SEQUENCE: 28

```
Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Lys Gln Thr Lys Tyr Arg Glu Lys Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Arg Glu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Gly Gly Ser Gly Gly
            260                 265                 270

Ser Gly Gly Ser Glu Glu Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300
```

Asn Ser Thr Tyr Arg Val Val Ser Val Leu Thr Val Leu His Gln Asp
305 310 315 320

Trp Leu Asn Gly Lys Glu Tyr Lys Cys Lys Val Ser Asn Asp Ala Leu
325 330 335

Pro Met Pro Ile Glu Glu Thr Ile Ser Lys Ala Lys Gly Gln Pro Arg
340 345 350

Glu Pro Gln Val Tyr Thr Leu Pro Pro Ser Arg Cys Glu Leu Thr Lys
355 360 365

Asn Gln Val Ser Leu Ser Cys Ala Val Lys Gly Phe Tyr Pro Ser Asp
370 375 380

Ile Ala Val Glu Trp Glu Ser Asn Gly Gln Pro Glu Asn Asn Tyr Lys
385 390 395 400

Thr Thr Pro Pro Val Leu Asp Ser Asp Gly Ser Phe Phe Leu Val Ser
405 410 415

Lys Leu Thr Val Asp Lys Ser Arg Trp Gln Gln Gly Asn Val Phe Ser
420 425 430

Cys Ser Val Met His Glu Ala Leu His Asn His Tyr Thr Gln Lys Ser
435 440 445

Leu Ser Leu Ser Pro
450

<210> SEQ ID NO 29
<211> LENGTH: 447
<212> TYPE: PRT
<213> ORGANISM: Artificial
<220> FEATURE:
<223> OTHER INFORMATION: An artificially synthesized peptide sequence

<400> SEQUENCE: 29

Gln Asp Gln Leu Val Gln Ser Gly Ala Glu Val Lys Lys Pro Gly Ala
1 5 10 15

Ser Val Lys Val Ser Cys Lys Ala Ser Gly Phe Asn Ile Lys Asp Thr
20 25 30

Tyr Ile Gln Trp Val Arg Gln Ala Pro Gly Gln Gly Leu Glu Trp Met
35 40 45

Gly Arg Ile Asp Pro Leu Arg Lys Gln Thr Lys Tyr Arg Glu Lys Phe
50 55 60

Glu Gly Arg Val Thr Ile Thr Ala Asp Thr Ser Thr Asn Thr Ala Tyr
65 70 75 80

Met Glu Leu Ser Ser Leu Arg Ser Glu Asp Thr Ala Val Tyr Tyr Cys
85 90 95

Val Arg Ser Gly Arg Glu Phe Asp Tyr Trp Gly Gln Gly Thr Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Ser Leu
180 185 190

Gly Thr Gln Thr Tyr Ile Cys Asn Val Asn His Lys Pro Ser Asn Thr
195 200 205

```
Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Glu Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Gly Gly Ser Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Asp Ala Leu Pro Met Pro Ile Glu Glu
                325                 330                 335

Thr Ile Ser Lys Ala Lys Gly Gln Pro Arg Glu Pro Gln Val Tyr Thr
            340                 345                 350

Leu Pro Pro Ser Arg Cys Glu Leu Thr Lys Asn Gln Val Ser Leu Ser
        355                 360                 365

Cys Ala Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445
```

<210> SEQ ID NO 30
<211> LENGTH: 450
<212> TYPE: PRT
<213> ORGANISM: Artificial
<220> FEATURE:
<223> OTHER INFORMATION: An artificially synthesized peptide sequence

<400> SEQUENCE: 30

```
Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Lys Gln Thr Lys Tyr Arg Glu Lys Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Arg Glu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125
```

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Glu Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Gly Gly Ser Gly Gly Ser
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Asp Ala Leu Pro Met Pro
                325                 330                 335

Ile Glu Glu Thr Ile Ser Lys Ala Lys Gly Gln Pro Arg Glu Pro Gln
            340                 345                 350

Val Tyr Thr Leu Pro Pro Ser Arg Cys Glu Leu Thr Lys Asn Gln Val
        355                 360                 365

Ser Leu Ser Cys Ala Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Val Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro
    450

<210> SEQ ID NO 31
<211> LENGTH: 453
<212> TYPE: PRT
<213> ORGANISM: Artificial
<220> FEATURE:
<223> OTHER INFORMATION: An artificially synthesized peptide sequence

<400> SEQUENCE: 31

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

```
Tyr Ile Gln Trp Val Arg Gln Ala Pro Gly Gln Gly Leu Glu Trp Met
        35                  40                  45

Gly Arg Ile Asp Pro Leu Arg Lys Gln Thr Lys Tyr Arg Glu Lys Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Arg Glu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Glu Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Gly Gly Ser Gly Gly Ser
    290                 295                 300

Gly Gly Ser Tyr Arg Val Val Ser Val Leu Thr Val Leu His Gln Asp
305                 310                 315                 320

Trp Leu Asn Gly Lys Glu Tyr Lys Cys Lys Val Ser Asn Asp Ala Leu
                325                 330                 335

Pro Met Pro Ile Glu Glu Thr Ile Ser Lys Ala Lys Gly Gln Pro Arg
            340                 345                 350

Glu Pro Gln Val Tyr Thr Leu Pro Pro Ser Arg Cys Glu Leu Thr Lys
        355                 360                 365

Asn Gln Val Ser Leu Ser Cys Ala Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Val Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445
```

Leu Ser Leu Ser Pro
450

<210> SEQ ID NO 32
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 32

Gln Asp Gln Leu Val Gln Ser Gly Ala Glu Val Lys Lys Pro Gly Ala
1 5 10 15

Ser Val Lys Val Ser Cys Lys Ala Ser Gly Phe Asn Ile Lys Asp Thr
20 25 30

Tyr Ile Gln Trp Val Arg Gln Ala Pro Gly Gln Gly Leu Glu Trp Met
35 40 45

Gly Arg Ile Asp Pro Leu Arg Lys Gln Thr Lys Tyr Arg Glu Lys Phe
50 55 60

Glu Gly Arg Val Thr Ile Thr Ala Asp Thr Ser Thr Asn Thr Ala Tyr
65 70 75 80

Met Glu Leu Ser Ser Leu Arg Ser Glu Asp Thr Ala Val Tyr Tyr Cys
85 90 95

Val Arg Ser Gly Arg Glu Phe Asp Tyr Trp Gly Gln Gly Thr Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Ser Leu
180 185 190

Gly Thr Gln Thr Tyr Ile Cys Asn Val Asn His Lys Pro Ser Asn Thr
195 200 205

Lys Val Asp Lys Lys Val Glu Pro Lys Ser Cys Asp Lys Thr His Thr
210 215 220

Cys Pro Pro Cys Pro Ala Pro Glu Tyr Gln Trp Gly Pro Met Val Phe
225 230 235 240

Leu Phe Pro Pro Lys Pro Lys Asp Thr Leu Met Ile Ser Arg Thr Pro
245 250 255

Glu Val Thr Cys Val Val Val Asp Val Ser Asp Glu Glu Pro Glu Val
260 265 270

Lys Phe Asn Trp Tyr Val Asp Gly Val Glu Val His Asn Ala Lys Thr
275 280 285

Lys Pro Arg Glu Glu Gln Tyr Asn Ala Thr Tyr Arg Val Val Ser Val
290 295 300

Leu Thr Val Leu His Gln Asp Trp Leu Asn Gly Lys Glu Tyr Lys Cys
305 310 315 320

Lys Val Ser Asn Gly Ser Gly Gly Ser Pro Ile Glu Lys Thr Ile Ser
325 330 335

Lys Ala Lys Gly Gln Pro Arg Glu Pro Gln Val Cys Thr Leu Pro Pro
340 345 350

Ser Arg Asp Glu Leu Thr Lys Asn Gln Val Ser Leu Trp Cys Leu Val
355 360 365

Lys Gly Phe Tyr Pro Ser Asp Ile Ala Val Glu Trp Glu Ser Asn Gly
370 375 380

Gln Pro Glu Asn Asn Tyr Lys Thr Thr Pro Pro Val Leu Asp Ser Asp
385 390 395 400

Gly Ser Phe Phe Leu Tyr Ser Lys Leu Thr Val Asp Lys Ser Arg Trp
405 410 415

Gln Gln Gly Asn Val Phe Ser Cys Ser Val Met His Glu Ala Leu His
420 425 430

Asn His Tyr Thr Gln Lys Ser Leu Ser Leu Ser Pro
435 440

<210> SEQ ID NO 33
<211> LENGTH: 446
<212> TYPE: PRT
<213> ORGANISM: Artificial
<220> FEATURE:
<223> OTHER INFORMATION: An artificially synthesized peptide sequence

<400> SEQUENCE: 33

Gln Asp Gln Leu Val Gln Ser Gly Ala Glu Val Lys Lys Pro Gly Ala
1 5 10 15

Ser Val Lys Val Ser Cys Lys Ala Ser Gly Phe Asn Ile Lys Asp Thr
20 25 30

Tyr Ile Gln Trp Val Arg Gln Ala Pro Gly Gln Gly Leu Glu Trp Met
35 40 45

Gly Arg Ile Asp Pro Leu Arg Lys Gln Thr Lys Tyr Arg Glu Lys Phe
50 55 60

Glu Gly Arg Val Thr Ile Thr Ala Asp Thr Ser Thr Asn Thr Ala Tyr
65 70 75 80

Met Glu Leu Ser Ser Leu Arg Ser Glu Asp Thr Ala Val Tyr Tyr Cys
85 90 95

Val Arg Ser Gly Arg Glu Phe Asp Tyr Trp Gly Gln Gly Thr Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Ser Leu
180 185 190

Gly Thr Gln Thr Tyr Ile Cys Asn Val Asn His Lys Pro Ser Asn Thr
195 200 205

Lys Val Asp Lys Lys Val Glu Pro Lys Ser Cys Asp Lys Thr His Thr
210 215 220

Cys Pro Pro Cys Pro Ala Pro Glu Tyr Gln Trp Gly Pro Met Val Phe
225 230 235 240

Leu Phe Pro Pro Lys Pro Lys Asp Thr Leu Met Ile Ser Arg Thr Pro
245 250 255

Glu Val Thr Cys Val Val Val Asp Val Ser Asp Glu Glu Pro Glu Val
260 265 270

Lys Phe Asn Trp Tyr Val Asp Gly Val Glu Val His Asn Ala Lys Thr
275 280 285

Lys Pro Arg Glu Glu Gln Tyr Asn Ala Thr Tyr Arg Val Val Ser Val
290 295 300

Leu Thr Val Leu His Gln Asp Trp Leu Asn Gly Lys Glu Tyr Lys Cys
305 310 315 320

Lys Val Ser Asn Gly Gly Ser Gly Gly Gly Ser Pro Ile Glu Lys Thr
325 330 335

Ile Ser Lys Ala Lys Gly Gln Pro Arg Glu Pro Gln Val Cys Thr Leu
340 345 350

Pro Pro Ser Arg Asp Glu Leu Thr Lys Asn Gln Val Ser Leu Trp Cys
355 360 365

Leu Val Lys Gly Phe Tyr Pro Ser Asp Ile Ala Val Glu Trp Glu Ser
370 375 380

Asn Gly Gln Pro Glu Asn Asn Tyr Lys Thr Thr Pro Pro Val Leu Asp
385 390 395 400

Ser Asp Gly Ser Phe Phe Leu Tyr Ser Lys Leu Thr Val Asp Lys Ser
405 410 415

Arg Trp Gln Gln Gly Asn Val Phe Ser Cys Ser Val Met His Glu Ala
420 425 430

Leu His Asn His Tyr Thr Gln Lys Ser Leu Ser Leu Ser Pro
435 440 445

<210> SEQ ID NO 34
<211> LENGTH: 450
<212> TYPE: PRT
<213> ORGANISM: Artificial
<220> FEATURE:
<223> OTHER INFORMATION: An artificially synthesized peptide sequence

<400> SEQUENCE: 34

Gln Asp Gln Leu Val Gln Ser Gly Ala Glu Val Lys Lys Pro Gly Ala
1 5 10 15

Ser Val Lys Val Ser Cys Lys Ala Ser Gly Phe Asn Ile Lys Asp Thr
20 25 30

Tyr Ile Gln Trp Val Arg Gln Ala Pro Gly Gln Gly Leu Glu Trp Met
35 40 45

Gly Arg Ile Asp Pro Leu Arg Lys Gln Thr Lys Tyr Arg Glu Lys Phe
50 55 60

Glu Gly Arg Val Thr Ile Thr Ala Asp Thr Ser Thr Asn Thr Ala Tyr
65 70 75 80

Met Glu Leu Ser Ser Leu Arg Ser Glu Asp Thr Ala Val Tyr Tyr Cys
85 90 95

Val Arg Ser Gly Arg Glu Phe Asp Tyr Trp Gly Gln Gly Thr Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Ser Leu
180 185 190

```
Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Tyr Gln Trp Gly Pro Met Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Asp Glu Glu Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ala Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Gly Gly Ser Gly Gly Gly Ser Gly Gly Gly Ser Pro
                325                 330                 335

Ile Glu Lys Thr Ile Ser Lys Ala Lys Gly Gln Pro Arg Glu Pro Gln
            340                 345                 350

Val Cys Thr Leu Pro Pro Ser Arg Asp Glu Leu Thr Lys Asn Gln Val
        355                 360                 365

Ser Leu Trp Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro
    450


<210> SEQ ID NO 35
<211> LENGTH: 447
<212> TYPE: PRT
<213> ORGANISM: Artificial
<220> FEATURE:
<223> OTHER INFORMATION: An artificially synthesized peptide sequence

<400> SEQUENCE: 35

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Lys Gln Thr Lys Tyr Arg Glu Lys Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95
```

```
Val Arg Ser Gly Arg Glu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Tyr Gln Trp Gly Pro Met Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Asp Glu Gly Gly Ser Glu
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ala Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Asp Glu Leu Thr Lys Asn Gln Val Ser Leu Trp
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445
```

<210> SEQ ID NO 36
<211> LENGTH: 450
<212> TYPE: PRT
<213> ORGANISM: Artificial
<220> FEATURE:
<223> OTHER INFORMATION: An artificially synthesized peptide sequence

<400> SEQUENCE: 36

```
Gln Asp Gln Leu Val Gln Ser Gly Ala Glu Val Lys Lys Pro Gly Ala
1               5                   10                  15
```

```
Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Lys Gln Thr Lys Tyr Arg Glu Lys Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Arg Glu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Tyr Gln Trp Gly Pro Met Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Asp Glu Gly Gly Ser Gly
            260                 265                 270

Gly Ser Glu Pro Glu Val Lys Phe Asn Trp Tyr Val Asp Gly Val Glu
        275                 280                 285

Val His Asn Ala Lys Thr Lys Pro Arg Glu Glu Gln Tyr Asn Ala Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Cys Thr Leu Pro Pro Ser Arg Asp Glu Leu Thr Lys Asn Gln Val
        355                 360                 365

Ser Leu Trp Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
```

```
        435                 440                 445

Ser Pro
    450


<210> SEQ ID NO 37
<211> LENGTH: 453
<212> TYPE: PRT
<213> ORGANISM: Artificial
<220> FEATURE:
<223> OTHER INFORMATION: An artificially synthesized peptide sequence

<400> SEQUENCE: 37

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Lys Gln Thr Lys Tyr Arg Glu Lys Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Arg Glu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Tyr Gln Trp Gly Pro Met Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Asp Glu Gly Gly Ser Gly
            260                 265                 270

Gly Ser Gly Gly Ser Glu Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ala Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
```

```
            340                 345                 350

Glu Pro Gln Val Cys Thr Leu Pro Pro Ser Arg Asp Glu Leu Thr Lys
        355                 360                 365

Asn Gln Val Ser Leu Trp Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro
    450


<210> SEQ ID NO 38
<211> LENGTH: 447
<212> TYPE: PRT
<213> ORGANISM: Artificial
<220> FEATURE:
<223> OTHER INFORMATION: An artificially synthesized peptide sequence

<400> SEQUENCE: 38

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Lys Gln Thr Lys Tyr Arg Glu Lys Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Arg Glu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Tyr Gln Trp Gly Pro Met Val Phe
225                 230                 235                 240

Leu Phe Pro Pro Lys Pro Lys Asp Thr Leu Met Ile Ser Arg Thr Pro
```

```
                245                 250                 255

Glu Val Thr Cys Val Val Val Asp Val Ser Asp Glu Glu Gly Gly Ser
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ala Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Asp Glu Leu Thr Lys Asn Gln Val Ser Leu Trp
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445


<210> SEQ ID NO 39
<211> LENGTH: 450
<212> TYPE: PRT
<213> ORGANISM: Artificial
<220> FEATURE:
<223> OTHER INFORMATION: An artificially synthesized peptide sequence

<400> SEQUENCE: 39

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Lys Gln Thr Lys Tyr Arg Glu Lys Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Arg Glu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
```

```
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Tyr Gln Trp Gly Pro Met Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Asp Glu Glu Gly Gly Ser
            260                 265                 270

Gly Gly Ser Pro Glu Val Lys Phe Asn Trp Tyr Val Asp Gly Val Glu
        275                 280                 285

Val His Asn Ala Lys Thr Lys Pro Arg Glu Glu Gln Tyr Asn Ala Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Cys Thr Leu Pro Pro Ser Arg Asp Glu Leu Thr Lys Asn Gln Val
        355                 360                 365

Ser Leu Trp Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro
    450
```

<210> SEQ ID NO 40
<211> LENGTH: 453
<212> TYPE: PRT
<213> ORGANISM: Artificial
<220> FEATURE:
<223> OTHER INFORMATION: An artificially synthesized peptide sequence

<400> SEQUENCE: 40

```
Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Lys Gln Thr Lys Tyr Arg Glu Lys Phe
    50                  55                  60

Glu Gly Arg Val Thr Ile Thr Ala Asp Thr Ser Thr Asn Thr Ala Tyr
```

```
65                  70                  75                  80

Met Glu Leu Ser Ser Leu Arg Ser Glu Asp Thr Ala Val Tyr Tyr Cys
                85                  90                  95

Val Arg Ser Gly Arg Glu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Tyr Gln Trp Gly Pro Met Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Asp Glu Glu Gly Gly Ser
            260                 265                 270

Gly Gly Ser Gly Gly Ser Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ala Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Cys Thr Leu Pro Pro Ser Arg Asp Glu Leu Thr Lys
        355                 360                 365

Asn Gln Val Ser Leu Trp Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro
    450
```

<210> SEQ ID NO 41
<211> LENGTH: 447
<212> TYPE: PRT
<213> ORGANISM: Artificial

<220> FEATURE:
<223> OTHER INFORMATION: An artificially synthesized peptide sequence

<400> SEQUENCE: 41

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Lys Gln Thr Lys Tyr Arg Glu Lys Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Arg Glu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Tyr Gln Trp Gly Pro Met Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Asp Glu Glu Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ala Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Gly Ser Ala Leu Pro Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Asp Glu Leu Thr Lys Asn Gln Val Ser Leu Trp
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

```
Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445


<210> SEQ ID NO 42
<211> LENGTH: 450
<212> TYPE: PRT
<213> ORGANISM: Artificial
<220> FEATURE:
<223> OTHER INFORMATION: An artificially synthesized peptide sequence

<400> SEQUENCE: 42

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Lys Gln Thr Lys Tyr Arg Glu Lys Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Arg Glu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Tyr Gln Trp Gly Pro Met Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Asp Glu Glu Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ala Thr Tyr Arg Val Val Ser Val
    290                 295                 300

Leu Thr Val Leu His Gln Asp Trp Leu Asn Gly Lys Glu Tyr Lys Cys
305                 310                 315                 320
```

Lys Val Ser Asn Lys Gly Gly Ser Gly Gly Ser Ala Leu Pro Ala Pro
325 330 335

Ile Glu Lys Thr Ile Ser Lys Ala Lys Gly Gln Pro Arg Glu Pro Gln
340 345 350

Val Cys Thr Leu Pro Pro Ser Arg Asp Glu Leu Thr Lys Asn Gln Val
355 360 365

Ser Leu Trp Cys Leu Val Lys Gly Phe Tyr Pro Ser Asp Ile Ala Val
370 375 380

Glu Trp Glu Ser Asn Gly Gln Pro Glu Asn Asn Tyr Lys Thr Thr Pro
385 390 395 400

Pro Val Leu Asp Ser Asp Gly Ser Phe Phe Leu Tyr Ser Lys Leu Thr
405 410 415

Val Asp Lys Ser Arg Trp Gln Gln Gly Asn Val Phe Ser Cys Ser Val
420 425 430

Met His Glu Ala Leu His Asn His Tyr Thr Gln Lys Ser Leu Ser Leu
435 440 445

Ser Pro
450

<210> SEQ ID NO 43
<211> LENGTH: 453
<212> TYPE: PRT
<213> ORGANISM: Artificial
<220> FEATURE:
<223> OTHER INFORMATION: An artificially synthesized peptide sequence

<400> SEQUENCE: 43

Gln Asp Gln Leu Val Gln Ser Gly Ala Glu Val Lys Lys Pro Gly Ala
1 5 10 15

Ser Val Lys Val Ser Cys Lys Ala Ser Gly Phe Asn Ile Lys Asp Thr
20 25 30

Tyr Ile Gln Trp Val Arg Gln Ala Pro Gly Gln Gly Leu Glu Trp Met
35 40 45

Gly Arg Ile Asp Pro Leu Arg Lys Gln Thr Lys Tyr Arg Glu Lys Phe
50 55 60

Glu Gly Arg Val Thr Ile Thr Ala Asp Thr Ser Thr Asn Thr Ala Tyr
65 70 75 80

Met Glu Leu Ser Ser Leu Arg Ser Glu Asp Thr Ala Val Tyr Tyr Cys
85 90 95

Val Arg Ser Gly Arg Glu Phe Asp Tyr Trp Gly Gln Gly Thr Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Ser Leu
180 185 190

Gly Thr Gln Thr Tyr Ile Cys Asn Val Asn His Lys Pro Ser Asn Thr
195 200 205

Lys Val Asp Lys Lys Val Glu Pro Lys Ser Cys Asp Lys Thr His Thr
210 215 220

Cys Pro Pro Cys Pro Ala Pro Glu Tyr Gln Trp Gly Pro Met Val Phe
225 230 235 240

Leu Phe Pro Pro Lys Pro Lys Asp Thr Leu Met Ile Ser Arg Thr Pro
245 250 255

Glu Val Thr Cys Val Val Val Asp Val Ser Asp Glu Glu Pro Glu Val
260 265 270

Lys Phe Asn Trp Tyr Val Asp Gly Val Glu Val His Asn Ala Lys Thr
275 280 285

Lys Pro Arg Glu Glu Gln Tyr Asn Ala Thr Tyr Arg Val Val Ser Val
290 295 300

Leu Thr Val Leu His Gln Asp Trp Leu Asn Gly Lys Glu Tyr Lys Cys
305 310 315 320

Lys Val Ser Asn Lys Gly Gly Ser Gly Gly Ser Gly Gly Ser Ala Leu
325 330 335

Pro Ala Pro Ile Glu Lys Thr Ile Ser Lys Ala Lys Gly Gln Pro Arg
340 345 350

Glu Pro Gln Val Cys Thr Leu Pro Pro Ser Arg Asp Glu Leu Thr Lys
355 360 365

Asn Gln Val Ser Leu Trp Cys Leu Val Lys Gly Phe Tyr Pro Ser Asp
370 375 380

Ile Ala Val Glu Trp Glu Ser Asn Gly Gln Pro Glu Asn Asn Tyr Lys
385 390 395 400

Thr Thr Pro Pro Val Leu Asp Ser Asp Gly Ser Phe Phe Leu Tyr Ser
405 410 415

Lys Leu Thr Val Asp Lys Ser Arg Trp Gln Gln Gly Asn Val Phe Ser
420 425 430

Cys Ser Val Met His Glu Ala Leu His Asn His Tyr Thr Gln Lys Ser
435 440 445

Leu Ser Leu Ser Pro
450

<210> SEQ ID NO 44
<211> LENGTH: 444
<212> TYPE: PRT
<213> ORGANISM: Homo sapiens

<400> SEQUENCE: 44

Gln Asp Gln Leu Val Gln Ser Gly Ala Glu Val Lys Lys Pro Gly Ala
1 5 10 15

Ser Val Lys Val Ser Cys Lys Ala Ser Gly Phe Asn Ile Lys Asp Thr
20 25 30

Tyr Ile Gln Trp Val Arg Gln Ala Pro Gly Gln Gly Leu Glu Trp Met
35 40 45

Gly Arg Ile Asp Pro Leu Arg Lys Gln Thr Lys Tyr Arg Glu Lys Phe
50 55 60

Glu Gly Arg Val Thr Ile Thr Ala Asp Thr Ser Thr Asn Thr Ala Tyr
65 70 75 80

Met Glu Leu Ser Ser Leu Arg Ser Glu Asp Thr Ala Val Tyr Tyr Cys
85 90 95

Val Arg Ser Gly Arg Glu Phe Asp Tyr Trp Gly Gln Gly Thr Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu

```
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
        435                 440
```

<210> SEQ ID NO 45
<211> LENGTH: 449
<212> TYPE: PRT
<213> ORGANISM: Artificial
<220> FEATURE:
<223> OTHER INFORMATION: An artificially synthesized peptide sequence

<400> SEQUENCE: 45

```
Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Lys Gln Thr Lys Tyr Arg Glu Lys Phe
```

```
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Arg Glu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gly Cys Arg Gly Asp Cys
            260                 265                 270

Leu Glu Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Asp Ala Leu Pro Met Pro Ile
                325                 330                 335

Glu Glu Thr Ile Ser Lys Ala Lys Gly Gln Pro Arg Glu Pro Gln Val
            340                 345                 350

Tyr Thr Leu Pro Pro Ser Arg Cys Glu Leu Thr Lys Asn Gln Val Ser
        355                 360                 365

Leu Ser Cys Ala Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro

<210> SEQ ID NO 46
<211> LENGTH: 449
```

<212> TYPE: PRT
<213> ORGANISM: Artificial
<220> FEATURE:
<223> OTHER INFORMATION: An artificially synthesized peptide sequence

<400> SEQUENCE: 46

```
Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Lys Gln Thr Lys Tyr Arg Glu Lys Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Arg Glu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Tyr Gln Trp Gly Pro Met Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gly Cys Arg Gly Asp Cys
            260                 265                 270

Leu Glu Pro Glu Val Lys Phe Asn Trp Tyr Val Asp Gly Val Glu Val
        275                 280                 285

His Asn Ala Lys Thr Lys Pro Arg Glu Glu Gln Tyr Asn Ala Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Asp Glu Leu Thr Lys Asn Gln Val Ser
        355                 360                 365

Leu Trp Cys Leu Val Lys Gly Phe Tyr Pro Ser Asp Ile Ala Val Glu
    370                 375                 380
```

Trp Glu Ser Asn Gly Gln Pro Glu Asn Asn Tyr Lys Thr Thr Pro Pro
385 390 395 400

Val Leu Asp Ser Asp Gly Ser Phe Phe Leu Tyr Ser Lys Leu Thr Val
405 410 415

Asp Lys Ser Arg Trp Gln Gln Gly Asn Val Phe Ser Cys Ser Val Met
420 425 430

His Glu Ala Leu His Asn His Tyr Thr Gln Lys Ser Leu Ser Leu Ser
435 440 445

Pro

<210> SEQ ID NO 47
<211> LENGTH: 448
<212> TYPE: PRT
<213> ORGANISM: Artificial
<220> FEATURE:
<223> OTHER INFORMATION: An artificially synthesized peptide sequence

<400> SEQUENCE: 47

Gln Asp Gln Leu Val Gln Ser Gly Ala Glu Val Lys Lys Pro Gly Ala
1 5 10 15

Ser Val Lys Val Ser Cys Lys Ala Ser Gly Phe Asn Ile Lys Asp Thr
20 25 30

Tyr Ile Gln Trp Val Arg Gln Ala Pro Gly Gln Gly Leu Glu Trp Met
35 40 45

Gly Arg Ile Asp Pro Leu Arg Lys Gln Thr Lys Tyr Arg Glu Lys Phe
50 55 60

Glu Gly Arg Val Thr Ile Thr Ala Asp Thr Ser Thr Asn Thr Ala Tyr
65 70 75 80

Met Glu Leu Ser Ser Leu Arg Ser Glu Asp Thr Ala Val Tyr Tyr Cys
85 90 95

Val Arg Ser Gly Arg Glu Phe Asp Tyr Trp Gly Gln Gly Thr Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Ser Leu
180 185 190

Gly Thr Gln Thr Tyr Ile Cys Asn Val Asn His Lys Pro Ser Asn Thr
195 200 205

Lys Val Asp Lys Lys Val Glu Pro Lys Ser Cys Asp Lys Thr His Thr
210 215 220

Cys Pro Pro Cys Pro Ala Pro Glu Tyr Gln Trp Gly Pro Met Val Phe
225 230 235 240

Leu Phe Pro Pro Lys Pro Lys Asp Thr Leu Met Ile Ser Arg Thr Pro
245 250 255

Glu Val Thr Cys Val Val Val Asp Val Ser Asp Glu Glu Pro Glu Val
260 265 270

Lys Phe Asn Trp Tyr Val Asp Gly Val Glu Val His Asn Ala Lys Thr
275 280 285

Lys Pro Arg Glu Glu Gln Tyr Asn Ala Thr Tyr Arg Val Val Ser Val 290 295 300

Leu Thr Val Leu His Gln Asp Trp Leu Asn Gly Lys Glu Tyr Lys Cys
305 310 315 320

Lys Val Ser Asn Lys Ala Leu Pro Ala Pro Ile Glu Lys Thr Ile Ser
325 330 335

Lys Ala Lys Gly Gln Pro Arg Glu Pro Gln Val Cys Thr Leu Pro Pro
340 345 350

Ser Arg Asp Glu Leu Thr Lys Asn Gln Val Ser Leu Trp Cys Leu Val
355 360 365

Lys Gly Phe Tyr Pro Ser Asp Ile Ala Val Glu Trp Glu Ser Gly Cys
370 375 380

Arg Gly Asp Cys Leu Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

<210> SEQ ID NO 48
<211> LENGTH: 448
<212> TYPE: PRT
<213> ORGANISM: Artificial
<220> FEATURE:
<223> OTHER INFORMATION: An artificially synthesized peptide sequence

<400> SEQUENCE: 48

Gln Asp Gln Leu Val Gln Ser Gly Ala Glu Val Lys Lys Pro Gly Ala
1 5 10 15

Ser Val Lys Val Ser Cys Lys Ala Ser Gly Phe Asn Ile Lys Asp Thr
20 25 30

Tyr Ile Gln Trp Val Arg Gln Ala Pro Gly Gln Gly Leu Glu Trp Met
35 40 45

Gly Arg Ile Asp Pro Leu Arg Lys Gln Thr Lys Tyr Arg Glu Lys Phe
50 55 60

Glu Gly Arg Val Thr Ile Thr Ala Asp Thr Ser Thr Asn Thr Ala Tyr
65 70 75 80

Met Glu Leu Ser Ser Leu Arg Ser Glu Asp Thr Ala Val Tyr Tyr Cys
85 90 95

Val Arg Ser Gly Arg Glu Phe Asp Tyr Trp Gly Gln Gly Thr Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Ser Leu
180 185 190

Gly Thr Gln Thr Tyr Ile Cys Asn Val Asn His Lys Pro Ser Asn Thr
195 200 205

Lys Val Asp Lys Lys Val Glu Pro Lys Ser Cys Asp Lys Thr His Thr

```
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Gly Cys
    370                 375                 380

Arg Gly Asp Cys Leu Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445


<210> SEQ ID NO 49
<211> LENGTH: 330
<212> TYPE: PRT
<213> ORGANISM: Homo sapiens

<400> SEQUENCE: 49

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140
```

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 50
<211> LENGTH: 326
<212> TYPE: PRT
<213> ORGANISM: Homo sapiens

<400> SEQUENCE: 50

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190
```

```
Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 51
<211> LENGTH: 377
<212> TYPE: PRT
<213> ORGANISM: Homo sapiens

<400> SEQUENCE: 51

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
```

225 230 235 240

Gln Asp Trp Leu Asn Gly Lys Glu Tyr Lys Cys Lys Val Ser Asn Lys
245 250 255

Ala Leu Pro Ala Pro Ile Glu Lys Thr Ile Ser Lys Thr Lys Gly Gln
260 265 270

Pro Arg Glu Pro Gln Val Tyr Thr Leu Pro Pro Ser Arg Glu Glu Met
275 280 285

Thr Lys Asn Gln Val Ser Leu Thr Cys Leu Val Lys Gly Phe Tyr Pro
290 295 300

Ser Asp Ile Ala Val Glu Trp Glu Ser Ser Gly Gln Pro Glu Asn Asn
305 310 315 320

Tyr Asn Thr Thr Pro Pro Met Leu Asp Ser Asp Gly Ser Phe Phe Leu
325 330 335

Tyr Ser Lys Leu Thr Val Asp Lys Ser Arg Trp Gln Gln Gly Asn Ile
340 345 350

Phe Ser Cys Ser Val Met His Glu Ala Leu His Asn Arg Phe Thr Gln
355 360 365

Lys Ser Leu Ser Leu Ser Pro Gly Lys
370 375

<210> SEQ ID NO 52
<211> LENGTH: 327
<212> TYPE: PRT
<213> ORGANISM: Homo sapiens

<400> SEQUENCE: 52

Ala Ser Thr Lys Gly Pro Ser Val Phe Pro Leu Ala Pro Cys Ser Arg
1 5 10 15

Ser Thr Ser Glu Ser Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Lys Thr
65 70 75 80

Tyr Thr Cys Asn Val Asp His Lys Pro Ser Asn Thr Lys Val Asp Lys
85 90 95

Arg Val Glu Ser Lys Tyr Gly Pro Pro Cys Pro Ser Cys Pro Ala Pro
100 105 110

Glu Phe Leu Gly Gly Pro Ser Val Phe Leu Phe Pro Pro Lys Pro Lys
115 120 125

Asp Thr Leu Met Ile Ser Arg Thr Pro Glu Val Thr Cys Val Val Val
130 135 140

Asp Val Ser Gln Glu Asp Pro Glu Val Gln Phe Asn Trp Tyr Val Asp
145 150 155 160

Gly Val Glu Val His Asn Ala Lys Thr Lys Pro Arg Glu Glu Gln Phe
165 170 175

Asn Ser Thr Tyr Arg Val Val Ser Val Leu Thr Val Leu His Gln Asp
180 185 190

Trp Leu Asn Gly Lys Glu Tyr Lys Cys Lys Val Ser Asn Lys Gly Leu
195 200 205

Pro Ser Ser Ile Glu Lys Thr Ile Ser Lys Ala Lys Gly Gln Pro Arg
210 215 220

```
Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 53
<211> LENGTH: 230
<212> TYPE: PRT
<213> ORGANISM: Artificial
<220> FEATURE:
<223> OTHER INFORMATION: An artificially synthesized peptide sequence

<400> SEQUENCE: 53

Glu Pro Lys Ser Ser Asp Lys Thr His Thr Cys Pro Pro Cys Pro Ala
1               5                   10                  15

Pro Glu Leu Leu Gly Gly Pro Asp Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Leu Pro Glu Glu Lys Thr Ile Ser Lys Ala Lys Gly Gln Pro
        115                 120                 125

Arg Glu Pro Gln Val Cys Thr Leu Pro Pro Ser Arg Asp Glu Leu Thr
    130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro
225                 230


<210> SEQ ID NO 54
<211> LENGTH: 230
```

```
<212> TYPE: PRT
<213> ORGANISM: Artificial
<220> FEATURE:
<223> OTHER INFORMATION: An artificially synthesized peptide sequence

<400> SEQUENCE: 54

Glu Pro Lys Ser Ser Asp Lys Thr His Thr Cys Pro Pro Cys Pro Ala
1               5                   10                  15

Pro Glu Tyr Leu Trp Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ala Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Cys Glu Leu Thr
    130                 135                 140

Lys Asn Gln Val Ser Leu Ser Cys Ala Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Val
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro
225                 230
```